(12) United States Patent
D'Souza et al.

(10) Patent No.: US 8,545,809 B2
(45) Date of Patent: *Oct. 1, 2013

(54) METHODS AND COMPOSITIONS FOR IMPROVED $^{18}$F LABELING OF PROTEINS, PEPTIDES AND OTHER MOLECULES

(75) Inventors: Christopher A. D'Souza, Pomona, NY (US); William J. McBride, Boonton, NJ (US); David M. Goldenberg, Mendham, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/323,139

(22) Filed: Dec. 12, 2011

(65) Prior Publication Data

US 2012/0134920 A1    May 31, 2012

Related U.S. Application Data

(63) Continuation-in-part of application No. 13/309,714, filed on Dec. 2, 2011, now Pat. No. 8,398,956, which is a continuation-in-part of application No. 12/958,889, filed on Dec. 2, 2010, now Pat. No. 8,202,509, which is a continuation-in-part of application No. 12/433,212, filed on Apr. 30, 2009, now Pat. No. 8,153,100, which is a continuation-in-part of application No. 12/343,655, filed on Dec. 24, 2008, now Pat. No. 7,993,626, which is a continuation-in-part of application No. 12/112,289, filed on Apr. 30, 2008, now Pat. No. 7,563,433, which is a continuation-in-part of application No. 11/960,262, filed on Dec. 19, 2007, now Pat. No. 7,597,876.

(60) Provisional application No. 61/419,082, filed on Dec. 2, 2010, provisional application No. 61/266,773, filed on Dec. 4, 2009, provisional application No. 61/302,280, filed on Feb. 8, 2010, provisional application No. 61/316,125, filed on Mar. 22, 2010, provisional application No. 61/347,486, filed on May 24, 2010, provisional application No. 61/381,720, filed on Sep. 10, 2010, provisional application No. 61/388,268, filed on Sep. 30, 2010, provisional application No. 61/884,521, filed on Jan. 11, 2007, provisional application No. 61/422,258, filed on Dec. 13, 2010, provisional application No. 61/479,660, filed on Apr. 27, 2011, provisional application No. 61/492,613, filed on Jun. 2, 2011, provisional application No. 61/523,668, filed on Aug. 15, 2011, provisional application No. 61/540,248, filed on Sep. 28, 2011, provisional application No. 61/547,434, filed on Oct. 14, 2011.

(51) Int. Cl.
*A61K 51/00* (2006.01)
*A61M 36/14* (2006.01)

(52) U.S. Cl.
USPC ....... 424/1.89; 424/1.11; 424/1.53; 424/1.65; 424/1.81; 424/1.85; 534/7; 534/14

(58) Field of Classification Search
USPC ................... 424/1.11, 1.49, 1.53, 1.65, 1.69, 424/1.73, 1.81, 1.85, 1.89, 9.1, 9.2, 9.3, 9.4, 424/9.5, 9.6, 9.7, 9.8; 534/7, 10–16; 514/1, 514/1.11; 530/300; 206/223, 569, 570
See application file for complete search history.

(56) References Cited

U.S. PATENT DOCUMENTS

| | | | |
|---|---|---|---|
| 5,256,395 | A | 10/1993 | Barbet et al. |
| 5,446,147 | A | 8/1995 | Kung et al. |
| 5,686,116 | A | 11/1997 | Bockman et al. |
| 6,056,939 | A | 5/2000 | Desreux et al. |
| 6,207,858 | B1 | 3/2001 | Chinn et al. |
| 6,469,162 | B1 | 10/2002 | Winchell et al. |
| 6,605,615 | B2 | 8/2003 | Medina et al. |
| 6,838,073 | B1 | 1/2005 | Collins et al. |
| 6,953,567 | B2 | 10/2005 | Griffiths et al. |
| 7,011,816 | B2 | 3/2006 | Griffiths et al. |
| 7,081,452 | B2 | 7/2006 | Brechbiel et al. |
| 7,163,935 | B2 | 1/2007 | Brechbiel et al. |
| 7,563,433 | B2 * | 7/2009 | McBride et al. ............. 424/1.89 |
| 7,597,876 | B2 * | 10/2009 | McBride et al. ............. 424/1.89 |

(Continued)

FOREIGN PATENT DOCUMENTS

| | | |
|---|---|---|
| KR | 1142153 | 5/2012 |
| WO | 2007027385 | 3/2007 |

(Continued)

OTHER PUBLICATIONS

D'Souza (Bioconjugate Chemistry, Jul. 30, 2011, vol. 22, pp. 1793-1803).*

(Continued)

*Primary Examiner* — D L Jones
(74) *Attorney, Agent, or Firm* — Richard A. Nakashima

(57) ABSTRACT

The present application discloses compositions and methods of synthesis and use of $^{18}$F or $^{19}$F-labeled molecules of use in PET, SPECT and/or MR imaging. Preferably, the $^{18}$F or $^{19}$F is conjugated to a targeting molecule by formation of a complex with a group IIIA metal and binding of the complex to a bifunctional chelating agent, which may be directly or indirectly attached to the targeting molecule. In other embodiments, the $^{18}$F or $^{19}$F labeled moiety may comprise a targetable construct used in combination with a bispecific antibody to target a disease-associated antigen. The disclosed methods and compositions allow the simple and reproducible labeling of molecules at very high efficiency and specific activity in 30 minutes or less. In preferred embodiments, the labeled molecule may be used for imaging in a subject without purification after labeling.

41 Claims, 30 Drawing Sheets

(56) References Cited

U.S. PATENT DOCUMENTS

| | | | |
|---|---|---|---|
| 7,842,279 B2 | 11/2010 | McBride et al. | |
| 7,993,626 B2* | 8/2011 | McBride et al. | 424/1.89 |
| 8,147,800 B2* | 4/2012 | McBride et al. | 424/1.89 |
| 8,153,100 B2* | 4/2012 | McBride et al. | 424/1.89 |
| 8,202,509 B2* | 6/2012 | McBride et al. | 424/1.89 |
| 2002/0006379 A1 | 1/2002 | Hansen et al. | |
| 2003/0064523 A1 | 4/2003 | Popov et al. | |
| 2005/0112060 A1 | 5/2005 | White et al. | |
| 2005/0136001 A1 | 6/2005 | McBride et al. | |
| 2006/0140858 A1 | 6/2006 | Goldenberg et al. | |
| 2006/0228300 A1 | 10/2006 | Chang et al. | |
| 2008/0027220 A1 | 1/2008 | Stossel et al. | |
| 2008/0038191 A1 | 2/2008 | Perrin et al. | |
| 2008/0089838 A1 | 4/2008 | Hansen et al. | |
| 2008/0170989 A1 | 7/2008 | McBride et al. | |
| 2008/0253964 A1 | 10/2008 | McBride et al. | |
| 2009/0246130 A1 | 10/2009 | McBride et al. | |
| 2009/0299033 A1 | 12/2009 | McBride et al. | |
| 2010/0008858 A1 | 1/2010 | McBride et al. | |
| 2010/0234338 A1 | 9/2010 | Delangle et al. | |
| 2010/0322855 A1 | 12/2010 | Chong et al. | |

FOREIGN PATENT DOCUMENTS

| | | |
|---|---|---|
| WO | 2008088648 | 7/2008 |
| WO | 2010011367 | 1/2010 |
| WO | 2010092114 | 8/2010 |
| WO | 2010109065 | 9/2010 |
| WO | 2010114308 | 10/2010 |

OTHER PUBLICATIONS

Cai et al., "Chemistry with [18F]Fluoride Ion", Eur. J. Org. Chem. 2008, pp. 2853-2873.

Clark et al., "The Preparation of Fluorine-18 Labelled Compounds Using a Recirculatory Neon Target", Radiochem. Radioanal. Letters 14(2):101-108 (1973).

D'Souza et al., "High-yielding aqueous 18F-labeling of peptides via Al18F chelation", Bioconjug Chem. Sep. 21, 2011;22(9):1793-803.

Imahori et al., "Fluorine-18-Labeled Fluoroboronophenylalanine PET in Patients with Glioma", J Nucl Med 1998; 39:325-333.

Karacay et al., "18F labeling of a peptide for PET imaging of receptor-expressing tumors", Abstract # 1567, 2009 SNM Annual Meeting Scientific Abstracts 50(Suppl. 2), p. 318P, May 2009.

Lang et al., "Comparison study of [18F]FAl-NOTA-PRGD2, [18F]FPPRGD2, and [68Ga]Ga-NOTA-PRGD2 for PET imaging of U87MG tumors in mice", Bioconjug Chem. Dec. 21, 2011;22(12):2415-22.

Laverman et al., "A novel facile method of labeling octreotide with (18)F-fluorine", J Nucl Med. Mar. 2010;51 (3):454-61.

Leyton et al., "Targeting somatostatin receptors: preclinical evaluation of novel 18F-fluoroethyltriazole-Tyr3-octreotate analogs for PET", J Nucl Med. Sep. 2011;52(9):1441-8.

Liu et al., "One-step radiosynthesis of $^{18}$F-AlF-NOTA-RGD$_2$ for tumor angiogenesis PET imaging", Eur J Nucl Med Mol Imaging. Sep. 2011;38(9)1732-41.

Mamat et al., "Recent Applications of Click Chemistry for the Synthesis of Radiotracers for Molecular Imaging", Mini-Reviews in Organic Chemistry, 2009, vol. 6, pp. 21-34.

Marik et al., "Click for PET: rapid preparation of [18F]fluoropeptides using CuI catalyzed 1,3-dipolar cycloaddition", Tetrahedron Letters 47 (2006) 6681-6684.

McBride et al., "A new method of labeling peptides and proteins with F-18 via a metal ligand", Abstract #384, J Nucl Med. 2008; 49 (Supplement 1):97P.

McBride et al., "A new method of labeling peptides and proteins with F-18 via a metal ligand", PowerPoint Presentation, 55th SNM Annual Meeting, New Orleans, LA, Jun. 17, 2008.

McBride et al., "A New Method of Labeling Peptides with F-18 Via a Metal Ligand", Abstract #04, Cancer Biother Radiopharm Aug. 2008; 23(4): 514.

McBride et al., "A New Method of Labeling Peptides with F-18 Via a Metal Ligand", PowerPoint Presentation, 19th Winter Fluorine Conference, St. Pete Beach, FL, Jan. 13, 2009.

McBride et al., "A New Method of Labeling Peptides with F-18 Via a Metal Ligand", Abstract #68, 19th Winter Fluorine Conference (Jan. 11-16, 2009) Abstract Book, p. 32.

McBride et al., "A novel method of radiolabeling peptides with aluminium-fluoride-18 (AlF-18) using various NOTA derivatives", Abstract # 202, 2009 SNM Annual Meeting Scientific Abstracts 50(Suppl. 2), pp. 52P-53P, May 2009.

McBride et al., "A novel method of 18F radiolabeling for PET", J Nucl Med. Jun. 2009;50(6):991-8.

McBride et al., "Improved 18F labeling of peptides with a fluoride-aluminum-chelate complex", Bioconjug Chem. Jul. 21, 2010;21(7):1331-40.

McBride et al., "The radiolabeling of proteins by the [18F]AlF method", Appl Radiat Isot. Jan. 2012;70(1):200-4.

McBride et al., "New Lyophilized Kit for Rapid Radiofluorination of Peptides", Bioconjug Chem. Feb. 10, 2012. [Epub ahead of print].

Miller et al., "Synthesis of 11C, 18F, 15O, and 13N Radiolabels for Positron Emission Tomography", Angew. Chem. Int. Ed. 2008, vol. 47, pp. 8998-9033.

Murata et al., "Formation of the Stable Myosin-ADP-Aluminum Fluoride and Myosin-ADP-Beryllium Fluoride Complexes and Their Analysis Using 19F NMR", J. Biol. Chem. 268(10):7093-7100 (1993).

Schirrmacher et al., "Recent Developments and Trends in 18F-Radiochemistry: Syntheses and Applications" Mini-Reviews in Organic Chemistry, 2007, vol. 4, pp. 317-329.

Schoffelen et al., "Pretargeted immunoPET for imaging colorectal cancer in a mouse model", Abstract # 381, 2009 NM Annual Meeting Scientific Abstracts 50(Suppl. 2), pp. 100P, May 2009.

Schoffelen et al., "Pretargeted immuno-positron emission tomography imaging of carcinoembryonic antigen-expressing tumors with a bispecific antibody and a 68Ga- and 18F-labeled hapten peptide in mice with human tumor xenografts", Mol Cancer Ther. Apr. 2010;9(4):1019-27.

Shetty et al., "Stable aluminium fluoride chelates with triazacyclononane derivatives proved by X-ray crystallography and 18F-labeling study", Chem Commun (Camb). Sep. 14, 2011;47(34):9732-4.

Ting et al., "Toward [18F]-Labeled Aryltrifluoroborate Radiotracers: In Vivo Positron Emission Tomography Imaging of Stable Aryltrifluoroborate Clearance in Mice", J. Am. Chem. Soc. 2008, 130, 12045-12055.

Ting et al., "Arylfruoroborates and Alkylfluorosilicates as Potential PET Imaging Agents: High-Yielding Aqueous Biomolecular 18F-Labeling", J. Am. Chem. Soc. 2005, 127, 13094-13095.

Wagner, Henry N. "Advancing a Molecular Theory of Disease", J Nulc Med 49(8):15N-34N. (2008).

Wester et al., "Fluorine-18 Labeling of Peptides and Proteins", Review, Ernst Schering Res. Found. Workshop 62:79-111 (2007).

Hatfield et al. "Structure change associated with the [M(II/III) 1,4,7-triazacyclononane-N,N',N"-triacetate (TCTA)] (-/0) electron transfers (M = Mn, Fe, and Ni): crystal structure for [Fe(II)(H2O)6][Fe(II)(TCTA)]2", Inorg Chem. Oct. 18, 2010;49(20):9312-20.

Pubchem CID 44623582. 2-[4-(carboxymethyl)-7-(2-hydroxyethyl)-1,4,7-triazonan-1-yl]acetic acid. Feb. 22, 2010. [Retrieved from the Internet Jun. 24, 2012: <http://pubchem.ncbi.nlm.nih.gov/summary/summary.cgi?cid=44623582&loc=ec_rcs>].

Pubchem CID 124326. 1,4,7-triazacyclononane-N,N',N"-triacetic acid. Mar. 27, 2005. [Retrieved from the Internet Mar. 1, 2012: http://pubchem.ncbi.nlm.nih.gov/summary/summary.cgi?cid=124326&loc=ec_rcs>].

Shetty et al. "Synthesis and evaluation of macrocyclic amino acid derivatives for tumor imaging by gallium-68 positron emission tomography", Bioorg Med Chem. Nov. 1, 2010;18(21):7338-47.

International Search Report for PCT/US11/64407, filed Dec. 12, 2011. Date of mailing Jul. 11, 2012.

* cited by examiner

F-18  Ga-68

IMP-479
Molecular Weight =1349.5446
Exact Mass =1348.7330
Molecular Formula =C62H96N18O16

HH22-168
NODA-HA-D-Ala-D-Lys(HSG)-D-Tyr-D-Lys(HSG)-NH₂

[M-H]⁻ 1347.7214

IMP-485

Molecular Weight =1312.4750
Exact Mass =1311.6724
Molecular Formula =C62H89N17O15
II14-137-11
NODA-MPAA-D-Lys(HSG)-D-Tyr-D-Lys(HSG)-NH₂

(M+H)⁺  1312.6838

IMP-487

Molecular Weight =1383.5229
Exact Mass =1382.7095
Molecular Formula =C65H94N18O16

Il14-150-13

NODA-EPA-succinyl-D-Lys(HSG)-D-Tyr-D-Lys(HSG)-NH₂

IMP-490
NODA-MPAA-D-Phe-c[Cys-Phe-D-Trp-Lys-Thr-Cys]-Thr(ol)

Molecular Weight =1394.69
Exact Mass =1393
Molecular Formula =C68H91N13O15S2

IMP-493

Molecular Weight = 1562.87
Exact Mass = 1561
Molecular Formula = C73H111N17O19S

NODA-MPAA-PEG4-Gln-Trp-Ala-Val-Gly-His-Leu-Met-NH2

IMP-495
NODA-EBA-D-Glu-D-Lys(HSG)-D-Tyr-D-Lys(HSG)-NH₂

Molecular Weight =1441.62
Exact Mass =1440
Molecular Formula =C67H96N18O18

IMP-496
NODA-MBA-D-Glu-D-Lys(HSG)-D-Tyr-D-Lys(HSG)-NH$_2$
Molecular Weight =1427.59
Exact Mass =1426
Molecular Formula =C66H94N18O18

NODA-HA         NODA-MPN         NODA-EPN

NODA-MBA        NODA-EPA         NODA-MPAA

NODA-BAEM              NODA-MPAEM

NODA-BM                NODA-MBEM $^{18}$F-hMN14-Fab (after spin column)

$^{18}$F-hMN14-Fab + human serum 37 °C (t = 1 h)

$^{18}$F-hMN14-Fab + human serum 37 °C (t = 3 h)

$^{18}$F-hMN14-Fab + human Serum (1 h 40 m) + CEA $^{18}$F-hMN14-Fab + human Serum (3 h 25 m) + CEA

METHODS AND COMPOSITIONS FOR IMPROVED $^{18}$F LABELING OF PROTEINS, PEPTIDES AND OTHER MOLECULES

RELATED APPLICATIONS

This application is a continuation-in-part of U.S patent application Ser. No. 13/309,714, filed Dec. 2, 2011, which was a continuation-in-part of U.S. patent application Ser. No. 12/958,889, filed Dec. 2, 2010, which was a continuation-in-part of U.S patent application Ser. No. 12/433,212, filed Apr. 30, 2009, which was a continuation-in-part of U.S patent application Ser. No. 12/343,655 (now U.S. Pat. No. 7,993,626), filed Dec. 24, 2008, which was a continuation-in-part of U.S patent application Ser. No. 12/112,289 (now U.S. Pat. No. 7,563,433), filed Apr. 30, 2008, which was a continuation-in-part of U.S. patent application Ser. No. 11/960,262 (now U.S. Pat. No. 7,597,876), filed Dec. 19, 2007. These applications claimed the benefit under 35 U.S.C. 119(e) of provisional U.S. Patent Application Nos. 61/419,082, filed Dec. 2, 2010; 61/388,268, filed Sep. 30, 2010; 61/381,720, filed Sep. 10, 2010; 61/347,486, filed May 24, 2010; 61/316,125, filed Mar. 22, 2010; 61/302,280, filed Feb. 8, 2010; 61/266,773, filed Dec. 4, 2009; 60/884,521, filed Jan. 11, 2007. This application claims the benefit under 35 U.S.C. 119(e) of provisional U.S. Patent Application Nos. 61/422,258, filed Dec. 13, 2010; 61/479,660, filed Apr. 27, 2011; 61/492,613, filed Jun. 2, 2011; 61/523,668, filed Aug. 15, 2011; 61/540,248, filed Sep. 28, 2011, and 61/547,434, filed Oct. 14, 2011. Each priority application is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Dec. 14, 2011, is named IMM310US.txt and is 27,535 bytes in size.

FIELD

The present invention concerns methods of labeling peptides or other molecules with $^{18}$F or $^{19}$F that are of use, for example, in PET or NMR in vivo imaging. Preferably, the $^{18}$F or $^{19}$F is attached as a complex with aluminum or another metal, such as a Group IIIA metal, via a chelating moiety, which may be covalently linked to a protein, peptide or other molecule. The chelating moiety may be attached to a protein, peptide or other molecule either before or after binding to the metal-$^{18}$F or metal-$^{19}$F complex. When labeling of heat sensitive molecules is performed, labeling may occur at a lower temperature, or alternatively a chelating moiety may be labeled at a higher temperature and then conjugated to the heat sensitive molecule. In certain embodiments, the labeled molecule may be used for targeting a cell, tissue, organ or pathogen to be imaged or detected. Exemplary targeting molecules include, but are not limited to, an antibody, antigen-binding antibody fragment, bispecific antibody, affibody, diabody, minibody, ScFvs, aptamer, avimer, targeting peptide, somatostatin, bombesin, octreotide, RGD peptide, folate, folate analog or any other molecule known to bind to a disease-associated target.

Using the techniques described herein, $^{18}$F-labeled molecules of high specific activity may be prepared in 30 minutes or less and are suitable for use in imaging techniques without the need for HPLC purification of the labeled molecule. Labeling may occur in a saline medium suitable for direct use in vivo. In alternative embodiments an organic solvent may be added to improve the labeling efficiency. The labeled molecules are stable under physiological conditions, although for certain purposes, such as kit formulations, a stabilizing agent such as ascorbic acid, trehalose, sorbitol or mannitol may be added. In other alternative embodiments, a chelating moiety may be preloaded with aluminum and lyophilized for storage, prior to labeling with $^{18}$F.

BACKGROUND

Positron Emission Tomography (PET) has become one of the most prominent functional imaging modalities in diagnostic medicine, with very high sensitivity (fmol), high resolution (4-10 mm) and tissue accretion that can be adequately quantitated (Volkow et al., 1988, Am. J. Physiol. Imaging 3:142). Although [$^{18}$F]2-deoxy-2-fluoro-D-glucose ([$^{18}$F]FDG) is the most widely used PET imaging agent in oncology (Fletcher et al., 2008, J. Nucl. Med. 49:480), there is a keen interest in developing other labeled compounds for functional imaging to complement and augment anatomic imaging methods (Torigian et al., 2007, CA Cancer J. Clin. 57:206), especially with the hybrid PET/computed tomography systems currently in use. Thus, there is a need to have facile methods of conjugating positron emitting radionuclides to various molecules of biological and medical interest.

Peptides or other targeting molecules can be labeled with the positron emitters $^{18}$F, $^{64}$Cu, $^{11}$C, $^{66}$Ga, $^{68}$Ga, $^{76}$Br, $^{94m}$Tc, $^{86}$Y, and $^{124}$I. A low ejection energy for a PET isotope is desirable to minimize the distance that the positron travels from the target site before it generates the two 511 keV gamma rays that are imaged by the PET camera. Many isotopes that emit positrons also have other emissions such as gamma rays, alpha particles or beta particles in their decay chain. It is desirable to have a PET isotope that is a pure positron emitter so that any dosimetry problems will be minimized. The half-life of the isotope is also important, since the half-life must be long enough to attach the isotope to a targeting molecule, analyze the product, inject it into the patient, and allow the product to localize, clear from non-target tissues and then image. $^{18}$F ($\beta^+$97%, 635 keV, $t_{1/2}$ 110 min) is one of the most widely used PET emitting isotopes because of its low positron emission energy, lack of side emissions and suitable half-life.

Conventionally, $^{18}$F is attached to compounds by binding it to a carbon atom (Miller et al., 2008, Angew Chem Int Ed 47:8998-9033), but attachments to silicon (Shirrmacher et al., 2007, Bioconj Chem 18:2085-89; Hohne et al., 2008, Bioconj Chem 19:1871-79) and boron (Ting et al., 2008, Fluorine Chem 129:349-58) have also been reported. Binding to carbon usually involves multistep syntheses, including multiple purification steps, which is problematic for an isotope with a 110-min half-life. Current methods for $^{18}$F-labeling of peptides typically involve the labeling of a reagent at low specific activity, HPLC purification of the reagent and then conjugation to the peptide of interest. The conjugate is often repurified after conjugation to obtain the desired specific activity of labeled peptide.

An example is the labeling method of Poethko et al. (J. Nucl. Med. 2004; 45: 892-902) in which 4-[$^{18}$F]fluorobenzaldehyde is first synthesized and purified (Wilson et al, J. Labeled Compounds and Radiopharm. 1990; XXVIII: 1189-1199) and then conjugated to the peptide. The peptide conjugate is then purified by HPLC to remove excess peptide that was used to drive the conjugation to completion. Other examples include labeling with succinimidyl [$^{18}$F]fluorobenzoate (SFB) (e.g., Vaidyanathan et al., 1992, Int. J. Rad. Appl. Instrum. B 19:275), other acyl compounds (Tada et al., 1989, Labeled Compd. Radiopharm. XXVII:1317; Wester et al., 1996, Nucl. Med. Biol. 23:365; Guhlke et al., 1994, Nucl. Med. Biol 21:819), or click chemistry adducts (Li et al., 2007, Bioconj Chem. 18:1987). The total synthesis and formulation time for these methods ranges between 1-3 hours, with most of the time dedicated to the HPLC purification of the labeled peptides to obtain the specific activity required for in vivo targeting. With a 2 hr half-life, all of the manipulations that are needed to attach the $^{18}F$ to the peptide are a significant burden. These methods are also tedious to perform and require the use of equipment designed specifically to produce the labeled product and/or the efforts of specialized professional chemists. They are also not conducive to kit formulations that could routinely be used in a clinical setting.

A need exists for a rapid, simple method of $^{18}F$ labeling of targeting moieties, such as proteins or peptides, which results in targeting constructs of suitable specific activity and in vivo stability for detection and/or imaging, while minimizing the requirements for specialized equipment or highly trained personnel and reducing operator exposure to high levels of radiation. More preferably a need exists for methods of preparing $^{18}F$-labeled targeting peptides of use in pretargeting technologies. A further need exists for prepackaged kits that could provide compositions required for performing such novel methods. An additional need exists for methods of efficiently labeling temperature sensitive molecules.

SUMMARY

In certain embodiments, the claimed compositions and methods relate to chelating moieties of a structure as shown in Structure 1 below, with values for R1,R2, and R3 as indicated below.

Structure 1

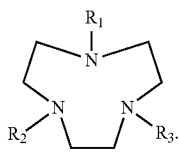

wherein $R_1$ and $R_2$ are independently selected from the group consisting of
—$CH_2$—COOH
—$CH^2$—$CH^2$—OH
—CH($C_3$)—COOH
—CH($C_6H_5$)—COOH

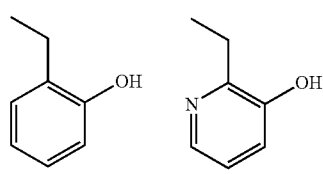

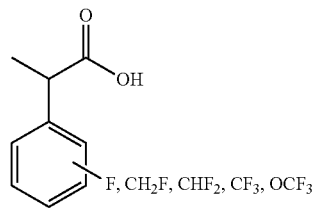

and $R_3$ is selected from the group consisting of:

—$CH_2$—$(CH_2)_n$—COOH   —$CH_2$—$(CH_2)_n$—OH
—$CH_2$—$(CH_2)_n$—$N_3$   —$CH_2$—$(CH_2)_n$—SH
—$CH_2$—$(CH_2)_n$—C≡CH   —$CH_2$—$(CH_2)_n$—$CONHNH_2$
—$CH_2$—$(CH_2)_n$—NH—$NH_2$   —$CH_2$—$(CH_2)_n$—$NH_2$
—$CH_2$—$(CH_2)_n$—N=C=S

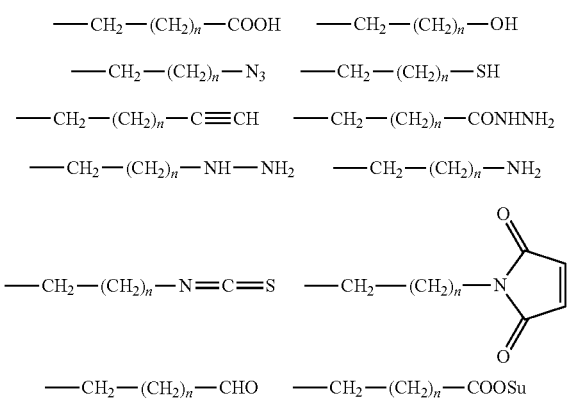

—$CH_2$—$(CH_2)_n$—CHO   —$CH_2$—$(CH_2)_n$—COOSu

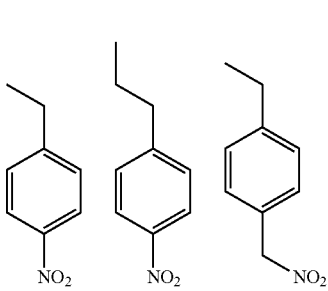

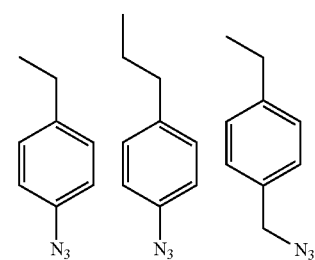

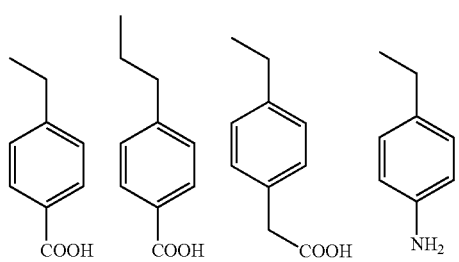

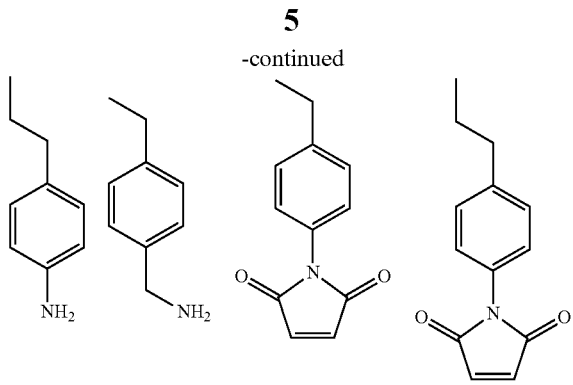
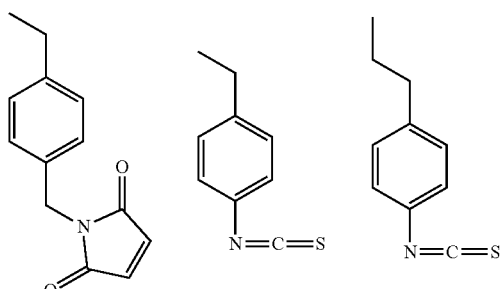
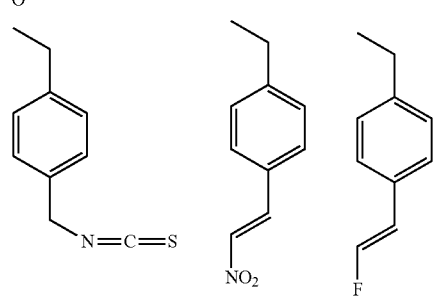
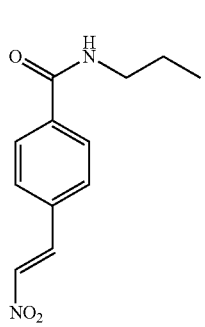
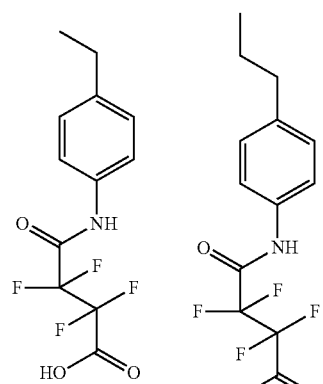
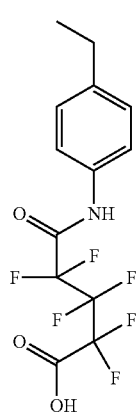
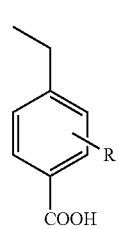
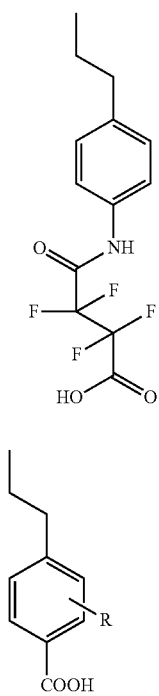
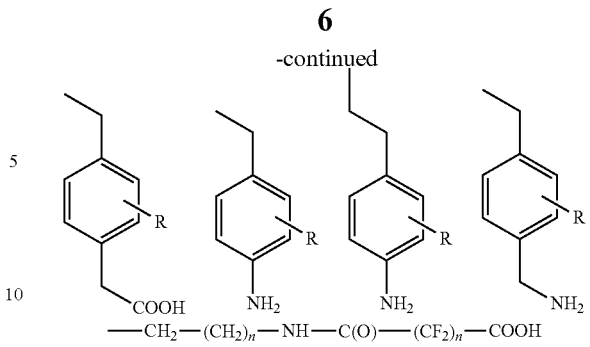
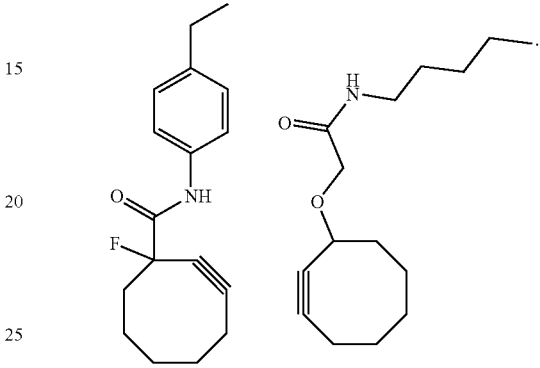

n = 1-9
R = F, CH$_2$F, CHF$_2$, CF$_3$, OCF$_3$

In various embodiments, the present invention concerns compositions and methods relating to $^{18}$F- or $^{19}$F-labeled molecules of use for PET or NMR imaging. As discussed herein, where the present application refers to $^{18}$F the skilled artisan will realize that either $^{18}$F, $^{19}$F or another radionuclide, such as $^{68}$Ga, may be utilized. In an exemplary approach, the $^{18}$F is bound to a metal and the $^{18}$F-metal complex is attached to a ligand on a peptide or other molecule. As described below, the metals of group IIIA (aluminum, gallium, indium, and thallium) are suitable for $^{18}$F binding, although aluminum is preferred. Lutetium may also be of use. The metal binding ligand is preferably a chelating agent, such as NOTA, NODA, NETA, DOTA, DTPA and other chelating groups discussed in more detail below. Alternatively, one can attach the metal to a molecule first and then add the $^{18}$F to bind to the metal. In still other embodiments, one may attach an $^{18}$F-metal to a chelating moiety first and then attach the labeled chelating moiety to a molecule, such as a temperature sensitive molecule. In this way, the $^{18}$F-metal may be attached to a chelating moiety at a higher temperature, such as between 90° to 110° C., more preferably between 95° to 105° C., and the $^{18}$F-labeled chelating moiety may be attached to a temperature sensitive molecule at a lower temperature, such as at room temperature.

The skilled artisan will realize that virtually any delivery molecule can be attached to $^{18}$F for imaging purposes, so long as it contains derivatizable groups that may be modified without affecting the ligand-receptor binding interaction between the delivery molecule and the cellular or tissue target receptor. Although the Examples below primarily concern $^{18}$F-labeled peptide moieties, many other types of delivery molecules, such as oligonucleotides, hormones, growth factors, cytokines, chemokines, angiogenic factors, anti-angiogenic factors, immunomodulators, proteins, nucleic acids, antibodies, antibody fragments, drugs, interleukins, interferons, oligosaccharides, polysaccharides, siderophores, lipids, etc. may be $^{18}$F-labeled and utilized for imaging purposes.

Exemplary targetable construct peptides described in the Examples below, of use for pre-targeting delivery of $^{18}$F or other agents, include but are not limited to IMP449, IMP460, IMP461, IMP467, IMP469, IMP470, IMP471, IMP479, IMP485, IMP486, IMP487, IMP488, IMP490, IMP493, IMP495, IMP497 and IMP500, comprising chelating moieties that include, but are not limited to, DTPA, NOTA, benzyl-NOTA, alkyl or aryl derivatives of NOTA, NODA, NODA-GA, C-NETA, succinyl-C-NETA and bis-t-butyl-NODA.

In certain embodiments, the exemplary $^{18}$F-labeled peptides may be of use as targetable constructs in a pre-targeting method, utilizing bispecific or multispecific antibodies or antibody fragments. In this case, the antibody or fragment will comprise one or more binding sites for a target associated with a disease or condition, such as a tumor-associated or autoimmune disease-associated antigen or an antigen produced or displayed by a pathogenic organism, such as a virus, bacterium, fungus or other microorganism. A second binding site will specifically bind to the targetable construct. Methods for pre-targeting using bispecific or multispecific antibodies are well known in the art (see, e.g., U.S. Pat. No. 6,962,702, the Examples section of which is incorporated herein by reference.) Similarly, antibodies or fragments thereof that bind to targetable constructs are also well known in the art, such as the 679 monoclonal antibody that binds to HSG (histamine succinyl glycine) or the 734 antibody that binds to In-DTPA (see U.S. Pat. Nos. 7,429,381; 7,563,439; 7,666,415; and 7,534,431, the Examples section of each incorporated herein by reference). Generally, in pretargeting methods the bispecific or multispecific antibody is administered first and allowed to bind to cell or tissue target antigens. After an appropriate amount of time for unbound antibody to clear from circulation, the e.g. labeled targetable construct is administered to the patient and binds to the antibody localized to target cells or tissues. Then an image is taken, for example by PET scanning.

In alternative embodiments, molecules that bind directly to receptors, such as somatostatin, octreotide, bombesin, folate or a folate analog, an RGD peptide or other known receptor ligands may be labeled and used for imaging. Receptor targeting agents may include, for example, TA138, a non-peptide antagonist for the integrin $\alpha_v\beta_3$ receptor (Liu et al., 2003, Bioconj. Chem. 14:1052-56). Other methods of receptor targeting imaging using metal chelates are known in the art and may be utilized in the practice of the claimed methods (see, e.g., Andre et al., 2002, J. Inorg. Biochem. 88:1-6; Pearson et al., 1996, J. Med., Chem. 39:1361-71).

The type of diseases or conditions that may be imaged is limited only by the availability of a suitable delivery molecule for targeting a cell or tissue associated with the disease or condition. Many such delivery molecules are known. For example, any protein or peptide that binds to a diseased tissue or target, such as cancer, may be labeled with $^{18}$F by the disclosed methods and used for detection and/or imaging. In certain embodiments, such proteins or peptides may include, but are not limited to, antibodies or antibody fragments that bind to tumor-associated antigens (TAAs). Any known TAA-binding antibody or fragment may be labeled with $^{18}$F by the described methods and used for imaging and/or detection of tumors, for example by PET scanning or other known techniques.

Certain alternative embodiments involve the use of "click" chemistry for attachment of $^{18}$F-labeled moieties to targeting molecules. Preferably, the click chemistry involves the reaction of a targeting molecule such as an antibody or antigen-binding antibody fragment, comprising a functional group such as an alkyne, nitrone or an azide group, with a $^{18}$F-labeled moiety comprising the corresponding reactive moiety such as an azide, alkyne or nitrone. Where the targeting molecule comprises an alkyne, the chelating moiety or carrier will comprise an azide, a nitrone or similar reactive moiety. The click chemistry reaction may occur in vitro to form a highly stable, $^{18}$F-labeled targeting molecule that is then administered to a subject.

In other alternative embodiments, a prosthetic group, such as a NODA-maleimide moiety, may be labeled with $^{18}$F-metal and then conjugated to a targeting molecule, for example by a maleimide-sulfhydryl reaction. Exemplary NODA-maleimide moieties include, but are not limited to, NODA-MPAEM, NODA-PM, NODA-PAEM, NODA-BAEM, NODA-BM, NODA-MPM, and NODA-MBEM.

BRIEF DESCRIPTION OF THE DRAWINGS

The following Figures are included to illustrate particular embodiments of the invention and are not meant to be limiting as to the scope of the claimed subject matter.

DETAILED DESCRIPTION

Figure 1:
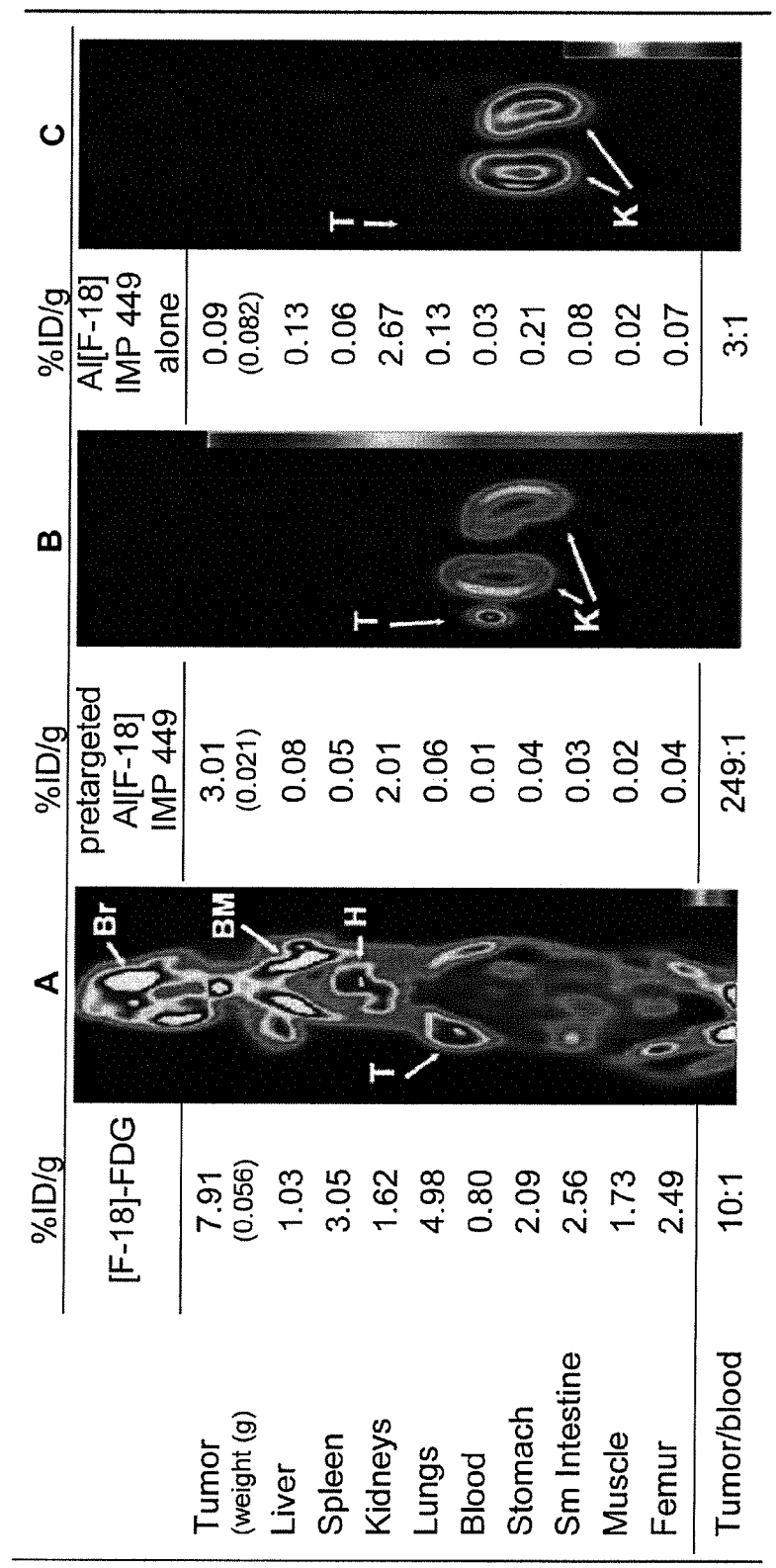
FIG. 1. Biodistribution of $^{18}$F-labeled agents in tumor-bearing nude mice by microPET imaging. Coronal slices of 3 nude mice bearing a small, subcutaneous LS174T tumor on each left flank after being injected with either (A) $^{18}$F-FDG, (B) Al$^{18}$F(IMP449) pretargeted with the anti-CEA×anti-HSG bsMAb, (C) Al$^{18}$F(IMP449) alone (not pretargeted with the bsMAb). Biodistribution data expressed as percent-injected dose per gram (% ID/g) are given for the tissues removed from the animals at the conclusion of the imaging session. Abbreviations: B, bone marrow; H, heart; K, kidney; T, tumor.

The following definitions are provided to facilitate understanding of the disclosure herein. Terms that are not explicitly defined are used according to their plain and ordinary meaning.

As used herein, "a" or "an" may mean one or more than one of an item.

As used herein, the terms "and" and "or" may be used to mean either the conjunctive or disjunctive. That is, both terms should be understood as equivalent to "and/or" unless otherwise stated.

As used herein, "about" means within plus or minus ten percent of a number. For example, "about 100" would refer to any number between 90 and 110.

As used herein, a "peptide" refers to any sequence of naturally occurring or non-naturally occurring amino acids of between 2 and 100 amino acid residues in length, more preferably between 2 and 10, more preferably between 2 and 6 amino acids in length. An "amino acid" may be an L-amino acid, a D-amino acid, an amino acid analogue, an amino acid derivative or an amino acid mimetic.

As used herein, the term "pathogen" includes, but is not limited to fungi, viruses, parasites and bacteria, including but not limited to human immunodeficiency virus (HIV), herpes virus, cytomegalovirus, rabies virus, influenza virus, hepatitis B virus, Sendai virus, feline leukemia virus, Reovirus, polio virus, human serum parvo-like virus, simian virus 40, respiratory syncytial virus, mouse mammary tumor virus, Varicella-Zoster virus, Dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus, blue tongue virus, *Streptococcus agalactiae*, *Legionella pneumophila*, *Streptococcus pyogenes*, *Escherichia coli*, *Neisseria gonorrhoeae*, *Neisseria meningitidis*, *Pneumococcus*, *Hemophilus influenzae* B, *Treponema pallidum*, Lyme disease spirochetes, *Pseudomonas aeruginosa*, *Mycobacterium leprae*, *Brucella abortus*, *Mycobacterium tuberculosis* and *Clostridium tetani*.

As used herein, a "radiolysis protection agent" refers to any molecule, compound or composition that may be added to an $^{18}$F-labeled complex or molecule to decrease the rate of breakdown of the $^{18}$F-labeled complex or molecule by radiolysis. Any known radiolysis protection agent, including but not limited to ascorbic acid, may be used.

$^{18}$F Labeling Techniques

A variety of techniques for labeling molecules with $^{18}$F are known. Table 1 lists the properties of several of the more commonly reported fluorination procedures. Peptide labeling through carbon often involves $^{18}$F-binding to a prosthetic group through nucleophilic substitution, usually in 2- or 3-steps where the prosthetic group is labeled and purified, attached to the compound, and then purified again. This general method has been used to attach prosthetic groups through amide bonds, aldehydes, and "click" chemistry (Marik et al., 2006, Bioconj Chem 17:1017-21; Poethko et al., 2004, J Nucl Med 45:892-902; Li et al., 2007, Bioconj Chem 18:989-93). The most common amide bond-forming reagent has been N-succinimidyl 4-$^{18}$F-fluorobenzoate ($^{18}$F-SFB), but a number of other groups have been tested (Marik et al., 2006). In some cases, such as when $^{18}$F-labeled active ester amide-forming groups are used, it may be necessary to protect certain groups on a peptide during the coupling reaction, after which they are cleaved. The synthesis of this $^{18}$F-SFB reagent and subsequent conjugation to the peptide requires many synthetic steps and takes about 2-3 h.

A simpler, more efficient $^{18}$F-peptide labeling method was developed by Poethko et al. (2004), where a 4-$^{18}$F-fluorobenzaldehyde reagent was conjugated to a peptide through an oxime linkage in about 75-90 min, including the dry-down step. The newer "click chemistry" method attaches $^{18}$F-labeled molecules onto peptides with an acetylene or azide in the presence of a copper catalyst (Li et al, 2007; Glaser and Arstad, 2007, Bioconj Chem 18:989-93). The reaction between the azide and acetylene groups forms a triazole connection, which is quite stable and forms very efficiently on peptides without the need for protecting groups. Click chemistry produces the $^{18}$F-labeled peptides in good yield (~50%) in about 75-90 min with the dry-down step.

TABLE 1

Summary of selected $^{18}$F-labeling methods.

| Author/Ref. | Schirrmacher et al. (2007) | Höhne et al. (2008) | Li et al. (2007) | Glaser & Arstad (2007) | Poethko et al. (2004) | Marik et al (2006) |
|---|---|---|---|---|---|---|
| Attachment | Silicon | Silicon | Click | Click | Aldehyde/oxime | Amide |
| Rx steps | 2 | 1 | 2 | 2 | 2 | many |
| Rx time (min)[a] | 40 | 115-155 | 110 | 65-80 (estimated) | 75-90 min (estimated) | 110+ |
| Yield[b] | 55% | 13% | 54% | 50% | 40% | 10% |
| HPLC-purification steps | 1 | 1 | 2 | 1 + distillation | 1 | 2 |
| Specific Activity (GBq/μmol) | 225-680 | 62 | high | high | high | high |

[a]Including dry-down time
[b]Decay corrected

A more recent method of binding $^{18}$F to silicon uses isotopic exchange to displace $^{19}$F with $^{18}$F (Shirrmacher et al., 2007). Performed at room temperature in 10 min, this reaction produces the $^{18}$F-prosthetic aldehyde group with high specific activity (225-680 GBq/μmol; 6,100-18,400 Ci/mmol). The $^{18}$F-labeled aldehyde is subsequently conjugated to a peptide and purified by HPLC, and the purified labeled peptide is obtained within 40 min (including dry-down) with ~55% yield. This was modified subsequently to a single-step process by incorporating the silicon into the peptide before the labeling reaction (Hohne et al, 2008). However, biodistribution studies in mice with an $^{18}$F-silicon-bombesin derivative showed bone uptake increasing over time (1.35±0.47% injected dose (ID)/g at 0.5 h vs. 5.14±2.71% ID/g at 4.0 h), suggesting a release of $^{18}$F from the peptide, since unbound $^{18}$F is known to localize in bone (Hohne et al., 2008). HPLC analysis of urine showed a substantial amount of $^{18}$F activity in the void volume, which presumably is due to fluoride anion ($^{18}$F$^-$) released from the peptide. It would therefore appear that the $^{18}$F-silicon labeled molecule was not stable in serum. Substantial hepatobiliary excretion was also reported, attributed to the lipophilic nature of the $^{18}$F-silicon-binding substrate, and requiring future derivatives to be more hydrophilic. Methods of attaching $^{18}$F to boron also have been explored; however, the current process produces conjugates with low specific activity (Ting et al., 2008).

Antibodies and peptides are coupled routinely with radiometals, typically in 15 min and in quantitative yields (Meares et al., 1984, Acc Chem Res 17:202-209; Scheinberg et al., 1982, Science 215:1511-13). For PET imaging, $^{64}$Cu and $^{68}$Ga have been bound to peptides via a chelate, and have shown reasonably good PET-imaging properties (Heppler et al., 2000, Current Med Chem 7:971-94). Since fluoride binds to most metals, we sought to determine if an $^{18}$F-metal complex could be bound to a chelator on a targeting molecule (Tewson, 1989, Nucl Med Biol. 16:533-51; Martin, 1996, Coordination Chem Rev 141:23-32). We have focused on the binding of an Al$^{18}$F complex, since aluminum-fluoride can be relatively stable in vivo (Li, 2003, Crit Rev Oral Biol Med 14:100-114; Antonny et al., 1992, J Biol Chem 267:6710-18). Initial studies showed the feasibility of this approach to prepare an $^{18}$F-labeled peptide for in vivo targeting of cancer with a bispecific antibody (bsMAb) pretargeting system, a highly sensitive and specific technique for localizing cancer, in some cases better than [$^{18}$F]FDG (fluorodeoxyglucose) (McBride et al., 2008, J Nucl Med (suppl) 49:97 P; Wagner, 2008, J Nucl Med 49:23 N-24N; Karacay et al., 2000, Bioconj Chem 11:842-54; Sharkey et al., 2008, Cancer Res 68; 5282-90; Gold Et al., 2008, Cancer Res 68:4819-26; Sharkey et al., 2005, Nature Med 11:1250-55; Sharkey et al., 2005, Clin Cancer Res 11:7109s-7121s; McBride et al., 2006, J Nucl Med 47:1678-88; Sharkey et al., 2008, Radiology 246:497-508). These studies revealed that an Al$^{18}$F complex could bind stably to a 1,4,7-triazacyclononane-1,4,7-triacetic acid (NOTA), but the yields were low.

In the Examples below, new labeling conditions and several new chelating moieties were examined that enhanced yields from about 10% to about 80%, providing a feasible method for $^{18}$F-labeling of peptides and other molecules of use in PET imaging.

Targetable Constructs

In certain embodiments, the moiety labeled with $^{18}$F or other diagnostic and/or therapeutic agents may comprise a peptide or other targetable construct. Labeled peptides (or proteins), for example RGD peptide, octreotide, bombesin or somatostatin, may be selected to bind directly to a targeted cell, tissue, pathogenic organism or other target for imaging, detection and/or diagnosis. In other embodiments, labeled peptides may be selected to bind indirectly, for example using a bispecific antibody with one or more binding sites for a targetable construct peptide and one or more binding sites for a target antigen associated with a disease or condition. Bispecific antibodies may be used, for example, in a pretargeting technique wherein the antibody may be administered first to a subject. Sufficient time may be allowed for the bispecific antibody to bind to a target antigen and for unbound antibody to clear from circulation. Then a targetable construct, such as a labeled peptide, may be administered to the subject and allowed to bind to the bispecific antibody and localize at the diseased cell or tissue. The distribution of $^{18}$F-labeled targetable constructs may be determined by PET scanning or other known techniques.

Such targetable constructs can be of diverse structure and are selected not only for the availability of an antibody or fragment that binds with high affinity to the targetable construct, but also for rapid in vivo clearance when used within the pre-targeting method and bispecific antibodies (bsAb) or multispecific antibodies. Hydrophobic agents are best at eliciting strong immune responses, whereas hydrophilic agents are preferred for rapid in vivo clearance. Thus, a balance between hydrophobic and hydrophilic character is established. This may be accomplished, in part, by using hydrophilic chelating agents to offset the inherent hydrophobicity of many organic moieties. Also, sub-units of the targetable construct may be chosen which have opposite solution properties, for example, peptides, which contain amino acids, some of which are hydrophobic and some of which are hydrophilic. Aside from peptides, carbohydrates may also be used.

Peptides having as few as two amino acid residues, preferably two to ten residues, may be used and may also be coupled to other moieties, such as chelating agents. The linker should be a low molecular weight conjugate, preferably having a molecular weight of less than 50,000 daltons, and advantageously less than about 20,000 daltons, 10,000 daltons or 5,000 daltons. More usually, the targetable construct peptide will have four or more residues, such as the peptide DOTA-Phe-Lys(HSG)-Tyr-Lys(HSG)-NH$_2$ (SEQ ID NO: 1), wherein DOTA is 1,4,7,10-tetraazacyclododecane-1,4,7,10-tetraacetic acid and HSG is the histamine succinyl glycyl group. Alternatively, DOTA may be replaced by NOTA (1,4,7-triazacyclononane-1,4,7-triacetic acid), TETA (p-bromoacetamido-benzyl-tetraethylaminetetraacetic acid), NETA ([2-(4,7-biscarboxymethyl[1,4,7]triazacyclononan-1-yl-ethyl]-2-carbonylmethyl-amino]acetic acid) or other known chelating moieties.

The targetable construct may also comprise unnatural amino acids, e.g., D-amino acids, in the backbone structure to increase the stability of the peptide in vivo. In alternative embodiments, other backbone structures such as those constructed from non-natural amino acids or peptoids may be used.

The peptides used as targetable constructs are conveniently synthesized on an automated peptide synthesizer using a solid-phase support and standard techniques of repetitive orthogonal deprotection and coupling. Free amino groups in the peptide, that are to be used later for conjugation of chelating moieties or other agents, are advantageously blocked with standard protecting groups such as a Boc group, while N-terminal residues may be acetylated to increase serum stability. Such protecting groups are well known to the skilled artisan. See Greene and Wuts Protective Groups in Organic Synthesis, 1999 (John Wiley and Sons, N.Y.). When the peptides are prepared for later use within the bispecific antibody system, they are advantageously cleaved from the resins to generate the corresponding C-terminal amides, in order to inhibit in vivo carboxypeptidase activity. Exemplary methods of peptide synthesis are disclosed in the Examples below.

Where pretargeting with bispecific antibodies is used, the antibody will contain a first binding site for an antigen produced by or associated with a target tissue and a second binding site for a hapten on the targetable construct. Exemplary haptens include, but are not limited to, HSG and In-DTPA. Antibodies raised to the HSG hapten are known (e.g. 679 antibody) and can be easily incorporated into the appropriate bispecific antibody (see, e.g., U.S. Pat. Nos. 6,962,702; 7,138,103 and 7,300,644, incorporated herein by reference with respect to the Examples sections). However, other haptens and antibodies that bind to them are known in the art and may be used, such as In-DTPA and the 734 antibody (e.g., U.S. Pat. No. 7,534,431, the Examples section incorporated herein by reference).

The skilled artisan will realize that although the majority of targetable constructs disclosed in the Examples below are peptides, other types of molecules may be used as targetable constructs. For example, polymeric molecules, such as polyethylene glycol (PEG) may be easily derivatized with chelating moieties to bind Al$^{18}$F. Many examples of such carrier molecules are known in the art and may be utilized, including but not limited to polymers, nanoparticles, microspheres, liposomes and micelles. For use in pretargeted delivery of $^{18}$F, the only requirement is that the carrier molecule comprise one or more chelating moieties for attachment of metal-$^{18}$F and one or more hapten moieties to bind to a bispecific or multispecific antibody or other targeting molecule.

Chelating Moieties

In some embodiments, an $^{18}$F-labeled molecule may comprise one or more hydrophilic chelating moieties, which can bind metal ions and also help to ensure rapid in vivo clearance. Chelators may be selected for their particular metal-binding properties, and may be readily interchanged.

Particularly useful metal-chelate combinations include 2-benzyl-DTPA and its monomethyl and cyclohexyl analogs. Macrocyclic chelators such as NOTA (1,4,7-triazacyclononane-1,4,7-triacetic acid), DOTA, TETA (p-bromoacetamido-benzyl-tetraethylaminetetraacetic acid) and NETA are also of use with a variety of metals, that may potentially be used as ligands for $^{18}$F-labeling.

DTPA and DOTA-type chelators, where the ligand includes hard base chelating functions such as carboxylate or amine groups, are most effective for chelating hard acid cations, especially Group IIa and Group IIIa metal cations. Such metal-chelate complexes can be made very stable by tailoring the ring size to the metal of interest. Other ring-type chelators such as macrocyclic polyethers are of interest for stably binding nuclides. Porphyrin chelators may be used with numerous metal complexes. More than one type of chelator may be conjugated to a carrier to bind multiple metal ions. Chelators such as those disclosed in U.S. Pat. No. 5,753,206, especially thiosemicarbazonylglyoxylcysteine (Tscg-Cys) and thiosemicarbazinyl-acetylcysteine (Tsca-Cys) chelators are advantageously used to bind soft acid cations of Tc, Re, Bi and other transition metals, lanthanides and actinides that are tightly bound to soft base ligands. It can be useful to link more than one type of chelator to a peptide. Because antibodies to a di-DTPA hapten are known (Barbet et al., U.S. Pat. No. 5,256,395) and are readily coupled to a targeting antibody to form a bispecific antibody, it is possible to use a peptide hapten with cold diDTPA chelator and another chelator for binding an $^{18}$F complex, in a pretargeting protocol. One example of such a peptide is Ac-Lys(DTPA)-Tyr-Lys(DTPA)-Lys(Tscg-Cys)-NH$_2$ (core peptide disclosed as SEQ ID NO:2). Other hard acid chelators such as DOTA, TETA and the like can be substituted for the DTPA and/or Tscg-Cys groups, and MAbs specific to them can be produced using analogous techniques to those used to generate the anti-di-DTPA MAb.

Another useful chelator may comprise a NOTA-type moiety, for example as disclosed in Chong et al. (*J. Med. Chem.*, 2008, 51:118-25). Chong et al. disclose the production and use of a bifunctional C-NETA ligand, based upon the NOTA structure, that when complexed with $^{177}$Lu or $^{205/206}$Bi showed stability in serum for up to 14 days. The chelators are not limiting and these and other examples of chelators that are known in the art and/or described in the following Examples may be used in the practice of the invention.

It will be appreciated that two different hard acid or soft acid chelators can be incorporated into the targetable construct, e.g., with different chelate ring sizes, to bind preferentially to two different hard acid or soft acid cations, due to the differing sizes of the cations, the geometries of the chelate rings and the preferred complex ion structures of the cations. This will permit two different metals, one or both of which may be attached to $^{18}$F, to be incorporated into a targetable construct for eventual capture by a pretargeted bispecific antibody.

Antibodies

Target Antigens

Targeting antibodies of use may be specific to or selective for a variety of cell surface or disease-associated antigens. Exemplary target antigens of use for imaging or treating various diseases or conditions, such as a malignant disease, a cardiovascular disease, an infectious disease, an inflammatory disease, an autoimmune disease, a metabolic disease, or a neurological (e.g., neurodegenerative) disease may include α-fetoprotein (AFP), A3, amyloid beta, CA125, colon-specific antigen-p (CSAp), carbonic anhydrase IX, CCCL19, CCCL21, CSAp, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, CXCR4, CXCR7, CXCL12, HIF-1α, AFP, CEACAM5, CEACAM6, c-met, B7, ED-B of fibronectin, EGP-1, EGP-2, Factor H, FHL-1, fibrin, Flt-3, folate receptor, glycoprotein GRO-β, human chorionic gonadotropin (HCG), HER-2/neu, HMGB-1, hypoxia inducible factor (HIF), HM1.24, HLA-DR, Ia, ICAM-1, insulin-like growth factor-1 (IGF-1), IGF-1R, IFN-γ, IFN-α, IFN-β, IL-2, IL-4R, IL-6R, IL-13R, IL-15R, IL-17R, IL-18R, IL-1, IL-6, IL-8, IL-12, IL-15, IL-17, IL-18, IL-25, IP-10, KS-1, Le(y), low-density lipoprotein (LDL), MAGE, mCRP, MCP-1, MIP-1A, MIP-1B, MIF, MUC1, MUC2, MUC3, MUC4, MUC5a-c, MUC16, NCA-95, NCA-90, as NF-κB, pancreatic cancer mucin, PAM4 antigen, placental growth factor, p53, PLAGL2, Pr1, prostatic acid phosphatase, PSA, PRAME, PSMA, PIGF, tenascin, RANTES, T101, TAC, TAG72, TF, Tn antigen, Thomson-Friedenreich antigens, thrombin, tumor necrosis antigens, TNF-α, TRAIL receptor (R1 and R2), TROP2, VEGFR, EGFR, complement factors C3, C3a, C3b, C5a, C5, and an oncogene product.

In certain embodiments, such as imaging or treating tumors, antibodies of use may target tumor-associated antigens. These antigenic markers may be substances produced by a tumor or may be substances which accumulate at a tumor site, on tumor cell surfaces or within tumor cells. Among such tumor-associated markers are those disclosed by Herberman, "Immunodiagnosis of Cancer", in Fleisher ed., "The Clinical Biochemistry of Cancer", page 347 (American Association of Clinical Chemists, 1979) and in U.S. Pat. Nos. 4,150,149; 4,361,544; and 4,444,744, the Examples section of each of which is incorporated herein by reference. Reports on tumor associated antigens (TAAs) include Mizukami et al., (2005, Nature Med. 11:992-97); Hatfield et al., (2005, Curr. Cancer Drug Targets 5:229-48); Vallbohmer et al. (2005, J. Clin. Oncol. 23:3536-44); and Ren et al. (2005, Ann. Surg. 242:55-63), each incorporated herein by reference with respect to the TAAs identified.

Tumor-associated markers have been categorized by Herberman, supra, in a number of categories including oncofetal antigens, placental antigens, oncogenic or tumor virus associated antigens, tissue associated antigens, organ associated antigens, ectopic hormones and normal antigens or variants thereof. Occasionally, a sub-unit of a tumor-associated marker is advantageously used to raise antibodies having higher tumor-specificity, e.g., the beta-subunit of human chorionic gonadotropin (HCG) or the gamma region of carcinoembryonic antigen (CEA), which stimulate the production of antibodies having a greatly reduced cross-reactivity to non-tumor substances as disclosed in U.S. Pat. Nos. 4,361,644 and 4,444,744.

Another marker of interest is transmembrane activator and CAML-interactor (TACI). See Yu et al. Nat. Immunol. 1:252-256 (2000). Briefly, TACI is a marker for B-cell malignancies (e.g., lymphoma). TACI and B-cell maturation antigen (BCMA) are bound by the tumor necrosis factor homolog—a proliferation-inducing ligand (APRIL). APRIL stimulates in vitro proliferation of primary B and T-cells and increases spleen weight due to accumulation of B-cells in vivo. APRIL also competes with TALL-I (also called BLyS or BAFF) for receptor binding. Soluble BCMA and TACI specifically prevent binding of APRIL and block APRIL-stimulated proliferation of primary B-cells. BCMA-Fc also inhibits production of antibodies against keyhole limpet hemocyanin and Pneumovax in mice, indicating that APRIL and/or TALL-I signaling via BCMA and/or TACI are required for generation of humoral immunity. Thus, APRIL-TALL-I and BCMA-TACI form a two ligand-two receptor pathway involved in stimulation of B and T-cell function.

Where the disease involves a lymphoma, leukemia or autoimmune disorder, targeted antigens may be selected from the group consisting of CD4, CD5, CD8, CD14, CD15, CD19, CD20, CD21, CD22, CD23, CD25, CD33, CD37, CD38, CD40, CD40L, CD46, CD52, CD54, CD67, CD74, CD79a, CD80, CD126, CD138, CD154, B7, MUC1, Ia, Ii, HM1.24, HLA-DR, tenascin, VEGF, PIGF, ED-B fibronectin, an oncogene (e.g., c-met or PLAGL2), an oncogene product, CD66a-d, necrosis antigens, IL-2, T101, TAG, IL-6, MIF, TRAIL-R1 (DR4) and TRAIL-R2 (DR5).

In some embodiments, target antigens may be selected from the group consisting of (A) proinflammatory effectors of the innate immune system, (B) coagulation factors, (C) complement factors and complement regulatory proteins, and (D) targets specifically associated with an inflammatory or immune-dysregulatory disorder or with a pathologic angiogenesis or cancer, wherein the latter target is not (A), (B), or (C). Suitable targets are described in U.S. patent application Ser. No. 11/296,432, filed Dec. 8, 2005, the Examples section of which is incorporated herein by reference.

The proinflammatory effector of the innate immune system may be a proinflammatory effector cytokine, a proinflammatory effector chemokine or a proinflammatory effector receptor. Suitable proinflammatory effector cytokines include MIF, HMGB-1 (high mobility group box protein 1), TNF-α, IL-1, IL-4, IL-5, IL-6, IL-8, IL-12, IL-15, and IL-18. Examples of proinflammatory effector chemokines include CCL19, CCL21, IL-8, MCP-1, RANTES, MIP-1A, MIP-1B, ENA-78, MCP-1, IP-10, GRO-β, and eotaxin. Proinflammatory effector receptors include IL-4R (interleukin-4 receptor), IL-6R (interleukin-6 receptor), IL-13R (interleukin-13 receptor), IL-15R (interleukin-15 receptor) and IL-18R (interleukin-18 receptor).

The targeting molecule may bind to a coagulation factor, such as tissue factor (TF) or thrombin. In other embodiments, the targeting molecule may bind to a complement factor or complement regulatory protein. In preferred embodiments, the complement factor is selected from the group consisting of C3, C5, C3a, C3b, and C5a. When the targeting molecule binds to a complement regulatory protein, the complement regulatory protein preferably is selected from the group consisting of CD46, CD55, CD59 and mCRP.

MIF is a pivotal cytokine of the innate immune system and plays an important part in the control of inflammatory responses. Originally described as a T lymphocyte-derived factor that inhibited the random migration of macrophages, the protein known as macrophage migration inhibitory factor (MIF) was an enigmatic cytokine for almost 3 decades. In recent years, the discovery of MIF as a product of the anterior pituitary gland and the cloning and expression of bioactive, recombinant MIF protein have led to the definition of its critical biological role in vivo. MIF has the unique property of being released from macrophages and T lymphocytes that have been stimulated by glucocorticoids. Once released, MIF overcomes the inhibitory effects of glucocorticoids on TNF-α, IL-1β, IL-6, and IL-8 production by LPS-stimulated monocytes in vitro and suppresses the protective effects of steroids against lethal endotoxemia in vivo. MIF also antagonizes glucocorticoid inhibition of T-cell proliferation in vitro by restoring IL-2 and IFN-gamma production. MIF is the first mediator to be identified that can counter-regulate the inhibitory effects of glucocorticoids and thus plays a critical role in the host control of inflammation and immunity. MIF is particularly of use in cancer, pathological angiogenesis, and sepsis or septic shock. More recently, CD74 has been identified as an endogenous receptor for MIF, along with CD44, CXCR2 and CXCR4 (see, e.g., Baron et al., 2011, J Neuroscience Res 89:711-17). Targeting molecules that bind to MIF, CD74, CD44, CXCR2 and/or CXCR4 may be of use for imaging various of these conditions.

HMGB-1, a DNA binding nuclear and cytosolic protein, is a proinflammatory cytokine released by monocytes and macrophages that have been activated by IL-1β, TNF, or LPS. Via its B box domain, it induces phenotypic maturation of DCs. It also causes increased secretion of the proinflammatory cytokines IL-1α, IL-6, IL-8, IL-12, TNF-α and RANTES. HMGB-1 released by necrotic cells may be a signal of tissue or cellular injury that, when sensed by DCs, induces and/or enhances an immune reaction. Palumbo et al. report that HMBG1 induces mesoangioblast migration and proliferation (J Cell Biol, 164:441-449, 2004). Targeting molecules that target HMBG-1 may be of use in detecting, diagnosing or treating arthritis, particularly collagen-induced arthritis, sepsis and/or septic shock. Yang et al., PNAS USA 101:296-301 (2004); Kokkola et al., Arthritis Rheum, 48:2052-8 (2003); Czura et al., J Infect Dis, 187 Suppl 2:S391-6 (2003); Treutiger et al., J Intern Med, 254:375-85 (2003).

TNF-α is an important cytokine involved in systemic inflammation and the acute phase response. TNF-α is released by stimulated monocytes, fibroblasts, and endothelial cells. Macrophages, T-cells and B-lymphocytes, granulocytes, smooth muscle cells, eosinophils, chondrocytes, osteoblasts, mast cells, glial cells, and keratinocytes also produce TNF-α after stimulation. Its release is stimulated by several other mediators, such as interleukin-1 and bacterial endotoxin, in the course of damage, e.g., by infection. It has a number of actions on various organ systems, generally together with interleukins-1 and -6. TNF-α is a useful target for sepsis or septic shock.

The complement system is a complex cascade involving proteolytic cleavage of serum glycoproteins often activated by cell receptors. The "complement cascade" is constitutive and non-specific but it must be activated in order to function. Complement activation results in a unidirectional sequence of enzymatic and biochemical reactions. In this cascade, a specific complement protein, C5, forms two highly active, inflammatory byproducts, C5a and C5b, which jointly activate white blood cells. This in turn evokes a number of other inflammatory byproducts, including injurious cytokines, inflammatory enzymes, and cell adhesion molecules. Together, these byproducts can lead to the destruction of tissue seen in many inflammatory diseases. This cascade ultimately results in induction of the inflammatory response, phagocyte chemotaxis and opsonization, and cell lysis.

The complement system can be activated via two distinct pathways, the classical pathway and the alternate pathway. Some of the components must be enzymatically cleaved to activate their function; others simply combine to form complexes that are active. Active components of the classical pathway include C1q, C1r, C1s, C2a, C2b, C3a, C3b, C4a, and C4b. Active components of the alternate pathway include C3a, C3b, Factor B, Factor Ba, Factor Bb, Factor D, and Properdin. The last stage of each pathway is the same, and involves component assembly into a membrane attack complex. Active components of the membrane attack complex include C5a, C5b, C6, C7, C8, and C9n.

While any of these components of the complement system can be targeted, certain of the complement components are preferred. C3a, C4a and C5a cause mast cells to release chemotactic factors such as histamine and serotonin, which attract phagocytes, antibodies and complement, etc. These form one group of preferred targets. Another group of preferred targets includes C3b, C4b and C5b, which enhance phagocytosis of foreign cells. Another preferred group of targets are the predecessor components for these two groups, i.e., C3, C4 and C5. C5b, C6, C7, C8 and C9 induce lysis of foreign cells (membrane attack complex) and form yet another preferred group of targets.

Coagulation factors also are preferred targets, particularly tissue factor (TF) and thrombin. TF is also known also as tissue thromboplastin, CD142, coagulation factor III, or factor III. TF is an integral membrane receptor glycoprotein and a member of the cytokine receptor superfamily. The ligand binding extracellular domain of TF consists of two structural modules with features that are consistent with the classification of TF as a member of type-2 cytokine receptors. TF is involved in the blood coagulation protease cascade and initiates both the extrinsic and intrinsic blood coagulation cascades by forming high affinity complexes between the extracellular domain of TF and the circulating blood coagulation factors, serine proteases factor VII or factor VIIa. These enzymatically active complexes then activate factor IX and factor X, leading to thrombin generation and clot formation.

TF is expressed by various cell types, including monocytes, macrophages and vascular endothelial cells, and is induced by IL-1, TNF-α or bacterial lipopolysaccharides. Protein kinase C is involved in cytokine activation of endothelial cell TF expression. Induction of TF by endotoxin and cytokines is an important mechanism for initiation of disseminated intravascular coagulation seen in patients with Gram-negative sepsis. TF also appears to be involved in a variety of non-hemostatic functions including inflammation, cancer, brain function, immune response, and tumor-associated angiogenesis. Thus, targeting molecules that target TF are of use in coagulopathies, sepsis, cancer, pathologic angiogenesis, and other immune and inflammatory dysregulatory diseases.

In other embodiments, the targeting molecule may bind to a MHC class I, MHC class II or accessory molecule, such as CD40, CD54, CD80 or CD86. The binding molecule also may bind to a T-cell activation cytokine, or to a cytokine mediator, such as NF-κB.

Targets associated with sepsis and immune dysregulation and other immune disorders include MIF, IL-1, IL-6, IL-8, CD74, CD83, and C5aR. Antibodies and inhibitors against C5aR have been found to improve survival in rodents with sepsis (Huber-Lang et al., FASEB J 2002; 16:1567-1574; Riedemann et al., J Clin Invest 2002; 110:101-108) and septic shock and adult respiratory distress syndrome in monkeys (Hangen et al., J Surg Res 1989; 46:195-199; Stevens et al., J Clin Invest 1986; 77:1812-1816). Thus, for sepsis, preferred targets are associated with infection, such as LPS/C5a. Other preferred targets include HMGB-1, TF, CD14, VEGF, and IL-6, each of which is associated with septicemia or septic shock.

In still other embodiments, a target may be associated with graft versus host disease or transplant rejection, such as MIF (Lo et al., Bone Marrow Transplant, 30(6):375-80 (2002)), CD74 or HLA-DR. A target also may be associated with acute respiratory distress syndrome, such as IL-8 (Bouros et al., PMC Pulm Med, 4(1):6 (2004), atherosclerosis or restenosis, such as MIF (Chen et al., Arterioscler Thromb Vasc Biol, 24(4):709-14 (2004), asthma, such as IL-18 (Hata et al., Int Immunol, Oct. 11, 2004 Epub ahead of print), a granulomatous disease, such as TNF-α (Ulbricht et al., Arthritis Rheum, 50(8):2717-8 (2004), a neuropathy, such as carbamylated EPO (erythropoietin) (Leist et al., Science 305(5681):164-5 (2004), or cachexia, such as IL-6 and TNF-α.

Other targets include C5a, LPS, IFN-gamma, B7; CD2, CD4, CD14, CD18, CD11a, CD11b, CD11c, CD14, CD18, CD27, CD29, CD38, CD40L, CD52, CD64, CD83, CD147, CD154. Activation of mononuclear cells by certain microbial antigens, including LPS, can be inhibited to some extent by antibodies to CD18, CD11b, or CD11c, which thus implicate $\beta_2$-integrins (Cuzzola et al., J Immunol 2000; 164:5871-5876; Medvedev et al., J Immunol 1998; 160: 4535-4542). CD83 has been found to play a role in giant cell arteritis (GCA), which is a systemic vasculitis that affects medium- and large-size arteries, predominately the extracranial branches of the aortic arch and of the aorta itself, resulting in vascular stenosis and subsequent tissue ischemia, and the severe complications of blindness, stroke and aortic arch syndrome (Weyand and Goronzy, N Engl J Med 2003; 349: 160-169; Hunder and Valente, In: Inflammatory Diseases of Blood Vessels. G. S. Hoffman and C. M. Weyand, eds, Marcel Dekker, New York, 2002; 255-265). Antibodies to CD83 were found to abrogate vasculitis in a SCID mouse model of human GCA (Ma-Krupa et al., J Exp Med 2004; 199:173-183), suggesting to these investigators that dendritic cells, which express CD83 when activated, are critical antigen-processing cells in GCA. In these studies, they used a mouse anti-CD83 MAb (IgG1 clone HB15e from Research Diagnostics). CD154, a member of the TNF family, is expressed on the surface of CD4-positive T-lymphocytes, and it has been reported that a humanized monoclonal antibody to CD154 produced significant clinical benefit in patients with active systemic lupus erythematosus (SLE) (Grammar et al., J Clin Invest 2003; 112:1506-1520). It also suggests that this antibody might be useful in other autoimmune diseases (Kelsoe, J Clin Invest 2003; 112:1480-1482). Indeed, this antibody was also reported as effective in patients with refractory immune thrombocytopenic purpura (Kuwana et al., Blood 2004; 103:1229-1236).

In rheumatoid arthritis, a recombinant interleukin-1 receptor antagonist, IL-1 Ra or anakinra, has shown activity (Cohen et al., Ann Rheum Dis 2004; 63:1062-8; Cohen, Rheum Dis Clin North Am 2004; 30:365-80). An improvement in treatment of these patients, which hitherto required concomitant treatment with methotrexate, is to combine anakinra with one or more of the anti-proinflammatory effector cytokines or anti-proinflammatory effector chemokines (as listed above). Indeed, in a review of antibody therapy for rheumatoid arthritis, Taylor (Curr Opin Pharmacol 2003; 3:323-328) suggests that in addition to TNF, other antibodies to such cytokines as IL-1, IL-6, IL-8, IL-15, IL-17 and IL-18, are useful.

Methods for Raising Antibodies

MAbs can be isolated and purified from hybridoma cultures by a variety of well-established techniques. Such isolation techniques include affinity chromatography with Protein-A or Protein-G Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992). After the initial raising of antibodies to the immunogen, the antibodies can be sequenced and subsequently prepared by recombinant techniques. Humanization and chimerization of murine antibodies and antibody fragments are well known to those skilled in the art, as discussed below.

Chimeric Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. General techniques for cloning murine immunoglobulin variable domains are disclosed, for example, in Orlandi et al., Proc. Nat'l Acad. Sci. USA 6: 3833 (1989). Techniques for constructing chimeric antibodies are well known to those of skill in the art. As an example, Leung et al., Hybridoma 13:469 (1994), produced an LL2 chimera by combining DNA sequences encoding the $V_\kappa$ and $V_H$ domains of murine LL2, an anti-CD22 monoclonal antibody, with respective human κ and $IgG_1$ constant region domains.

Humanized Antibodies

Techniques for producing humanized MAbs are well known in the art (see, e.g., Jones et al., Nature 321: 522 (1986), Riechmann et al., Nature 332: 323 (1988), Verhoeyen et al., Science 239: 1534 (1988), Carter et al., Proc. Nat'l Acad. Sci. USA 89: 4285 (1992), Sandhu, Crit. Rev. Biotech. 12: 437 (1992), and Singer et al., J. Immun. 150: 2844 (1993)). A chimeric or murine monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. As simply transferring mouse CDRs into human FRs often results in a reduction or even loss of antibody affinity, additional modification might be required in order to restore the original affinity of the murine antibody. This can be accomplished by the replacement of one or more human residues in the FR regions with their murine counterparts to obtain an antibody that possesses good binding affinity to its epitope. See, for example, Tempest et al., Biotechnology 9:266 (1991) and Verhoeyen et al., Science 239: 1534 (1988). Preferred residues for substitution include FR residues that are located within 1, 2, or 3 Angstroms of a CDR residue side chain, that are located adjacent to a CDR sequence, or that are predicted to interact with a CDR residue.

Human Antibodies

Methods for producing fully human antibodies using either combinatorial approaches or transgenic animals transformed with human immunoglobulin loci are known in the art (e.g., Mancini et al., 2004, New Microbiol. 27:315-28; Conrad and Scheller, 2005, Comb. Chem. High Throughput Screen. 8:117-26; Brekke and Loset, 2003, Curr. Opin. Pharmacol. 3:544-50). A fully human antibody also can be constructed by genetic or chromosomal transfection methods, as well as phage display technology, all of which are known in the art. See for example, McCafferty et al., Nature 348:552-553 (1990). Such fully human antibodies are expected to exhibit even fewer side effects than chimeric or humanized antibodies and to function in vivo as essentially endogenous human antibodies.

In one alternative, the phage display technique may be used to generate human antibodies (e.g., Dantas-Barbosa et al., 2005, *Genet. Mol. Res.* 4:126-40). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.). Recombinant Fab were cloned from the µ, γ and κ chain antibody repertoires and inserted into a phage display library (Id.). RNAs were converted to cDNAs and used to make Fab cDNA libraries using specific primers against the heavy and light chain immunoglobulin sequences (Marks et al., 1991, *J. Mol. Biol.* 222:581-97). Library construction was performed according to Andris-Widhopf et al. (2000, In: *Phage Display Laboratory Manual*, Barbas et al. (eds), 1$^{st}$ edition, Cold Spring Harbor Laboratory Press, Cold Spring Harbor, N.Y. pp. 9.1 to 9.22). The final Fab fragments were digested with restriction endonucleases and inserted into the bacteriophage genome to make the phage display library. Such libraries may be screened by standard phage display methods, as known in the art. Phage display can be performed in a variety of formats, for their review, see e.g. Johnson and Chiswell, *Current Opinion in Structural Biology* 3:5564-571 (1993).

Human antibodies may also be generated by in vitro activated B-cells. See U.S. Pat. Nos. 5,567,610 and 5,229,275, incorporated herein by reference in their entirety. The skilled artisan will realize that these techniques are exemplary and any known method for making and screening human antibodies or antibody fragments may be utilized.

In another alternative, transgenic animals that have been genetically engineered to produce human antibodies may be used to generate antibodies against essentially any immunogenic target, using standard immunization protocols. Methods for obtaining human antibodies from transgenic mice are disclosed by Green et al., *Nature Genet.* 7:13 (1994), Lonberg et al., *Nature* 368:856 (1994), and Taylor et al., *Int. Immun.* 6:579 (1994). A non-limiting example of such a system is the XenoMouse® (e.g., Green et al., 1999, *J. Immunol. Methods* 231:11-23, incorporated herein by reference) from Abgenix (Fremont, Calif.). In the XenoMouse® and similar animals, the mouse antibody genes have been inactivated and replaced by functional human antibody genes, while the remainder of the mouse immune system remains intact.

The XenoMouse® was transformed with germline-configured YACs (yeast artificial chromosomes) that contained portions of the human IgH and Igkappa loci, including the majority of the variable region sequences, along with accessory genes and regulatory sequences. The human variable region repertoire may be used to generate antibody producing B-cells, which may be processed into hybridomas by known techniques. A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

Known Antibodies

The skilled artisan will realize that the targeting molecules of use for imaging, detection and/or diagnosis may incorporate any antibody or fragment known in the art that has binding specificity for a target antigen associated with a disease state or condition. Such known antibodies include, but are not limited to, hR1 (anti-IGF-1R, U.S. patent application Ser. No. 12/772,645, filed Mar. 12, 2010) hPAM4 (anti-pancreatic cancer mucin, U.S. Pat. No. 7,282,567), hA20 (anti-CD20, U.S. Pat. No. 7,251,164), hA19 (anti-CD19, U.S. Pat. No. 7,109,304), hIMMU31 (anti-AFP, U.S. Pat. No. 7,300,655), hLL1 (anti-CD74, U.S. Pat. No. 7,312,318), hLL2 (anti-CD22, U.S. Pat. No. 7,074,403), hMu-9 (anti-CSAp, U.S. Pat. No. 7,387,773), hL243 (anti-HLA-DR, U.S. Pat. No. 7,612,180), hMN-14 (anti-CEACAM5, U.S. Pat. No. 6,676,924), hMN-15 (anti-CEACAM6, U.S. Pat. No. 7,662,378, U.S. patent application Ser. No. 12/846,062, filed Jul. 29, 2010), hRS7 (anti-TROP2), U.S. Pat. No. 7,238,785), hMN-3 (anti-CEACAM6, U.S. Pat. No. 7,541,440), Ab124 and Ab125 (anti-CXCR4, U.S. Pat. No. 7,138,496) the Examples section of each cited patent or application incorporated herein by reference.

Alternative antibodies of use include, but are not limited to, abciximab (anti-glycoprotein IIb/IIIa), alemtuzumab (anti-CD52), bevacizumab (anti-VEGF), cetuximab (anti-EGFR), gemtuzumab (anti-CD33), ibritumomab tiuxetan (anti-CD20), panitumumab (anti-EGFR), rituximab (anti-CD20), tositumomab (anti-CD20), trastuzumab (anti-ErbB2), abagovomab (anti-CA-125), adecatumumab (anti-EpCAM), atlizumab (anti-IL-6 receptor), benralizumab (anti-CD125), CC49 (anti-TAG-72), AB-PG1-XG1-026 (anti-PSMA, U.S. patent application Ser. No. 11/983,372, deposited as ATCC PTA-4405 and PTA-4406), D2/B (anti-PSMA, WO 2009/130575), tocilizumab (anti-IL-6 receptor), basiliximab (anti-CD25), daclizumab (anti-CD25), efalizumab (anti-CD11a), GA101 (anti-CD20; Glycart Roche), muromonab-CD3 (anti-CD3 receptor), natalizumab (anti-α4 integrin), omalizumab (anti-IgE); anti-TNF-α antibodies such as CDP571 (Ofei et al., 2011, Diabetes 45:881-85), MTNFAI, M2TNFAI, M3TNFAI, M3TNFABI, M302B, M303 (Thermo Scientific, Rockford, Ill.), infliximab (CENTOCOR, Malvern, Pa.), certolizumab pegol (UCB, Brussels, Belgium), anti-CD70L (UCB, Brussels, Belgium), adalimumab (Abbott, Abbott Park, Ill.), Benlysta (Human Genome Sciences); and antibodies against pathogens such as CR6261 (anti-influenza), exbivirumab (anti-hepatitis B), felvizumab (anti-respiratory syncytial virus), foravirumab (anti-rabies virus), motavizumab (anti-respiratory syncytial virus), palivizumab (anti-respiratory syncytial virus), panobacumab (anti-*Pseudomonas*), rafivirumab (anti-rabies virus), regavirumab (anti-cytomegalovirus), sevirumab (anti-cytomegalovirus), tivirumab (anti-hepatitis B), and urtoxazumab (anti-*E. coli*).

Other antibodies are known to target antigens associated with diseased cells, tissues or organs. For example, bapineuzumab is in clinical trials for therapy of Alzheimer's disease. Other antibodies proposed for Alzheimer's disease include Alz 50 (Ksiezak-Reding et al., 1987, J Biol Chem 263:7943-47), gantenerumab, and solanezumab. Anti-CD3 antibodies have been proposed for type 1 diabetes (Cernea et al., 2010, Diabetes Metab Rev 26:602-05). Antibodies to fibrin (e.g., scFv(59D8); T2G1s; MH1) are known and in clinical trials as imaging agents for disclosing fibrin clots and pulmonary emboli, while anti-granulocyte antibodies, such as MN-3, MN-15, anti-NCA95, and anti-CD15 antibodies, can target myocardial infarcts and myocardial ischemia. (See, e.g., U.S. Pat. Nos. 5,487,892; 5,632,968; 6,294,173; 7,541,440, the Examples section of each incorporated herein by reference) Anti-macrophage, anti-low-density lipoprotein (LDL) and anti-CD74 (e.g., hLL1) antibodies can be used to target atherosclerotic plaques. Abciximab (anti-glycoprotein IIb/IIIa) has been approved for adjuvant use for prevention of restenosis in percutaneous coronary interventions and the treatment of unstable angina (Waldmann et al., 2000, Hematol 1:394-408). Anti-CD3 antibodies have been reported to reduce development and progression of atherosclerosis (Steffens et al., 2006, Circulation 114:1977-84). Antibodies against oxidized LDL induced a regression of established atherosclerosis in a mouse model (Ginsberg, 2007, J Am Coll Cardiol 52:2319-21). Anti-ICAM-1 antibody was shown to reduce ischemic cell damage after cerebral artery occlusion in rats (Zhang et al., 1994, Neurology 44:1747-51). Commercially available monoclonal antibodies to leukocyte antigens are represented by: OKT anti-T cell monoclonal antibodies (available from Ortho Pharmaceutical Company) which bind to normal T-lymphocytes; the monoclonal antibodies produced by the hybridomas having the ATCC accession numbers HB44, HB55, HB12, HB78 and HB2; G7E11, W8E7, NKP15 and GO22 (Becton Dickinson); NEN9.4 (New England Nuclear); and FMC11 (Sera Labs). A description of antibodies against fibrin and platelet antigens is contained in Knight, Semin. Nucl. Med., 20:52-67 (1990).

Known antibodies of use may bind to antigens produced by or associated with pathogens, such as HIV. Such antibodies may be used to detect, diagnose and/or treat infectious disease. Candidate anti-HIV antibodies include the anti-envelope antibody described by Johansson et al. (AIDS. 2006 Oct. 3; 20(15):1911-5), as well as the anti-HIV antibodies described and sold by Polymun (Vienna, Austria), also described in U.S. Pat. Nos. 5,831,034, 5,911,989, and Vcelar et al., AIDS 2007; 21(16):2161-2170 and Joos et al., Antimicrob. Agents Chemother. 2006; 50(5):1773-9, all incorporated herein by reference.

Antibodies against malaria parasites can be directed against the sporozoite, merozoite, schizont and gametocyte stages. Monoclonal antibodies have been generated against sporozoites (cirumsporozoite antigen), and have been shown to bind to sporozoites in vitro and in rodents (N. Yoshida et al., Science 207:71-73, 1980). Several groups have developed antibodies to *T. gondii*, the protozoan parasite involved in toxoplasmosis (Kasper et al., J. Immunol. 129:1694-1699, 1982; Id., 30:2407-2412, 1983). Antibodies have been developed against schistosomular surface antigens and have been found to bind to schistosomulae in vivo or in vitro (Simpson et al., Parasitology, 83:163-177, 1981; Smith et al., Parasitology, 84:83-91, 1982: Gryzch et al., J. Immunol., 129:2739-2743, 1982; Zodda et al., J. Immunol. 129:2326-2328, 1982; Dissous et al., J. Immunol., 129:2232-2234, 1982)

*Trypanosoma cruzi* is the causative agent of Chagas' disease, and is transmitted by blood-sucking reduviid insects. An antibody has been generated that specifically inhibits the differentiation of one form of the parasite to another (epimastigote to trypomastigote stage) in vitro and which reacts with a cell-surface glycoprotein; however, this antigen is absent from the mammalian (bloodstream) forms of the parasite (Sher et al., Nature, 300:639-640, 1982).

Anti-fungal antibodies are known in the art, such as anti-Sclerotinia antibody (U.S. Pat. No. 7,910,702); antiglucuronoxylomannan antibody (Zhong and Priofski, 1998, Clin Diag Lab Immunol 5:58-64); anti-Candida antibodies (Matthews and Burnie, 2001, 2:472-76); and anti-glycosphingolipid antibodies (Toledo et al., 2010, BMC Microbiol 10:47).

Where bispecific antibodies are used, the second MAb may be selected from any anti-hapten antibody known in the art, including but not limited to h679 (U.S. Pat. No. 7,429,381) and 734 (U.S. Pat. Nos. 7,429,381; 7,563,439; 7,666,415; and 7,534,431), the Examples section of each of which is incorporated herein by reference.

Various other antibodies of use are known in the art (e.g., U.S. Pat. Nos. 5,686,072; 5,874,540; 6,107,090; 6,183,744; 6,306,393; 6,653,104; 6,730.300; 6,899,864; 6,926,893; 6,962,702; 7,074,403; 7,230,084; 7,238,785; 7,238,786; 7,256,004; 7,282,567; 7,300,655; 7,312,318; 7,585,491; 7,612,180; 7,642,239 and U.S. Patent Application Publ. No. 20060193865; each incorporated herein by reference.) Such known antibodies are of use for detection and/or imaging of a variety of disease states or conditions (e.g., hMN-14 or TF2 (CEA-expressing carcinomas), hA20 or TF-4 (lymphoma), hPAM4 or TF-10 (pancreatic cancer), RS7 (lung, breast, ovarian, prostatic cancers), hMN-15 or hMN3 (inflammation), anti-gp120 and/or anti-gp41 (HIV), anti-platelet and anti-thrombin (clot imaging), anti-myosin (cardiac necrosis), anti-CXCR4 (cancer and inflammatory disease)).

Antibodies of use may be commercially obtained from a wide variety of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312, 318; 7,282,567; 7,151,164; 7,074,403; 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 6,783,758; 6,770,450; 6,767,711; 6,764,688; 6,764,681; 6,764,679; 6,743,898; 6,733,981; 6,730,307; 6,720,155; 6,716,966; 6,709,653; 6,693,176; 6,692,908; 6,689,607; 6,689,362; 6,689,355; 6,682,737; 6,682,736; 6,682,734; 6,673,344; 6,653,104; 6,652,852; 6,635,482; 6,630,144; 6,610,833; 6,610,294; 6,605,441; 6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040, 6,451,310; 6,444,206; 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393; 6,254,868; 6,187,287; 6,183,744; 6,129,914; 6,120,767; 6,096,289; 6,077,499; 5,922,302; 5,874,540; 5,814,440; 5,798,229; 5,789,554; 5,776,456; 5,736,119; 5,716,595; 5,677,136; 5,587,459; 5,443,953, 5,525,338. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art.

Antibody Fragments

Antibody fragments which recognize specific epitopes can be generated by known techniques. The antibody fragments are antigen binding portions of an antibody, such as F(ab')$_2$, Fab', F(ab)$_2$, Fab, Fv, sFv and the like. F(ab')$_2$ fragments can be produced by pepsin digestion of the antibody molecule and Fab' fragments can be generated by reducing disulfide bridges of the F(ab')$_2$ fragments. Alternatively, Fab' expression libraries can be constructed (Huse et al., 1989, *Science*, 246:1274-1281) to allow rapid and easy identification of monoclonal Fab' fragments with the desired specificity. An antibody fragment can be prepared by proteolytic hydrolysis of the full length antibody or by expression in *E. coli* or another host of the DNA coding for the fragment. These methods are described, for example, by Goldenberg, U.S. Pat. Nos. 4,036,945 and 4,331,647 and references contained therein, which patents are incorporated herein in their entireties by reference. Also, see Nisonoff et al., *Arch Biochem. Biophys.* 89: 230 (1960); Porter, *Biochem. J.* 73: 119 (1959), Edelman et al., in METHODS IN ENZYMOLOGY VOL. 1, page 422 (Academic Press 1967), and Coligan at pages 2.8.1-2.8.10 and 2.10.-2.10.4.

A single chain Fv molecule (scFv) comprises a $V_L$ domain and a $V_H$ domain. The $V_L$ and $V_H$ domains associate to form a target binding site. These two domains are further covalently linked by a peptide linker (L). Methods for making scFv molecules and designing suitable peptide linkers are described in U.S. Pat. No. 4,704,692, U.S. Pat. No. 4,946,778, R. Raag and M. Whitlow, "Single Chain Fvs." FASEB Vol 9:73-80 (1995) and R. E. Bird and B. W. Walker, "Single Chain Antibody Variable Regions," TIBTECH, Vol 9: 132-137 (1991), incorporated herein by reference.

An scFv library with a large repertoire can be constructed by isolating V-genes from non-immunized human donors using PCR primers corresponding to all known $V_H$, $V_{kappa}$ and $V_{80}$ gene families. See, e.g., Vaughn et al., Nat. Biotechnol., 14: 309-314 (1996). Following amplification, the $V_{kappa}$ and $V_{lambda}$ pools are combined to form one pool. These fragments are ligated into a phagemid vector. The scFv linker is then ligated into the phagemid upstream of the $V_L$ fragment. The $V_H$ and linker-$V_L$ fragments are amplified and assembled on the $J_H$ region. The resulting $V_H$-linker-$V_L$ fragments are ligated into a phagemid vector. The phagemid library can be panned for binding to the selected antigen.

Other antibody fragments, for example single domain antibody fragments, are known in the art and may be used in the claimed constructs. Single domain antibodies (VHH) may be obtained, for example, from camels, alpacas or llamas by standard immunization techniques. (See, e.g., Muyldermans et al., TIBS 26:230-235, 2001; Yau et al., J Immunol Methods 281:161-75, 2003; Maass et al., J Immunol Methods 324:13-25, 2007). The VHH may have potent antigen-binding capacity and can interact with novel epitopes that are inaccessible to conventional VH-VL pairs. (Muyldermans et al., 2001) Alpaca serum IgG contains about 50% camelid heavy chain only IgG antibodies (Cabs) (Maass et al., 2007). Alpacas may be immunized with known antigens and VHHs can be isolated that bind to and neutralize the target antigen (Maass et al., 2007). PCR primers that amplify virtually all alpaca VHH coding sequences have been identified and may be used to construct alpaca VHH phage display libraries, which can be used for antibody fragment isolation by standard biopanning techniques well known in the art (Maass et al., 2007). These and other known antigen-binding antibody fragments may be utilized in the claimed methods and compositions.

General Techniques for Antibody Cloning and Production

Various techniques, such as production of chimeric or humanized antibodies, may involve procedures of antibody cloning and construction. The antigen-binding $V_\kappa$ (variable light chain) and $V_H$ (variable heavy chain) sequences for an antibody of interest may be obtained by a variety of molecular cloning procedures, such as RT-PCR, 5'-RACE, and cDNA library screening. The V genes of a MAb from a cell that expresses a murine MAb can be cloned by PCR amplification and sequenced. To confirm their authenticity, the cloned $V_L$ and $V_H$ genes can be expressed in cell culture as a chimeric Ab as described by Orlandi et al., (*Proc. Natl. Acad. Sci.*, USA, 86: 3833 (1989)). Based on the V gene sequences, a humanized MAb can then be designed and constructed as described by Leung et al. (*Mol. Immunol.*, 32: 1413 (1995)).

cDNA can be prepared from any known hybridoma line or transfected cell line producing a murine MAb by general molecular cloning techniques (Sambrook et al., Molecular Cloning, A laboratory manual, $2^{nd}$ Ed (1989)). The $V_\kappa$ sequence for the MAb may be amplified using the primers VK1BACK and VK1FOR (Orlandi et al., 1989) or the extended primer set described by Leung et al. (*BioTechniques*, 15: 286 (1993)). The $V_H$ sequences can be amplified using the primer pair VH1BACK/VH1FOR (Orlandi et al., 1989) or the primers annealing to the constant region of murine IgG described by Leung et al. (Hybridoma, 13:469 (1994)). Humanized V genes can be constructed by a combination of long oligonucleotide template syntheses and PCR amplification as described by Leung et al. (*Mol. Immunol.*, 32: 1413 (1995)).

PCR products for $V_\kappa$ can be subcloned into a staging vector, such as a pBR327-based staging vector, VKpBR, that contains an Ig promoter, a signal peptide sequence and convenient restriction sites. PCR products for $V_H$ can be subcloned into a similar staging vector, such as the pBluescript-based VHpBS. Expression cassettes containing the $V_\kappa$ and $V_H$ sequences together with the promoter and signal peptide sequences can be excised from VKpBR and VHpBS and ligated into appropriate expression vectors, such as pKh and pG1g, respectively (Leung et al., Hybridoma, 13:469 (1994)). The expression vectors can be co-transfected into an appropriate cell and supernatant fluids monitored for production of a chimeric, humanized or human MAb. Alternatively, the $V_\kappa$ and $V_H$ expression cassettes can be excised and subcloned into a single expression vector, such as pdHL2, as described by Gillies et al. (*J. Immunol. Methods* 125:191 (1989) and also shown in Losman et al., *Cancer*, 80:2660 (1997)).

In an alternative embodiment, expression vectors may be transfected into host cells that have been pre-adapted for transfection, growth and expression in serum-free medium. Exemplary cell lines that may be used include the Sp/EEE, Sp/ESF and Sp/ESF-X cell lines (see, e.g., U.S. Pat. Nos. 7,531,327; 7,537,930 and 7,608,425; the Examples section of each of which is incorporated herein by reference). These exemplary cell lines are based on the Sp2/0 myeloma cell line, transfected with a mutant Bcl-EEE gene, exposed to methotrexate to amplify transfected gene sequences and pre-adapted to serum-free cell line for protein expression.

Bispecific and Multispecific Antibodies

Certain embodiments concern pretargeting methods with bispecific antibodies and hapten-bearing targetable constructs. Numerous methods to produce bispecific or multispecific antibodies are known, as disclosed, for example, in U.S. Pat. No. 7,405,320, the Examples section of which is incorporated herein by reference. Bispecific antibodies can be produced by the quadroma method, which involves the fusion of two different hybridomas, each producing a monoclonal antibody recognizing a different antigenic site (Milstein and Cuello, Nature, 1983; 305:537-540).

Another method for producing bispecific antibodies uses heterobifunctional cross-linkers to chemically tether two different monoclonal antibodies (Staerz, et al. Nature. 1985; 314:628-631; Perez, et al. Nature. 1985; 316:354-356). Bispecific antibodies can also be produced by reduction of each of two parental monoclonal antibodies to the respective half molecules, which are then mixed and allowed to reoxidize to obtain the hybrid structure (Staerz and Bevan. Proc Natl Acad Sci USA. 1986; 83:1453-1457). Other methods include improving the efficiency of generating hybrid hybridomas by gene transfer of distinct selectable markers via retrovirus-derived shuttle vectors into respective parental hybridomas, which are fused subsequently (DeMonte, et al. Proc Natl Acad Sci USA. 1990, 87:2941-2945); or transfection of a hybridoma cell line with expression plasmids containing the heavy and light chain genes of a different antibody.

Cognate $V_H$ and $V_L$ domains can be joined with a peptide linker of appropriate composition and length (usually consisting of more than 12 amino acid residues) to form a single-chain Fv (scFv), as discussed above. Reduction of the peptide linker length to less than 12 amino acid residues prevents pairing of $V_H$ and $V_L$ domains on the same chain and forces pairing of $V_H$ and $V_L$ domains with complementary domains on other chains, resulting in the formation of functional multimers. Polypeptide chains of $V_H$ and $V_L$ domains that are joined with linkers between 3 and 12 amino acid residues form predominantly dimers (termed diabodies). With linkers between 0 and 2 amino acid residues, trimers (termed triabody) and tetramers (termed tetrabody) are favored, but the exact patterns of oligomerization appear to depend on the composition as well as the orientation of V-domains ($V_H$-linker-$V_L$ or $V_L$-linker-$V_H$), in addition to the linker length.

These techniques for producing multispecific or bispecific antibodies exhibit various difficulties in terms of low yield, necessity for purification, low stability or the labor-intensiveness of the technique. More recently, a technique known as "dock and lock" (DNL), discussed in more detail below, has been utilized to produce combinations of virtually any desired antibodies, antibody fragments and other effector molecules (see, e.g., U.S. Patent Application Publ. Nos. 20060228357; 20060228300; 20070086942; 20070140966 and 20070264265, the Examples section of each incorporated herein by reference). The DNL technique allows the assembly of monospecific, bispecific or multispecific antibodies, either as naked antibody moieties or in combination with a wide range of other effector molecules such as immunomodulators, enzymes, chemotherapeutic agents, chemokines, cytokines, diagnostic agents, therapeutic agents, radionuclides, imaging agents, anti-angiogenic agents, growth factors, oligonucleotides, siderophores, hormones, peptides, toxins, pro-apoptotic agents, or a combination thereof. Any of the techniques known in the art for making bispecific or multispecific antibodies may be utilized in the practice of the presently claimed methods.

Dock-and-Lock (DNL)

In preferred embodiments, bispecific or multispecific antibodies or other constructs may be produced using the dock-and-lock technology (see, e.g., U.S. Pat. Nos. 7,550,143; 7,521,056; 7,534,866; 7,527,787 and 7,666,400, the Examples section of each incorporated herein by reference). The DNL method exploits specific protein/protein interactions that occur between the regulatory (R) subunits of cAMP-dependent protein kinase (PKA) and the anchoring domain (AD) of A-kinase anchoring proteins (AKAPs) (Baillie et al., FEBS Letters. 2005; 579: 3264. Wong and Scott, Nat. Rev. Mol. Cell. Biol. 2004; 5: 959). PKA, which plays a central role in one of the best studied signal transduction pathways triggered by the binding of the second messenger cAMP to the R subunits, was first isolated from rabbit skeletal muscle in 1968 (Walsh et al., J. Biol. Chem. 1968; 243:3763). The structure of the holoenzyme consists of two catalytic subunits held in an inactive form by the R subunits (Taylor, J. Biol. Chem. 1989; 264:8443). Isozymes of PKA are found with two types of R subunits (RI and RII), and each type has α and β isoforms (Scott, Pharmacol. 1991; 50:123). The R subunits have been isolated only as stable dimers and the dimerization domain has been shown to consist of the first 44 amino-terminal residues (Newlon et al., Nat. Struct. Biol. 1999; 6:222). Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., J. Biol. Chem. 1990; 265; 21561)

Since the first AKAP, microtubule-associated protein-2, was characterized in 1984 (Lohmann et al., Proc. Natl. Acad. Sci. USA. 1984; 81:6723), more than 50 AKAPs that localize to various sub-cellular sites, including plasma membrane, actin cytoskeleton, nucleus, mitochondria, and endoplasmic reticulum, have been identified with diverse structures in species ranging from yeast to humans (Wong and Scott, Nat. Rev. Mol. Cell. Biol. 2004; 5:959). The AD of AKAPs for PKA is an amphipathic helix of 14-18 residues (Carr et al., J. Biol. Chem. 1991; 266:14188). The amino acid sequences of the AD are quite varied among individual AKAPs, with the binding affinities reported for RII dimers ranging from 2 to 90 nM (Alto et al., Proc. Natl. Acad. Sci. USA. 2003; 100:4445). AKAPs will only bind to dimeric R subunits. For human RIIα, the AD binds to a hydrophobic surface formed by the 23 amino-terminal residues (Colledge and Scott, Trends Cell Biol. 1999; 6:216). Thus, the dimerization domain and AKAP binding domain of human RIIα are both located within the same N-terminal 44 amino acid sequence (Newlon et al., Nat. Struct. Biol. 1999; 6:222; Newlon et al., EMBO J. 2001; 20:1651), which is termed the DDD herein.

We have developed a platform technology to utilize the DDD of human RIIα and the AD of AKAP as an excellent pair of linker modules for docking any two entities, referred to hereafter as A and B, into a noncovalent complex, which could be further locked into a binding molecule through the introduction of cysteine residues into both the DDD and AD at strategic positions to facilitate the formation of disulfide bonds. The general methodology of the "dock-and-lock" approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2$b. This binding event is made irreversible with a subsequent reaction to covalently secure the two entities via disulfide bridges, which occurs very efficiently based on the principle of effective local concentration because the initial binding interactions should bring the reactive thiol groups placed onto both the DDD and AD into proximity (Chmura et al., Proc. Natl. Acad. Sci. USA. 2001; 98:8480) to ligate site-specifically. Using various combinations of linkers, adaptor modules and precursors, a wide variety of DNL constructs of different stoichiometry may be produced and used, including but not limited to dimeric, trimeric, tetrameric, pentameric and hexameric DNL constructs (see, e.g., U.S. Pat. Nos. 7,550,143; 7,521,056; 7,534,866; 7,527,787 and 7,666,400.)

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances, including peptides, proteins, antibodies, antibody fragments, and other effector moieties with a wide range of activities. Utilizing the fusion protein method of constructing AD and DDD conjugated effectors described in the Examples below, virtually any protein or peptide may be incorporated into a DNL construct. However, the technique is not limiting and other methods of conjugation may be utilized.

A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., Molecular Cloning, A laboratory manual, $2^{nd}$ Ed, 1989). In such preferred embodiments, the AD and/or DDD moiety may be attached to either the N-terminal or C-terminal end of an effector protein or peptide. However, the skilled artisan will realize that the site of attachment of an AD or DDD moiety to an effector moiety may vary, depending on the chemical nature of the effector moiety and the part(s) of the effector moiety involved in its physiological activity. Site-specific attachment of a variety of effector moieties may be performed using techniques known in the art, such as the use of bivalent cross-linking reagents and/or other chemical conjugation techniques.

Pre-Targeting

Bispecific or multispecific antibodies may be utilized in pre-targeting techniques. Pre-targeting is a multistep process originally developed to resolve the slow blood clearance of directly targeting antibodies, which contributes to undesirable toxicity to normal tissues such as bone marrow. With pre-targeting, a radionuclide or other diagnostic or therapeutic agent is attached to a small delivery molecule (targetable construct) that is cleared within minutes from the blood. A pre-targeting bispecific or multispecific antibody, which has binding sites for the targetable construct as well as a target antigen, is administered first, free antibody is allowed to clear from circulation and then the targetable construct is administered.

Pre-targeting methods are disclosed, for example, in Goodwin et al., U.S. Pat. No. 4,863,713; Goodwin et al., J. Nucl. Med. 29:226, 1988; Hnatowich et al., J. Nucl. Med. 28:1294, 1987; Oehr et al., J. Nucl. Med. 29:728, 1988; Klibanov et al., J. Nucl. Med. 29:1951, 1988; Sinitsyn et al., J. Nucl. Med. 30:66, 1989; Kalofonos et al., J. Nucl. Med. 31:1791, 1990; Schechter et al., Int. J. Cancer 48:167, 1991; Paganelli et al., Cancer Res. 51:5960, 1991; Paganelli et al., Nucl. Med. Commun. 12:211, 1991; U.S. Pat. No. 5,256,395; Stickney et al., Cancer Res. 51:6650, 1991; Yuan et al., Cancer Res. 51:3119, 1991; U.S. Pat. Nos. 6,077,499; 7,011,812; 7,300,644; 7,074, 405; 6,962,702; 7,387,772; 7,052,872; 7,138,103; 6,090,381; 6,472,511; 6,962,702; and 6,962,702, each incorporated herein by reference.

A pre-targeting method of treating or diagnosing a disease or disorder in a subject may be provided by: (1) administering to the subject a bispecific antibody or antibody fragment; (2) optionally administering to the subject a clearing composition, and allowing the composition to clear the antibody from circulation; and (3) administering to the subject the targetable construct, containing one or more chelated or chemically bound therapeutic or diagnostic agents.

Immunoconjugates

Any of the antibodies, antibody fragments or antibody fusion proteins described herein may be conjugated to a chelating moiety or other carrier molecule to form an immunoconjugate. Methods for covalent conjugation of chelating moieties and other functional groups are known in the art and any such known method may be utilized.

For example, a chelating moiety or carrier can be attached at the hinge region of a reduced antibody component via disulfide bond formation. Alternatively, such agents can be attached using a heterobifunctional cross-linker, such as N-succinyl 3-(2-pyridyldithio)propionate (SPDP). Yu et al., Int. J. Cancer 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995).

Alternatively, the chelating moiety or carrier can be conjugated via a carbohydrate moiety in the Fc region of the antibody. Methods for conjugating peptides to antibody components via an antibody carbohydrate moiety are well-known to those of skill in the art. See, for example, Shih et al., Int. J. Cancer 41: 832 (1988); Shih et al., Int. J. Cancer 46: 1101 (1990); and Shih et al., U.S. Pat. No. 5,057,313, the Examples section of which is incorporated herein by reference. The general method involves reacting an antibody component having an oxidized carbohydrate portion with a carrier polymer that has at least one free amine function. This reaction results in an initial Schiff base (imine) linkage, which can be stabilized by reduction to a secondary amine to form the final conjugate.

The Fc region may be absent if the antibody used as the antibody component of the immunoconjugate is an antibody fragment. However, it is possible to introduce a carbohydrate moiety into the light chain variable region of a full length antibody or antibody fragment. See, for example, Leung et al., J. Immunol. 154: 5919 (1995); U.S. Pat. Nos. 5,443,953 and 6,254,868, the Examples section of which is incorporated herein by reference. The engineered carbohydrate moiety is used to attach the functional group to the antibody fragment.

Other methods of conjugation of chelating agents to proteins are well known in the art (see, e.g., U.S. Pat. No. 7,563, 433, the Examples section of which is incorporated herein by reference). Chelates may be directly linked to antibodies or peptides, for example as disclosed in U.S. Pat. No. 4,824,659, incorporated herein in its entirety by reference.

Click Chemistry

In various embodiments, immunoconjugates may be prepared using the click chemistry technology. The click chemistry approach was originally conceived as a method to rapidly generate complex substances by joining small subunits together in a modular fashion. (See, e.g., Kolb et al., 2004, Angew Chem Int Ed 40:3004-31; Evans, 2007, Aust J Chem 60:384-95.) Various forms of click chemistry reaction are known in the art, such as the Huisgen 1,3-dipolar cycloaddition copper catalyzed reaction (Tornoe et al., 2002, J Organic Chem 67:3057-64), which is often referred to as the "click reaction." Other alternatives include cycloaddition reactions such as the Diels-Alder, nucleophilic substitution reactions (especially to small strained rings like epoxy and aziridine compounds), carbonyl chemistry formation of urea compounds and reactions involving carbon-carbon double bonds, such as alkynes in thiol-yne reactions.

The azide alkyne Huisgen cycloaddition reaction uses a copper catalyst in the presence of a reducing agent to catalyze the reaction of a terminal alkyne group attached to a first molecule. In the presence of a second molecule comprising an azide moiety, the azide reacts with the activated alkyne to form a 1,4-disubstituted 1,2,3-triazole. The copper catalyzed reaction occurs at room temperature and is sufficiently specific that purification of the reaction product is often not required. (Rostovstev et al., 2002, Angew Chem Int Ed 41:2596; Tornoe et al., 2002, J Org Chem 67:3057.) The azide and alkyne functional groups are largely inert towards biomolecules in aqueous medium, allowing the reaction to occur in complex solutions. The triazole formed is chemically stable and is not subject to enzymatic cleavage, making the click chemistry product highly stable in biological systems. However, the copper catalyst is toxic to living cells, precluding biological applications.

A copper-free click reaction has been proposed for covalent modification of biomolecules in living systems. (See, e.g., Agard et al., 2004, J Am Chem Soc 126:15046-47.) The copper-free reaction uses ring strain in place of the copper catalyst to promote a [3+2] azide-alkyne cycloaddition reaction (Id.) For example, cyclooctyne is a 8-carbon ring structure comprising an internal alkyne bond. The closed ring structure induces a substantial bond angle deformation of the acetylene, which is highly reactive with azide groups to form a triazole. Thus, cyclooctyne derivatives may be used for copper-free click reactions, without the toxic copper catalyst (Id.)

Another type of copper-free click reaction was reported by Ning et al. (2010, Angew Chem Int Ed 49:3065-68), involving strain-promoted alkyne-nitrone cycloaddition. To address the slow rate of the original cyclooctyne reaction, electron-withdrawing groups are attached adjacent to the triple bond (Id.) Examples of such substituted cyclooctynes include difluorinated cyclooctynes, 4-dibenzocyclooctynol and azacyclooctyne (Id.) An alternative copper-free reaction involved strain-promoted alkyne-nitrone cycloaddition to give N-alkylated isoxazolines (Id.) The reaction was reported to have exceptionally fast reaction kinetics and was used in a one-pot three-step protocol for site-specific modification of peptides and proteins (Id.) Nitrones were prepared by the condensation of appropriate aldehydes with N-methylhydroxylamine and the cycloaddition reaction took place in a mixture of acetonitrile and water (Id.) However, an attempt to use the reaction with nitrone-labeled monosaccharide derivatives and metabolic labeling in Jurkat cells was unsuccessful (Id.)

In some cases, activated groups for click chemistry reactions may be incorporated into biomolecules using the endogenous synthetic pathways of cells. For example, Agard et al. (2004, J Am Chem Soc 126:15046-47) demonstrated that a recombinant glycoprotein expressed in CHO cells in the presence of peracetylated N-azidoacetylmannosamine resulted in the incorporation of the corresponding N-azidoacetyl sialic acid in the carbohydrates of the glycoprotein. The azido-derivatized glycoprotein reacted specifically with a biotinylated cyclooctyne to form a biotinylated glycoprotein, while control glycoprotein without the azido moiety remained unlabeled (Id.) Laughlin et al. (2008, Science 320:664-667) used a similar technique to metabolically label cell-surface glycans in zebrafish embryos incubated with peracetylated N-azidoacetylgalactosamine. The azido-derivatized glycans reacted with difluorinated cyclooctyne (DIFO) reagents to allow visualization of glycans in vivo.

The Diels-Alder reaction has also been used for in vivo labeling of molecules. Rossin et al. (2010, Angew Chem Int Ed 49:3375-78) reported a 52% yield in vivo between a tumor-localized anti-TAG72 (CC49) antibody carrying a trans-cyclooctene (TCO) reactive moiety and an $^{111}$In-labeled tetrazine DOTA derivative. The TCO-labeled CC49 antibody was administered to mice bearing colon cancer xenografts, followed 1 day later by injection of $^{111}$In-labeled tetrazine probe (Id.) The reaction of radiolabeled probe with tumor localized antibody resulted in pronounced radioactivity localized in the tumor, as demonstrated by SPECT imaging of live mice three hours after injection of radiolabeled probe, with a tumor-to-muscle ratio of 13:1 (Id.) The results confirmed the in vivo chemical reaction of the TCO and tetrazine-labeled molecules.

Antibody labeling techniques using biological incorporation of labeling moieties are further disclosed in U.S. Pat. No. 6,953,675 (the Examples section of which is incorporated herein by reference). Such "landscaped" antibodies were prepared to have reactive ketone groups on glycosylated sites. The method involved expressing cells transfected with an expression vector encoding an antibody with one or more N-glycosylation sites in the CH1 or $V_\kappa$ domain in culture medium comprising a ketone derivative of a saccharide or saccharide precursor. Ketone-derivatized saccharides or precursors included N-levulinoyl mannosamine and N-levulinoyl fucose. The landscaped antibodies were subsequently reacted with agents comprising a ketone-reactive moiety, such as hydrazide, hydrazine, hydroxylamino or thiosemicarbazide groups, to form a labeled targeting molecule. Exemplary agents attached to the landscaped antibodies included chelating agents like DTPA, large drug molecules such as doxorubicin-dextran, and acyl-hydrazide containing peptides. However, the landscaping technique is not limited to producing antibodies comprising ketone moieties, but may be used instead to introduce a click chemistry reactive group, such as a nitrone, an azide or a cyclooctyne, onto an antibody or other biological molecule.

Modifications of click chemistry reactions are suitable for use in vitro or in vivo. Reactive targeting molecule may be formed either by either chemical conjugation or by biological incorporation. The targeting molecule, such as an antibody or antibody fragment, may be activated with an azido moiety, a substituted cyclooctyne or alkyne group, or a nitrone moiety. Where the targeting molecule comprises an azido or nitrone group, the corresponding targetable construct will comprise a substituted cyclooctyne or alkyne group, and vice versa. Such activated molecules may be made by metabolic incorporation in living cells, as discussed above. Alternatively, methods of chemical conjugation of such moieties to biomolecules are well known in the art, and any such known method may be utilized. The disclosed techniques may be used in combination with the $^{18}$F or $^{19}$F labeling methods described below for PET or NMR imaging, or alternatively may be utilized for delivery of any therapeutic and/or diagnostic agent that may be conjugated to a suitable activated targetable construct and/or targeting molecule.

Affibodies

Affibodies are small proteins that function as antibody mimetics and are of use in binding target molecules. Affibodies were developed by combinatorial engineering on an alpha helical protein scaffold (Nord et al., 1995, Protein Eng 8:601-8; Nord et al., 1997, Nat Biotechnol 15:772-77). The affibody design is based on a three helix bundle structure comprising the IgG binding domain of protein A (Nord et al., 1995; 1997). Affibodies with a wide range of binding affinities may be produced by randomization of thirteen amino acids involved in the Fc binding activity of the bacterial protein A (Nord et al., 1995; 1997). After randomization, the PCR amplified library was cloned into a phagemid vector for screening by phage display of the mutant proteins.

A $^{177}$Lu-labeled affibody specific for HER2/neu has been demonstrated to target HER2-expressing xenografts in vivo (Tolmachev et al., 2007, Cancer Res 67:2773-82). Although renal toxicity due to accumulation of the low molecular weight radiolabeled compound was initially a problem, reversible binding to albumin reduced renal accumulation, enabling radionuclide-based therapy with labeled affibody (Id.)

The feasibility of using radiolabeled affibodies for in vivo tumor imaging has been recently demonstrated (Tolmachev et al., 2011, Bioconjugate Chem 22:894-902). A maleimide-derivatized NOTA was conjugated to the anti-HER2 affibody and radiolabeled with $^{111}$In (Id.) Administration to mice bearing the HER2-expressing DU-145 xenograft, followed by gamma camera imaging, allowed visualization of the xenograft (Id.)

The skilled artisan will realize that affibodies may be used as targeting molecules in the practice of the claimed methods and compositions. Labeling with metal-conjugated $^{18}$F may be performed as described in the Examples below. Affibodies are commercially available from Affibody AB (Solna, Sweden).

Phage Display Peptides

In some alternative embodiments, binding peptides may be produced by phage display methods that are well known in the art. For example, peptides that bind to any of a variety of disease-associated antigens may be identified by phage display panning against an appropriate target antigen, cell, tissue or pathogen and selecting for phage with high binding affinity.

Various methods of phage display and techniques for producing diverse populations of peptides are well known in the art. For example, U.S. Pat. Nos. 5,223,409; 5,622,699 and 6,068,829, each of which is incorporated herein by reference, disclose methods for preparing a phage library. The phage display technique involves genetically manipulating bacteriophage so that small peptides can be expressed on their surface (Smith and Scott, 1985, Science 228:1315-1317; Smith and Scott, 1993, Meth. Enzymol. 21:228-257).

The past decade has seen considerable progress in the construction of phage-displayed peptide libraries and in the development of screening methods in which the libraries are used to isolate peptide ligands. For example, the use of peptide libraries has made it possible to characterize interacting sites and receptor-ligand binding motifs within many proteins, such as antibodies involved in inflammatory reactions or integrins that mediate cellular adherence. This method has also been used to identify novel peptide ligands that may serve as leads to the development of peptidomimetic drugs or imaging agents (Arap et al., 1998a, Science 279:377-380). In addition to peptides, larger protein domains such as single-chain antibodies may also be displayed on the surface of phage particles (Arap et al., 1998a).

Targeting amino acid sequences selective for a given target molecule may be isolated by panning (Pasqualini and Ruoslahti, 1996, Nature 380:364-366; Pasqualini, 1999, The Quart. J. Nucl. Med. 43:159-162). In brief, a library of phage containing putative targeting peptides is administered to target molecules and samples containing bound phage are collected. Target molecules may, for example, be attached to the bottom of microtiter wells in a 96-well plate. Phage that bind to a target may be eluted and then amplified by growing them in host bacteria.

In certain embodiments, the phage may be propagated in host bacteria between rounds of panning. Rather than being lysed by the phage, the bacteria may instead secrete multiple copies of phage that display a particular insert. If desired, the amplified phage may be exposed to the target molecule again and collected for additional rounds of panning. Multiple rounds of panning may be performed until a population of selective or specific binders is obtained. The amino acid sequence of the peptides may be determined by sequencing the DNA corresponding to the targeting peptide insert in the phage genome. The identified targeting peptide may then be produced as a synthetic peptide by standard protein chemistry techniques (Arap et al., 1998a, Smith et al., 1985).

Aptamers

In certain embodiments, a targeting molecule may comprise an aptamer. Methods of constructing and determining the binding characteristics of aptamers are well known in the art. For example, such techniques are described in U.S. Pat. Nos. 5,582,981, 5,595,877 and 5,637,459, each incorporated herein by reference.

Aptamers may be prepared by any known method, including synthetic, recombinant, and purification methods, and may be used alone or in combination with other ligands specific for the same target. In general, a minimum of approximately 3 nucleotides, preferably at least 5 nucleotides, are necessary to effect specific binding. Aptamers of sequences shorter than 10 bases may be feasible, although aptamers of 10, 20, 30 or 40 nucleotides may be preferred.

Aptamers need to contain the sequence that confers binding specificity, but may be extended with flanking regions and otherwise derivatized. In preferred embodiments, the binding sequences of aptamers may be flanked by primer-binding sequences, facilitating the amplification of the aptamers by PCR or other amplification techniques. In a further embodiment, the flanking sequence may comprise a specific sequence that preferentially recognizes or binds a moiety to enhance the immobilization of the aptamer to a substrate.

Aptamers may be isolated, sequenced, and/or amplified or synthesized as conventional DNA or RNA molecules. Alternatively, aptamers of interest may comprise modified oligomers. Any of the hydroxyl groups ordinarily present in aptamers may be replaced by phosphonate groups, phosphate groups, protected by a standard protecting group, or activated to prepare additional linkages to other nucleotides, or may be conjugated to solid supports. One or more phosphodiester linkages may be replaced by alternative linking groups, such as P(O)O replaced by P(O)S, P(O)NR.sub.2, P(O)R, P(O)OR', CO, or CNR.sub.2, wherein R is H or alkyl (1-20 C) and R' is alkyl (1-20 C); in addition, this group may be attached to adjacent nucleotides through O or S. Not all linkages in an oligomer need to be identical.

Methods for preparation and screening of aptamers that bind to particular targets of interest are well known, for example U.S. Pat. Nos. 5,475,096 and 5,270,163, each incorporated by reference. The technique generally involves selection from a mixture of candidate aptamers and step-wise iterations of binding, separation of bound from unbound aptamers and amplification. Because only a small number of sequences (possibly only one molecule of aptamer) corresponding to the highest affinity aptamers exist in the mixture, it is generally desirable to set the partitioning criteria so that a significant amount of aptamers in the mixture (approximately 5-50%) is retained during separation. Each cycle results in an enrichment of aptamers with high affinity for the target. Repetition for between three to six selection and amplification cycles may be used to generate aptamers that bind with high affinity and specificity to the target.

Avimers

In certain embodiments, the targeting molecules may comprise one or more avimer sequences. Avimers are a class of binding proteins somewhat similar to antibodies in their affinities and specificities for various target molecules. They were developed from human extracellular receptor domains by in vitro exon shuffling and phage display. (Silverman et al., 2005, Nat. Biotechnol. 23:1493-94; Silverman et al., 2006, Nat. Biotechnol. 24:220.) The resulting multidomain proteins may comprise multiple independent binding domains, that may exhibit improved affinity (in some cases sub-nanomolar) and specificity compared with single-epitope binding proteins. (Id.) Additional details concerning methods of construction and use of avimers are disclosed, for example, in U.S. Patent Application Publication Nos. 20040175756, 20050048512, 20050053973, 20050089932 and 20050221384, the Examples section of each of which is incorporated herein by reference.

Methods of Administration

In various embodiments, bispecific antibodies and targetable constructs may be used for imaging normal or diseased tissue and organs (see, e.g. U.S. Pat. Nos. 6,126,916; 6,077,499; 6,010,680; 5,776,095; 5,776,094; 5,776,093; 5,772,981; 5,753,206; 5,746,996; 5,697,902; 5,328,679; 5,128,119; 5,101,827; and 4,735,210, each incorporated herein by reference in its Examples section).

The administration of a bispecific antibody (bsAb) and an $^{18}$F-labeled targetable construct may be conducted by administering the bsAb antibody at some time prior to administration of the targetable construct. The doses and timing of the reagents can be readily devised by a skilled artisan, and are dependent on the specific nature of the reagents employed. If a bsAb-F(ab')$_2$ derivative is given first, then a waiting time of 24-72 hr (alternatively 48-96 hours) before administration of the targetable construct would be appropriate. If an IgG-Fab' bsAb conjugate is the primary targeting vector, then a longer waiting period before administration of the targetable construct would be indicated, in the range of 3-10 days. After sufficient time has passed for the bsAb to target to the diseased tissue, the $^{18}$F-labeled targetable construct is administered. Subsequent to administration of the targetable construct, imaging can be performed.

Certain embodiments concern the use of multivalent target binding proteins which have at least three different target binding sites as described in patent application Ser. No. 60/220,782. Multivalent target binding proteins have been made by cross-linking several Fab-like fragments via chemical linkers. See U.S. Pat. Nos. 5,262,524; 5,091,542 and Landsdorp et al. Euro. J. Immunol. 16: 679-83 (1986). Multivalent target binding proteins also have been made by covalently linking several single chain Fv molecules (scFv) to form a single polypeptide. See U.S. Pat. No. 5,892,020. A multivalent target binding protein which is basically an aggregate of scFv molecules has been disclosed in U.S. Pat. Nos. 6,025,165 and 5,837,242. A trivalent target binding protein comprising three scFv molecules has been described in Krott et al. Protein Engineering 10(4): 423-433 (1997).

Alternatively, a technique known as "dock-and-lock" (DNL), described in more detail below, has been demonstrated for the simple and reproducible construction of a variety of multivalent complexes, including complexes comprising two or more different antibodies or antibody fragments. (See, e.g., U.S. Pat. Nos. 7,550,143; 7,521,056; 7,534,866; 7,527,787 and 7,666,400, the Examples section of each of which is incorporated herein by reference.) Such constructs are also of use for the practice of the claimed methods and compositions described herein.

A clearing agent may be used which is given between doses of the bispecific antibody (bsAb) and the targetable construct. A clearing agent of novel mechanistic action may be used, namely a glycosylated anti-idiotypic Fab' fragment targeted against the disease targeting arm(s) of the bsAb. In one example, anti-CEA (MN-14 Ab)×anti-peptide bsAb is given and allowed to accrete in disease targets to its maximum extent. To clear residual bsAb from circulation, an anti-idiotypic Ab to MN-14, termed WI2, is given, preferably as a glycosylated Fab' fragment. The clearing agent binds to the bsAb in a monovalent manner, while its appended glycosyl residues direct the entire complex to the liver, where rapid metabolism takes place. Then the $^{18}$F-labeled targetable construct is given to the subject. The WI2 Ab to the MN-14 arm of the bsAb has a high affinity and the clearance mechanism differs from other disclosed mechanisms (see Goodwin et al., ibid), as it does not involve cross-linking, because the WI2-Fab' is a monovalent moiety. However, alternative methods and compositions for clearing agents are known and any such known clearing agents may be used.

Formulation and Administration

The $^{18}$F-labeled molecules may be formulated to obtain compositions that include one or more pharmaceutically suitable excipients, one or more additional ingredients, or some combination of these. These can be accomplished by known methods to prepare pharmaceutically useful dosages, whereby the active ingredients (i.e., the $^{18}$F-labeled molecules) are combined in a mixture with one or more pharmaceutically suitable excipients. Sterile phosphate-buffered saline is one example of a pharmaceutically suitable excipient. Other suitable excipients are well known to those in the art. See, e.g., Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The preferred route for administration of the compositions described herein is parenteral injection. Injection may be intravenous, intraarterial, intralymphatic, intrathecal, subcutaneous or intracavitary (i.e., parenterally). In parenteral administration, the compositions will be formulated in a unit dosage injectable form such as a solution, suspension or emulsion, in association with a pharmaceutically acceptable excipient. Such excipients are inherently nontoxic and nontherapeutic. Examples of such excipients are saline, Ringer's solution, dextrose solution and Hank's solution. Nonaqueous excipients such as fixed oils and ethyl oleate may also be used. A preferred excipient is 5% dextrose in saline. The excipient may contain minor amounts of additives such as substances that enhance isotonicity and chemical stability, including buffers and preservatives. Other methods of administration, including oral administration, are also contemplated.

Formulated compositions comprising $^{18}$F-labeled molecules can be used for intravenous administration via, for example, bolus injection or continuous infusion. Compositions for injection can be presented in unit dosage form, e.g., in ampoules or in multi-dose containers, with an added preservative. Compositions can also take such forms as suspensions, solutions or emulsions in oily or aqueous vehicles, and can contain formulatory agents such as suspending, stabilizing and/or dispersing agents. Alternatively, the compositions can be in powder form for constitution with a suitable vehicle, e.g., sterile pyrogen-free water, before use.

The compositions may be administered in solution. The pH of the solution should be in the range of pH 5 to 9.5, preferably pH 6.5 to 7.5. The formulation thereof should be in a solution having a suitable pharmaceutically acceptable buffer such as phosphate, TRIS (hydroxymethyl)aminomethane-HCl or citrate and the like. In certain preferred embodiments, the buffer is potassium biphthalate (KHP), which may act as a transfer ligand to facilitate $^{18}$F-labeling. Buffer concentrations should be in the range of 1 to 100 mM. The formulated solution may also contain a salt, such as sodium chloride or potassium chloride in a concentration of 50 to 150 mM. An effective amount of a stabilizing agent such as glycerol, albumin, a globulin, a detergent, a gelatin, a protamine or a salt of protamine may also be included. The compositions may be administered to a mammal subcutaneously, intravenously, intramuscularly or by other parenteral routes. Moreover, the administration may be by continuous infusion or by single or multiple boluses.

Where bispecific antibodies are administered, for example in a pretargeting technique, the dosage of an administered antibody for humans will vary depending upon such factors as the patient's age, weight, height, sex, general medical condition and previous medical history. Typically, for imaging purposes it is desirable to provide the recipient with a dosage of bispecific antibody that is in the range of from about 1 mg to 200 mg as a single intravenous infusion, although a lower or higher dosage also may be administered as circumstances dictate. Typically, it is desirable to provide the recipient with a dosage that is in the range of from about 10 mg per square meter of body surface area or 17 to 18 mg of the antibody for the typical adult, although a lower or higher dosage also may be administered as circumstances dictate. Examples of dosages of bispecific antibodies that may be administered to a human subject for imaging purposes are 1 to 200 mg, more preferably 1 to 70 mg, most preferably 1 to 20 mg, although higher or lower doses may be used.

In general, the dosage of $^{18}$F label to administer will vary depending upon such factors as the patient's age, weight, height, sex, general medical condition and previous medical history. Preferably, a saturating dose of the $^{18}$F-labeled molecules is administered to a patient. For administration of $^{18}$F-labeled molecules, the dosage may be measured by millicuries. A typical range for $^{18}$F imaging studies would be five to 10 mCi.

Administration of Peptides

Various embodiments of the claimed methods and/or compositions may concern one or more $^{18}$F-labeled peptides to be administered to a subject. Administration may occur by any route known in the art, including but not limited to oral, nasal, buccal, inhalational, rectal, vaginal, topical, orthotopic, intradermal, subcutaneous, intramuscular, intraperitoneal, intraarterial, intrathecal or intravenous injection. Where, for example, $^{18}$F-labeled peptides are administered in a pretargeting protocol, the peptides would preferably be administered i.v.

In certain embodiments, the standard peptide bond linkage may be replaced by one or more alternative linking groups, such as $CH_2$—NH, $CH_2$—S, $CH_2$—$CH_2$, CH=CH, CO—$CH_2$, CHOH—$CH_2$ and the like. Methods for preparing peptide mimetics are well known (for example, Hruby, 1982, *Life Sci* 31:189-99; Holladay et al., 1983, *Tetrahedron Lett.* 24:4401-04; Jennings-White et al., 1982, *Tetrahedron Lett.* 23:2533; Almquiest et al., 1980, *J. Med. Chem.* 23:1392-98; Hudson et al., 1979, *Int. J. Pept. Res.* 14:177-185; Spatola et al., 1986, *Life Sci* 38:1243-49; U.S. Pat. Nos. 5,169,862; 5,539,085; 5,576,423, 5,051,448, 5,559,103.) Peptide mimetics may exhibit enhanced stability and/or absorption in vivo compared to their peptide analogs.

Peptide stabilization may also occur by substitution of D-amino acids for naturally occurring L-amino acids, particularly at locations where endopeptidases are known to act. Endopeptidase binding and cleavage sequences are known in the art and methods for making and using peptides incorporating D-amino acids have been described (e.g., U.S. Patent Application Publication No. 20050025709, McBride et al., filed Jun. 14, 2004, the Examples section of which is incorporated herein by reference).

Imaging Using Labeled Molecules

Methods of imaging using labeled molecules are well known in the art, and any such known methods may be used with the $^{18}$F-labeled molecules disclosed herein. See, e.g., U.S. Pat. Nos. 6,241,964; 6,358,489; 6,953,567 and published U.S. Patent Application Publ. Nos. 20050003403; 20040018557; 20060140936, the Examples section of each incorporated herein by reference. See also, Page et al., Nuclear Medicine And Biology, 21:911-919, 1994; Choi et al., Cancer Research 55:5323-5329, 1995; Zalutsky et al., J. Nuclear Med., 33:575-582, 1992; Woessner et. al. Magn. Reson. Med. 2005, 53: 790-99.

In certain embodiments, $^{18}$F-labeled molecules may be of use in imaging normal or diseased tissue and organs, for example using the methods described in U.S. Pat. Nos. 6,126, 916; 6,077,499; 6,010,680; 5,776,095; 5,776,094; 5,776,093; 5,772,981; 5,753,206; 5,746,996; 5,697,902; 5,328,679; 5,128,119; 5,101,827; and 4,735,210, each incorporated herein by reference. Such imaging can be conducted by direct $^{18}$F labeling of the appropriate targeting molecules, or by a pretargeted imaging method, as described in Goldenberg et al. (2007, Update Cancer Ther. 2:19-31); Sharkey et al. (2008, Radiology 246:497-507); Goldenberg et al. (2008, J. Nucl. Med. 49:158-63); Sharkey et al. (2007, Clin. Cancer Res. 13:5777s-5585s); McBride et al. (2006, J. Nucl. Med. 47:1678-88); Goldenberg et al. (2006, J. Clin. Oncol. 24:823-85), see also U.S. Patent Publication Nos. 20050002945, 20040018557, 20030148409 and 20050014207, each incorporated herein by reference.

Methods of diagnostic imaging with labeled peptides or MAbs are well-known. For example, in the technique of immunoscintigraphy, ligands or antibodies are labeled with a gamma-emitting radioisotope and introduced into a patient. A gamma camera is used to detect the location and distribution of gamma-emitting radioisotopes. See, for example, Srivastava (ed.), RADIOLABELED MONOCLONAL ANTIBODIES FOR IMAGING AND THERAPY (Plenum Press 1988), Chase, "Medical Applications of Radioisotopes," in REMINGTON'S PHARMACEUTICAL SCIENCES, 18th Edition, Gennaro et al. (eds.), pp. 624-652 (Mack Publishing Co., 1990), and Brown, "Clinical Use of Monoclonal Antibodies," in BIOTECHNOLOGY AND PHARMACY 227-49, Pezzuto et al. (eds.) (Chapman & Hall 1993). Also preferred is the use of positron-emitting radionuclides (PET isotopes), such as with an energy of 511 keV, such as $^{18}$F, $^{68}$Ga, $^{64}$Cu, and $^{124}$I. Such radionuclides may be imaged by well-known PET scanning techniques.

In preferred embodiments, the $^{18}$F-labeled peptides, proteins and/or antibodies are of use for imaging of cancer. Examples of cancers include, but are not limited to, carcinoma, lymphoma, blastoma, sarcoma, and leukemia or lymphoid malignancies. More particular examples of such cancers are noted below and include: squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Purpura, Parathyroid Cancer, Penile Cancer, Pheochromocytoma, Pituitary Tumor, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

The methods and compositions described and claimed herein may be used to detect or diagnose malignant or pre-malignant conditions. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W. B. Saunders Co., Philadelphia, pp. 68-79 (1976)).

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. Dysplastic disorders which can be detected include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be detected include, but are not limited to, benign dysproliferative disorders (e.g., benign tumors, fibrocystic conditions, tissue hypertrophy, intestinal polyps, colon polyps, and esophageal dysplasia), leukoplakia, keratoses, Bowen's disease, Farmer's Skin, solar cheilitis, and solar keratosis.

Additional hyperproliferative diseases, disorders, and/or conditions include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, menangioma, melanoma, neuroblastoma, and retinoblastoma.

In a preferred embodiment, diseases that may be diagnosed, detected or imaged using the claimed compositions and methods include cardiovascular diseases, such as fibrin clots, atherosclerosis, myocardial ischemia and infarction. Antibodies to fibrin (e.g., scFv(59D8); T2G1s; MH1) are known and in clinical trials as imaging agents for disclosing said clots and pulmonary emboli, while anti-granulocyte antibodies, such as MN-3, MN-15, anti-NCA95, and anti-CD15 antibodies, can target myocardial infarcts and myocardial ischemia. (See, e.g., U.S. Pat. Nos. 5,487,892; 5,632,968; 6,294,173; 7,541,440, the Examples section of each incorporated herein by reference) Anti-macrophage, anti-low-density lipoprotein (LDL) and anti-CD74 (e.g., hLL1) antibodies can be used to target atherosclerotic plaques. Abciximab (anti-glycoprotein IIb/IIIa) has been approved for adjuvant use for prevention of restenosis in percutaneous coronary interventions and the treatment of unstable angina (Waldmann et al., 2000, Hematol 1:394-408). Anti-CD3 antibodies have been reported to reduce development and progression of atherosclerosis (Steffens et al., 2006, Circulation 114:1977-84). Treatment with blocking MIF antibody has been reported to induce regression of established atherosclerotic lesions (Sanchez-Madrid and Sessa, 2010, Cardiovasc Res 86:171-73). Antibodies against oxidized LDL also induced a regression of established atherosclerosis in a mouse model (Ginsberg, 2007, J Am Coll Cardiol 52:2319-21). Anti-ICAM-1 antibody was shown to reduce ischemic cell damage after cerebral artery occlusion in rats (Zhang et al., 1994, Neurology 44:1747-51). Commercially available monoclonal antibodies to leukocyte antigens are represented by: OKT anti-T-cell monoclonal antibodies (available from Ortho Pharmaceutical Company) which bind to normal T-lymphocytes; the monoclonal antibodies produced by the hybridomas having the ATCC accession numbers HB44, HB55, HB12, HB78 and HB2; G7E11, W8E7, NKP15 and GO22 (Becton Dickinson); NEN9.4 (New England Nuclear); and FMC11 (Sera Labs). A description of antibodies against fibrin and platelet antigens is contained in Knight, Semin. Nucl. Med., 20:52-67 (1990).

In one embodiment, a pharmaceutical composition may be used to diagnose a subject having a metabolic disease, such amyloidosis, or a neurodegenerative disease, such as Alzheimer's disease, amyotrophic lateral sclerosis (ALS), Parkinson's disease, Huntington's disease, olivopontocerebellar atrophy, multiple system atrophy, progressive supranuclear palsy, corticodentatonigral degeneration, progressive familial myoclonic epilepsy, strionigral degeneration, torsion dystonia, familial tremor, Gilles de la Tourette syndrome or Hallervorden-Spatz disease. Bapineuzumab is in clinical trials for Alzheimer's disease therapy. Other antibodies proposed for Alzheimer's disease include Alz 50 (Ksiezak-Reding et al., 1987, J Biol Chem 263:7943-47), gantenerumab, and solanezumab. Infliximab, an anti-TNF-α antibody, has been reported to reduce amyloid plaques and improve cognition. Antibodies against mutant SOD1, produced by hybridoma cell lines deposited with the International Depositary Authority of Canada (accession Nos. ADI-290806-01, ADI-290806-02, ADI-290806-03) have been proposed for therapy of ALS, Parkinson's disease and Alzheimer's disease (see U.S. Patent Appl. Publ. No. 20090068194). Anti-CD3 antibodies have been proposed for therapy of type 1 diabetes (Cernea et al., 2010, Diabetes Metab Rev 26:602-05). In addition, a pharmaceutical composition of the present invention may be used on a subject having an immune-dysregulatory disorder, such as graft-versus-host disease or organ transplant rejection.

The exemplary conditions listed above that may be detected, diagnosed and/or imaged are not limiting. The skilled artisan will be aware that antibodies, antibody fragments or targeting peptides are known for a wide variety of conditions, such as autoimmune disease, cardiovascular disease, neurodegenerative disease, metabolic disease, cancer, infectious disease and hyperproliferative disease. Any such condition for which an $^{18}$F-labeled molecule, such as a protein or peptide, may be prepared and utilized by the methods described herein, may be imaged, diagnosed and/or detected as described herein.

Kits

Various embodiments may concern kits containing components suitable for imaging, diagnosing and/or detecting diseased tissue in a patient using labeled compounds. Exemplary kits may contain an antibody, fragment or fusion protein, such as a bispecific antibody of use in pretargeting methods as described herein. Other components may include a targetable construct for use with such bispecific antibodies. In preferred embodiments, the targetable construct is pre-conjugated to a chelating group that may be used to attach an Al$^{18}$F complex or a complex of $^{18}$F with a different metal. However, in alternative embodiments it is contemplated that a targetable construct may be attached to one or more different diagnostic agents, such as $^{68}$Ga.

A device capable of delivering the kit components may be included. One type of device, for applications such as parenteral delivery, is a syringe that is used to inject the composition into the body of a subject. Inhalation devices may also be used for certain applications.

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

EXAMPLES

Example 1

$^{18}$F-Labeling of Peptide IMP272

The first peptide that was prepared and $^{18}$F-labeled was IMP272:

```
                                        (SEQ ID NO: 3)
DTPA-Gln-Ala-Lys(HSG)-D-Tyr-Lys(HSG)-NH₂
```

Acetate buffer solution—Acetic acid, 1.509 g was diluted in ~160 mL water and the pH was adjusted by the addition of 1 M NaOH then diluted to 250 mL to make a 0.1 M solution at pH 4.03.

Aluminum acetate buffer solution—A solution of aluminum was prepared by dissolving 0.1028 g of AlCl$_3$ hexahydrate in 42.6 mL DI water. A 4 mL aliquot of the aluminum solution was mixed with 16 mL of a 0.1 M NaOAc solution at pH 4 to provide a 2 mM Al stock solution.

IMP272 acetate buffer solution—Peptide, 0.0011 g, 7.28×10$^{-7}$ mol IMP272 was dissolved in 364 μL, of the 0.1 M pH 4 acetate buffer solution to obtain a 2 mM stock solution of the peptide.

$^{18}$F-Labeling of IMP272—A 3 μL aliquot of the aluminum stock solution was placed in a REACTI-VIAL™ and mixed with 50 μL $^{18}$F (as received) and 3 μL of the IMP272 solution. The solution was heated in a heating block at 110° C. for 15 min and analyzed by reverse phase HPLC. The HPLC trace (not shown) showed 93% free $^{18}$F and 7% bound to the peptide. An additional 10 μL of the IMP272 solution was added to the reaction and it was heated again and analyzed by reverse phase HPLC (not shown). The HPLC trace showed 8% $^{18}$F at the void volume and 92% of the activity attached to the peptide. The remainder of the peptide solution was incubated at room temperature with 150 μL PBS for ~1 hr and then examined by reverse phase HPLC. The HPLC (not shown) showed 58% $^{18}$F unbound and 42% still attached to the peptide. The data indicate that Al$^{18}$F(DTPA) complex may be unstable when mixed with phosphate.

Example 2

IMP272 $^{18}$F-Labeling with Other Metals

A ~3 μL aliquot of the metal stock solution (6×10$^{-9}$ mol) was placed in a polypropylene cone vial and mixed with 75 μL $^{18}$F (as received), incubated at room temperature for ~2 min and then mixed with 20 μL of a 2 mM (4×10$^{-8}$ mol) IMP272 solution in 0.1 M NaOAc pH 4 buffer. The solution was heated in a heating block at 100° C. for 15 min and analyzed by reverse phase HPLC. IMP272 was labeled with indium (24%), gallium (36%), zirconium (15%), lutetium (37%) and yttrium (2%) (not shown). These results demonstrate that the $^{18}$F metal labeling technique is not limited to an aluminum ligand, but can also utilize other metals as well. With different metal ligands, different chelating moieties may be utilized to optimize binding of an $^{18}$F-metal conjugate.

Example 3

Production and Use of a Serum-Stable $^{18}$F-Labeled Peptide IMP449

```
                                            (SEQ ID NO: 4)
NOTA-benzyl-ITC-D-Ala-D-Lys(HSG)-D-Tyr-D-Lys(HSG)-
NH₂
```

The peptide, IMP448 D-Ala-D-Lys(HSG)-D-Tyr-D-Lys (HSG)-NH$_2$ (SEQ ID NO:5) was made on Sieber Amide resin by adding the following amino acids to the resin in the order shown: Aloc-D-Lys(Fmoc)-OH, Trt-HSG-OH, the Aloc was cleaved, Fmoc-D-Tyr(But)-OH, Aloc-D-Lys(Fmoc)-OH, Trt-HSG-OH, the Aloc was cleaved, Fmoc-D-Ala-OH with final Fmoc cleavage to make the desired peptide. The peptide was then cleaved from the resin and purified by HPLC to produce IMP448, which was then coupled to ITC-benzyl NOTA.

IMP448 (0.0757 g, 7.5×10$^{-5}$ mol) was mixed with 0.0509 g (9.09×10$^{-5}$ mol) ITC benzyl NOTA and dissolved in 1 mL water. Potassium carbonate anhydrous (0.2171 g) was then slowly added to the stirred peptide/NOTA solution. The reaction solution was pH 10.6 after the addition of all the carbonate. The reaction was allowed to stir at room temperature overnight. The reaction was carefully quenched with 1 M HCl after 14 hr and purified by HPLC to obtain 48 mg of IMP449.

$^{18}$F-Labeling of IMP449

IMP449 (0.002 g, 1.37×10$^{-6}$ mol) was dissolved in 686 μL (2 mM peptide solution) 0.1 M NaOAc pH 4.02. Three microliters of a 2 mM solution of Al in a pH 4 acetate buffer was mixed with 15 μL, 1.3 mCi of $^{18}$F. The solution was then mixed with 20 μL of the 2 mM IMP449 solution and heated at 105° C. for 15 min. Reverse Phase HPLC analysis showed 35% (t$_R$~10 min) of the activity was attached to the peptide and 65% of the activity was eluted at the void volume of the column (3.1 min, not shown) indicating that the majority of activity was not associated with the peptide. The crude labeled mixture (5 μL) was mixed with pooled human serum and incubated at 37° C. An aliquot was removed after 15 min and analyzed by HPLC. The HPLC showed 9.8% of the activity was still attached to the peptide (down from 35%). Another aliquot was removed after 1 hr and analyzed by HPLC. The HPLC showed 7.6% of the activity was still attached to the peptide (down from 35%), which was essentially the same as the 15 min trace (data not shown).

High Dose $^{18}$F-Labeling of IMP449

Further studies with purified IMP449 demonstrated that the $^{18}$F-labeled peptide was highly stable (91%, not shown) in human serum at 37° C. for at least one hour and was partially stable (76%, not shown) in human serum at 37° C. for at least four hours. Additional studies were performed in which the IMP449 was prepared in the presence of ascorbic acid as a stabilizing agent. In those studies (not shown), the $^{18}$F-metal-peptide complex showed no detectable decomposition in serum after 4 hr at 37° C. The mouse urine 30 min after injection of $^{18}$F-labeled peptide was found to contain $^{18}$F bound to the peptide (not shown). These results demonstrate that the $^{18}$F-labeled peptides disclosed herein exhibit sufficient stability under approximated in vivo conditions to be used for $^{18}$F imaging studies.

Since IMP449 peptide contains a thiourea linkage, which is sensitive to radiolysis, several products are observed by RP-HPLC. However, when ascorbic acid is added to the reaction mixture, the side products generated are markedly reduced.

Example 4

Preparation of DNL Constructs for $^{18}$F Imaging by Pretargeting

The DNL technique may be used to make dimers, trimers, tetramers, hexamers, etc. comprising virtually any antibodies or fragments thereof or other effector moieties. For certain preferred embodiments, IgG antibodies, Fab fragments or other proteins or peptides may be produced as fusion proteins containing either a DDD (dimerization and docking domain) or AD (anchoring domain) sequence. Bispecific antibodies may be formed by combining a Fab-DDD fusion protein of a first antibody with a Fab-AD fusion protein of a second antibody. Alternatively, constructs may be made that combine IgG-AD fusion proteins with Fab-DDD fusion proteins. For purposes of $^{18}$F detection, an antibody or fragment containing a binding site for an antigen associated with a target tissue to be imaged, such as a tumor, may be combined with a second antibody or fragment that binds a hapten on a targetable construct, such as IMP 449, to which a metal-$^{18}$F can be attached. The bispecific antibody (DNL construct) is administered to a subject, circulating antibody is allowed to clear from the blood and localize to target tissue, and the $^{18}$F-labeled targetable construct is added and binds to the localized antibody for imaging.

Independent transgenic cell lines may be developed for each Fab or IgG fusion protein. Once produced, the modules can be purified if desired or maintained in the cell culture supernatant fluid. Following production, any DDD$_2$-fusion protein module can be combined with any corresponding AD-fusion protein module to generate a bispecific DNL construct. For different types of constructs, different AD or DDD sequences may be utilized. The following DDD sequences are based on the DDD moiety of PKA RIM, while the AD sequences are based on the AD moiety of the optimized synthetic AKAP-IS sequence (Alto et al., Proc. Natl. Acad. Sci. USA. 2003; 100:4445).

DDD1:
(SEQ ID NO: 6)
SHIQIPPGLTELLQGYTVEVLRQQPPDLVEFAVEYFTRLREARA

DDD2:
(SEQ ID NO: 7)
CGHIQIPPGLTELLQGYTVEVLRQQPPDLVEFAVEYFTRLREARA

-continued

AD1:
(SEQ ID NO: 8)
QIEYLAKQIVDNAIQQA

AD2:
(SEQ ID NO: 9)
CGQIEYLAKQIVDNAIQQAGC

The plasmid vector pdHL2 has been used to produce a number of antibodies and antibody-based constructs. See Gillies et al., J Immunol Methods (1989), 125:191-202; Losman et al., Cancer (Phila) (1997), 80:2660-6. The di-cistronic mammalian expression vector directs the synthesis of the heavy and light chains of IgG. The vector sequences are mostly identical for many different IgG-pdHL2 constructs, with the only differences existing in the variable domain (VH and VL) sequences. Using molecular biology tools known to those skilled in the art, these IgG expression vectors can be converted into Fab-DDD or Fab-AD expression vectors. To generate Fab-DDD expression vectors, the coding sequences for the hinge, CH2 and CH3 domains of the heavy chain are replaced with a sequence encoding the first 4 residues of the hinge, a 14 residue Gly-Ser linker and the first 44 residues of human RIIα (referred to as DDD1). To generate Fab-AD expression vectors, the sequences for the hinge, CH2 and CH3 domains of IgG are replaced with a sequence encoding the first 4 residues of the hinge, a 15 residue Gly-Ser linker and a 17 residue synthetic AD called AKAP-IS (referred to as AD1), which was generated using bioinformatics and peptide array technology and shown to bind RIIα dimers with a very high affinity (0.4 nM). See Alto, et al. Proc. Natl. Acad. Sci., U.S.A (2003), 100:4445-50.

Two shuttle vectors were designed to facilitate the conversion of IgG-pdHL2 vectors to either Fab-DDD1 or Fab-AD1 expression vectors, as described below.

Preparation of CH1

The CH1 domain was amplified by PCR using the pdHL2 plasmid vector as a template. The left PCR primer consisted of the upstream (5') end of the CH1 domain and a SacII restriction endonuclease site, which is 5' of the CH1 coding sequence. The right primer consisted of the sequence coding for the first 4 residues of the hinge followed by four glycines and a serine, with the final two codons (GS) comprising a Bam HI restriction site. The 410 bp PCR amplimer was cloned into the pGemT PCR cloning vector (Promega, Inc.) and clones were screened for inserts in the T7 (5') orientation.

A duplex oligonucleotide was synthesized by to code for the amino acid sequence of DDD1 preceded by 11 residues of a linker peptide, with the first two codons comprising a BamHI restriction site. A stop codon and an EagI restriction site are appended to the 3' end. The encoded polypeptide sequence is shown below, with the DDD1 sequence underlined.

(SEQ ID NO: 10)
GSGGGGSGGGG<u>SHIQIPPGLTELLQGYTVEVLRQQPPDLVEFAVEYFTR</u>

<u>LREARA</u>

Two oligonucleotides, designated RIIA1-44 top and RIIA1-44 bottom, that overlap by 30 base pairs on their 3' ends, were synthesized (Sigma Genosys) and combined to comprise the central 154 base pairs of the 174 bp DDD1 sequence. The oligonucleotides were annealed and subjected to a primer extension reaction with Taq polymerase. Following primer extension, the duplex was amplified by PCR. The amplimer was cloned into pGemT and screened for inserts in the T7 (5') orientation.

A duplex oligonucleotide was synthesized to code for the amino acid sequence of AD1 preceded by 11 residues of the linker peptide with the first two codons comprising a BamHI restriction site. A stop codon and an EagI restriction site are appended to the 3' end. The encoded polypeptide sequence is shown below, with the sequence of AD1 underlined.

(SEQ ID NO: 11)
GSGGGGSGGGGS<u>QIEYLAKQIVDNAIQQA</u>

Two complimentary overlapping oligonucleotides encoding the above peptide sequence, designated AKAP-IS Top and AKAP-IS Bottom, were synthesized and annealed. The duplex was amplified by PCR. The amplimer was cloned into the pGemT vector and screened for inserts in the T7 (5') orientation.

Ligating DDD1 with CH1

A 190 bp fragment encoding the DDD1 sequence was excised from pGemT with BamHI and NotI restriction enzymes and then ligated into the same sites in CH1-pGemT to generate the shuttle vector CH1-DDD1-pGemT.

Ligating AD1 with CH1

A 110 bp fragment containing the AD1 sequence was excised from pGemT with BamHI and NotI and then ligated into the same sites in CH1-pGemT to generate the shuttle vector CH1-AD1-pGemT.

Cloning CH1-DDD1 or CH1-AD1 into pdHL2-Based Vectors

With this modular design either CH1-DDD1 or CH1-AD1 can be incorporated into any IgG construct in the pdHL2 vector. The entire heavy chain constant domain is replaced with one of the above constructs by removing the SacII/EagI restriction fragment (CH1-CH3) from pdHL2 and replacing it with the SacII/EagI fragment of CH1-DDD1 or CH1-AD1, which is excised from the respective pGemT shuttle vector.

Construction of h679-Fd-AD1-pdHL2 h679-Fd-AD1-pdHL2 is an expression vector for production of h679 Fab with AD1 coupled to the carboxyl terminal end of the CH1 domain of the Fd via a flexible Gly/Ser peptide spacer composed of 14 amino acid residues. A pdHL2-based vector containing the variable domains of h679 was converted to h679-Fd-AD1-pdHL2 by replacement of the SacII/EagI fragment with the CH1-AD1 fragment, which was excised from the CH1-AD1-SV3 shuttle vector with SacII and EagI.

Construction of C-DDD1-Fd-hMN-14-pdHL2

C-DDD1-Fd-hMN-14-pdHL2 is an expression vector for production of a stable dimer that comprises two copies of a fusion protein C-DDD1-Fab-hMN-14, in which DDD1 is linked to hMN-14 Fab at the carboxyl terminus of CH1 via a flexible peptide spacer. The plasmid vector hMN14(I)-pdHL2, which has been used to produce hMN-14 IgG, was converted to C-DDD1-Fd-hMN-14-pdHL2 by digestion with SacII and EagI restriction endonucleases to remove the CH1-CH3 domains and insertion of the CH1-DDD1 fragment, which was excised from the CH1-DDD1-SV3 shuttle vector with SacII and EagI.

The same technique has been utilized to produce plasmids for Fab expression of a wide variety of known antibodies, such as hLL1, hLL2, hPAM4, hR1, hRS7, hMN-14, hMN-15, hA19, hA20 and many others. Generally, the antibody variable region coding sequences were present in a pdHL2 expression vector and the expression vector was converted for production of an AD- or DDD-fusion protein as described above. The AD- and DDD-fusion proteins comprising a Fab fragment of any of such antibodies may be combined, in an approximate ratio of two DDD-fusion proteins per one AD-fusion protein, to generate a trimeric DNL construct comprising two Fab fragments of a first antibody and one Fab fragment of a second antibody.

C-DDD2-Fd-hMN-14-pdHL2

C-DDD2-Fd-hMN-14-pdHL2 is an expression vector for production of C-DDD2-Fab-hMN-14, which possesses a dimerization and docking domain sequence of DDD2 appended to the carboxyl terminus of the Fd of hMN-14 via a 14 amino acid residue Gly/Ser peptide linker. The fusion protein secreted is composed of two identical copies of hMN-14 Fab held together by non-covalent interaction of the DDD2 domains.

Two overlapping, complimentary oligonucleotides, which comprise the coding sequence for part of the linker peptide and residues 1-13 of DDD2, were made synthetically. The oligonucleotides were annealed and phosphorylated with T4 PNK, resulting in overhangs on the 5' and 3' ends that are compatible for ligation with DNA digested with the restriction endonucleases BamHI and PstI, respectively.

The duplex DNA was ligated with the shuttle vector CH1-DDD1-pGemT, which was prepared by digestion with BamHI and PstI, to generate the shuttle vector CH1-DDD2-pGemT. A 507 bp fragment was excised from CH1-DDD2-pGemT with SacII and EagI and ligated with the IgG expression vector hMN14(I)-pdHL2, which was prepared by digestion with SacII and EagI. The final expression construct was designated C-DDD2-Fd-hMN-14-pdHL2. Similar techniques have been utilized to generated DDD2-fusion proteins of the Fab fragments of a number of different humanized antibodies.

H679-Fd-AD2-pdHL2 h679-Fab-AD2, was designed to pair as B to C-DDD2-Fab-hMN-14 as A. h679-Fd-AD2-pdHL2 is an expression vector for the production of h679-Fab-AD2, which possesses an anchor domain sequence of AD2 appended to the carboxyl terminal end of the CH1 domain via a 14 amino acid residue Gly/Ser peptide linker. AD2 has one cysteine residue preceding and another one following the anchor domain sequence of AD1.

The expression vector was engineered as follows. Two overlapping, complimentary oligonucleotides (AD2 Top and AD2 Bottom), which comprise the coding sequence for AD2 and part of the linker sequence, were made synthetically. The oligonucleotides were annealed and phosphorylated with T4 PNK, resulting in overhangs on the 5' and 3' ends that are compatible for ligation with DNA digested with the restriction endonucleases BamHI and SpeI, respectively.

The duplex DNA was ligated into the shuttle vector CH1-AD1-pGemT, which was prepared by digestion with BamHI and SpeI, to generate the shuttle vector CH1-AD2-pGemT. A 429 base pair fragment containing CH1 and AD2 coding sequences was excised from the shuttle vector with SacII and EagI restriction enzymes and ligated into h679-pdHL2 vector that prepared by digestion with those same enzymes. The final expression vector is h679-Fd-AD2-pdHL2.

Example 5

Generation of TF2 DNL Construct

A trimeric DNL construct designated TF2 was obtained by reacting C-DDD2-Fab-hMN-14 with h679-Fab-AD2. A pilot batch of TF2 was generated with >90% yield as follows. Protein L-purified C-DDD2-Fab-hMN-14 (200 mg) was mixed with h679-Fab-AD2 (60 mg) at a 1.4:1 molar ratio. The total protein concentration was 1.5 mg/ml in PBS containing 1 mM EDTA. Subsequent steps involved TCEP reduction, HIC chromatography, DMSO oxidation, and IMP 291 affinity chromatography. Before the addition of TCEP, SE-HPLC did not show any evidence of $a_2b$ formation. Addition of 5 mM TCEP rapidly resulted in the formation of $a_2b$ complex consistent with a 157 kDa protein expected for the binary structure. TF2 was purified to near homogeneity by IMP 291 affinity chromatography (not shown). IMP 291 is a synthetic peptide containing the HSG hapten to which the 679 Fab binds (Rossi et al., 2005, Clin Cancer Res 11:7122s-29s). SE-HPLC analysis of the IMP 291 unbound fraction demonstrated the removal of $a_4$, $a_2$ and free kappa chains from the product (not shown).

Non-reducing SDS-PAGE analysis demonstrated that the majority of TF2 exists as a large, covalent structure with a relative mobility near that of IgG (not shown). The additional bands suggest that disulfide formation is incomplete under the experimental conditions (not shown). Reducing SDS-PAGE shows that any additional bands apparent in the non-reducing gel are product-related (not shown), as only bands representing the constituent polypeptides of TF2 are evident. MALDI-TOF mass spectrometry (not shown) revealed a single peak of 156,434 Da, which is within 99.5% of the calculated mass (157,319 Da) of TF2.

The functionality of TF2 was determined by BIACORE assay. TF2, C-DDD1-hMN-14+h679-AD1 (used as a control sample of noncovalent $a_2b$ complex), or C-DDD2-hMN-14+h679-AD2 (used as a control sample of unreduced $a_2$ and b components) were diluted to 1 µg/ml (total protein) and passed over a sensorchip immobilized with HSG. The response for TF2 was approximately two-fold that of the two control samples, indicating that only the h679-Fab-AD component in the control samples would bind to and remain on the sensorchip. Subsequent injections of WI2 IgG, an anti-idiotype antibody for hMN-14, demonstrated that only TF2 had a DDD-Fab-hMN-14 component that was tightly associated with h679-Fab-AD as indicated by an additional signal response. The additional increase of response units resulting from the binding of WI2 to TF2 immobilized on the sensorchip corresponded to two fully functional binding sites, each contributed by one subunit of C-DDD2-Fab-hMN-14. This was confirmed by the ability of TF2 to bind two Fab fragments of WI2 (not shown).

Example 6

Production of TF10 DNL Construct

A similar protocol was used to generate a trimeric TF10 DNL construct, comprising two copies of a C-DDD2-Fab-hPAM4 and one copy of C-AD2-Fab-679. The TF10 bispecific ([hPAM4]$_2$×h679) antibody was produced using the method disclosed for production of the (anti CEA)$_2$×anti HSG bsAb TF2, as described above. The TF10 construct bears two humanized PAM4 Fabs and one humanized 679 Fab.

The two fusion proteins (hPAM4-DDD2 and h679-AD2) were expressed independently in stably transfected myeloma cells. The tissue culture supernatant fluids were combined, resulting in a two-fold molar excess of hPAM4-DDD2. The reaction mixture was incubated at room temperature for 24 hours under mild reducing conditions using 1 mM reduced glutathione. Following reduction, the DNL reaction was completed by mild oxidation using 2 mM oxidized glutathione. TF10 was isolated by affinity chromatography using IMP 291-affigel resin, which binds with high specificity to the h679 Fab.

Example 7

Sequence Variants for DNL

In certain preferred embodiments, the AD and DDD sequences incorporated into the cytokine-MAb DNL complex comprise the amino acid sequences of AD1 or AD2 and DDD1 or DDD2, as discussed above. However, in alternative embodiments sequence variants of AD and/or DDD moieties may be utilized in construction of the DNL complexes. For example, there are only four variants of human PKA DDD sequences, corresponding to the DDD moieties of PKA RIα, RIIα, RIβ and RIIβ. The RIIα DDD sequence is the basis of DDD1 and DDD2 disclosed above. The four human PKA DDD sequences are shown below. The DDD sequence represents residues 1-44 of RIIα, 1-44 of RIIβ, 12-61 of RIα and 13-66 of RIβ. (Note that the sequence of DDD1 is modified slightly from the human PKA RIIα DDD moiety.)

PKA RIα
(SEQ ID NO: 12)
SLRECELYVQKHNIQALLKDVSIVQLCTARPERPMAFLREYFEKLEKEE
AK

PKA RIβ
(SEQ ID NO: 13)
SLKGCELYVQLHGIQQVLKDCIVHLCISKPERPMKFLREHFEKLEKEE
NRQILA

PKA RIIα
(SEQ ID NO: 14)
SHIQIPPGLTELLQGYTVEVGQQPPDLVDFAVEYFTRLREARRQ

PKA RIIβ
(SEQ ID NO: 15)
SIEIPAGLTELLQGFTVEVLRHQPADLLEFALQHFTRLQQENER

The structure-function relationships of the AD and DDD domains have been the subject of investigation. (See, e.g., Burns-Hamuro et al., 2005, Protein Sci 14:2982-92; Can et al., 2001, J Biol Chem 276:17332-38; Alto et al., 2003, Proc Natl Acad Sci USA 100:4445-50; Hundsrucker et al., 2006, Biochem J 396:297-306; Stokka et al., 2006, Biochem J 400: 493-99; Gold et al., 2006, Mol Cell 24:383-95; Kinderman et al., 2006, Mol Cell 24:397-408, the entire text of each of which is incorporated herein by reference.)

For example, Kinderman et al. (2006, Mol Cell 24:397-408) examined the crystal structure of the AD-DDD binding interaction and concluded that the human DDD sequence contained a number of conserved amino acid residues that were important in either dimer formation or AKAP binding, underlined in SEQ ID NO:6 below. (See FIG. 1 of Kinderman et al., 2006, incorporated herein by reference.) The skilled artisan will realize that in designing sequence variants of the DDD sequence, one would desirably avoid changing any of the underlined residues, while conservative amino acid substitutions might be made for residues that are less critical for dimerization and AKAP binding.

(SEQ ID NO: 6)
SH<u>I</u>Q<u>I</u>PPG<u>L</u>TE<u>LL</u>QGYT<u>V</u>E<u>V</u>LRQQPPD<u>L</u>VE<u>FA</u>V<u>E</u>Y<u>F</u>TR<u>L</u>REARA

As known in the art, conservative amino acid substitutions have been characterized for each of the twenty common L-amino acids. Thus, based on the data of Kinderman (2006) and conservative amino acid substitutions, potential alternative DDD sequences based on SEQ ID NO:6 are shown in Table 2. In devising Table 2, only highly conservative amino acid substitutions were considered. For example, charged residues were only substituted for residues of the same charge, residues with small side chains were substituted with residues of similar size, hydroxyl side chains were only substituted with other hydroxyls, etc. Because of the unique effect of proline on amino acid secondary structure, no other residues were substituted for proline. Even with such conservative substitutions, there are over twenty million possible alternative sequences for the 44 residue peptide (2×3×2×2×2×2×2×2×2×2×2×2×2×2×4×2×2×2×2×2×4×2×4). The skilled artisan will realize that an almost unlimited number of alternative species within the genus of DDD moieties can be constructed by standard techniques, for example using a commercial peptide synthesizer or well known site-directed mutagenesis techniques. The effect of the amino acid substitutions on AD moiety binding may also be readily determined by standard binding assays, for example as disclosed in Alto et al. (2003, Proc Natl Acad Sci USA 100:4445-50).

TABLE 2

Conservative Amino Acid Substitutions in DDD1 (SEQ ID NO: 6). Consensus sequence disclosed as SEQ ID NO: 16.

| S | H | I | Q | I | P | P | G | L | T | E | L | L | Q | G | Y | T | V | E | V | L | R |
|---|---|---|---|---|---|---|---|---|---|---|---|---|---|---|---|---|---|---|---|---|---|
| T | K |   | N |   |   |   | A |   | S | D |   |   |   | N | A |   | S |   | D |   | K |
|   | R |   |   |   |   |   |   |   |   |   |   |   |   |   |   |   |   |   |   |   |   |

| Q | Q | P | P | D | L | V | E | F | A | V | E | Y | F | T | R | L | R | E | A | R | A |
|---|---|---|---|---|---|---|---|---|---|---|---|---|---|---|---|---|---|---|---|---|---|
| N | N |   |   | E |   |   | D | L | D |   |   | S | K |   | K | D | L | K | L |   |   |
|   |   |   |   |   |   |   |   | I |   |   |   |   |   |   |   |   | I |   | I |   |   |
|   |   |   |   |   |   |   |   | V |   |   |   |   |   |   |   |   | V |   | V |   |   |

TABLE 3

Conservative Amino Acid Substitutuins in AD1 (SEQ ID NO: 8). Consensus sequence disclosed as SEQ ID NO: 17.

| Q | I | E | Y | L | A | K | Q | I | V | D | N | A | I | Q | Q | A |
|---|---|---|---|---|---|---|---|---|---|---|---|---|---|---|---|---|
| N | L | D | F | I |   | R | N |   |   | E | Q |   |   | N | N | L |
|   | V | T | V |   |   |   |   |   |   |   |   |   |   |   |   | I |
|   |   | S |   |   |   |   |   |   |   |   |   |   |   |   |   | V |

Gold (2006, Mol Cell 24:383-95) utilized crystallography and peptide screening to develop a SuperAKAP-IS sequence (SEQ ID NO:18), exhibiting a five order of magnitude higher selectivity for the RII isoform of PKA compared with the RI isoform. Underlined residues indicate the positions of amino acid substitutions, relative to the AKAP-IS sequence, which increased binding to the DDD moiety of RIIα. In this Alto et al. (2003, Proc Natl Acad Sci USA 100:4445-50) performed a bioinformatic analysis of the AD sequence of various AKAP proteins to design an RII selective AD sequence called AKAP-IS (SEQ ID NO:8), with a binding constant for DDD of 0.4 nM. The AKAP-IS sequence was designed as a peptide antagonist of AKAP binding to PKA. Residues in the AKAP-IS sequence where substitutions tended to decrease binding to DDD are underlined in SEQ ID NO:8 below. The skilled artisan will realize that in designing sequence variants of the AD sequence, one would desirably avoid changing any of the underlined residues, while conservative amino acid substitutions might be made for residues that are less critical for DDD binding. Table 3 shows potential conservative amino acid substitutions in the sequence of AKAP-IS (AD1, SEQ ID NO:8), similar to that shown for DDD1 (SEQ ID NO:6) in Table 2 above.

Even with such conservative substitutions, there are over thirty-five thousand possible alternative sequences for the 17 residue AD1 (SEQ ID NO:8) peptide sequence (2×3×2×4×3×2×2×2×2×2×2×4). Again, a very large number of species within the genus of possible AD moiety sequences could be made, tested and used by the skilled artisan, based on the data of Alto et al. (2003). It is noted that FIG. 2 of Alto (2003) shows an even larger number of potential amino acid substitutions that may be made, while retaining binding activity to DDD moieties, based on actual binding experiments.

AKAP-IS
(SEQ ID NO: 8)
QIEYLAKQIVDNAIQQA sequence, the N-terminal Q residue is numbered as residue number 4 and the C-terminal A residue is residue number 20. Residues where substitutions could be made to affect the affinity for RIM were residues 8, 11, 15, 16, 18, 19 and 20 (Gold et al., 2006). It is contemplated that in certain alternative embodiments, the SuperAKAP-IS sequence may be substituted for the AKAP-IS AD moiety sequence to prepare DNL constructs. Other alternative sequences that might be substituted for the AKAP-IS AD sequence are shown in SEQ ID NO:19-21. Substitutions relative to the AKAP-IS sequence are underlined. It is anticipated that, as with the AD2 sequence shown in SEQ ID NO:9, the AD moiety may also include the additional N-terminal residues cysteine and glycine and C-terminal residues glycine and cysteine.

SuperAKAP-IS
(SEQ ID NO: 18)
QIEYVAKQIVDYAIHQA

Figure 2:
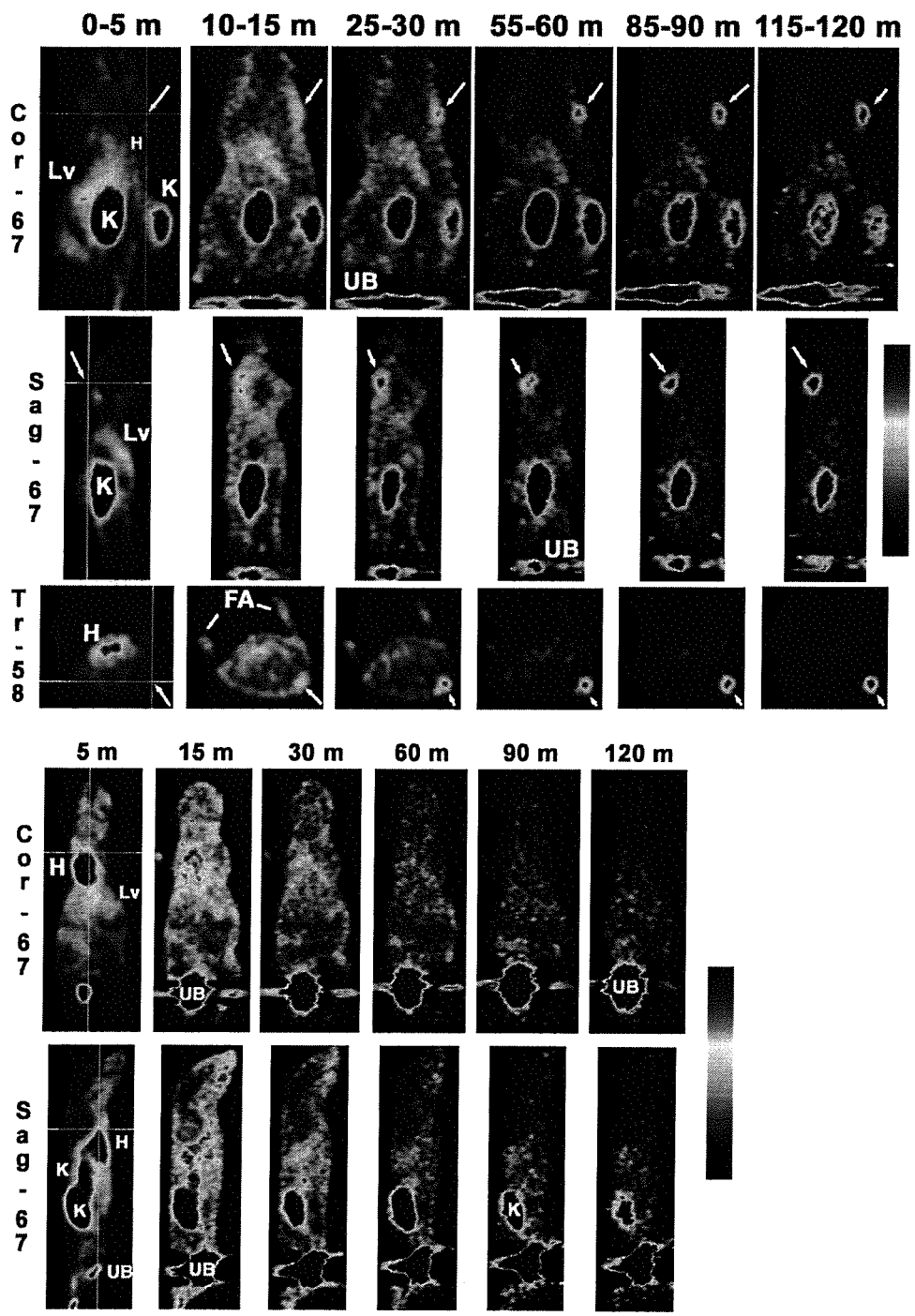
FIG. 2. Dynamic imaging study of pretargeted Al$^{18}$F (IMP449) given to a nude mouse bearing a 35-mg LS174T human colorectal cancer xenograft in the upper flank. The top 3 panels show coronal, sagittal, and transverse sections, respectively, taken of a region of the body centering on the tumor's peripheral location at 6 different 5-min intervals over the 120-min imaging session. The first image on the left in each sectional view shows the positioning of the tumor at the intersection of the crosshairs, which is highlighted by arrows. The animal was partially tilted to its right side during the imaging session. The bottom 2 panels show additional coronal and sagittal sections that focus on a more anterior plane in the coronal section to highlight distribution in the liver and intestines, while the sagittal view crosses more centrally in the body. Abbreviations: Cor, coronal; FA, forearms; H, heart; K, kidney; Lv, liver; Sag, sagittal; Tr, transverse; UB, urinary bladder.

Alternative AKAP sequences
(SEQ ID NO: 19)
QIEYKAKQIVDHAIHQA (SEQ ID NO: 20)
QIEYHAKQIVDHAIHQA (SEQ ID NO: 21)
QIEYVAKQIVDHAIHQA FIG. 2 of Gold et al. disclosed additional DDD-binding sequences from a variety of AKAP proteins, any of which could be utilized to design a DNL construct.

Stokka et al. (2006, Biochem J 400:493-99) also developed peptide competitors of AKAP binding to PKA, shown in SEQ ID NO:22-24. The peptide antagonists were designated as Ht31 (SEQ ID NO:22), RIAD (SEQ ID NO:23) and PV-38 (SEQ ID NO:24). The Ht-31 peptide exhibited a greater affinity for the RII isoform of PKA, while the RIAD and PV-38 showed higher affinity for RI.

```
Ht31
                                        (SEQ ID NO: 22)
DLIEEAASRIVDAVIEQVKAAGAY

RIAD
                                        (SEQ ID NO: 23)
LEQYANQLADQIIKEATE

PV-38
                                        (SEQ ID NO: 24)
FEELAWKIAKMIWSDVFQQC
```

Hundsrucker et al. (2006, Biochem J 396:297-306) developed still other peptide competitors for AKAP binding to PKA, with a binding constant as low as 0.4 nM to the DDD of the RII form of PKA. The sequences of various AKAP antagonistic peptides are provided in Table 1 of Hundsrucker et al., reproduced in Table 4 below. AKAPIS represents a synthetic RII subunit-binding peptide. All other peptides are derived from the RII-binding domains of the indicated AKAPs.

TABLE 4

AKAP Peptide sequences

| | Peptide Sequence |
|---|---|
| AKAPIS | QIEYLAKQIVDNAIQQA (SEQ ID NO: 8) |
| AKAPIS-P | QIEYLAKQIPDNAIQQA (SEQ ID NO: 25) |
| Ht31 | KGADLIEEAASRIVDAVIEQVKAAG (SEQ ID NO: 26) |
| Ht31-P | KGADLIEEAASRIPDAPIEQVKAAG (SEQ ID NO: 27) |
| AKAP7δ-wt-pep | PEDAELVRLSKRLVENAVLKAVQQY (SEQ ID NO: 28) |
| AKAP7δ-L304T-pep | PEDAELVRTSKRLVENAVLKAVQQY (SEQ ID NO: 29) |
| AKAP7δ-L308D-pep | PEDAELVRLSKRDVENAVLKAVQQY (SEQ ID NO: 30) |
| AKAP7δ-P-pep | PEDAELVRLSKRLPENAVLKAVQQY (SEQ ID NO: 31) |
| AKAP7δ-PP-pep | PEDAELVRLSKRLPENAPLKAVQQY (SEQ ID NO: 32) |
| AKAPδ-L314E-pep | PEDAELVRLSKRLVENAVEKAVQQY (SEQ ID NO: 33) |
| AKAP1-pep | EEGLDRNEEIKRAAFQIISQVISEA (SEQ ID NO: 34) |
| AKAP2-pep | LVDDPLEYQAGLLVQNAIQQAIAEQ (SEQ ID NO: 35) |
| AKAP5-pep | QYETLLIETASSLVKNAIQLSIEQL (SEQ ID NO: 36) |
| AKAP9-pep | LEKQYQEQLEEEVAKVIVSMSIAFA (SEQ ID NO: 37) |
| AKAP10-pep | NTDEAQEELAWKIAKMIVSDIMQQA (SEQ ID NO: 38) |

TABLE 4-continued

AKAP Peptide sequences

| | Peptide Sequence |
|---|---|
| AKAP11-pep | VNLDKKAVLAEKIVAEAIEKAEREL (SEQ ID NO: 39) |
| AKAP12-pep | NGILELETKSSKLVQNIIQTAVDQF (SEQ ID NO: 40) |
| AKAP14-pep | TQDKNYEDELTQVALALVEDVINYA (SEQ ID NO: 41) |
| Rab32-pep | ETSAKDNINIEEAARFLVEKILVNH (SEQ ID NO: 42) |

Residues that were highly conserved among the AD domains of different AKAP proteins are indicated below by underlining with reference to the AKAP IS sequence (SEQ ID NO:8). The residues are the same as observed by Alto et al. (2003), with the addition of the C-terminal alanine residue. (See FIG. 4 of Hundsrucker et al. (2006), incorporated herein by reference.) The sequences of peptide antagonists with particularly high affinities for the RII DDD sequence were those of AKAP-IS, AKAP7δ-wt-pep, AKAP7δ-L304T-pep and AKAP7δ-L308D-pep.

```
                AKAP-IS
                                        (SEQ ID NO: 8)
           QIEYLAKQIVDNAIQQA
```

Carr et al. (2001, J Biol Chem 276:17332-38) examined the degree of sequence homology between different AKAP-binding DDD sequences from human and non-human proteins and identified residues in the DDD sequences that appeared to be the most highly conserved among different DDD moieties. These are indicated below by underlining with reference to the human PKA RIIα DDD sequence of SEQ ID NO:6. Residues that were particularly conserved are further indicated by italics. The residues overlap with, but are not identical to those suggested by Kinderman et al. (2006) to be important for binding to AKAP proteins. The skilled artisan will realize that in designing sequence variants of DDD, it would be most preferred to avoid changing the most conserved residues (italicized), and it would be preferred to also avoid changing the conserved residues (underlined), while conservative amino acid substitutions may be considered for residues that are neither underlined nor italicized.

```
                                        (SEQ ID NO: 6)
SHIQIPPGLTELLQGYTVEVLRQQPPDLVEFAVEYFTRLREARA
```

A modified set of conservative amino acid substitutions for the DDD1 (SEQ ID NO:6) sequence, based on the data of Carr et al. (2001) is shown in Table 5. Even with this reduced set of substituted sequences, there are over 65,000 possible alternative DDD moiety sequences that may be produced, tested and used by the skilled artisan without undue experimentation. The skilled artisan could readily derive such alternative DDD amino acid sequences as disclosed above for Table 2 and Table 3.

TABLE 5

Conservative Amino Acid Substitutions in DDD1 (SEQ ID NO: 6).
Consensus sequence disclosed as SEQ ID NO: 43.

| S | H | I | Q | I | P | P | G | L | T | E | L | L | Q | G | Y | T | V | E | V | L | R |
|---|---|---|---|---|---|---|---|---|---|---|---|---|---|---|---|---|---|---|---|---|---|
| T |   | N |   |   |   |   |   | S |   |   |   |   |   |   |   |   |   | I |   |   |   |
|   |   |   |   |   |   |   |   |   |   |   |   |   |   |   |   |   |   | L |   |   |   |
|   |   |   |   |   |   |   |   |   |   |   |   |   |   |   |   |   |   | A |   |   |   |

| Q | Q | P | P | D | L | V | E | F | A | V | E | Y | F | T | R | L | R | E | A | R | A |
|---|---|---|---|---|---|---|---|---|---|---|---|---|---|---|---|---|---|---|---|---|---|
|   | N |   |   |   |   |   |   | I | D |   |   | S | K |   |   | K |   | L |   | L |   |
|   |   |   |   |   |   |   |   | L |   |   |   |   |   |   |   |   |   | I |   | I |   |
|   |   |   |   |   |   |   |   | A |   |   |   |   |   |   |   |   |   | V |   | V |   |

The skilled artisan will realize that these and other amino acid substitutions in the DDD or AD amino acid sequences may be utilized to produce alternative species within the genus of AD or DDD moieties, using techniques that are standard in the field and only routine experimentation.

Example 8

In Vivo Imaging Using $^{18}$F-Labeled Peptides and Comparison with $^{18}$F-FDG In vivo imaging techniques using pretargeting with bispecific antibodies and labeled targeting peptides were used to successfully detect tumors of relatively small size. The $^{18}$F was purified on a WATERS® ACCELL™ Plus QMA Light cartridge. The $^{18}$F eluted with 0.4 M KHCO$_3$ was mixed with 3 µL 2 mM Al$^{3+}$ in a pH 4 acetate buffer. The Al$^{18}$F solution was then injected into the ascorbic acid IMP449 labeling vial and heated to 105° C. for 15 min. The reaction solution was cooled and mixed with 0.8 mL DI water. The reaction contents were loaded on a WATERS® OASIS® 1 cc HLB Column and eluted with 2×200 µL 1:1 EtOH/H$_2$O. TF2 was prepared as described above. TF2 binds divalently to carcinoembryonic antigen (CEA) and monovalently to the synthetic hapten, HSG (histamine-succinyl-glycine).

Biodistribution and microPET Imaging.

Six-week-old NCr nu-m female nude mice were implanted s.c. with the human colonic cancer cell line, LS174T (ATCC, Manassas, Va.). When tumors were visibly established, pretargeted animals were injected intravenously with 162 µg (~1 nmole/0.1 mL) TF2 or TF10 (control non-targeting tri-Fab bsMAb), and then 16-18 h later, ~0.1 nmol of Al$^{18}$F(IMP449) (84 µCi, 3.11 MBq/0.1 mL) was injected intravenously. Other non-pretargeted control animals received $^{18}$F alone (150 µCi, 5.5 MBq), Al$^{18}$F complex alone (150 µCi, 5.55 MBq), the Al$^{18}$F(IMP449) peptide alone (84 µCi, 3.11 MBq), or $^{18}$F-FDG (150 µCi, 5.55 MBq). $^{18}$F and $^{18}$F-FDG were obtained on the day of use from IBA Molecular (Somerset, N.J.). Animals receiving $^{18}$F-FDG were fasted overnight, but water was given ad libitum.

At 1.5 h after the radiotracer injection, animals were anesthetized, bled intracardially, and necropsied. Tissues were weighed and counted together with a standard dilution prepared from each of the respective products. Due to the short physical half-life of $^{18}$F, standards were interjected between each group of tissues from each animal. Uptake in the tissues is expressed as the counts per gram divided by the total injected activity to derive the percent-injected dose per gram (% ID/g).

Two types of imaging studies were performed. In one set, 3 nude mice bearing small LS174T subcutaneous tumors received either the pretargeted Al$^{18}$F(IMP449), Al$^{18}$F (IMP449) alone (not pretargeted), both at 135 µCi (5 MBq; 0.1 nmol), or $^{18}$F-FDG (135 µCi, 5 MBq). At 2 h after the intravenous radiotracer injection, the animals were anesthetized with a mixture of O$_2$/N$_2$O and isoflurane (2%) and kept warm during the scan, performed on an INVEON® animal PET scanner (Siemens Preclinical Solutions, Knoxville, Tenn.).

Representative coronal cross-sections (0.8 mm thick) in a plane located approximately in the center of the tumor were displayed, with intensities adjusted until pixel saturation occurred in any region of the body (excluding the bladder) and without background adjustment.

In a separate dynamic imaging study, a single LS174T bearing nude mouse that was given the TF2 bsMAb 16 h earlier was anesthetized with a mixture of O$_2$/N$_2$O and isoflurane (2%), placed supine on the camera bed, and then injected intravenously with 219 µCi (8.1 MBq) Al$^{18}$F (IMP449) (0.16 nmol). Data acquisition was immediately initiated over a period of 120 minutes. The scans were reconstructed using OSEM3D/MAP. For presentation, time-frames ending at 5, 15, 30, 60, 90, and 120 min were displayed for each cross-section (coronal, sagittal, and transverse). For sections containing tumor, at each interval the image intensity was adjusted until pixel saturation first occurred in the tumor. Image intensity was increased as required over time to maintain pixel saturation within the tumor. Coronal and sagittal cross-sections without tumor taken at the same interval were adjusted to the same intensity as the transverse section containing the tumor. Background activity was not adjusted.

Results

While $^{18}$F alone and [Al$^{18}$F] complexes had similar uptake in all tissues, considerable differences were found when the complex was chelated to IMP449 (Table 6). The most striking differences were found in the uptake in the bone, where the non-chelated $^{18}$F was 60- to nearly 100-fold higher in the scapula and ~200-fold higher in the spine. This distribution is expected since $^{18}$F, or even a metal-fluoride complex, is known to accrete in bone (Franke et al. 1972, Radiobiol. Radiother. (Berlin) 13:533). Higher uptake was also observed in the tumor and intestines as well as in muscle and blood. The chelated Al$^{18}$F(IMP449) had significantly lower uptake in all the tissues except the kidneys, illustrating the ability of the chelate-complex to be removed efficiently from the body by urinary excretion.

Pretargeting the Al$^{18}$F(IMP449) using the TF2 anti-CEA bsMAb shifted uptake to the tumor, increasing it from 0.20±0.05 to 6.01±1.72% injected dose per gram at 1.5 h, while uptake in the normal tissues was similar to the Al$^{18}$F (IMP449) alone. Tumor/nontumor ratios were 146±63, 59±24, 38±15, and 2.0±1.0 for the blood, liver, lung, and kidneys, respectively, with other tumor/tissue ratios >100:1 at this time. Although both $^{18}$F alone and [Al$^{18}$F] alone had higher uptake in the tumor than the chelated Al$^{18}$F(IMP449), yielding tumor/blood ratios of 6.7±2.7 and 11.0±4.6 vs. 5.1±1.5, respectively, tumor uptake and tumor/blood ratios were significantly increased with pretargeting (all P values <0.001).

Biodistribution was also compared to the most commonly used tumor imaging agent, [$^{18}$F]FDG, which targets tissues with high glucose consumption and metabolic activity (Table 6). Its uptake was appreciably higher than the Al$^{18}$F(IMP449) in all normal tissues, except the kidney. Tumor uptake was similar for both the pretargeted Al$^{18}$F(IMP449) and $^{18}$F-FDG, but because of the higher accretion of [$^{18}$F]FDG in most normal tissues, tumor/nontumor ratios with $^{18}$F-FDG were significantly lower than those in the pretargeted animals (all P values <0.001).

2006, J. Nucl. Med. 47:1678; Sharkey et al., 2008, Radiology 246:497), with considerably more background activity in the body (FIG. 1). Tissue uptake measured in the 3 animals necropsied at the conclusion of the static imaging study confirmed much higher tissue $^{18}$F radioactivity in all tissues (not shown). While tumor uptake with $^{18}$F-FDG was higher in this animal than in the pretargeted one, tumor/blood ratios were more favorable for pretargeting; and with much less residual activity in the body, tumor visualization was enhanced by pretargeting.

These studies demonstrate that a hapten-peptide used in pretargeted imaging can be rapidly labeled (60 min total preparation time) with $^{18}$F by simply forming an aluminum-fluoride complex that can then be bound by a suitable chelate and incorporated into the hapten-peptide. This can be made

TABLE 6

Biodistribution of TF2-pretargeted Al$^{18}$F(IMP449) and other control $^{18}$F-labeled agents in nude mice bearing LS174T human colonic xenografts. For pretargeting, animals were given TF2 16 h before the injection of the Al$^{18}$F(IMP449). All injections were administered intravenously.

Percent Injected Dose Per Gram (Mean ± SD) at 1.5 hr Post-Injection

|  | $^{18}$F alone | [Al$^{18}$F] alone | Al$^{18}$F(IMP449) alone | TF2-pretargeted Al$^{18}$F(IMP449) | $^{18}$F-FDG |
|---|---|---|---|---|---|
| Tumor | 1.02 ± 0.45 | 1.38 ± 0.39 | 0.20 ± 0.05 | 6.01 ± 1.72 | 7.25 ± 2.54 |
| Liver | 0.11 ± 0.02 | 0.12 ± 0.02 | 0.08 ± 0.03 | 0.11 ± 0.03 | 1.34 ± 0.36 |
| Spleen | 0.13 ± 0.06 | 0.10 ± 0.03 | 0.08 ± 0.02 | 0.08 ± 0.02 | 2.62 ± 0.73 |
| Kidney | 0.29 ± 0.07 | 0.25 ± 0.07 | 3.51 ± 0.56 | 3.44 ± 0.99 | 1.50 ± 0.61 |
| Lung | 0.26 ± 0.08 | 0.38 ± 0.19 | 0.11 ± 0.03 | 0.17 ± 0.04 | 3.72 ± 1.48 |
| Blood | 0.15 ± 0.03 | 0.13 ± 0.03 | 0.04 ± 0.01 | 0.04 ± 0.02 | 0.66 ± 0.19 |
| Stomach | 0.21 ± 0.13 | 0.15 ± 0.05 | 0.20 ± 0.32 | 0.12 ± 0.18 | 2.11 ± 1.04 |
| Small Int. | 1.53 ± 0.33 | 1.39 ± 0.34 | 0.36 ± 0.23 | 0.27 ± 0.10 | 1.77 ± 0.61 |
| Large Int. | 1.21 ± 0.13 | 1.78 ± 0.70 | 0.05 ± 0.04 | 0.03 ± 0.01 | 2.90 ± 0.79 |
| Scapula | 6.13 ± 1.33 | 9.83 ± 2.31 | 0.08 ± 0.06 | 0.04 ± 0.02 | 10.63 ± 5.88 |
| Spine | 19.88 ± 2.12 | 19.03 ± 2.70 | 0.13 ± 0.14 | 0.08 ± 0.03 | 4.21 ± 1.79 |
| Muscle | 0.16 ± 0.05 | 0.58 ± 0.36 | 0.06 ± 0.05 | 0.10 ± 0.20 | 4.35 ± 3.01 |
| Brain | 0.15 ± 0.06 | 0.13 ± 0.03 | 0.01 ± 0.01 | 0.01 ± 0.00 | 10.71 ± 4.53 |
| Tumor wt (g) | 0.29 ± 0.07 | 0.27 ± 0.10 | 0.27 ± 0.08 | 0.33 ± 0.11 | 0.25 ± 0.21 |
| N | 6 | 7 | 8 | 7 | 5 |

Several animals were imaged to further analyze the biodistribution of Al$^{18}$F(IMP449) alone or Al$^{18}$F(IMP449) pretargeted with TF2, as well [$^{18}$F]FDG. Static images initiated at 2.0 h after the radioactivity was injected corroborated the previous tissue distribution data showing uptake almost exclusively in the kidneys (FIG. 1). A 21-mg tumor was easily visualized in the pretargeted animal, while the animal given the Al$^{18}$F(IMP449) alone failed to localize the tumor, having only renal uptake. No evidence of bone accretion was observed, suggesting that the Al$^{18}$F was bound firmly to IMP 449. This was confirmed in another pretargeted animal that underwent a dynamic imaging study that monitored the distribution of the Al$^{18}$F(IMP449) in 5-min intervals over 120 minutes (FIG. 2). Coronal and sagittal slices showed primarily cardiac, renal, and some hepatic uptake over the first 5 min, but heart and liver activity decreased substantially over the next 10 min, while the kidneys remained prominent throughout the study. There was no evidence of activity in the intestines or bone over the full 120-min scan. Uptake in a 35-mg LS174T tumor was first observed at 15 min, and by 30 min, the signal was very clearly delineated from background, with intense tumor activity being prominent during the entire 120-min scanning.

In comparison, static images from an animal given $^{18}$F-FDG showed the expected pattern of radioactivity in the bone, heart muscle, and brain observed previously (McBride et al., more general by simply coupling the [Al$^{18}$F]-chelate to any molecule that can be attached to the chelating moiety and be subsequently purified.

This report describes a direct, facile, and rapid method of binding $^{18}$F to various compounds via an aluminum conjugate. The [Al$^{18}$F] peptide was stable in vitro and in vivo when bound by a NOTA-based chelate. Yields were within the range found with conventional $^{18}$F labeling procedures. These results further demonstrate the feasibility of PET imaging using metal $^{18}$F chelated to a wide variety of targeting molecules.

Example 9

Preparation and Labeling of IMP460 with Al—$^{18}$F

IMP460 NODA-Ga-D-Ala-D-Lys(HSG)-D-Tyr-D-Lys(HSG)-NH$_2$ (SEQ ID NO:44) was chemically synthesized. The NODA-Ga ligand was purchased from CHEMATECH® and attached on the peptide synthesizer like the other amino acids. The peptide was synthesized on Sieber amide resin with the amino acids and other agents added in the following order Aloc-D-Lys(Fmoc)-OH, Trt-HSG-OH, Aloc removal, Fmoc-D-Tyr(But)-OH, Aloc-D-Lys(Fmoc)-OH, Trt-HSG-OH, Aloc removal, Fmoc-D-Ala-OH, and NODA-GA(tBu)$_3$. The peptide was then cleaved and purified by HPLC to afford the product.

Radiolabeling of IMP460

IMP 460 (0.0020 g) was dissolved in 732 pH 4, 0.1 M NaOAc. The $^{18}$F was purified as described above, neutralized with glacial acetic acid and mixed with the Al solution. The peptide solution, 20 µL was then added and the solution was heated at 99° C. for 25 min. The crude product was then purified on a WATERS® HLB column. The [Al$^{18}$F] labeled peptide was in the 1:1 EtOH/H$_2$O column eluent. The reverse phase HPLC trace in 0.1% TFA buffers showed a clean single HPLC peak at the expected location for the labeled peptide (not shown).

Example 10

Synthesis and Labeling of IMP461 and IMP462 NOTA-Conjugated Peptides

The simplest possible NOTA ligand (protected for peptide synthesis) was prepared and incorporated into two peptides for pretargeting—IMP461 and IMP462.

Synthesis of Bis-t-butyl-NOTA

NO2AtBu (0.501 g 1.4×10$^{-3}$ mol) was dissolved in 5 mL anhydrous acetonitrile. Benzyl-2-bromoacetate (0.222 mL, 1.4×10$^{-3}$ mol) was added to the solution followed by 0.387 g of anhydrous K$_2$CO$_3$. The reaction was allowed to stir at room temperature overnight. The reaction mixture was filtered and concentrated to obtain 0.605 g (86% yield) of the benzyl ester conjugate. The crude product was then dissolved in 50 mL of isopropanol, mixed with 0.2 g of 10% Pd/C (under Ar) and placed under 50 psi H$_2$ for 3 days. The product was then filtered and concentrated under vacuum to obtain 0.462 g of the desired product ESMS [M−H]$^-$ 415.

Synthesis of IMP461

The peptide was synthesized on Sieber amide resin with the amino acids and other agents added in the following order Aloc-D-Lys(Fmoc)-OH, Trt-HSG-OH, Aloc removal, Fmoc-D-Tyr(But)-OH, Aloc-D-Lys(Fmoc)-OH, Trt-HSG-OH, Aloc removal, Fmoc-D-Ala-OH, and Bis-t-butylNOTA. The peptide was then cleaved and purified by HPLC to afford the product IMP461 ESMS MH$^+$1294 NOTA-D-Ala-D-Lys (HSG)-D-Tyr-D-Lys(HSG)-NH$_2$; SEQ ID NO:45).

Synthesis of IMP 462

The peptide was synthesized on Sieber amide resin with the amino acids and other agents added in the following order Aloc-D-Lys(Fmoc)-OH, Trt-HSG-OH, Aloc removal, Fmoc-D-Tyr(But)-OH, Aloc-D-Lys(Fmoc)-OH, Trt-HSG-OH, Aloc removal, Fmoc-D-Asp(But)-OH, and Bis-t-butyl NOTA. The peptide was then cleaved and purified by HPLC to afford the product IMP462 ESMS MH$^+$1338 (NOTA-D-Asp-D-Lys(HSG)-D-Tyr-D-Lys(HSG)-NH$_2$; SEQ ID NO:46).

$^{18}$F Labeling of IMP461 & IMP462

The peptides were dissolved in pH 4.13, 0.5 M NaOAc to make a 0.05 M peptide solution, which was stored in the freezer until needed. The F-18 was received in 2 mL of water and trapped on a SEP-PAK® Light, WATERS® ACCELL™ Plus QMA Cartridge. The $^{18}$F was eluted from the column with 200 µL aliquots of 0.4 M KHCO$_3$. The bicarbonate was neutralized to ~pH 4 by the addition of 10 µL of glacial acetic acid to the vials before the addition of the activity. A 100 µL aliquot of the purified $^{18}$F solution was removed and mixed with 3 µL, 2 mM Al in pH 4, 0.1 M NaOAc. The peptide, 10 µL (0.05 M) was added and the solution was heated at ~100° C. for 15 min. The crude reaction mixture was diluted with 700 µL DI water and placed on an HLB column and after washing the $^{18}$F was eluted with 2×100 µL of 1:1 EtOH/H$_2$O to obtain the purified $^{18}$F-labeled peptide.

Example 11

Preparation and $^{18}$F-Labeling of IMP467

IMP467

(SEQ ID NO: 47)
C-NETA-succinyl-D-Lys(HSG)-D-Tyr-D-Lys(HSG)-NH$_2$

Tetra tert-butyl C-NETA-succinyl was produced. The tert-Butyl {4-[2-(Bis-(tert-butyoxycarbonyl)methyl-3-(4-nitrophenyl)propyl]-7-tert-butyoxycarbonyl[1,4,7]triazanonan-1-yl} was prepared as described in Chong et al. (J. Med. Chem. 2008, 51:118-125).

The peptide, IMP467 C-NETA-succinyl-D-Lys(HSG)-D-Tyr-D-Lys(HSG)-NH$_2$ (SEQ ID NO:47) was made on Sieber Amide resin by adding the following amino acids to the resin in the order shown: Aloc-D-Lys(Fmoc)-OH, Trt-HSG-OH, the Aloc was cleaved Fmoc-D-Tyr(But)-OH, Aloc-D-Lys (Fmoc)-OH, Trt-HSG-OH, the Aloc was cleaved, tert-Butyl{4-[Bis-(tert-butoxycarbonylmethyl)amino)-3-(4-succinylamidophenyl)propyl]-7-tert-butoxycarbonylmethyl[1,4,7]triazanonan-1-yl}acetate. The peptide was then cleaved from the resin and purified by RP-HPLC to yield 6.3 mg of IMP467. The crude peptide was purified by high performance liquid chromatography (HPLC) using a C18 column.

Radiolabeling

A 2 mM solution of IMP467 was prepared in pH 4, 0.1 M NaOAc. The $^{18}$F$^-$, 139 mCi, was eluted through a WATERS® ACCELL™ Plus SEP-PAK® Light QMA cartridge and the $^{18}$F was eluted with 1 mL of 0.4 M KHCO$_3$. The labeled IMP467 was purified by HLB R-HPLC. The RP-HPLC showed two peaks eluting (not shown), which are believed to be diastereomers of Al$^{18}$F(IMP467). Supporting this hypothesis, there appeared to be some interconversion between the two HLB peaks when IMP467 was incubated at 37° C. (not shown). In pretargeting techniques as discussed below, since the [Al$^{18}$F]-chelator complex is not part of the hapten site for antibody binding, the presence of diastereomers does not appear to affect targeting of the $^{18}$F-labeled peptide to diseased tissues.

Comparison of Yield of Radiolabeled Peptides

In an attempt to improve labeling yields while maintaining in vivo stability, 3 NOTA derivatives of pretargeting peptide were synthesized (IMP460, IMP461 and IMP467). Of these, IMP467 nearly doubled the labeling yields of the other peptides (Table 7). All of the labeling studies in Table 7 were performed with the same number of moles of peptide and aluminum. The results shown in Table 7 represent an exemplary labeling experiment with each peptide.

The $^{18}$F-labeling yield of IMP467 was ~70% when only 40 nmol (~13-fold less than IMP449) was used with 1.3 GBq (35 mCi) of $^{18}$F, indicating this ligand has improved binding properties for the Al$^{18}$F complex. By enhancing the kinetics of ligand binding, yields were substantially improved (average 65-75% yield), while using fewer moles of IMP467 (40 nmol), relative to IMP449 (520 nmol, 44% yield).

TABLE 7

Comparison of yields of different NOTA containing peptides

| Peptide | Yield |
|---------|-------|
| IMP449 | 44% |
| IMP460 | 5.8% |
| IMP461 | 31% |
| IMP467 | 87% |

Example 12

Factors Affecting Yield and Stability of IMP467 Labeling

Peptide Concentration

To examine the effect of varying peptide concentration on yield, the amount of binding of $Al^{18}F$ to peptide was determined in a constant volume (63 µL) with a constant amount of $Al^{3+}$ (6 nmol) and $^{18}F$, but varying the amount of peptide added. The yield of labeled peptide IMP467 decreased with a decreasing concentration of peptide as follows: 40 nmol peptide (82% yield); 30 nmol (79% yield); 20 nmol (75% yield); 10 nmol (49% yield). Thus, varying the amount of peptide between 20 and 40 nmol had little effect on yield with IMP467. However, a decreased yield was observed starting at 10 nmol of peptide in the labeling mix.

Aluminum Concentration

When IMP467 was labeled in the presence of increasing amounts of $Al^{3+}$ (0, 5, 10, 15, 20 µL of 2 mM Al in pH 4 acetate buffer and keeping the total volume constant), yields of 3.5%, 80%, 77%, 78% and 74%, respectively, were achieved. These results indicated that (a) non-specific binding of $^{18}F$ to this peptide in the absence of $Al^{3+}$ is minimal, (b) 10 nmol of $Al^{3+}$ was sufficient to allow for maximum $^{18}F$-binding, and (c) higher amounts of $Al^{3+}$ did not reduce binding substantially, indicating that there was sufficient chelation capacity at this peptide concentration.

Kinetics of $Al^{18}F$(IMP467) Radiolabeling

Kinetic studies showed that binding was complete within 5 min at 107° C. (5 min, 68%; 10 min, 61%; 15 min, 71%; and 30 min, 75%) with only moderate increases in isolated yield with reaction times as long as 30 min. A radiolabeling reaction of IMP467 performed at 50° C. showed that no binding was achieved at the lower temperature. Additional experiments, disclosed in the Examples below, show that under some conditions a limited amount of labeling can occur at reduced temperatures.

Effect of pH

The optimal pH for labeling was between 4.3 and 5.5. Yield ranged from 54% at pH 2.88; 70-77% at pH 3.99; 70% at pH 5; 41% at pH 6 to 3% at pH 7.3. The process could be expedited by eluting the $^{18}F$ from the anion exchange column with nitrate or chloride ion instead of carbonate ion, which eliminates the need for adjusting the eluent to pH 4 with glacial acetic acid before mixing with the $AlCl_3$.

High-Dose Radiolabeling of IMP467

Five microliters of 2 mM $Al^{3+}$ stock solution were mixed with 50 µL of $^{18}F$ 1.3 GBq (35 mCi) followed by the addition of 20 µL of 2 mM IMP467 in 0.1 mM, pH 4.1 acetate buffer. The reaction solution was heated to 104° C. for 15 min and then purified on an HLB column (~10 min) as described above, isolating 0.68 GBq (18.4 mCi) of the purified peptide in 69% radiochemical yield with a specific activity of 17 GBq/µmol (460 Ci/mmol). The reaction time was 15 min and the purification time was 12 min. The reaction was started 10 min after the 1.3 GBq (35 mCi) $^{18}F^-$ was purified, so the total time from the isolation of the $^{18}F^-$ to the purified final product was 37 min with a 52% yield without correcting for decay.

Human Serum Stability Test

An aliquot of the HLB purified peptide (~30 µL) was diluted with 200 µL human serum (previously frozen) and placed in the 37° C. HPLC sample chamber. Aliquots were removed at various time points and analyzed by HPLC. The HPLC analysis showed very high stability of the $^{18}F$-labeled peptides in serum at 37° C. for at least five hours (not shown). There was no detectable breakdown of the $^{18}F$-labeled peptide after a five hour incubation in serum (not shown).

The IMP461 and IMP462 ligands have two carboxyl groups available to bind the aluminum whereas the NOTA ligand in IMP467 had four carboxyl groups. The serum stability study showed that the complexes with IMP467 were stable in serum under conditions replicating in vivo use. In vivo biodistribution studies with labeled IMP467 show that the $Al^{18}F$-labeled peptide is stable under actual in vivo conditions (not shown).

Peptides can be labeled with $^{18}F$ rapidly (30 min) and in high yield by forming $Al^{18}F$ complexes that can be bound to a NOTA ligand on a peptide and at a specific activity of at least 17 GBq/µmol, without requiring HPLC purification. The $Al^{18}F$(NOTA)-peptides are stable in serum and in vivo. Modifications of the NOTA ligand can lead to improvements in yield and specific activity, while still maintaining the desired in vivo stability of the $Al^{18}F$(NOTA) complex, and being attached to a hydrophilic linker aids in the renal clearance of the peptide. Further, this method avoids the dry-down step commonly used to label peptides with $^{18}F$. As shown in the following Examples, this new $^{18}F$-labeling method is applicable to labeling of a broad spectrum of targeting peptides.

Optimized Labeling of $Al^{18}F$(IMP467)

Optimized conditions for $^{18}F$-labeling of IMP467 were identified. These consisted of eluting $^{18}F$ with commercial sterile saline (pH 5-7), mixing with 20 nmol of $AlCl_3$ and 40 nmol IMP467 in pH 4 acetate buffer in a total volume of 100 µL, heating to 102° C. for 15 min, and performing SPE separation. High-yield (85%) and high specific activity (115 GBq/µmol) were obtained with IMP467 in a single step, 30-min procedure after a simple solid-phase extraction (SPE) separation without the need for HPLC purification. $Al^{18}F$(IMP467) was stable in PBS or human serum, with 2% loss of $^{18}F$ after incubation in either medium for 6 h at 37° C.

Concentration and Purification of $^{18}F^-$

Radiochemical-grade $^{18}F^-$ needs to be purified and concentrated before use. We examined 4 different SPE purification procedures to process the $^{18}F^-$ prior to its use. Most of the radiolabeling procedures were performed using $^{18}F^-$ prepared by a conventional process. The $^{18}F^-$ in 2 mL of water was loaded onto a SEP-PAK® Light, Waters Accell™ QMA Plus Cartridge that was pre-washed with 10 mL of 0.4M $KHCO_3$, followed by 10 mL water. After loading the $^{18}F^-$ onto the cartridge, it was washed with 5 mL water to remove any dissolved metal and radiometal impurities. The isotope was then eluted with ~1 mL of 0.4M $KHCO_3$ in several fractions to isolate the fraction with the highest concentration of activity. The eluted fractions were neutralized with 5 µL of glacial acetic acid per 100 µL of solution to adjust the eluent to pH 4-5.

In the second process, the QMA cartridge was washed with 10 mL pH 8.4, 0.5 M NaOAc followed by 10 mL DI $H_2O$. $^{18}F^-$ was loaded onto the column as described above and eluted with 1 mL, pH 6, 0.05 M $KNO_3$ in 200-µL fractions with 60-70% of the activity in one of the fractions. No pH adjustment of this solution was needed.

In the third process, the QMA cartridge was washed with 10 mL pH 8.4, 0.5 M NaOAc followed by 10 mL DI H$_2$O. The $^{18}$F$^-$ was loaded onto the column as described above and eluted with 1 mL, pH 5-7, 0.154 M commercial normal saline in 200-4 fractions with 80% of the activity in one of the 5 fractions. No pH adjustment of this solution was needed.

Finally, we devised a method to prepare a more concentrated and high-activity $^{18}$F$^-$ solution, using tandem ion exchange. Briefly, Tygon tubing (1.27 cm long, 0.64 cm OD) was inserted into a TRICORN™ 5/20 column and filled with ~200 µL of AG 1-X8 resin, 100-200 mesh. The resin was washed with 6 mL 0.4 M K$_2$CO$_3$ followed by 6 mL H$_2$O. A SEP-PAK® light Waters ACCELL™ Plus CM cartridge was washed with DI H$_2$O. Using a syringe pump, the crude $^{18}$F$^-$ that was received in 5-mL syringe in 2 mL DI H$_2$O flowed slowly through the CM cartridge and the TRICORN™ column over ~5 min followed by a 6 mL wash with DI H$_2$O through both ion-binding columns. Finally, 0.4 M K$_2$CO$_3$ was pushed through only the TRICORN™ column in 50-µL fractions. Typically, 40 to 60% of the eluted activity was in one 50-µL fraction. The fractions were collected in 2.0 mL free-standing screw-cap microcentrifuge tubes containing 5 µL glacial acetic acid to neutralize the carbonate solution. The elution vial with the most activity was then used as the reaction vial.

Example 13

Labeling by Addition of $^{18}$F$^-$ to a Peptide Complexed with Aluminum

An HSG containing peptide (IMP 465, Al(NOTA)-D-Ala-D-Lys(HSG)-D-Tyr-D-Lys(HSG)-NH$_2$) (SEQ ID NO:48) linked to macrocyclic NOTA complexed with aluminum, was successfully labeled with F-18. $^{18}$F incorporation using 40 nmol of IMP 465 was 13.20%. An intermediate peptide, IMP 461, was made as described above. Then 25.7 mg of IMP461 was dissolved in 2 mL DI water to which was added 10.2 mg AlCl$_3$.3H$_2$O and the resultant solution heated to 100° C. for 1 h. The crude reaction mixture was purified by RP-HPLC to yield 19.6 mg of IMP465.

For $^{18}$F-labeling, 50 µL $^{18}$F solution [0.702 mCi of $^{18}$F$^-$] and 20 µL (40 nmol) 2 mM IMP465 solution (0.1 M NaOAc, pH 4.18) was heated to 101° C. for 17 minutes. Reverse Phase HPLC analysis showed 15.38% (RT about 8.60 min) of the activity was attached to the peptide and 84.62% of the activity eluted at the void volume of the column (2.60 min).

In a separate experiment, the percent yield of $^{18}$F-labeled peptide could be improved by varying the amount of peptide added. The percent yield observed for IMP465 was 0.27% at 10 nmol peptide, 1.8% at 20 nmol of peptide and 49% at 40 nmol of peptide.

IMP467 showed higher yield than IMP461 when peptide was pre-incubated with aluminum before exposure to $^{18}$F. IMP467 was incubated with aluminum at room temperature and then frozen and lyophilized. The amount of aluminum added for the pre-incubation was varied.

TABLE 8

Labeling of IMP467 Pre-Incubated with Aluminum Before $^{18}$F$^-$ is Added

| IMP467 + Al Premixed, Frozen and Lyophilized | Isolated Labeling Yield |
|---|---|
| 40 nmol IMP467 + 10 nmol Al Premix | 82% |
| 40 nmol IMP467 + 20 nmol Al Premix | 64% |
| 40 nmol IMP467 + 30 nmol Al Premix | 74% |
| 40 nmol IMP467 + 6 nmol Al Normal Labeling (Mix Al + $^{18}$F first) | 77% |

The yields were comparable to those obtained when IMP467 is labeled by addition of an Al$^{18}$F complex. Thus, $^{18}$F labeling by addition of $^{18}$F to a peptide with aluminum already bound to the chelating moiety is a feasible alternative approach to pre-incubating the metal with $^{18}$F$^-$ prior to addition to the chelating moiety.

Example 14

Synthesis and Labeling of IMP468 Bombesin Peptide

The $^{18}$F labeled targeting moieties are not limited to antibodies or antibody fragments, but rather can include any molecule that binds specifically or selectively to a cellular target that is associated with or diagnostic of a disease state or other condition that may be imaged by $^{18}$F PET. Bombesin is a 14 amino acid peptide that is homologous to neuromedin B and gastrin releasing peptide, as well as a tumor marker for cancers such as lung and gastric cancer and neuroblastoma. IMP468 (NOTA-NH—(CH$_2$)$_7$CO-Gln-Trp-Val-Trp-Ala-Val-Gly-His-Leu-Met-NH$_2$; SEQ ID NO:49) was synthesized as a bombesin analogue and labeled with $^{18}$F to target the gastrin-releasing peptide receptor.

The peptide was synthesized by Fmoc based solid phase peptide synthesis on Sieber amide resin, using a variation of a synthetic scheme reported in the literature (Prasanphanich et al., 2007, PNAS USA 104:12463-467). The synthesis was different in that a bis-t-butyl NOTA ligand was add to the peptide during peptide synthesis on the resin.

IMP468 (0.0139 g, 1.02×10$^{-5}$ mol) was dissolved in 203 µL of 0.5 M pH 4.13 NaOAc buffer. The peptide dissolved but formed a gel on standing so the peptide gel was diluted with 609 µL of 0.5 M pH 4.13 NaOAc buffer and 406 µL of ethanol to produce an 8.35×10$^{-3}$ M solution of the peptide. The $^{18}$F was purified on a QMA cartridge and eluted with 0.4 M KHCO$_3$ in 200 µL fractions, neutralized with 10 µL of glacial acetic acid. The purified $^{18}$F, 40 µL, 1.13 mCi was mixed with 3 µL of 2 mM AlCl$_3$ in pH 4, 0.1 M NaOAc buffer. IMP468 (59.2 µL, 4.94×10$^{-7}$ mol) was added to the Al$^{18}$F solution and placed in a 108° C. heating block for 15 min. The crude product was purified on an HLB column, eluted with 2×200 µL of 1:1 EtOH/H$_2$O to obtain the purified $^{18}$F-labeled peptide in 34% yield.

Example 15

Imaging of Tumors Using $^{18}$F Labeled Bombesin

A NOTA-conjugated bombesin derivative (IMP468) was prepared as described above. We began testing its ability to block radiolabeled bombesin from binding to PC-3 cells as was done by Prasanphanich et al. (PNAS 104:12462-12467, 2007). Our initial experiment was to determine if IMP468 could specifically block bombesin from binding to PC-3 cells. We used IMP333 as a non-specific control. In this experiment, 3×10⁶ PC-3 cells were exposed to a constant amount (~50,000 cpms) of $^{125}$I-Bombesin (Perkin-Elmer) to which increasing amounts of either IMP468 or IMP333 was added. A range of 56 to 0.44 nM was used as our inhibitory concentrations.

The results showed that we could block the binding of $^{125}$I-BBN with IMP468 but not with the control peptide (IMP333) (not shown), thus demonstrating the specificity of IMP468. Prasanphanich indicated an IC$_{50}$ for their peptide at 3.2 nM, which is approximately 7-fold lower than what we found with IMP468 (21.5 nM).

This experiment was repeated using a commercially available BBN peptide. We increased the amount of inhibitory peptide from 250 to 2 nM to block the $^{125}$I-BBN from binding to PC-3 cells. We observed very similar IC$_{50}$-values for IMP468 and the BBN positive control with an IC$_{50}$-value higher (35.9 nM) than what was reported previously (3.2 nM) but close to what the BBN control achieved (24.4 nM).

To examine in vivo targeting, the distribution of Al$^{18}$F (IMP468) was examined in scPC3 prostate cancer xenograft bearing nude male mice; alone vs. blocked with bombesin. For radiolabeling, aluminum chloride (10 μL, 2 mM), 51.9 mCi of $^{18}$F (from QMA cartridge), acetic acid, and 60 μL of IIMP468 (8.45 mM in ethanol/NaOAc) were heated at 100° C. for 15 min. The reaction mixture was purified on reverse phase HPLC. Fractions 40 and 41 (3.56, 1.91 mCi) were pooled and applied to HLB column for solvent exchange. The product was eluted in 800 μL (3.98 mCi) and 910 μCi remained on the column. iTLC developed in saturated NaCl showed 0.1% unbound activity.

Figure 3:
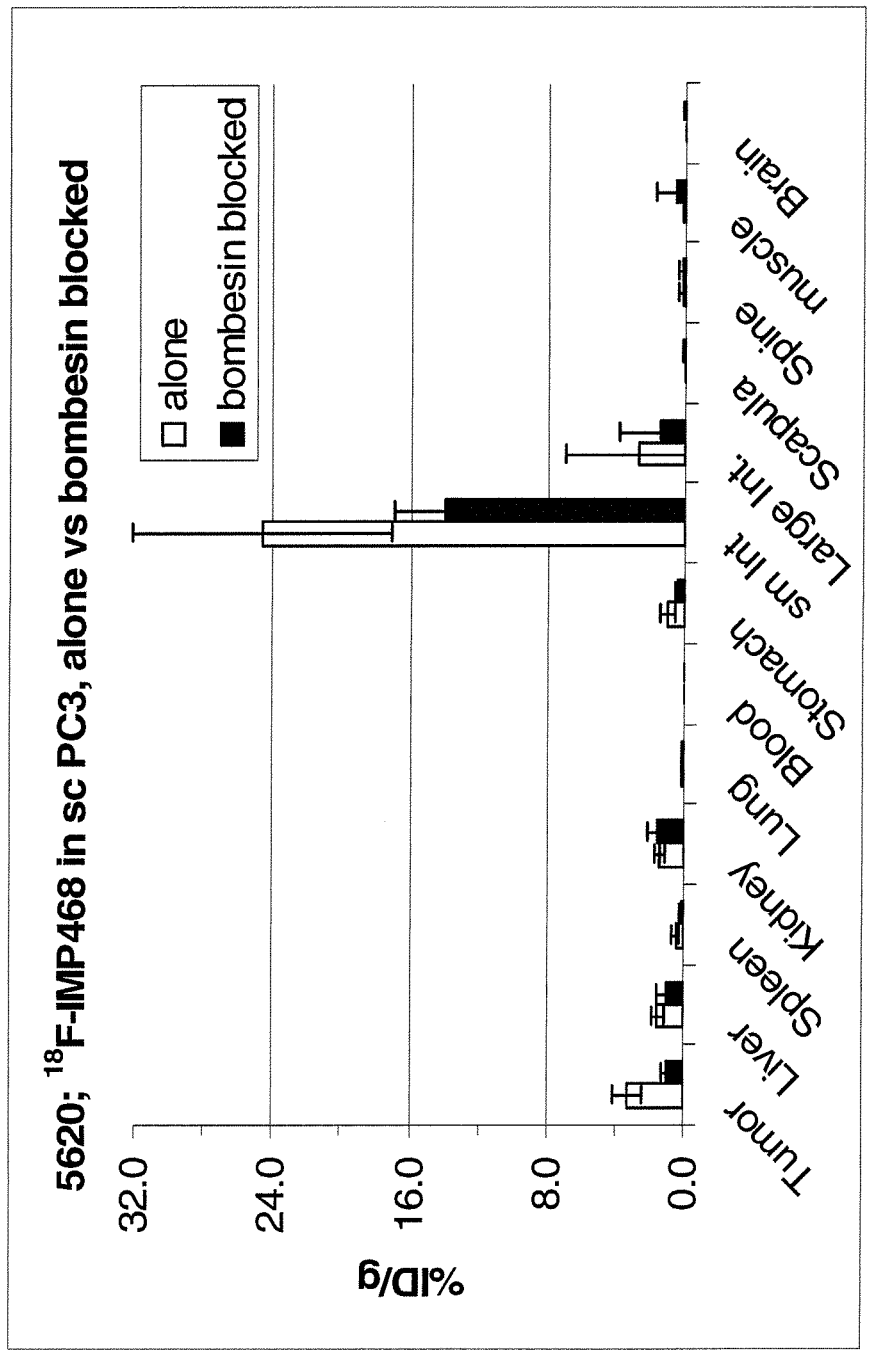
FIG. 3. In vivo tissue distribution with Al$^{18}$F(IMP466) bombesin analogue.

A group of six tumor-bearing mice were injected with Al$^{18}$F(IMP468) (167 μCi, ~9×10$^{-10}$ mol) and necropsied 1.5 h later. Another group of six mice were injected iv with 100 μg (6.2×10$^{-8}$ mol) of bombesin 18 min before administering Al$^{18}$F(IMP468). The second group was also necropsied 1.5 h post injection. The data shows specific targeting of the tumor with [Al$^{18}$F] IMP 468 (FIG. 3). Tumor uptake of the peptide is reduced when bombesin was given 18 min before the Al$^{18}$F (IMP468) (FIG. 3). Biodistribution data indicates in vivo stability of Al$^{18}$F(IMP468) for at least 1.5 h (not shown).

Larger tumors showed higher uptake of Al$^{18}$F(IMP468), possibly due to higher receptor expression in larger tumors (not shown). The biodistribution data showed Al$^{18}$F(IMP468) tumor targeting that was in the same range as reported for the same peptide labeled with $^{68}$Ga by Prasanphanich et al. (not shown). The results demonstrate that the $^{18}$F peptide labeling method can be used in vivo to target receptors that are upregulated in tumors, using targeting molecules besides antibodies. In this case, the IMP468 targeting took advantage of a naturally occurring ligand-receptor interaction. The tumor targeting was significant with a P value of P=0.0013. Many such ligand-receptor pairs are known and any such targeting interaction may form the basis for $^{18}$F imaging, using the methods described herein Example 16

Synthesis and Labeling of Somatostatin Analog IMP466

Somatostatin is another non-antibody targeting peptide that is of use for imaging the distribution of somatostatin receptor protein. $^{123}$I-labeled octreotide, a somatostatin analog, has been used for imaging of somatostatin receptor expressing tumors (e.g., Kvols et al., 1993, Radiology 187: 129-33; Leitha et al., 1993, J Nucl Med 34:1397-1402). However, $^{123}$I has not been of extensive use for imaging because of its expense, short physical half-life and the difficulty of preparing the radiolabeled compounds. The $^{18}$F-labeling methods described herein are preferred for imaging of somatostatin receptor expressing tumors.

IMP466
(SEQ ID NO: 50)
NOTA-D-Phe-Cys-Phe-D-Trp-Lys-Thr-Cys-Throl

A NOTA-conjugated derivative of the somatostatin analog octreotide (IMP466) was made by standard Fmoc based solid phase peptide synthesis to produce a linear peptide. The C-terminal Throl residue is threoninol. The peptide was cyclized by treatment with DMSO overnight. The peptide, 0.0073 g, 5.59×10$^{-6}$ mol was dissolved in 111.9 μL of 0.5 M pH 4 NaOAc buffer to make a 0.05 M solution of IMP466. The solution formed a gel over time so it was diluted to 0.0125 M by the addition of more 0.5 M NaOAc buffer.

$^{18}$F was purified and concentrated with a QMA cartridge to provide 200 μL of $^{18}$F in 0.4 M KHCO$_3$. The bicarbonate solution was neutralized with 10 μL of glacial acetic acid. A 40 μL aliquot of the neutralized $^{18}$F eluent was mixed with 3 μL of 2 mM AlCl$_3$, followed by the addition of 40 μL of 0.0125 M IMP466 solution. The mixture was heated at 105° C. for 17 min. The reaction was then purified on a Waters 1 cc (30 mg) HLB column by loading the reaction solution onto the column and washing the unbound $^{18}$F away with water (3 mL) and then eluting the radiolabeled peptide with 2×200 μL 1:1 EtOH water. The yield of the radiolabeled peptide after HLB purification was 34.6%.

Effect of Ionic Strength

To lower the ionic strength of the reaction mixture escalating amounts of acetonitrile were added to the labeling mixture (final concentration: 0-80%). The yield of radiolabeled IMP466 increased with increasing concentration of acetonitrile in the medium. The optimal radiolabeling yield (98%) was obtained in a final concentration of 80% acetonitrile, despite the increased volume (500 μL in 80% vs. 200 μL in 0% acetonitrile). In 0% acetonitrile the radiolabeling yield ranged from 36% to 55% in three experiments.

Example 17

Imaging of Neuroendocrine Tumors with an $^{18}$F- and $^{68}$Ga-Labeled IMP466

Studies were performed to compare the PET images obtained using an $^{18}$F versus $^{68}$Ga-labeled somatostatin analogue peptide and direct targeting to somatostatin receptor expressing tumors.

Methods $^{18}$F labeling—IMP466 was synthesized and $^{18}$F-labeled by a variation of the method described in the Example above. A QMA SEPPAK® light cartridge (Waters, Milford, Mass.) with 2-6 GBq $^{18}$F$^-$ (BV Cyclotron VU, Amsterdam, The Netherlands) was washed with 3 mL metal-free water. $^{18}$F$^-$ was eluted from the cartridge with 0.4 M KHCO$_3$ and fractions of 200 μL were collected. The pH of the fractions was adjusted to pH 4, with 10 μL metal-free glacial acid. Three μL of 2 mM AlCl$_3$ in 0.1 M sodium acetate buffer, pH 4 were added. Then, 10-50 μL IMP 466 (10 mg/mL) were added in 0.5 M sodium acetate, pH 4.1. The reaction mixture was incubated at 100° C. for 15 min unless stated otherwise. The radiolabeled peptide was purified on RP-HPLC. The Al$^{18}$F (IMP466) containing fractions were collected and diluted two-fold with H$_2$O and purified on a 1-cc Oasis HLB cartridge (Waters, Milford, Mass.) to remove acetonitrile and TFA. In brief, the fraction was applied on the cartridge and the cartridge was washed with 3 mL $H_2O$. The radiolabeled peptide was then eluted with 2×200 μL 50% ethanol. For injection in mice, the peptide was diluted with 0.9% NaCl. A maximum specific activity of 45,000 GBq/mmol was obtained.

$^{68}$Ga labeling—IMP466 was labeled with $^{68}$GaCl$_3$ eluted from a TiO$_2$-based 1,110 MBq $^{68}$Ge/$^{68}$Ga generator (Cyclotron Co. Ltd., Obninsk, Russia) using 0.1 M ultrapure HCl (J. T. Baker, Deventer, The Netherlands). IMP466 was dissolved in 1.0 M HEPES buffer, pH 7.0. Four volumes of $^{68}$Ga eluate (120-240 MBq) were added and the mixture was heated at 95° C. for 20 min. Then 50 mM EDTA was added to a final concentration of 5 mM to complex the non-incorporated $^{68}$Ga$^{3+}$. The $^{68}$Ga-labeled IMP466 was purified on an Oasis HLB cartridge and eluted with 50% ethanol.

Octanol-water partition coefficient (log $P_{oct/water}$)—To determine the lipophilicity of the radiolabeled peptides, approximately 50,000 dpm of the radiolabeled peptide was diluted in 0.5 mL phosphate-buffered saline (PBS). An equal volume of octanol was added to obtain a binary phase system. After vortexing the system for 2 min, the two layers were separated by centrifugation (100×g, 5 min). Three 100 μL samples were taken from each layer and radioactivity was measured in a well-type gamma counter (Wallac Wizard 3", Perkin-Elmer, Waltham, Mass.).

Stability—Ten μL of the $^{18}$F-labeled IMP466 was incubated in 500 μL of freshly collected human serum and incubated for 4 h at 37° C. Acetonitrile was added and the mixture was vortexed followed by centrifugation at 1000×g for 5 min to precipitate serum proteins. The supernatant was analyzed on RP-HPLC as described above.

Cell culture—The AR42J rat pancreatic tumor cell line was cultured in Dulbecco's Modified Eagle's Medium (DMEM) medium (Gibco Life Technologies, Gaithersburg, Md., USA) supplemented with 4500 mg/L D-glucose, 10% (v/v) fetal calf serum, 2 mmol/L glutamine, 100 U/mL penicillin and 100 μg/mL streptomycin. Cells were cultured at 37° C. in a humidified atmosphere with 5% $CO_2$.

$IC_{50}$ determination—The apparent 50% inhibitory concentration ($IC_{50}$) for binding the somatostatin receptors on AR42J cells was determined in a competitive binding assay using Al$^{19}$F(IMP466), $^{69}$Ga(IMP466) or $^{115}$In(DTPA-octreotide) to compete for the binding of $^{111}$In(DTPA-octreotide).

Al$^{19}$F(IMP466) was formed by mixing an aluminium fluoride (Al$^{19}$F) solution (0.02 M AlCl$_3$ in 0.5 M NaAc, pH 4, with 0.1 M NaF in 0.5 M NaAc, pH 4) with IMP466 and heating at 100° C. for 15 min. The reaction mixture was purified by RP-HPLC on a C-18 column as described above.

$^{69}$Ga(IMP466) was prepared by dissolving gallium nitrate (2.3×10$^{-8}$ mol) in 30 μL mixed with 20 μL IMP466 (1 mg/mL) in 10 mM NaAc, pH 5.5, and heated at 90° C. for 15 min. Samples of the mixture were used without further purification.

$^{115}$In(DTPA-octreotide) was made by mixing indium chloride (1×10$^{-5}$ mol) with 10 μL DTPA-octreotide (1 mg/mL) in 50 mM NaAc, pH 5.5, and incubated at room temperature (RT) for 15 min. This sample was used without further purification. $^{111}$In(DTPA-octreotide) (OCTREOSCAN®) was radiolabeled according to the manufacturer's protocol.

AR42J cells were grown to confluency in 12-well plates and washed twice with binding buffer (DMEM with 0.5% bovine serum albumin). After 10 min incubation at RT in binding buffer, Al$^{19}$F(IMP466), $^{69}$Ga(IMP466) or $^{115}$In (DTPA-octreotide) was added at a final concentration ranging from 0.1-1000 nM, together with a trace amount (10,000 cpm) of $^{111}$In(DTPA-octreotide) (radiochemical purity >95%). After incubation at RT for 3 h, the cells were washed twice with ice-cold PBS. Cells were scraped and cell-associated radioactivity was determined. Under these conditions, a limited extent of internalization may occur. We therefore describe the results of this competitive binding assay as "apparent $IC_{50}$" values rather than $IC_{50}$. The apparent $IC_{50}$ was defined as the peptide concentration at which 50% of binding without competitor was reached.

Biodistribution studies—Male nude BALB/c mice (6-8 weeks) were injected subcutaneously in the right flank with 0.2 mL AR42J cell suspension of 10$^7$ cells/mL. Approximately two weeks after tumor cell inoculation when tumors were 5-8 mm in diameter, 370 kBq $^{18}$F or $^{68}$Ga-labeled IMP466 was administered intravenously (n=5). Separate groups (n=5) were injected with a 1,000-fold molar excess of unlabeled IMP466. One group of three mice was injected with unchelated [Al$^{18}$F]. All mice were killed by $CO_2/O_2$ asphyxiation 2 h post-injection (p.i.). Organs of interest were collected, weighed and counted in a gamma counter. The percentage of the injected dose per gram tissue (% ID/g) was calculated for each tissue. The animal experiments were approved by the local animal welfare committee and performed according to national regulations.

PET/CT imaging—Mice with s.c. AR42J tumors were injected intravenously with 10 MBq Al$^{18}$F(IMP466) or $^{68}$Ga (IMP466). One and two hours after the injection of peptide, mice were scanned on an Inveon animal PET/CT scanner (Siemens Preclinical Solutions, Knoxville, Tenn.) with an intrinsic spatial resolution of 1.5 mm (Visser et al, JNM, 2009). The animals were placed in a supine position in the scanner. PET emission scans were acquired over 15 minutes, followed by a CT scan for anatomical reference (spatial resolution 113 μm, 80 kV, 500 μA). Scans were reconstructed using Inveon Acquisition Workplace software version 1.2 (Siemens Preclinical Solutions, Knoxville, Tenn.) using an ordered set expectation maximization-3D/maximum a posteriori (OSEM3D/MAP) algorithm with the following parameters: matrix 256×256×159, pixel size 0.43×0.43×0.8 mm$^3$ and MAP prior of 0.5 mm.

Results

Effect of buffer—The effect of the buffer on the labeling efficiency of IMP466 was investigated. IMP466 was dissolved in sodium citrate buffer, sodium acetate buffer, 2-(N-morpholino)ethanesulfonic acid (MES) or 4-(2-hydroxyethyl)-1-piperazineethanesulfonic acid (HEPES) buffer at 10 mg/mL (7.7 mM). The molarity of all buffers was 1 M and the pH was 4.1. To 200 μg (153 nmol) of IMP466 was added 100 μL [Al$^{18}$F] (pH 4) and incubated at 100° C. for 15 min. Radiolabeling yield and specific activity was determined with RP-HPLC. When using sodium acetate, MES or HEPES, radiolabeling yield was 49%, 44% and 46%, respectively. In the presence of sodium citrate, no labeling was observed (<1%). When the labeling reaction was carried out in sodium acetate buffer, the specific activity of the preparations was 10,000 GBq/mmol, whereas in MES and HEPES buffer a specific activity of 20,500 and 16,500 GBq/mmol was obtained, respectively.

Effect of AlCl$_3$ concentration—Three stock solutions of AlCl$_3$ in sodium acetate, pH 4.1 were prepared: 0.2, 2.0 and 20 mM. From these solutions, 3 μL was added to 200 μL of $^{18}$F$^-$ to form [Al$^{18}$F]. To these samples, 153 nmol of peptide was added and incubated for 15 min at 100° C. Radiolabeling yield was 49% after incubation at a final concentration of 6 nmol AlCl$_3$. Incubation with 0.6 nmol AlCl$_3$ and 60 nmol AlCl$_3$ resulted in a strong reduction of the radiolabeling yield: 10% and 6%, respectively.

Effect of amount of peptide—The effect of the amount of peptide on the labeling efficiency was investigated. IMP466 was dissolved in sodium acetate buffer, pH 4.1 at a concentration of 7.7 mM (10 mg/mL) and 38, 153 or 363 nmol of IMP466 was added to 200 μL [Al$^{18}$F] (581-603 MBq). The radiolabeling yield increased with increasing amounts of peptide. At 38 nmol, radiolabeling yield ranged from 4-8%, at 153 nmol, the yield had increased to 42-49% and at the highest concentration the radiolabeling yield was 48-52%.

Octanol-water partition coefficient—To determine the lipophilicity of the $^{18}$F and $^{68}$Ga-labeled IMP466, the octanol-water partition coefficients were determined. The log P$_{octanol/water}$ value for the Al$^{18}$F(IMP466) was −2.44±0.12 and that of $^{68}$Ga(IMP466) was −3.79±0.07, indicating that the $^{18}$F-labeled IMP 466 was slightly less hydrophilic.

Stability—The $^{18}$F-labeled IMP466 did not show release of $^{18}$F after incubation in human serum at 37° C. for 4 h, indicating excellent stability of the Al[$^{18}$F]NOTA complex.

IC$_{50}$ determination—The apparent IC$_{50}$ of Al$^{19}$F(IMP466) was 3.6±0.6 nM, whereas that for $^{69}$Ga(IMP466) was 13±3 nM. The apparent IC$_{50}$ of the reference peptide, $^{115}$In(DTPA-octeotride) (OCTREOSCAN®), was 6.3±0.9 nM.

Figure 4:
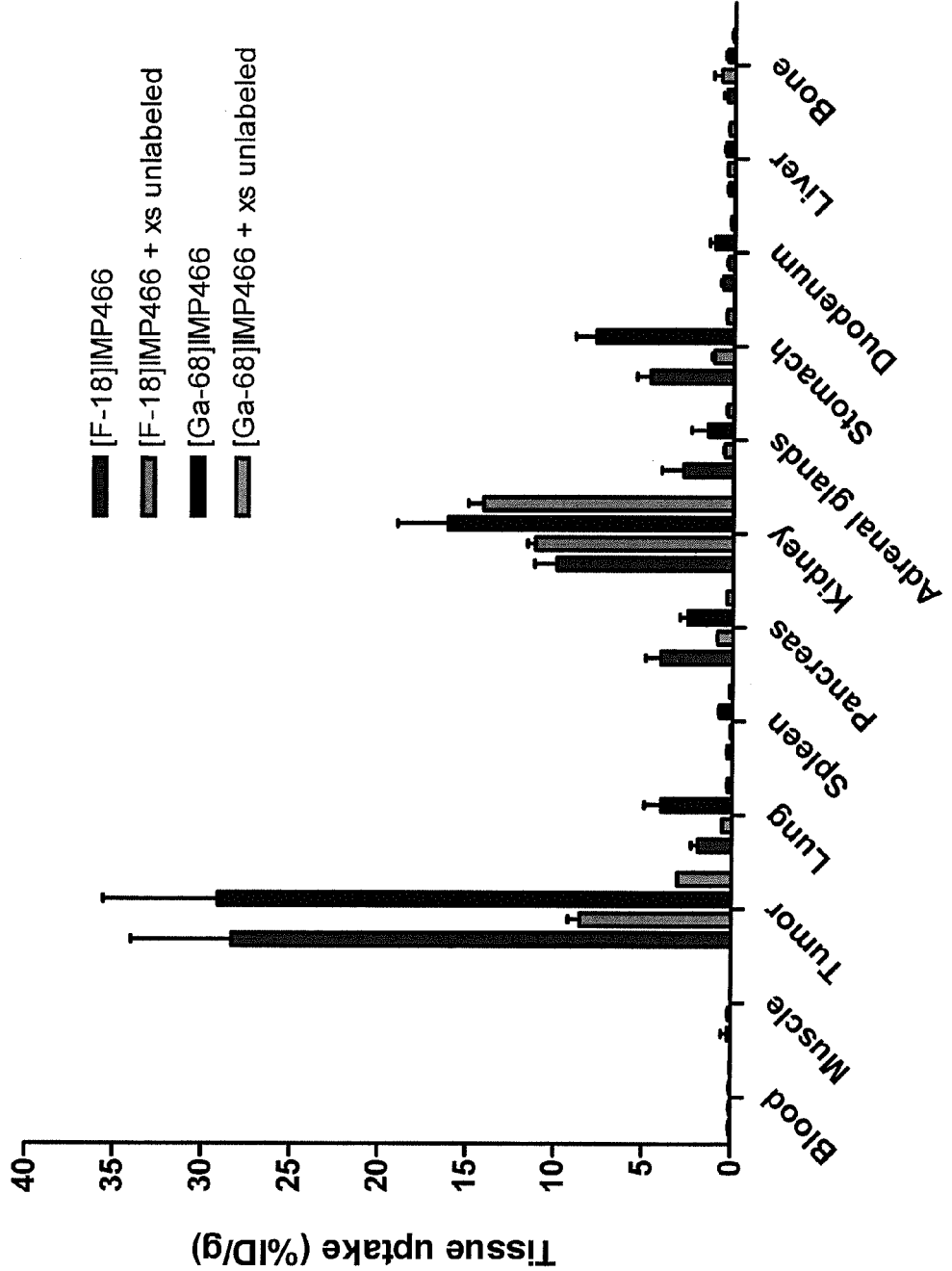
FIG. 4. Comparison of biodistribution of Al$^{18}$F(IMP466) and $^{68}$Ga(IMP466) at 2 hours post-injection in AR42J tumor-bearing mice (n=5). As a control, mice in separate groups (n=5) received an excess of unlabeled octreotide to demonstrate receptor specificity.

Biodistribution studies—The biodistribution of both Al$^{18}$F (IMP466) and $^{68}$Ga(IMP466) was studied in nude BALB/c mice with s.c. AR42J tumors at 2 h p.i. (FIG. 4). Al$^{18}$F was included as a control. Tumor targeting of the Al$^{18}$F(IMP466) was high with 28.3±5.7% ID/g accumulated at 2 h p.i. Uptake in the presence of an excess of unlabeled IMP466 was 8.6±0.7% ID/g, indicating that tumor uptake was receptor-mediated. Blood levels were very low (0.10±0.07% ID/g, 2 h pi), resulting in a tumor-to-blood ratio of 299±88. Uptake in the organs was low, with specific uptake in receptor expressing organs such as adrenal glands, pancreas and stomach. Bone uptake of Al$^{18}$F(IMP466) was negligible as compared to uptake of non-chelated Al$^{18}$F (0.33±0.07 vs. 36.9±5.0% ID/g at 2 h p.i., respectively), indicating good in vivo stability of the $^{18}$F-labeled NOTA-peptide.

The biodistribution of Al$^{18}$F(IMP466) was compared to that of $^{68}$Ga(IMP466) (FIG. 4). Tumor uptake of $^{68}$Ga (IMP466) (29.2±0.5% ID/g, 2 h pi) was similar to that of Al$^{18}$F-IMP 466 (p<0.001). Lung uptake of $^{68}$Ga(IMP466) was two-fold higher than that of Al$^{18}$F(IMP466) (4.0±0.9% ID/g vs. 1.9±0.4% ID/g, respectively). In addition, kidney retention of $^{68}$Ga(IMP466) was slightly higher than that of Al$^{18}$F(IMP466) (16.2±2.86% ID/g vs. 9.96±1.27% ID/g, respectively).

Figure 5:
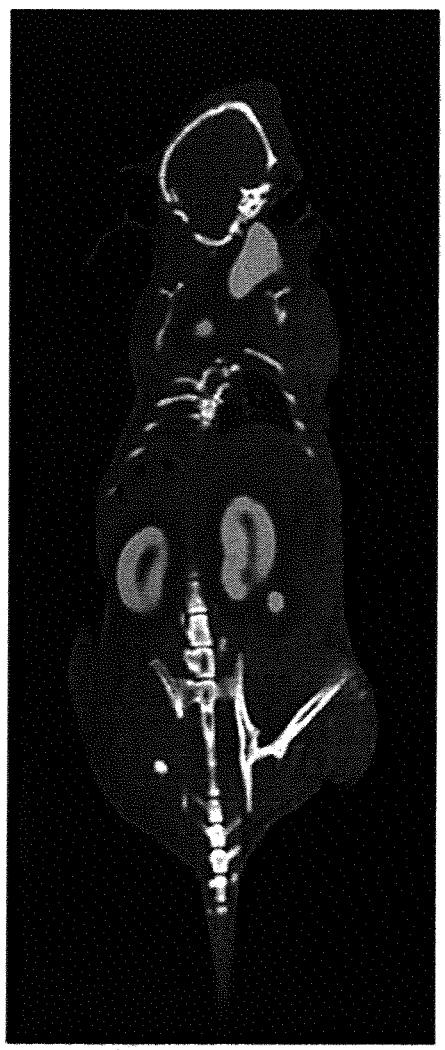
FIG. 5. Coronal slices of PET/CT scan of Al$^{18}$F(IMP466) and $^{68}$Ga(IMP466) at 2 hours post-injection in mice with an s.c. AR42J tumor in the neck. Accumulation in tumor and kidneys is clearly visualized.
Figure 5:
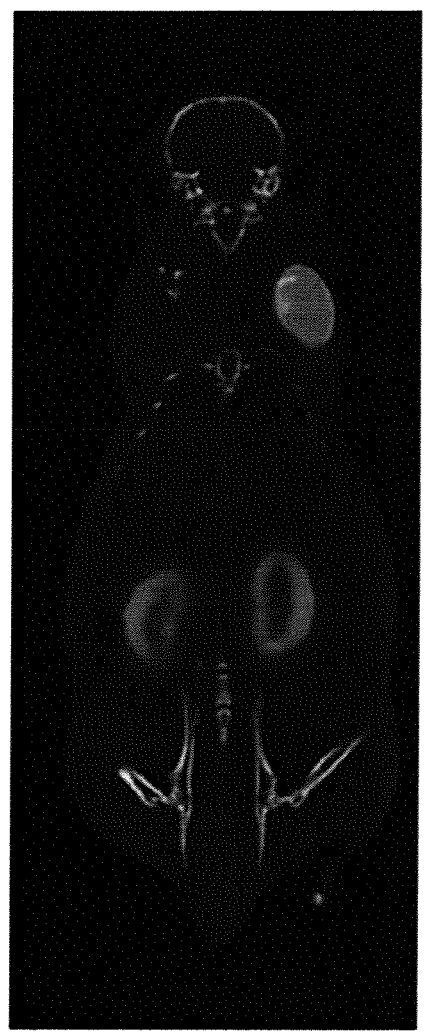

Fused PET and CT scans are shown in FIG. 5. PET scans corroborated the biodistribution data. Both Al$^{18}$F(IMP466) and $^{68}$Ga(IMP466) showed high uptake in the tumor and retention in the kidneys. The activity in the kidneys was mainly localized in the renal cortex. Again, the [Al$^{18}$F] proved to be stably chelated by the NOTA chelator, since no bone uptake was observed.

FIG. 5 clearly shows that the distribution of an $^{18}$F-labeled analog of somatostatin (octreotide) mimics that of a $^{68}$Ga-labeled somatostatin analog. These results are significant, since $^{68}$Ga-labeled octreotide PET imaging in human subjects with neuroendocrine tumors has been shown to have a significantly higher detection rate compared with conventional somatostatin receptor scintigraphy and diagnostic CT, with a sensitivity of 97%, a specificity of 92% and an accuracy of 96% (e.g., Gabriel et al., 2007, J Nucl Med 48:508-18). PET imaging with $^{68}$Ga-labeled octreotide is reported to be superior to SPECT analysis with $^{111}$In-labeled octreotide and to be highly sensitive for detection of even small meningiomas (Henze et al., 2001, J Nucl Med 42:1053-56). Because of the higher energy of $^{68}$Ga compared with $^{18}$F, it is expected that $^{18}$F based PET imaging would show even better spatial resolution than $^{68}$Ga based PET imaging. This is illustrated in FIG. 5 by comparing the kidney images obtained with $^{18}$F-labeled IMP466 (FIG. 5, left) vs. $^{68}$Ga-labeled IMP466 (FIG. 5, right). The PET images obtained with $^{68}$Ga show more diffuse margins and lower resolution than the images obtained with $^{18}$F. These results demonstrate the superior images obtained with $^{18}$F-labeled targeting moieties prepared using the methods and compositions described herein and confirm the utility of the described $^{18}$F-labeling techniques for non-antibody targeting peptides.

Example 18

Comparison of $^{68}$Ga and $^{18}$F PET Imaging Using Pretargeting

We compared PET images obtained using $^{68}$Ga- or $^{18}$F-labeled peptides that were pretargeted with the bispecific TF2 antibody, prepared as described above. The half-lives of $^{68}$Ga (t$_{1/2}$=68 minutes) and $^{18}$F (t$_{1/2}$=110 minutes) match with the pharmacokinetics of the radiolabeled peptide, since its maximum accretion in the tumor is reached within hours. Moreover, $^{68}$Ga is readily available from $^{68}$Ge/$^{68}$Ga generators, whereas $^{18}$F is the most commonly used and widely available radionuclide in PET.

Methods

Mice with s.c. CEA-expressing LS174T tumors received TF2 (6.0 nmol; 0.94 mg) and 5 MBq $^{68}$Ga(IMP288) (0.25 nmol) or Al$^{18}$F(IMP449) (0.25 nmol) intravenously, with an interval of 16 hours between the injection of the bispecific antibody and the radiolabeled peptide. One or two hours after the injection of the radiolabeled peptide, PET/CT images were acquired and the biodistribution of the radiolabeled peptide was determined. Uptake in the LS174T tumor was compared with that in an s.c. CEA-negative SK-RC 52 tumor. Pretargeted immunoPET imaging was compared with $^{18}$F-FDG PET imaging in mice with an s.c. LS174T tumor and contralaterally an inflamed thigh muscle.

```
IMP288
                                            (SEQ ID NO: 51)
DOTA-D-Tyr-D-Lys(HSG)-D-Glu-D-Lys(HSG)-NH2
```

Pretargeting—The bispecific TF2 antibody was made by the DNL method, as described above. TF2 is a trivalent bispecific antibody comprising an HSG-binding Fab fragment from the h679 antibody and two CEA-binding Fab fragments from the hMN-14 antibody. The DOTA-conjugated, HSG-containing peptide IMP288 was synthesized by peptide synthesis as described above. The IMP449 peptide, synthesized as described above, contains a 1,4,7-triazacyclononane-1,4,7-triacetic acid (NOTA) chelating moiety to facilitate labeling with $^{18}$F. As a tracer for the antibody component, TF2 was labeled with $^{125}$I (Perkin Elmer, Waltham, Mass.) by the iodogen method (Fraker and Speck, 1978, Biochem Biophys Res Comm 80:849-57), to a specific activity of 58 MBq/nmol.

Labeling of IMP288—IMP288 was labeled with $^{111}$In (Covidien, Petten, The Netherlands) for biodistribution studies at a specific activity of 32 MBq/nmol under strict metal-free conditions. IMP288 was labeled with $^{68}$Ga eluted from a TiO-based 1,110 MBq $^{68}$Ge/$^{68}$Ga generator (Cyclotron Co. Ltd., Obninsk Russia) using 0.1 M ultrapure HCl. Five 1 ml fractions were collected and the second fraction was used for labeling the peptide. One volume of 1.0 M HEPES buffer, pH 7.0 was added to 3.4 nmol IMP 288. Four volumes of $^{68}$Ga eluate (380 MBq) were added and the mixture was heated to 95° C. for 20 min. Then 50 mM EDTA was added to a final concentration of 5 mM to complex the non-chelated $^{68}Ga^{3+}$. The $^{68}Ga$(IMP288) peptide was purified on a 1-mL Oasis HLB-cartridge (Waters, Milford, Mass.). After washing the cartridge with water, the peptide was eluted with 25% ethanol. The procedure to label IMP288 with $^{68}Ga$ was performed within 45 minutes, with the preparations being ready for in vivo use.

Labeling of IMP449—IMP449 was labeled with $^{18}F$ as described above. 555-740 MBq $^{18}F$ (B.V. Cyclotron VU, Amsterdam, The Netherlands) was eluted from a QMA cartridge with 0.4 M $KHCO_3$. The $Al^{18}F$ activity was added to a vial containing the peptide (230 μg) and ascorbic acid (10 mg). The mixture was incubated at 100° C. for 15 min. The reaction mixture was purified by RP-HPLC. After adding one volume of water, the peptide was purified on a 1-mL Oasis HLB cartridge. After washing with water, the radiolabeled peptide was eluted with 50% ethanol. $Al^{18}F$(IMP449) was prepared within 60 minutes, with the preparations being ready for in vivo use.

Radiochemical purity of $^{125}I$-TF2, $^{111}In$(IMP288) and $^{68}Ga$(IMP288) and $Al^{18}F$(IMP449) preparations used in the studies always exceeded 95%.

Animal experiments—Experiments were performed in male nude BALB/c mice (6-8 weeks old), weighing 20-25 grams. Mice received a subcutaneous injection with 0.2 mL of a suspension of 1×10⁶ LS174T-cells, a CEA-expressing human colon carcinoma cell line (American Type Culture Collection, Rockville, Md., USA). Studies were initiated when the tumors reached a size of about 0.1-0.3 g (10-14 days after tumor inoculation).

The interval between TF2 and IMP288 injection was 16 hours, as this period was sufficient to clear unbound TF2 from the circulation. In some studies $^{125}I$-TF2, (0.4 MBq) was co-injected with unlabeled TF2. IMP288 was labeled with either $^{111}In$ or $^{68}Ga$. IMP449 was labeled with $^{18}F$. Mice received TF2 and IMP288 intravenously (0.2 mL). One hour after the injection of $^{68}Ga$-labeled peptide, and two hours after injection of $Al^{18}F$(IMP449), mice were euthanized by $CO_2/O_2$, and blood was obtained by cardiac puncture and tissues were dissected.

PET images were acquired with an Inveon animal PET/CT scanner (Siemens Preclinical Solutions, Knoxville, Tenn.). PET emission scans were acquired for 15 minutes, preceded by CT scans for anatomical reference (spatial resolution 113 μm, 80 kV, 500 μA, exposure time 300 msec).

After imaging, tumor and organs of interest were dissected, weighed and counted in a gamma counter with appropriate energy windows for $^{125}I$, $^{111}In$, $^{68}Ga$ or $^{18}F$. The percentage-injected dose per gram tissue (% ID/g) was calculated.

Results

Within 1 hour, pretargeted immunoPET resulted in high and specific targeting of $^{68}Ga$-IMP288 in the tumor (10.7±3.6% ID/g), with very low uptake in the normal tissues (e.g., tumor/blood 69.9±32.3), in a CEA-negative tumor (0.35±0.35% ID/g), and inflamed muscle (0.72±0.20% ID/g). Tumors that were not pretargeted with TF2 also had low $^{68}Ga$(IMP288) uptake (0.20±0.03% ID/g). [$^{18}F$]FDG accreted efficiently in the tumor (7.42±0.20% ID/g), but also in the inflamed muscle (4.07±1.13% ID/g) and a number of normal tissues, and thus pretargeted $^{68}Ga$-IMP 288 provided better specificity and sensitivity. The corresponding PET/CT images of mice that received $^{68}Ga$(IMP288) or $Al^{18}F$(IMP449) following pretargeting with TF2 clearly showed the efficient targeting of the radiolabeled peptide in the subcutaneous LS174T tumor, while the inflamed muscle was not visualized. In contrast, with $^{18}F$-FDG the tumor as well as the inflammation was clearly delineated.

Dose optimization—The effect of the TF2 bsMAb dose on tumor targeting of a fixed 0.01 nmol (15 ng) dose of IMP288 was determined. Groups of five mice were injected intravenously with 0.10, 0.25, 0.50 or 1.0 nmol TF2 (16, 40, 80 or 160 μg respectively), labeled with a trace amount of $^{125}I$ (0.4 MBq). One hour after injection of $^{111}In$(IMP288) (0.01 nmol, 0.4 MBq), the biodistribution of the radiolabels was determined.

TF2 cleared rapidly from the blood and the normal tissues. Eighteen hours after injection the blood concentration was less than 0.45% ID/g at all TF2 doses tested. Targeting of TF2 in the tumor was 3.5% ID/g at 2 h p.i. and independent of TF2 dose (data not shown). At all TF2 doses $^{111}In$(IMP288) accumulated effectively in the tumor (not shown). At higher TF2 doses enhanced uptake of $^{111}In$(IMP288) in the tumor was observed: at 1.0 nmol TF2 dose maximum targeting of IMP288 was reached (26.2±3.8% ID/g). Thus at the 0.01 nmol peptide dose highest tumor targeting and tumor-to-blood ratios were reached at the highest TF2 dose of 1.0 nmol (TF2:IMP288 molar ratio=100:1). Among the normal tissues, the kidneys had the highest uptake of $^{111}In$(IMP288) (1.75±0.27% ID/g) and uptake in the kidneys was not affected by the TF2 dose (not shown). All other normal tissues had very low uptake, resulting in extremely high tumor-to-nontumor ratios, exceeding 50:1 at all TF2 doses tested (not shown).

For PET imaging using $^{68}Ga$-labeled IMP288, a higher peptide dose is required, because a minimum activity of 5-10 MBq $^{68}Ga$ needs to be injected per mouse if PET imaging is performed 1 h after injection. The specific activity of the $^{68}Ga$(IMP288) preparations was 50-125 MBq/nmol at the time of injection. Therefore, for PET imaging at least 0.1-0.25 nmol of IMP288 had to be administered. The same TF2:IMP288 molar ratios were tested at 0.1 nmol IMP288 dose. LS174T tumors were pretargeted by injecting 1.0, 2.5, 5.0 or 10.0 nmol TF2 (160, 400, 800 or 1600 μg). In contrast to the results at the lower peptide dose, $^{111}In$(IMP288) uptake in the tumor was not affected by the TF2 doses (15% ID/g at all doses tested, data not shown). TF2 targeting in the tumor in terms of % ID/g decreased at higher doses (3.21±0.61% ID/g versus 1.16±0.27% Dig at an injected dose of 1.0 nmol and 10.0 nmol, respectively) (data not shown). Kidney uptake was also independent of the bsMAb dose (2% ID/g). Based on these data we selected a bsMAb dose of 6.0 nmol for targeting 0.1-0.25 nmol of IMP288 to the tumor.

PET imaging—To demonstrate the effectiveness of pretargeted immunoPET imaging with TF2 and $^{68}Ga$(IMP288) to image CEA-expressing tumors, subcutaneous tumors were induced in five mice. In the right flank an s.c. LS174T tumor was induced, while at the same time in the same mice 1×10⁶ SK-RC 52 cells were inoculated in the left flank to induce a CEA-negative tumor. Fourteen clays later, when tumors had a size of 0.1-0.2 g, the mice were pretargeted with 6.0 nmol $^{125}I$-TF2 intravenously. After 16 hours the mice received 5 MBq $^{68}Ga$(IMP288) (0.25 nmol, specific activity of 20 MBq/nmol). A separate group of three mice received the same amount of $^{68}Ga$-IMP 288 alone, without pretargeting with TF2. PET/CT scans of the mice were acquired 1 h after injection of the $^{68}Ga$(IMP288).

Figure 6:
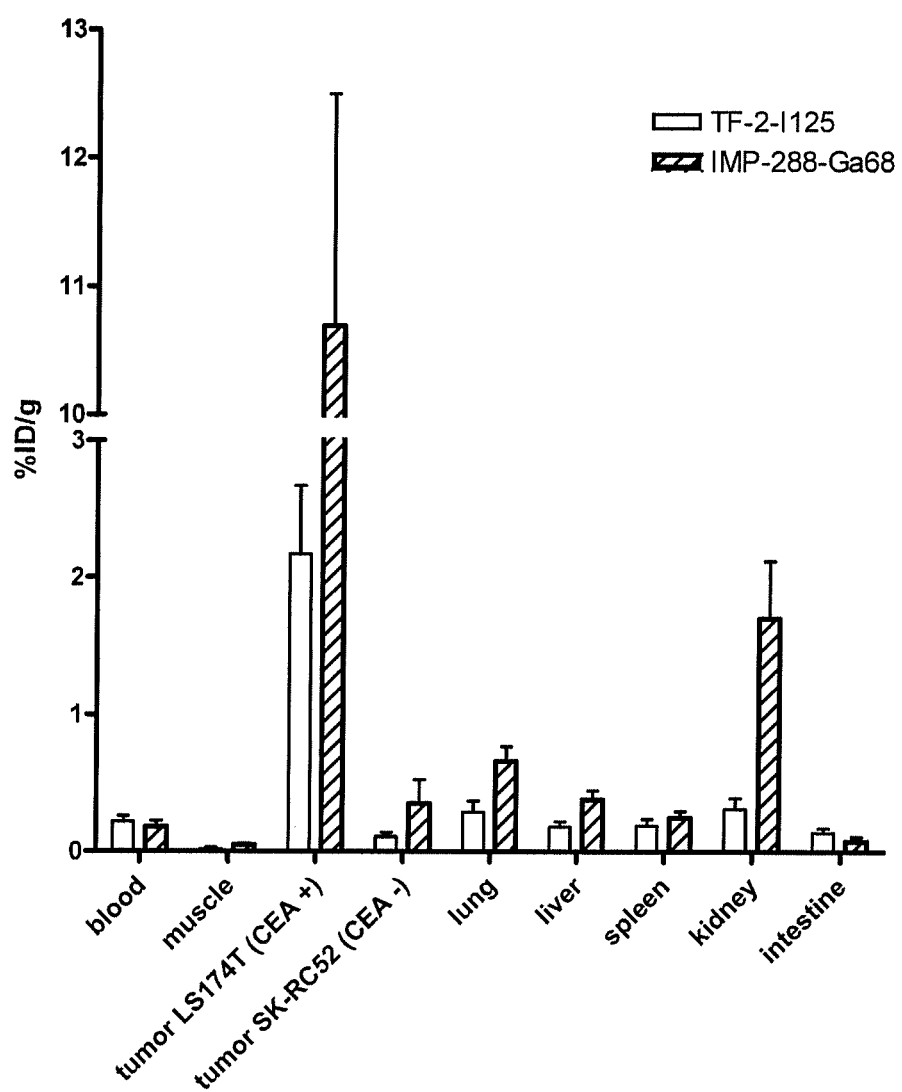
FIG. 6. Biodistribution of 6.0 nmol $^{125}$I-TF2 (0.37 MBq) and 0.25 nmol $^{68}$Ga(IMP288) (5 MBq), 1 hour after i.v. injection of $^{68}$Ga(IMP288) in BALB/c nude mice with a subcutaneous LS174T and SK-RC52 tumor. Values are given as means±standard deviation (n=5).

The biodistribution of $^{125}I$-TF2 and [$^{68}Ga$]IMP288 in the mice are shown in FIG. 6. Again high uptake of the bsMAb (2.17±0.50% ID/g) and peptide (10.7±3.6% ID/g) in the tumor was observed, with very low uptake in the normal tissues (tumor-to-blood ratio: 64±22). Targeting of $^{68}Ga$(IMP288) in the CEA-negative tumor SK-RC 52 was very low (0.35±0.35% ID/g). Likewise, tumors that were not pretargeted with TF2 had low uptake of $^{68}$Ga(IMP288) (0.20±0.03% TD/g), indicating the specific accumulation of IMP288 in the CEA-expressing LS174T tumor.

The specific uptake of $^{68}$Ga(IMP288) in the CEA-expressing tumor pretargeted with TF2 was clearly visualized in a PET image acquired 1 h after injection of the $^{68}$Ga-labeled peptide (not shown). Uptake in the tumor was evaluated quantitatively by drawing regions of interest (ROI), using a 50% threshold of maximum intensity. A region in the abdomen was used as background region. The tumor-to-background ratio in the image of the mouse that received TF2 and $^{68}$Ga (IMP288) was 38.2.

We then examined pretargeted immunoPET with $^{18}$F-FDG. In two groups of five mice a s.c. LS174T tumor was induced on the right hind leg and an inflammatory focus in the left thigh muscle was induced by intramuscular injection of 50 µL turpentine (18). Three days after injection of the turpentine, one group of mice received 6.0 nmol TF2, followed 16 h later by 5 MBq $^{68}$Ga(IMP288) (0.25 nmol). The other group received $^{18}$F-FDG (5 MBq). Mice were fasted during 10 hours prior to the injection and anaesthetized and kept warm at 37° C. until euthanasia, 1 h postinjection.

Figure 7:
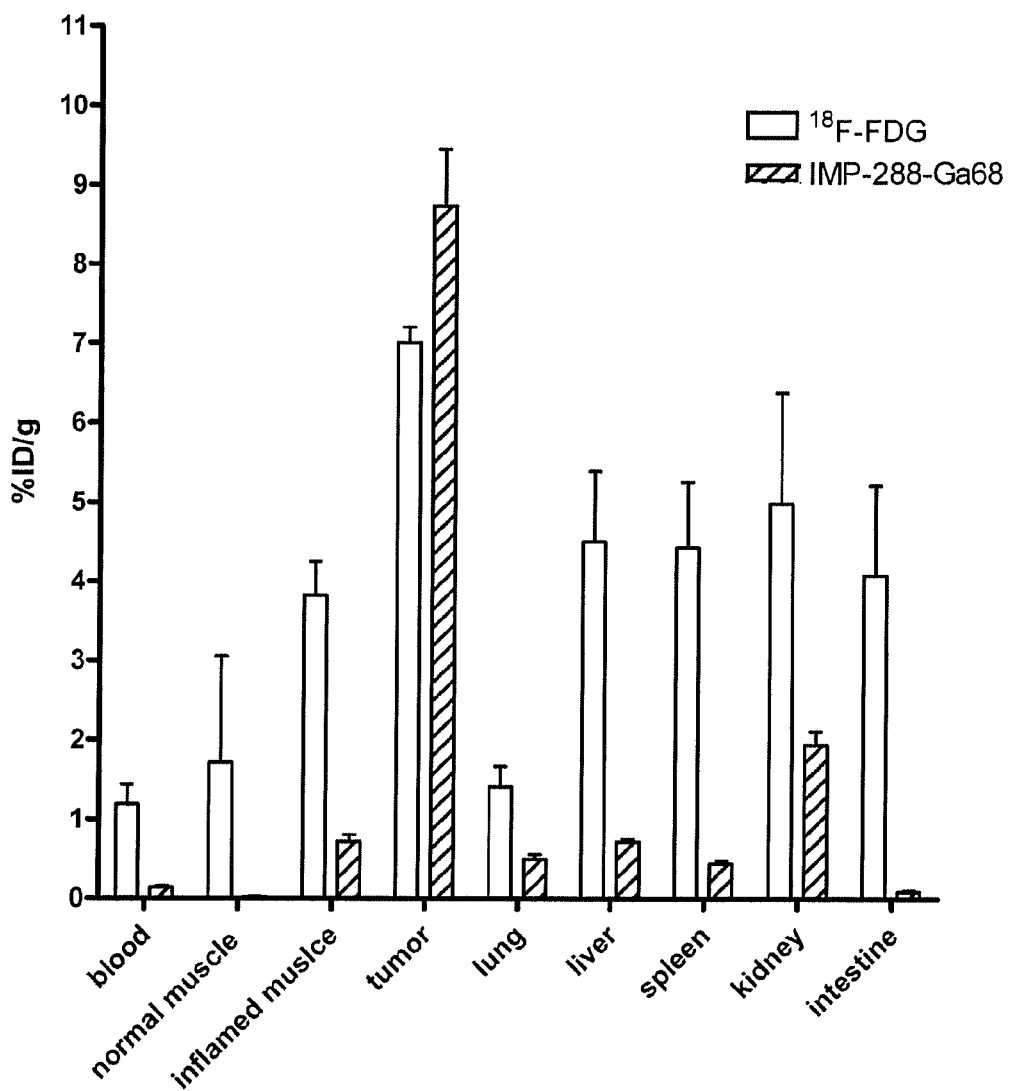
FIG. 7. Biodistribution of 5 MBq FDG and of 5 MBq $^{68}$Ga(IMP288) (0.25 nmol) 1 hour after i.v. injection following pretargeting with 6.0 nmol TF2. Values are given as means±standard deviation (n=5).

Uptake of $^{68}$Ga(IMP288) in the inflamed muscle was very low, while uptake in the tumor in the same animal was high (0.72±0.20% ID/g versus 8.73±1.60% ID/g, p<0.05, FIG. 7). Uptake in the inflamed muscle was in the same range as uptake in the lungs, liver and spleen (0.50±0.14% ID/g, 0.72±0.07% ID/g, 0.44±0.10% ID/g, respectively). Tumor-to-blood ratio of $^{68}$Ga(IMP288) in these mice was 69.9±32.3; inflamed muscle-to-blood ratio was 5.9±2.9; tumor-to-inflamed muscle ratio was 12.5±2.1. In the other group of mice $^{18}$F-FDG accreted efficiently in the tumor (7.42±0.20% ID/g, tumor-to-blood ratio 6.24±1.5, FIG. 4). $^{18}$F-FDG also substantially accumulated in the inflamed muscle (4.07±1.13% ID/g), with inflamed muscle-to-blood ratio of 3.4±0.5, and tumor-to-inflamed muscle ratio of 1.97±0.71.

Figure 8:
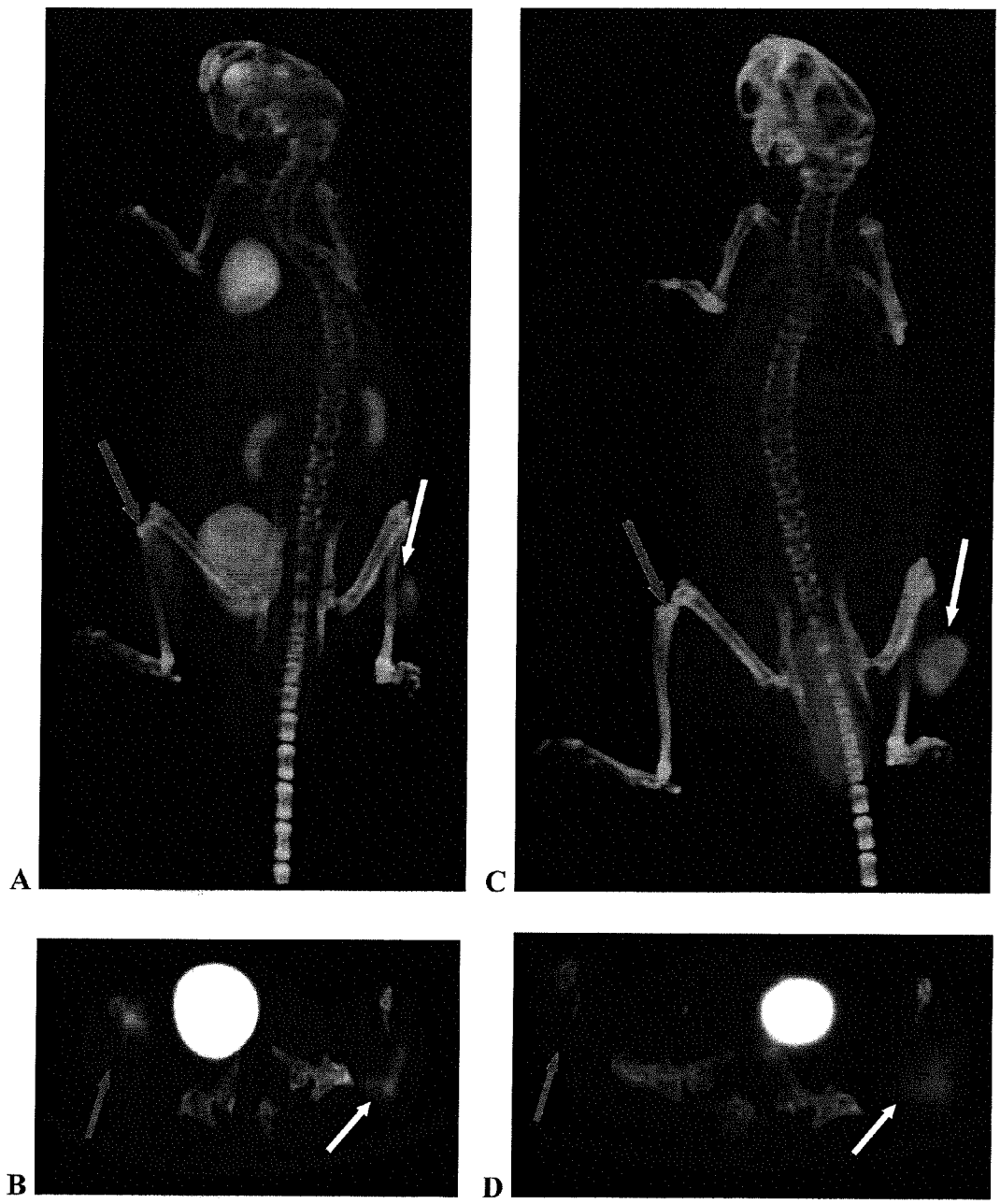
FIG. 8. PET/CT images of a BALB/c nude mouse with a subcutaneous LS174T tumor (0.1 g) on the right hind leg (light arrow) and a inflammation in the left thigh muscle (dark arrow), that received 5 MBq $^{18}$F-FDG, and one day later 6.0 nmol TF2 and 5 MBq $^{68}$Ga(IMP288) (0.25 nmol) with a 16 hour interval. The animal was imaged one hour after the $^{18}$F-FDG and $^{68}$Ga(IMP288) injection. The panel shows the 3D volume rendering (A), transverse sections of the tumor region (B) of the FDG-PET scan, and the 3D volume rendering (C), transverse sections of the tumor region (D) of the pretargeted immunoPET scan.

The corresponding PET/CT image of a mouse that received $^{68}$Ga(IMP288), following pretargeting with TF2, clearly showed the efficient accretion of the radiolabeled peptide in the tumor, while the inflamed muscle was not visualized (FIG. 8). In contrast, on the images of the mice that received $^{18}$F-FDG, the tumor as well as the inflammation was visible (FIG. 8). In the mice that received $^{68}$Ga(IMP288), the tumor-to-inflamed tissue ratio was 5.4; tumor-to-background ratio was 48; inflamed muscle-to-background ratio was 8.9. $^{18}$F-FDG uptake had a tumor-to-inflamed muscle ratio of 0.83; tumor-to-background ratio was 2.4; inflamed muscle-to-background ratio was 2.9.

Figure 9:
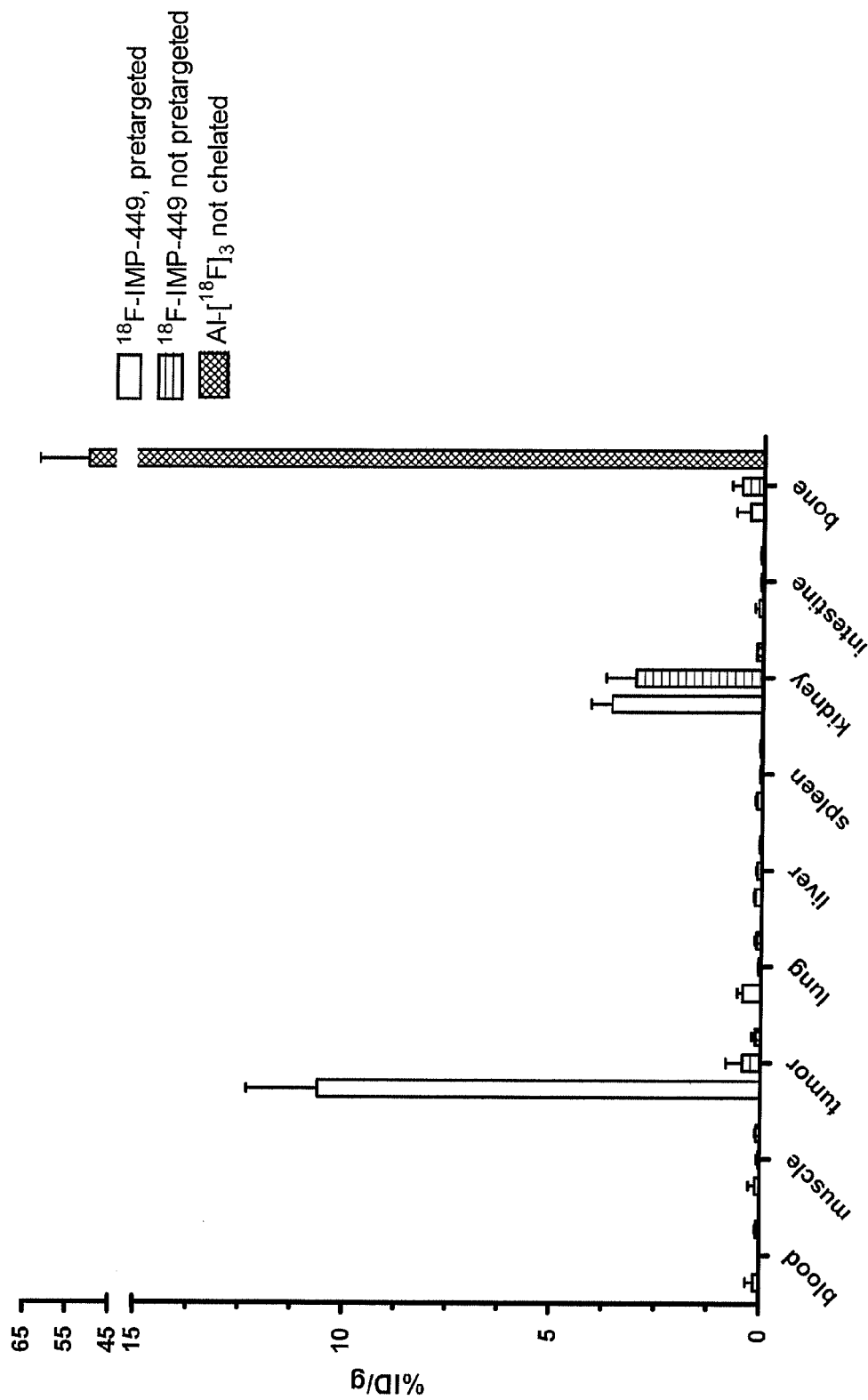
FIG. 9. Biodistribution of 0.25 nmol Al$^{18}$F(IMP449) (5 MBq) 1 hour after i.v. injection, following 6.0 nmol TF2 administered 16 hours earlier. Biodistribution of Al$^{18}$F (IMP449) without pretargeting, or biodistribution of [Al$^{18}$F]. Values are given as means±standard deviation.

The pretargeted immunoPET imaging method was tested using the Al$^{18}$F(IMP449). Five mice received 6.0 nmol TF2, followed 16 h later by 5 MBq Al[$^{18}$F]IMP449 (0.25 nmol). Three additional mice received 5 MBq Al$^{18}$F(IMP449) without prior administration of TF2, while two control mice were injected with [Al$^{18}$F] (3 MBq). The results of this experiment are summarized in FIG. 9. Uptake of Al$^{18}$F(IMP449) in tumors pretargeted with TF2 was high (10.6±1.7% ID/g), whereas it was very low in the non-pretargeted mice (0.45±0.38% ID/g). [Al$^{18}$F] accumulated in the bone (50.9±11.4% ID/g), while uptake of the radiolabeled IMP449 peptide in the bone was very low (0.54±0.2% ID/g), indicating that the Al$^{18}$F(IMP449) was stable in vivo. The biodistribution of Al$^{18}$F(IMP449) in the TF2 pretargeted mice with s.c. LS174T tumors were highly similar to that of $^{68}$Ga (MP288).

Figure 10:
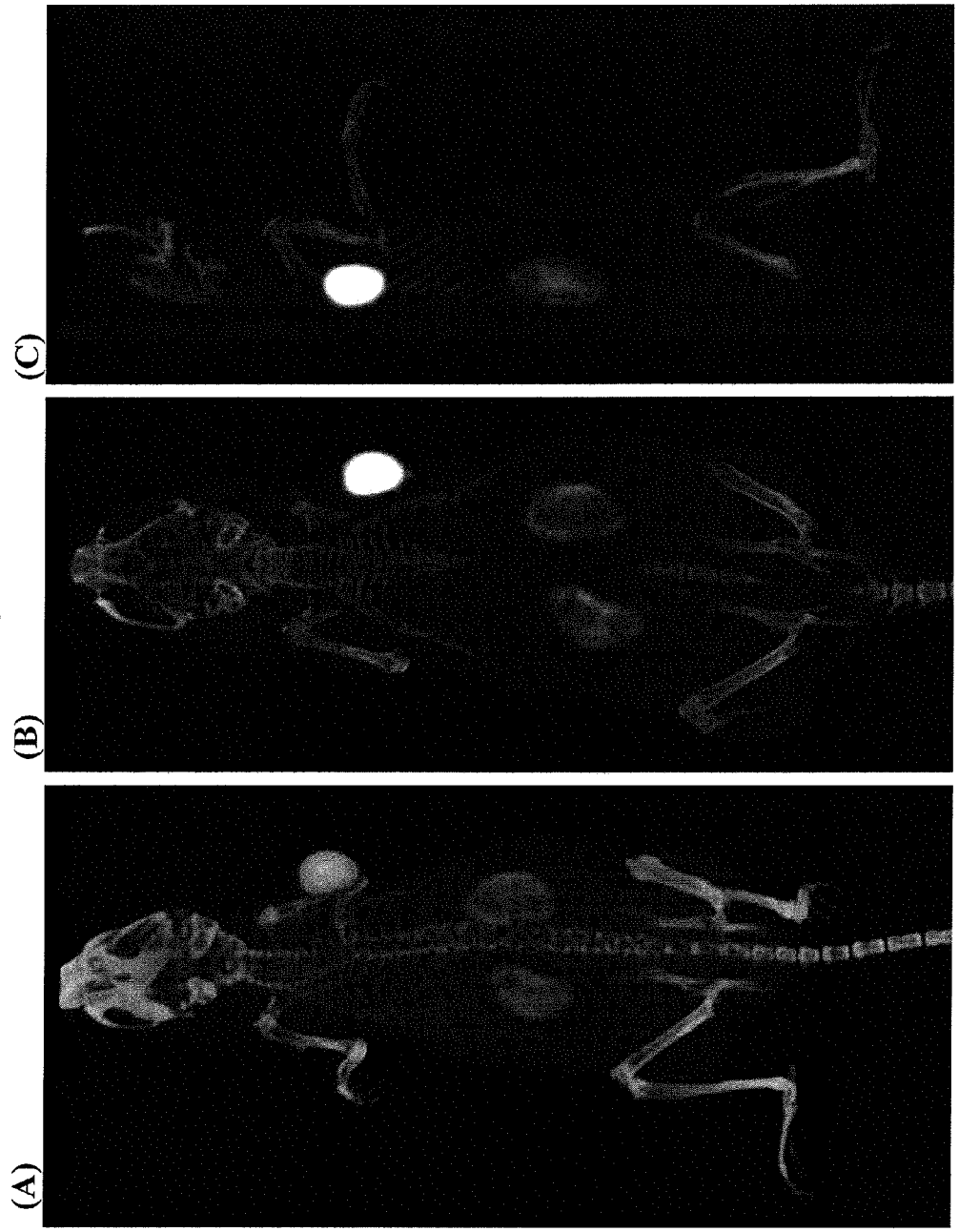
FIG. 10. Static PET/CT imaging study of a BALB/c nude mouse with a subcutaneous LS174T tumor (0.1 g) on the right side (arrow), that received 6.0 nmol TF2 and 0.25 nmol Al$^{18}$F (IMP449) (5 MBq) intravenously with a 16 hour interval. The animal was imaged one hour after injection of Al$^{18}$F (IMP449). The panel shows the 3D volume rendering (A) posterior view, and cross sections at the tumor region, (B) coronal, (C) sagittal.

The PET-images of pretargeted immunoPET with Al$^{18}$F (IMP449) show the same intensity in the tumor as those with $^{68}$Ga(IMP288), but the resolution of the $^{18}$F PET images were superior to those of the $^{68}$Ga. (FIG. 10). The tumor-to-background ratio of the Al$^{18}$F(IMP449) signal was 66.

Conclusions

The present study showed that pretargeted immunoPET with the anti-CEA×anti-HSG bispecific antibody TF2 in combination with a $^{68}$Ga- or $^{18}$F-labeled di-HSG-DOTA-peptide is a rapid and specific technique for PET imaging of CEA-expressing tumors.

Pretargeted immunoPET with TF2 in combination with $^{68}$Ga(IMP288) or Al$^{18}$F(IMP449) involves two intravenous administrations. An interval between the infusion of the bsMAb and the radiolabeled peptide of 16 h was used. After 16 h most of the TP2 had cleared from the blood (blood concentration <1% ID/g), preventing complexation of TF2 and IMP288 in the circulation.

For these studies the procedure to label IMP288 with $^{68}$Ga was optimized, resulting in a one-step labeling technique. We found that purification on a C18/HLB cartridge was needed to remove the $^{68}$Ga colloid that is formed when the peptide was labeled at specific activities exceeding 150 GBq/nmol at 95° C. If a preparation contains a small percentage of colloid and is administered intravenously, the $^{68}$Ga colloid accumulates in tissues of the mononuclear phagocyte system (liver, spleen, and bone marrow), deteriorating image quality. The $^{68}$Ga-labeled peptide could be rapidly purified on a C18-cartridge. Radiolabeling and purification for administration could be accomplished within 45 minutes.

The half-life of $^{68}$Ga matches with the kinetics of the IMP288 peptide in the pretargeting system: maximum accretion in the tumor is reached within 1 h. $^{68}$Ga can be eluted twice a day form a $^{68}$Ge/$^{68}$Ga generator, avoiding the need for an on-site cyclotron. However, the high energy of the positrons emitted by $^{68}$Ga (1.9 MeV) limits the spatial resolution of the acquired images to 3 mm, while the intrinsic resolution of the microPET system is as low as 1.5 mm.

$^{18}$F, the most widely used radionuclide in PET, has an even more favorable half-life for pretargeted PET imaging ($t_{1/2}$=110 min). The NOTA-conjugated peptide IMP449 was labeled with $^{18}$F, as described above. Like labeling with $^{68}$Ga, it is a one-step procedure. Labeling yields as high as 50% were obtained. The biodistribution of Al$^{18}$F(IMP449) was highly similar to that of $^{68}$Ga-labeled IMP288, suggesting that with this labeling method $^{18}$F is a residualizing radionuclide.

In contrast with FDG-PET, pretargeted radioimmunodetection is a tumor specific imaging modality. Although a high sensitivity and specificity for FDG-PET in detecting recurrent colorectal cancer lesions has been reported in patients (Huebner et al., 2000, J Nucl Med 41:11277-89), FDG-PET images could lead to diagnostic dilemmas in discriminating malignant from benign lesions, as indicated by the high level of labeling observed with inflammation. In contrast, the high tumor-to-background ratio and clear visualization of CEA-positive tumors using pretargeted immunoPET with TF2 $^{68}$Ga- or $^{18}$F-labeled peptides supports the use of the described methods for clinical imaging of cancer and other conditions. Apart from detecting metastases and discriminating CEA-positive tumors from other lesions, pretargeted immunoPET could also be used to estimate radiation dose delivery to tumor and normal tissues prior to pretargeted radioimmunotherapy. As TF2 is a humanized antibody, it has a low immunogenicity, opening the way for multiple imaging or treatment cycles.

Example 19

Synthesis of Folic Acid NOTA Conjugate

Folic acid is activated as described (Wang et. al. Bioconjugate Chem. 1996, 7, 56-62.) and conjugated to Boc-NH—CH$_2$—CH$_2$—NH$_2$. The conjugate is purified by chromatography. The Boc group is then removed by treatment with TFA. The amino folate derivative is then mixed with p-SCN-Bn-NOTA (Macrocyclics) in a carbonate buffer. The product is then purified by HPLC. The folate-NOTA derivative is labeled with Al$^{18}$F as described in the preceding Examples and then HPLC purified. The $^{18}$F-labeled folate is injected i.v. into a subject and successfully used to image the distribution of folate receptors, for example in cancer or inflammatory diseases (see, e.g., Ke et al., Advanced Drug Delivery Reviews, 56:1143-60, 2004).

Example 20

Pretargeted PET Imaging in Humans

A patient (1.7 m$^2$ body surface area) with a suspected recurrent tumor is injected with 17 mg of bispecific monoclonal antibody (bsMab). The bsMab is allowed to localize to the target and clear from the blood. The $^{18}$F-labeled peptide (5-10 mCi on 5.7×10$^{-9}$ mol) is injected when 99% of the bsMab has cleared from the blood. PET imaging shows the presence of micrometastatic tumors.

Example 21

Imaging of Angiogenesis Receptors by $^{18}$F-Labeling

Labeled Arg-Gly-Asp (RGD) peptides have been used for imaging of angiogenesis, for example in ischemic tissues, where $\alpha_v\beta_3$ integrin is involved. (Jeong et al., J. Nucl. Med. 2008, Apr. 15 epub). RGD is conjugated to SCN-Bn-NOTA according to Jeong et al. (2008). [Al$^{18}$F] is attached to the NOTA-derivatized RGD peptide as described above, by mixing aluminum stock solution with $^{18}$F and the derivatized RGD peptide and heating at 110° C. for 15 min, using an excess of peptide to drive the labeling reaction towards completion. The $^{18}$F labeled RGD peptide is used for in vivo biodistribution and PET imaging as disclosed in Jeong et al. (2008). The [Al$^{18}$F] conjugate of RGD-NOTA is taken up into ischemic tissues and provides PET imaging of angiogenesis.

Example 22

Carbohydrate Labeling

A NOTA thiosemicarbazide derivative is prepared by reacting the p-SCN-Bn-NOTA with hydrazine and then purifying the ligand by HPLC. [Al$^{18}$F] is prepared as described in the preceding Examples and the [Al$^{18}$F] is added to the NOTA thiosemicarbazide and heated for 15 min. Optionally the Al$^{18}$F(NOTA thiosemicarbazide) complex is purified by HPLC. The Al$^{18}$F(NOTA thiosemicarbazide) is conjugated to oxidized carbohydrates by known methods. The $^{18}$F-labeled carbohydrate is successfully used for imaging studies using PET scanning.

Example 23

Effect of Organic Solvents on F-18 Labeling

The affinity of chelating moieties such as NETA and NOTA for aluminum is much higher than the affinity of aluminum for $^{18}$F. The affinity of Al for $^{18}$F is affected by factors such as the ionic strength of the solution, since the presence of other counter-ions tends to shield the positively charged aluminum and negatively charged fluoride ions from each other and therefore to decrease the strength of ionic binding. Therefore low ionic strength medium should increase the effective binding of Al and $^{18}$F.

An initial study adding ethanol to the $^{18}$F reaction was found to increase the yield of radiolabeled peptide. IMP461 was prepared as described above.

TABLE 9

$^{18}$F-labeling of IMP461 in ethanol

| # | 2 mM AlCl$_3$ | $^{18}$F$^-$ | 2 mM IMP 461 | Solvent | | Yield* |
|---|---|---|---|---|---|---|
| 1 | 10 µL | 741 µCi | 20 µL | EtOH | 60 µL | 64.9% |
| 2 | 10 µL | 739 µCi | 20 µL | H$_2$O | 60 µL | 21.4% |
| 3 | 10 µL | 747 µCi | 20 µL | EtOH | 60 µL | 46.7% |
| 4 | 5 µL | 947 µCi | 10 µL | EtOH | 60 µL | 43.2% |

*Yield after HLB column purification, Rxn # 1, 2 and 4 were heated to 101° C. for 5 minutes, Rxn # 3 was heated for 1 minute in a microwave oven.

Preliminary results showed that addition of ethanol to the reaction mixture more than doubled the yield of $^{18}$F-labeled peptide. Table 9 also shows that microwave irradiation can be used in place of heating to promote incorporation of [Al$^{18}$F] into the chelating moiety of IMP461. Sixty seconds of microwave radiation (#3) appeared to be slightly less (18%) effective than heating to 101° C. for 5 minutes (#1).

The effect of additional solvents on Al$^{19}$F complexation of peptides was examined. In each case, the concentration of reactants was the same and only the solvent varied. Reaction conditions included mixing 25 µL Na$^{19}$F+20 µL AlCl$_3$+20 µL IMP461+60 µL solvent, followed by heating at 101° C. for 5 min. Table 10 shows that the presence of a solvent does improve the yields of Al$^{19}$F(IMP461) (i.e., IMP473) considerably.

TABLE 10

Complexation of IMP 461 with Al$^{19}$F in various solvents

| Solvent | H$_2$O | MeOH | EtOH | CH$_3$CN |
|---|---|---|---|---|
| Al-IMP461 | 2.97 | 3.03 | 2.13 | 1.54 |
| IMP465 | 52.46 | 34.19 | 31.58 | 24.58 |
| IMP473 | 14.99 | 30.96 | 33.00 | 37.48 |
| IMP473 | 15.96 | 31.81 | 33.29 | 36.40 |
| IMP461 | 13.63 | — | — | — |

| Solvent | IPA | Acetone | THF | Dioxane |
|---|---|---|---|---|
| Al-IMP461 | 2.02 | 2.05 | 2.20 | 16.67 |
| IMP465 | 32.11 | 28.47 | 34.76 | 10.35 |
| IMP473 | 27.31 | 34.35 | 29.38 | 27.09 |
| IMP473 | 27.97 | 35.13 | 29.28 | 11.62 |
| IMP461 | 10.58 | — | 4.37 | 34.27 |

| Solvent | DMF | DMSO | t$_R$ (min) |
|---|---|---|---|
| Al-IMP461 | — | — | 9.739 |
| IMP465 | 19.97 | 37.03 | 10.138 |
| IMP473 | 27.77 | 31.67 | 11.729 |
| IMP473 | 27.34 | 31.29 | 11.952 |
| IMP461 | — | — | 12.535 |

Al[$^{19}$F]IMP461 = IMP473

Example 24

Elution of $^{18}F^-$ with Bicarbonate $^{18}F$, 10.43 mCi, was received in 2 mL in a syringe. The solution was passed through a SEP-PAK® Light, WATERS® ACCELL™ Plus QMA Cartridge. The column was then washed with 5 mL of DI water. The $^{18}F$ was eluted with 0.4 M $KHCO_3$ in fractions as shown in Table 11 below.

TABLE 11

Elution of QMA Cartridge with $KHCO_3$

| Vial | Vol. Acetic acid μL | Vol. 0.4M $KHCO_3$ μL | Activity mCi |
|---|---|---|---|
| 1 | 7.5 | 150 | 0.0208 |
| 2 | 10 | 200 | 7.06 |
| 3 | 5 | 100 | 1.653 |
| 4 | 25 | 500 | 0.548 |

The effects of the amount of additional solvent ($CH_3CN$) on $^{18}F$-labeling of IMP461 was examined. In each case, the concentration of reactants was the same and only the amount of solvent varied. Reaction conditions included mixing 10 μL $AlCl_3$+20 μL $^{18}F$+20 μL IMP461+$CH_3CN$ followed by heating at 101° C. for 5 min. Table 12 shows that following an initial improvement the labeling efficiency decreases in the presence of excess solvent.

TABLE 12

$^{18}F$-labeling of IMP461 using varying amounts of $CH_3CN$

| $CH_3CN$ (μL) | $^{18}F^-$ mCi | $t_R$ 2.70 min (%) | $t_R$ 8.70 min (%) | RCY % (HLB) |
|---|---|---|---|---|
| 0 | 0.642 | 13.48 | 86.52 | 50.7 |
| 100 | 0.645 | 1.55 | 98.45 | 81.8* |
| 200 | 0.642 | 2.85 | 97.15 | 80.8 |
| 400 | 0.645 | 14.51 | 85.49 | 57.8 |

*Aqueous wash contains labeled peptide. RCY = radiochemical yield after HLB purification

Example 25

High Dose Radiolabeling of IMP461

$^{18}F^-$, 163 mCi, was received in 2 mL in a syringe. The solution was passed through a SEP-PAK® Light, WATERS® ACCELL™ Plus QMA Cartridge. The column was then washed with 5 mL of DI water. The $^{18}F$ was eluted with 0.4 M $K_2CO_3$ in fractions as shown in Table 13.

TABLE 13

High Dose Labeling

| Vial | Vol. Acetic acid μL | Vol. 0.4M $K_2CO_3$ μL | Activity mCi |
|---|---|---|---|
| 1 | 18.5 | 185 | 5.59 |
| 2 | 5 | 50 | 35.8 |
| 3 | 5 | 50 | 59.9 |
| 4 | 5 | 50 | 20.5 |
| 5 | 5 | 50 | 5.58 |
| 6 | 50 | 500 | 4.21 |

An aluminum chloride solution (10 μL, 2 mM in pH 4, 2 mM NaOAc) was added to vial number 3 from Table 13. The peptide (20 μL, 2 mM in pH 4, 2 mM NaOAc) was added to the vial followed by the addition of 170 μL of $CH_3CN$. The solution was heated for 10 min at 103° C. the diluted with 6 mL of water. The solution was pulled into a 10 mL syringe and injected onto two WATERS® HLB Plus Cartridges arranged in tandem. The cartridges were washed with 8 mL water. The radiolabeled peptide $Al^{18}F$(IMP461) was then eluted with 10 mL 1:1 $EtOH/H_2O$, 30.3 mCi, 63.5% yield, specific activity 750 Ci/mmol. The labeled peptide was free of unbound $^{18}F$ by HPLC. The total reaction and purification time was 20 min.

Example 26

Preparation of $Al^{19}F$ Peptides

Products containing $^{27}Al$ and/or $^{19}F$ are useful for certain applications like MR imaging. An improved method for preparing $[Al^{19}F]$ compounds was developed. IMP461 was prepared as described above and labeled with $^{19}F$. Reacting IMP461 with $AlCl_3$+NaF resulted in the formation of three products (not shown). However, by reacting IMP461 with $AlF_3.3H_2O$ we obtained a higher yield of $Al^{19}F$(IMP461).

Synthesis of IMP 473: $[Al^{19}F$(IMP461)$]$ To (14.1 mg, 10.90 μmol) IMP461 in 2 mL NaOAc (2 mM, pH 4.18) solution added (4.51 mg, 32.68 μmol) $AlF_3.3H_2O$ and 500 μL ethanol. The pH of the solution to adjusted to 4.46 using 3 μL 1 N NaOH and heated in a boiling water bath for 30 minutes. The crude reaction mixture was purified by preparative RP-HPLC to yield 4.8 mg (32.9%) of IMP 473. HRMS (ESI-TOF) $MH^+$ expected 1337.6341; found 1337.6332

These results demonstrate that $^{19}F$ labeled molecules may be prepared by forming metal-$^{19}F$ complexes and binding the metal-$^{19}F$ to a chelating moiety, as discussed above for $^{18}F$ labeling. The instant Example shows that a targeting peptide of use for pretargeting detection, diagnosis and/or imaging may be prepared using the instant methods.

Example 27

Synthesis and Labeling of IMP479, IMP485 and IMP487

Figure 11:
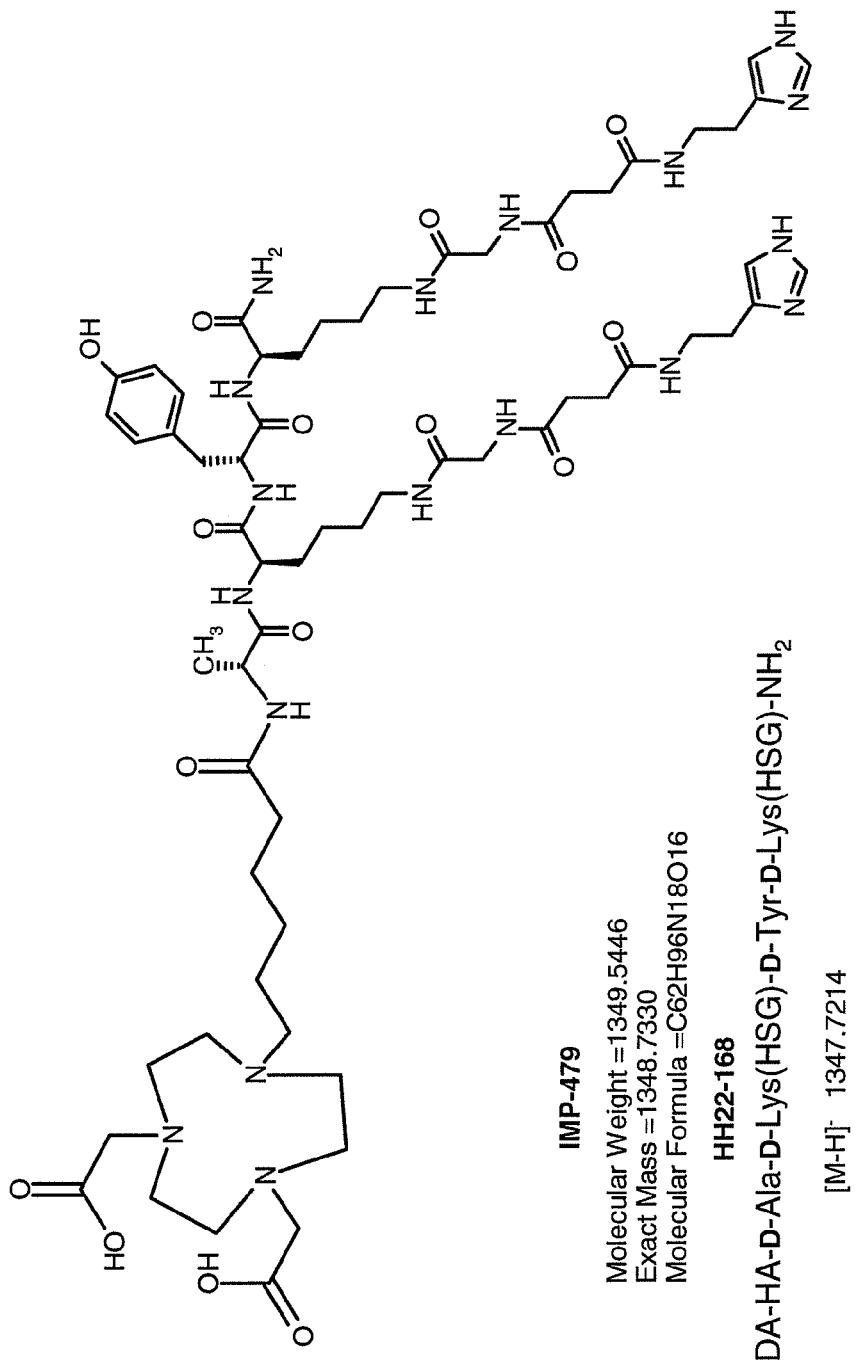
FIG. 11. Structure of IMP479 (SEQ ID NO:54).
Figure 12:
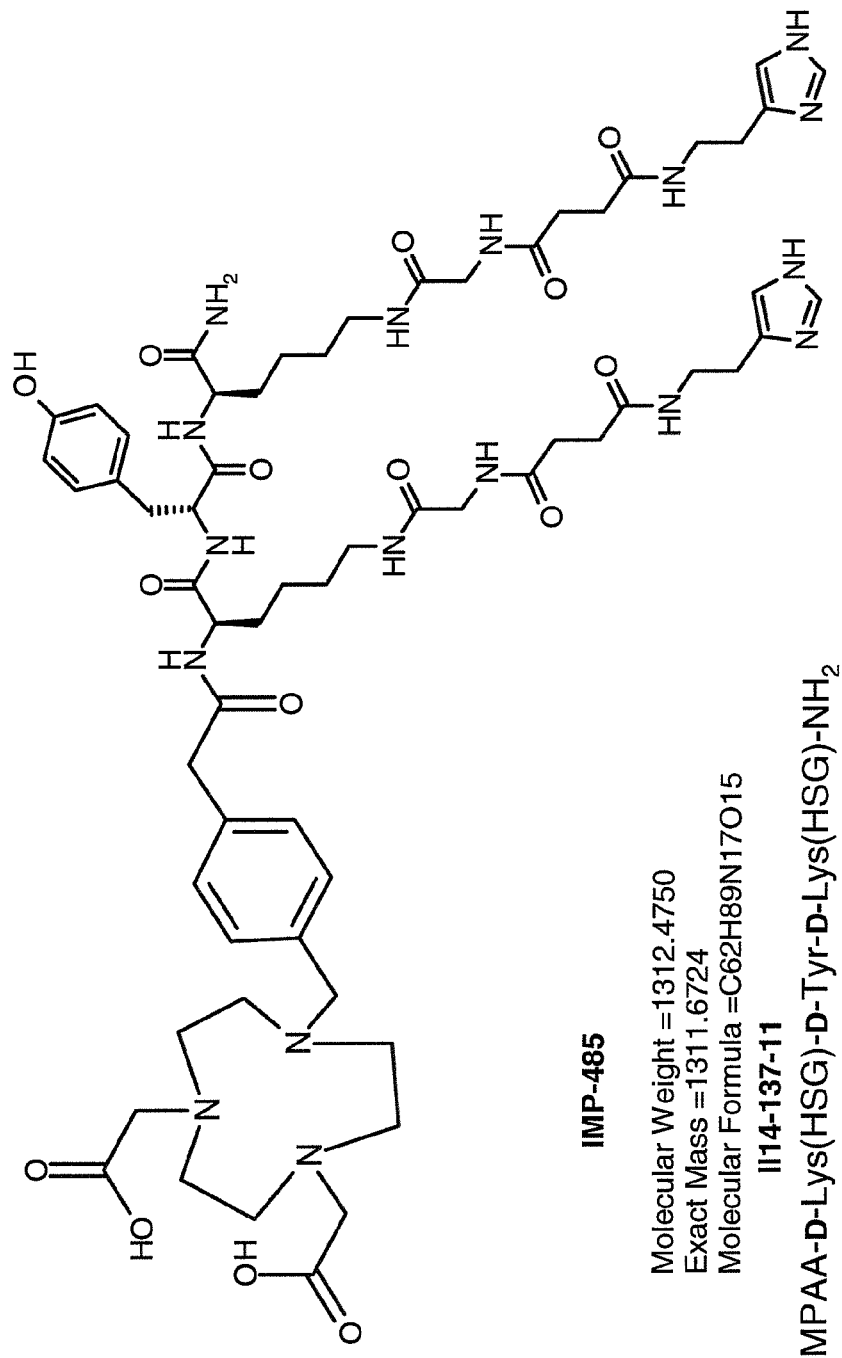
FIG. 12. Structure of IMP485 (SEQ ID NO:55).
Figure 13A:
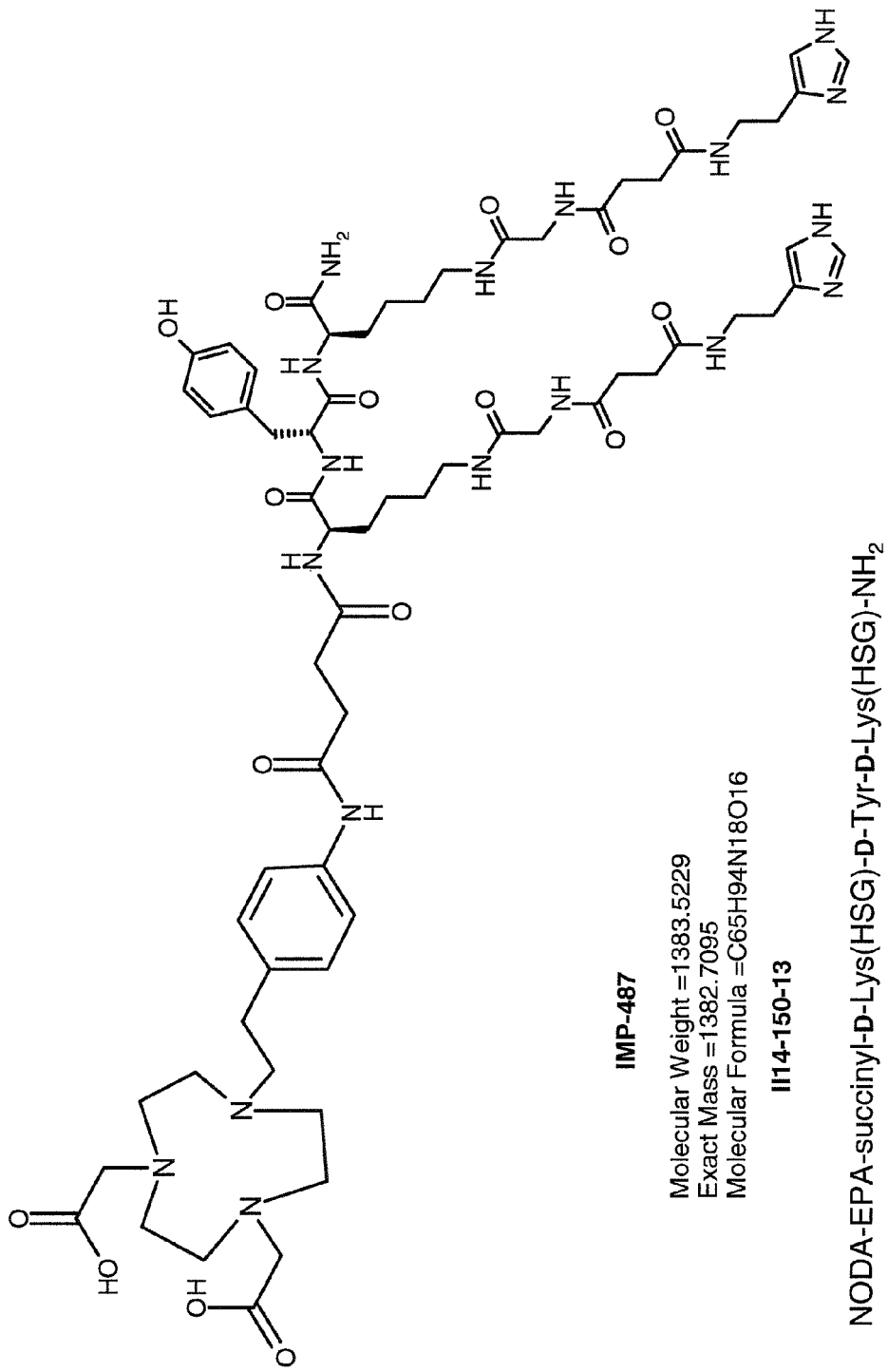
FIG. 13. Structures of (A) IMP487 (SEQ ID NO:56); (B) IMP490 (SEQ ID NO:52); (C) IMP493 (SEQ ID NO:53); (D) IMP495 (SEQ ID NO: 57); (E) IMP496 (SEQ ID NO: 58); and (F) IMP500.
Figure 13B:
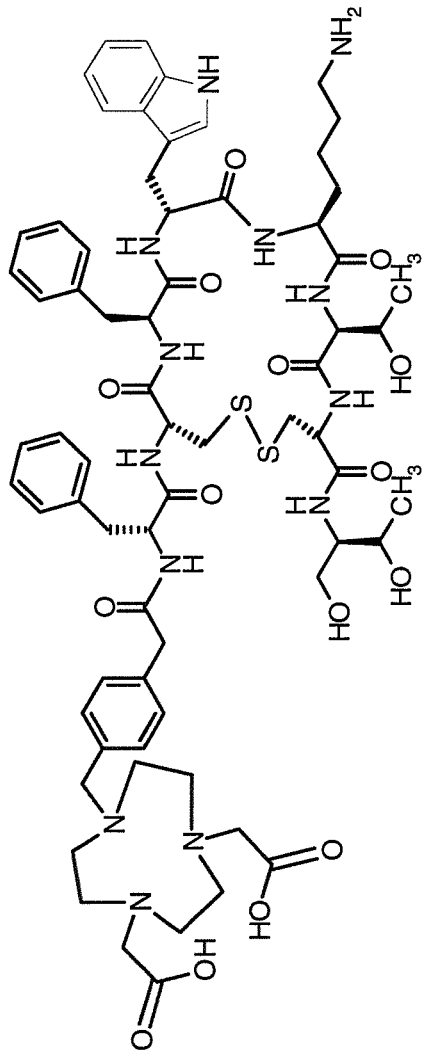
Figure 13C:
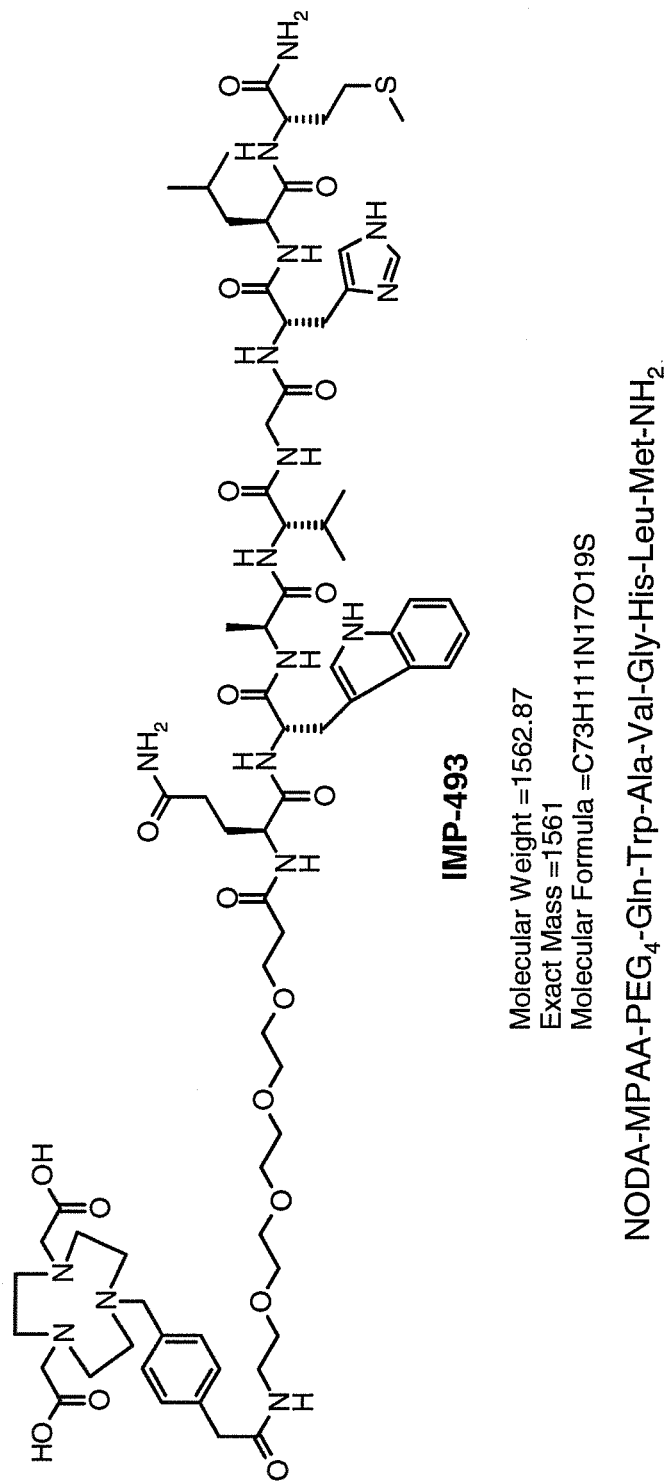
Figure 13D:
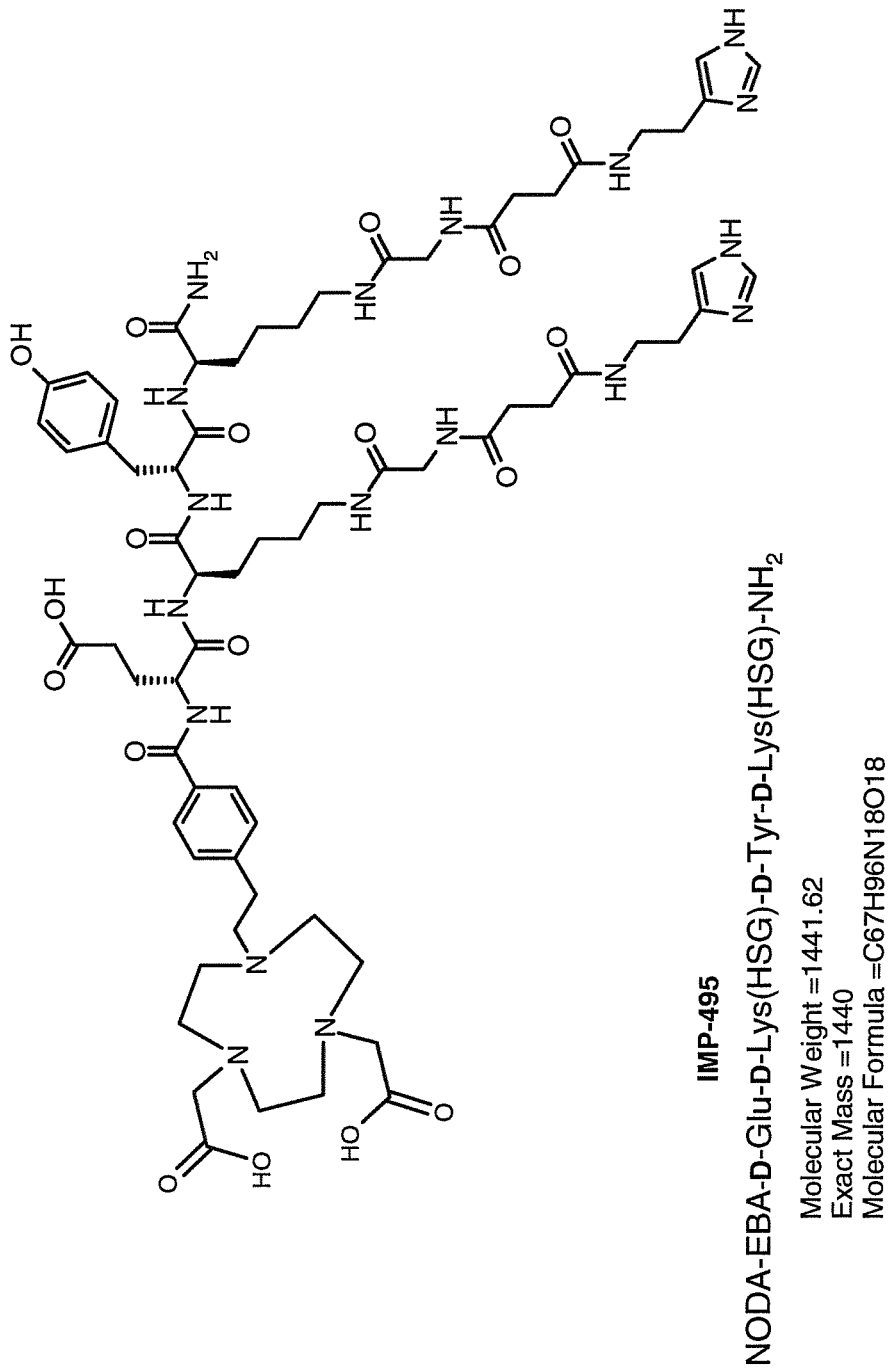
Figure 13E:
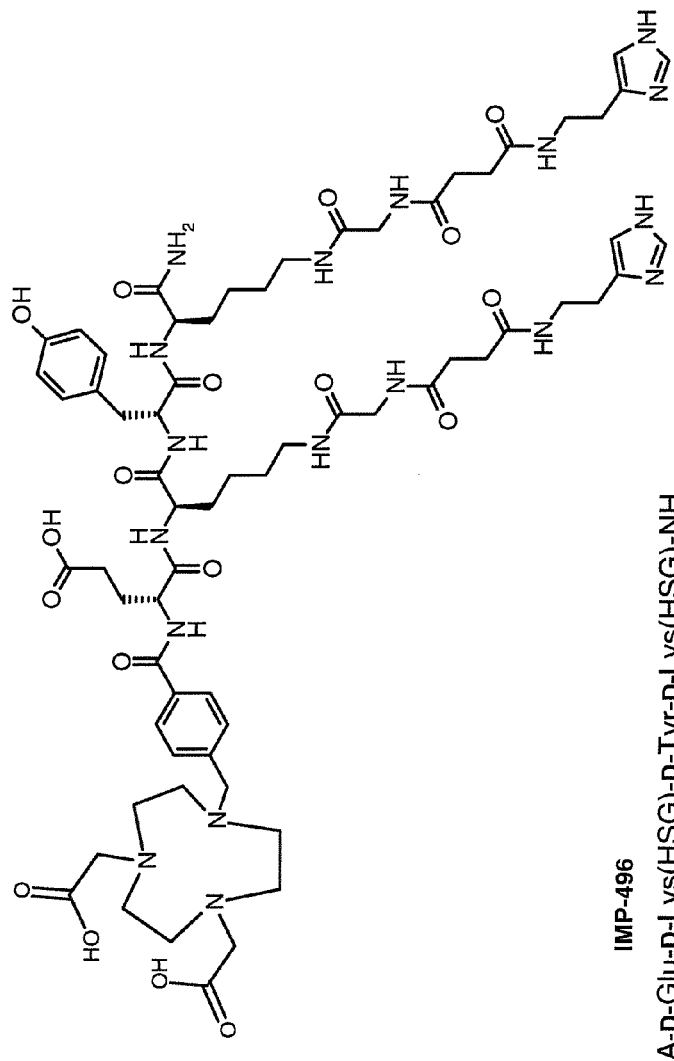
Figure 13F:
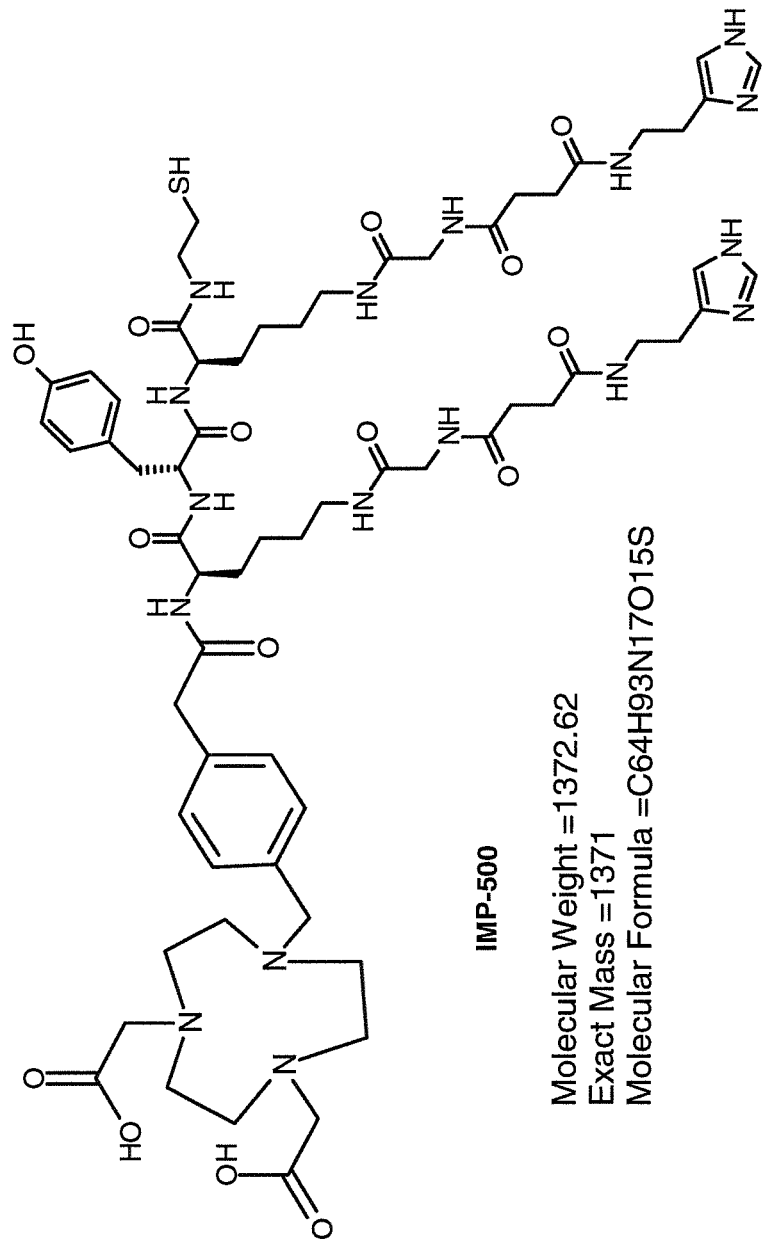

The structures of additional peptides (IMP479, IMP485, and IMP487) designed for $^{18}F$-labeling are shown in FIG. 11 to FIG. 13. IMP485 is shown in FIG. 12. IMP485 was made on Sieber Amide resin by adding the following amino acids to the resin in the order shown: Aloc-D-Lys(Fmoc)-OH, Trt-HSG-OH, the Aloc was cleaved, Fmoc-D-Tyr(But)-OH, Aloc-D-Lys(Fmoc)-OH, Trt-HSG-OH, the Aloc was cleaved, (tent-Butyl)$_2$NODA-MPAA (methyl phenyl acetic acid). The peptide was then cleaved from the resin and purified by RP-HPLC to yield 44.8 mg of IMP485.

Synthesis of Bis-t-butyl-NODA-MPAA: (tBu)$_2$NODA-MPAA for IMP485 Synthesis

To a solution of 4-(bromomethyl)phenyl acetic acid (Aldrich 310417) (0.5925 g, 2.59 mmol) in $CH_3CN$ (anhydrous) (50 mL) at 0° C. was added dropwise over 1 h a solution of NO2AtBu (1.0087 g, 2.82 mmol) in $CH_3CN$ (50 mL). After 4 h anhydrous $K_2CO_3$ (0.1008 g, 0.729 mmol) was added to the reaction mixture and allowed to stir at room temperature overnight. Solvent was evaporated and the crude mixture was purified by preparative RP-HPLC to yield a white solid (0.7132 g, 54.5%).

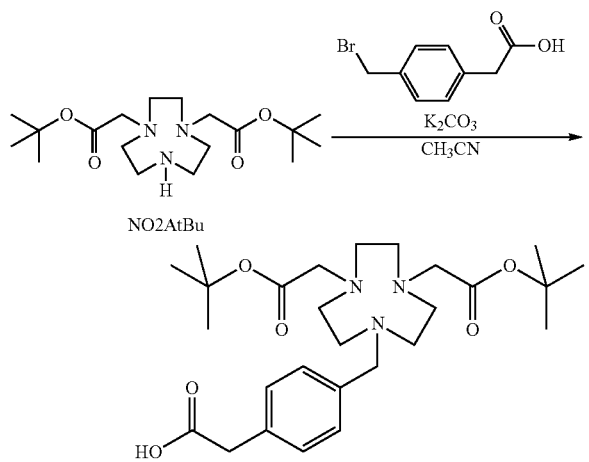

Figure 14:
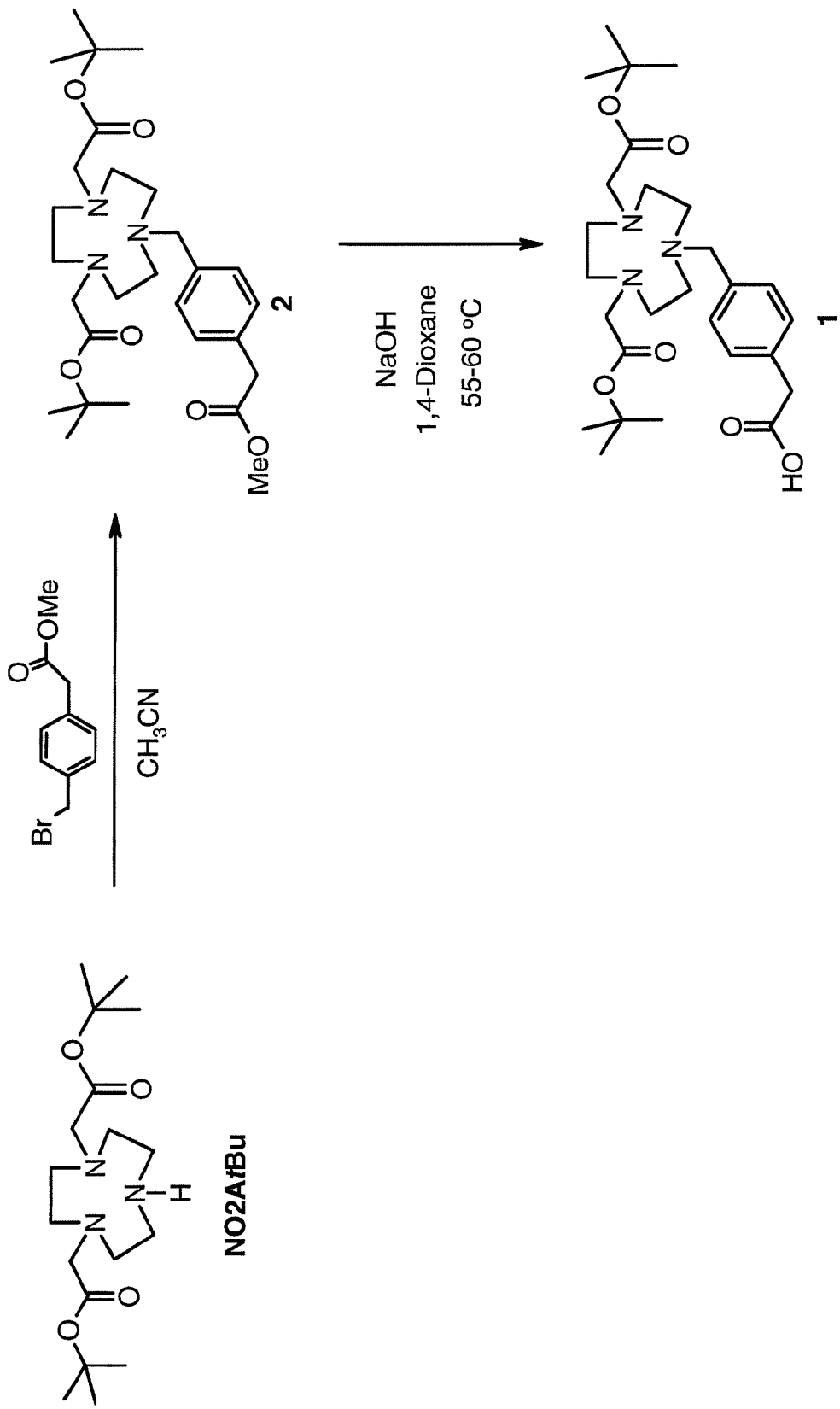
FIG. 14. Synthesis of bis-t-butyl-NODA-MPAA.

Although this is a one step synthesis, yields were low due to esterification of the product by 4-(bromomethyl)phenylacetic acid. Alkylation of NO2AtBu using methyl(4-bromomethyl)phenylacetate was employed to prevent esterification (FIG. 14).

$^{18}$F-Labeling

For $^{18}$F labeling studies in water, to 40 nmol of IMP479/485/487 (formulated using trehalose+ascorbic acid+AlCl$_3$) was added 250 μL $^{18}$F solution [~919-1112 μCi of $^{18}$F$^-$] and heated to 101° C. for 15 minutes. In ethanol, to 40 nmol of IMP479/485/487 (formulated using trehalose+ascorbic acid+AlCl$_3$) was added 250 μL $^{18}$F$^-$ solution [1.248-1.693 mCi of $^{18}$F$^-$], 100 μL EtOH and heated to 101° C. for 15 minutes. An exemplary experiment showing labeling of different peptides is shown in Table 14. With minimal optimization, radiolabeling of IMP485 has been observed with up to an 88% yield and a specific activity of 2,500 Ci/mmol. At this specific activity, HPLC purification of the radiolabeled peptide is not required for in vivo PET imaging using the radiolabeled peptide.

TABLE 14

Labeling of IMP479, IMP485 and IMP487

| IMP # | Isolated yields after HLB purification | |
|---|---|---|
| | H$_2$O | EtOH |
| IMP479 | 44.0% | 57.5% |
| IMP485 | 74.4% | 79.7% |
| IMP487 | 63.6% | 81.6% |

Stability in Serum

A kit containing 40 nmol of IMP485 or IMP487, 20 nmol AlCl$_3$, 0.1 mg ascorbic acid and 0.1 g trehalose adjusted to pH 3.9 was reconstituted with purified $^{18}$F$^-$ in 200 μL saline and heated 106° C. for 15 min. The reaction mixture was then diluted with 800 water and placed on an HLB column. After washing, the column was eluted with 2×200 μL 1:1 EtOH/H$_2$O to obtain the purified Al$^{18}$F(IMP485) in 64.6% isolated yield. The radiolabeled peptide in 50 μL was mixed with 250 μL of fresh human serum in a vial and incubated at 37° C.

Both radiolabeled peptides were stable at 37° C. in fresh human serum over the four hours tested (not shown).

Effect of Bulking Agents on Yield of Lyophilized Peptide

An experiment was performed to compare yield using IMP485 kits (40 nmol) with different bulking agents labeled with 2 mCi of F-18 (from the same batch of F-18) in 200 microliters of saline. The bulking agents were introduced at a concentration of 5% by weight in water with a dose of 200 microliters/vial. We tested sorbitol, trehalose, sucrose, mannitol and glycine as bulking agents. Results are shown in Table 15

TABLE 15

Effects of Bulking Agents on Radiolabeling Yield

| Bulking Agent | Activity mCi | Yield % |
|---|---|---|
| Sorbitol | 2.17 | 82.9 |
| Glycine | 2.17 | 41.5 |
| Mannitol | 2.11 | 81.8 |
| Sucrose | 2.11 | 66.1 |
| Trehalose | 2.10 | 81.3 |

Sorbitol, mannitol and trehalose all gave radiolabeled product in the same yield. The mannitol kit and the trehalose kit both formed nice cakes. The sucrose kit and the glycine kit both had significantly lower yields. We also recently tested 2-hydroxypropyl-beta-cyclodextrin as a bulking agent and obtained a 58% yield for the 40 nmol kit. We have found that radiolabeling is very pH sensitive and needs to be tuned to the ligand and possibly even to the peptide+the ligand. In the case of IMP485 the optimal pH is pH 4.0±0.2 whereas the optimal pH for IMP467 was pH 4.5±0.5. In both cases the yields drop off rapidly outside the ideal pH zone.

Time Course of Labeling

The time course for labeling of IMP485 was examined. To 40 nmol of IMP485 (formulated using trehalose+AlCl$_3$ (20 nmol)+ascorbic acid) was added ~200-250 μL $^{18}$F$^-$ solution (0.9% saline) and heated to 104° C. for 5 to 15 minutes. The results for labeling yield were: 5 min (28.9%), 10 min (57.9%), 15 min (83.7%) and 30 min (88.9%). Thus, the time course for labeling was approximately 15 minutes.

Biodistribution of IMP485 Alone

The biodistribution of IMP485 in the absence of any pretargeting antibody was examined in female Taconic nude mice (10 week old) bearing small or no BXPC3 pancreatic cancer xenografts. The mice were injected i.v. with Al$^{18}$F (IMP485), (340 μCi, 2.29×10$^{-9}$ mol, 100 μL in saline). The mice, 6 per time point, were necropsied at 30 min and 90 min post injection. In the absence of pretargeting antibody a low level of accumulation was seen in tumor and most normal tissues. The substantial majority of radiolabel was found in the bladder and to a lesser extent in kidney. Most of the activity was cleared before the 90 min time point.

Pretargeting of IMP485 with TF2 DNL Targeting Molecule

IMP485 Radiolabeling—$^{18}$F$^-$ (218 mCi) was purified to isolate 145.9 mCi. The purified $^{18}$F$^-$ (135 mCi) was added to a lyophilized vial containing 40 nmol of pre-complexed Al(IMP485). The reaction vial was heated at 110° C. for 17 min. Water (0.8 mL) was added to the reaction mixture before HLB purification. The product (22 mCi) was eluted with 0.6 mL of water:ethanol (1:1) mixture into a vial containing lyophilized ascorbic acid. The product was diluted with saline. The Al$^{18}$F(IMP485) specific activity used for injection was 550 Ci/mmol.

Biodistribution of Al$^{18}$F(IMP485) alone—Mice bearing sc LS174T xenografts were injected with Al$^{18}$F(IMP485) (28 μCi, 5.2×10$^{-11}$ mol, 100 μL. Mice were necropsied at 1 and 3 h post injection, 6 mice per time point.

Biodistribution of TF2+Al$^{18}$F(IMP485) With Pretargeting at 20:1 bsMAb to peptide ratio—Mice bearing sc LS174T xenografts were injected with TF2 (163.2 µg, 1.03×10$^{-9}$ mol, iv) and allowed 16.3 h for clearance before injecting Al$^{18}$F (IMP485) (28 µCi, 5.2×10$^{-11}$ mol, 100 µL iv). Mice were necropsied at 1 and 3 h post injection, 7 mice per time point.

Urine stability—Ten mice bearing s.c. Capan-1 xenografts were injected with Al$^{18}$F(IMP485) (400 µCi, in saline, 100 µL). Urine was collected from 3 mice at 55 min post injection. The urine samples were analyzed by reverse phase and SE-HPLC. Stability of the radiolabeled IMP485 in urine was observed.

TABLE 16

Al$^{18}$F(IMP485) Alone at 1 h post injection:

| Tissue | n | Weight | STD WT | % ID/g | STD % ID/g | % ID/org | STD % ID/org | T/NT | STD T/NT |
|---|---|---|---|---|---|---|---|---|---|
| Tumor | 6 | 0.235 | 0.147 | 0.316 | 0.114 | 0.081 | 0.063 | 1.0 | 0.0 |
| Liver | 6 | 1.251 | 0.139 | 0.176 | 0.032 | 0.220 | 0.043 | 1.8 | 0.4 |
| Spleen | 6 | 0.085 | 0.019 | 0.210 | 0.181 | 0.018 | 0.017 | 1.9 | 0.9 |
| Kidney | 6 | 0.149 | 0.013 | 3.328 | 0.556 | 0.499 | 0.119 | 0.1 | 0.0 |
| Lung | 6 | 0.141 | 0.039 | 0.238 | 0.048 | 0.033 | 0.010 | 1.3 | 0.3 |
| Blood | 6 | 0.222 | 0.006 | 0.165 | 0.062 | 0.268 | 0.101 | 2.0 | 0.4 |
| Stomach | 6 | 0.478 | 0.083 | 0.126 | 0.110 | 0.057 | 0.045 | 3.5 | 1.6 |
| Sm Int. | 6 | 0.896 | 0.098 | 0.396 | 0.128 | 0.353 | 0.110 | 0.8 | 0.3 |
| Lg Int. | 6 | 0.504 | 0.056 | 0.081 | 0.019 | 0.041 | 0.010 | 3.9 | 0.9 |
| Muscle | 6 | 0.103 | 0.029 | 0.114 | 0.079 | 0.011 | 0.008 | 4.1 | 2.5 |
| Scapula | 6 | 0.057 | 0.015 | 0.107 | 0.019 | 0.006 | 0.001 | 2.9 | 0.7 |

TABLE 17

Al$^{18}$F(IMP485) Alone at 3 h post injection:

| Tissue | n | Weight | STD WT | % ID/g | STD % ID/g | % ID/org | STD % ID/org | T/NT | STD T/NT |
|---|---|---|---|---|---|---|---|---|---|
| Tumor | 6 | 0.265 | 0.126 | 0.088 | 0.020 | 0.022 | 0.011 | 1.0 | 0.0 |
| Liver | 6 | 1.219 | 0.091 | 0.095 | 0.047 | 0.114 | 0.056 | 13.6 | 31.4 |
| Spleen | 6 | 0.091 | 0.015 | 0.065 | 0.009 | 0.006 | 0.001 | 1.4 | 0.2 |
| Kidney | 6 | 0.154 | 0.013 | 2.265 | 0.287 | 0.345 | 0.028 | 0.0 | 0.0 |
| Lung | 6 | 0.142 | 0.008 | 0.073 | 0.019 | 0.010 | 0.003 | 1.3 | 0.6 |
| Blood | 6 | 0.236 | 0.019 | 0.008 | 0.005 | 0.013 | 0.007 | 21.0 | 27.9 |
| Stomach | 6 | 0.379 | 0.054 | 0.041 | 0.017 | 0.016 | 0.008 | 2.5 | 1.0 |
| Sm. Int. | 6 | 0.870 | 0.042 | 0.137 | 0.031 | 0.119 | 0.029 | 0.7 | 0.3 |
| Lg. Int. | 6 | 0.557 | 0.101 | 0.713 | 0.215 | 0.408 | 0.194 | 0.1 | 0.0 |
| Muscle | 6 | 0.134 | 0.038 | 0.013 | 0.007 | 0.002 | 0.001 | 203.9 | 486.6 |
| Scapula | 6 | 0.074 | 0.009 | 0.079 | 0.026 | 0.006 | 0.002 | 1.2 | 0.6 |

TABLE 18

TF2 + Al$^{18}$F(IMP485), at 1 h post peptide injection:

| Tissue | n | Weight | STD WT | % ID/g | STD % ID/g | % ID/org | STD % ID/org | T/NT | STD T/NT |
|---|---|---|---|---|---|---|---|---|---|
| Tumor | 7 | 0.291 | 0.134 | 28.089 | 4.545 | 8.025 | 3.357 | 1 | 0 |
| Liver | 7 | 1.261 | 0.169 | 0.237 | 0.037 | 0.295 | 0.033 | 123 | 38 |
| Spleen | 7 | 0.081 | 0.013 | 0.254 | 0.108 | 0.020 | 0.008 | 139 | 87 |
| Kidney | 7 | 0.140 | 0.018 | 3.193 | 0.730 | 0.444 | 0.098 | 9 | 4 |
| Lung | 7 | 0.143 | 0.014 | 0.535 | 0.147 | 0.075 | 0.018 | 57 | 22 |
| Blood | 7 | 0.205 | 0.029 | 0.278 | 0.071 | 0.456 | 0.129 | 110 | 43 |
| Stomach | 7 | 0.473 | 0.106 | 0.534 | 1.175 | 0.265 | 0.598 | 381 | 318 |
| Sm. Int. | 7 | 0.877 | 0.094 | 0.686 | 0.876 | 0.586 | 0.725 | 75 | 39 |
| Lg. Int. | 7 | 0.531 | 0.068 | 0.104 | 0.028 | 0.055 | 0.015 | 291 | 121 |
| Muscle | 7 | 0.090 | 0.014 | 0.136 | 0.102 | 0.012 | 0.009 | 348 | 274 |
| Scapula | 6 | 0.189 | 0.029 | 0.500 | 0.445 | 0.095 | 0.092 | 120 | 108 |

TABLE 19

TF2 + Al$^{18}$F(IMP485), at 3 h post peptide injection:

| Tissue | n | Weight | STD WT | % ID/g | STD % ID/g | % ID/org | STD ID/org | T/NT | STD T/NT |
|---|---|---|---|---|---|---|---|---|---|
| Tumor | 7 | 0.320 | 0.249 | 26.518 | 5.971 | 8.127 | 5.181 | 1 | 0 |
| Liver | 7 | 1.261 | 0.048 | 0.142 | 0.019 | 0.178 | 0.025 | 189 | 43 |
| Spleen | 7 | 0.079 | 0.012 | 0.138 | 0.031 | 0.011 | 0.002 | 195 | 41 |

TABLE 19-continued

TF2 + Al[18]F(IMP485), at 3 h post peptide injection:

| Tissue | n | Weight | STD WT | % ID/g | STD % ID/g | % ID/org | STD ID/org | T/NT | STD T/NT |
|---|---|---|---|---|---|---|---|---|---|
| Kidney | 7 | 0.144 | 0.012 | 2.223 | 0.221 | 0.319 | 0.043 | 12 | 3 |
| Lung | 7 | 0.145 | 0.014 | 0.244 | 0.056 | 0.035 | 0.005 | 111 | 24 |
| Blood | 7 | 0.229 | 0.014 | 0.023 | 0.008 | 0.037 | 0.012 | 1240 | 490 |
| Stomach | 7 | 0.430 | 0.069 | 0.025 | 0.017 | 0.010 | 0.005 | 1389 | 850 |
| Sm. Int. | 7 | 0.818 | 0.094 | 0.071 | 0.029 | 0.059 | 0.028 | 438 | 207 |
| Lg. Int. | 7 | 0.586 | 0.101 | 0.353 | 0.160 | 0.206 | 0.103 | 86 | 33 |
| Muscle | 7 | 0.094 | 0.014 | 0.025 | 0.006 | 0.002 | 0.001 | 1129 | 451 |
| Scapula | 7 | 0.140 | 0.030 | 0.058 | 0.018 | 0.008 | 0.002 | 502 | 193 |

Conclusions

The IMP485 labels as well as or better than IMP467, with equivalent stability in serum. However, IMP485 is much easier to synthesize than IMP467. Preliminary studies have shown that $^{18}$F-labeling of lyophilized IMP485 works as well as non-lyophilized peptide (data not shown). The presence of alkyl or aryl groups in the linker joining the chelating moiety to the rest of the peptide was examined. The presence of aryl groups in the linker appears to increase the radiolabeling yield relative to the presence of alkyl groups in the linker.

Biodistribution of IMP485 in the presence or absence of pretargeting antibody resembles that observed with IMP467. In the absence of pretargeting antibody, distribution of radiolabeled peptide in tumor and most normal tissues is low and the peptide is removed from circulation by kidney excretion. In the presence of the 112 antibody, radiolabeled IMP485 is found primarily in the tumor, with little distribution to normal tissues. Kidney radiolabeling is substantially decreased in the presence of the pretargeting antibody. We conclude that IMP485 and other peptides with aryl groups in the linker are highly suitable for PET imaging with $^{18}$F-labeling.

Example 28

Kit Formulation of IMP485 for Imaging

We report a simple, general kit formulation for labeling peptides with [18]F. A ligand that contains 1,4,7-triazacyclononane-1,4-diacetate (NODA) attached to a methyl phenylacetic acid (MPAA) group was used to form a single stable complex with (AlF)$^{2+}$. The lyophilized kit contained IMP485, a di-HSG hapten-peptide used for pretargeting. The kit was reconstituted with an aqueous solution of [18]F−, heated at 100-110° C. for 15 min, followed by a rapid purification by solid-phase extraction (SPE). In vitro and in vivo stability and tumor targeting of the Al[18]F(IMP485) were examined in nude mice bearing human colon cancer xenografts pretargeted with an anti-CEACAM5 bispecific antibody. $^{18}$F-labeling of MPAA-bombesin and somatostatin peptides also was evaluated.

The HSG peptide was labeled with [18]F− as a single isomer complex, in high yield (50-90%) and high specific activity (up to 153 GBq/μmol), within 30 min. It was stable in human serum at 37° C. for 4 h, and in vivo showed low uptake (0.06%±0.02 ID/g) in bone. At 3 h, pretargeted animals had high Al[18]F(IMP485) tumor uptake (26.5%±6.0 ID/g), with ratios of 12±3, 189±43, 1240±490 and 502±193 for kidney, liver, blood and bone, respectively. Bombesin and octreotide analogs were labeled with comparable yields. In conclusion, $^{18}$F-labeled peptides can be produced as a stable, single [Al[18]F] complex with good radiochemical yields and high specific activity in a simple one-step kit.

Reagents List

Reagents were obtained from the following sources: Acetic acid (JT Baker 6903-05 or 9522-02), Sodium hydroxide (Aldrich semiconductor grade 99.99% 30, 657-6), α,α-Trehalose (JT Baker 4226-04), Aluminum chloride hexahydrate (Aldrich 99% 237078), Ascorbic acid (Aldrich 25, 556-4).

Acetate Buffer 2 mM—Acetic acid, 22.9 μL (4.0×10$^{-4}$ mol) was diluted with 200 mL water and neutralized with 6 N NaOH (~15 μL) to adjust the solution to pH 4.22.

Aluminum Solution 2 mM—Aluminum hexahydrate, 0.0225 g (9.32×10$^{-5}$ mol) was dissolved in 47 mL DI water.

α,α-Trehalose Solution—α,α-Trehalose, 4.004 g was dissolved in 40 mL DI water to make a 10% solution.

Peptide Solution, IMP485 2 mM—The peptide IMP485 (0.0020 g, 1.52 μmol) was dissolved in 762 μL of 2 mM acetate buffer. The pH was 2.48 (the peptide was lyophilized as the TFA salt). The pH of the peptide solution was adjusted to pH 4.56 by the addition of 4.1 μL of 1 M NaOH.

Ascorbic Acid Solution 5 mg/mL—Ascorbic acid, 0.0262 g (1.49×10$^{-4}$ mol) was dissolved in 5.24 mL DI water.

Formulation of Peptide Kit

The peptide, 20 μL (40 nmol) was mixed with 12 μL (24 nmol) of Al, 100 μL of trehalose, 20 μL (0.1 mg) ascorbic acid and 900 μL of DI water in a 3 mL lyophilization vial. The final pH of the solution was about pH 4.0. The vial was frozen, lyophilized and sealed under vacuum. Ten and 20 nmol kits have also been made. These kits are made the same as the 40 nmol kits keeping the peptide to Al$^{3+}$ ratio of 1 peptide to 0.6 Al$^{3+}$ but formulated in 2 mL vials with a total fill of 0.5 mL.

Purification of [18]F−

The crude [18]F− was received in 2 mL of DI water in a syringe. The syringe was placed on a syringe pump and the liquid pushed through a Waters CM cartridge followed by a QMA cartridge. Both cartridges were washed with 10 mL DI water. A sterile disposable three way valve between the two cartridges was switched and 1 mL commercial sterile saline was pushed through the QMA cartridge in 200 μL fractions. The second fraction usually contains ~80% of the [18]F− regardless of the amount of [18]F− applied (10-300 mCi loads were tested).

We alternatively use commercial [18]F− in saline, which has been purified on a QMA cartridge. This is a concentrated version of the commercial bone imaging agent so it is readily available and used in humans. The activity is supplied in 200 μL in a 0.5 mL tuberculin syringe.

Radiolabeling

The peptide was radiolabeled by adding [18]F− in 200 μL saline to the lyophilized peptide in a crimp sealed vial and then heating the solution to 90-110° C. for 15 min. The peptide was purified by adding 800 mL of DI water in a 1 mL syringe to the reaction vial, removing the liquid with the 1 mL syringe and applying the liquid to a Waters HLB column (1 cc, 30 mg). The HLB column was placed on a crimp sealed 5 mL vial and the liquid was drawn into the vial under vacuum supplied by a remote (using a sterile disposable line) 10 mL syringe. The reaction vial was washed with two one mL aliquots of DI water, which were also drawn through the column. The column was then washed with 1 mL more of DI water. The column was then moved to a vial containing buffered lyophilized ascorbic acid (~pH 5.5, 15 mg). The radiolabeled product was eluted with three 200 µL portions of 1:1 EtOH/DI water. The yield was determined by measuring the activity on the HLB cartridge, in the reaction vial, in the water wash and in the product vial to get the percent yield.

Adding ethanol to the radiolabeling reaction can increase the labeling yield. A 20 nmol kit can be reconstituted with a mixture of 200 µL $^{18}F^-$ in saline and 200 µL ethanol. The solution is then heated to 110° C. in the crimp sealed vial for 16 min. After heating, 0.8 mL of water was added to the reaction vial and the activity was removed with a syringe and placed in a dilution vial containing 2 mL of DI water. The reaction vial was washed with 2×1 mL DI water and each wash was added to the dilution vial. The solution in the dilution vial was applied to the HLB column in 1-mL aliquots. The column and the dilution vial were then washed with 2×1-mL water. The radiolabeled peptide was then eluted from the column with 3×200 µL of 1:1 ethanol/water in fractions. The peptide can be labeled in good yield and up to 4,100 Ci/mmol specific activity using this method.

The yield for this kit and label as described was 80-90% when labeled with 1.0 mCi of $^{18}F^-$. When higher doses of $^{18}F^-$ (~100 mCi) were used the yield dropped. However if ethanol is added to the labeling mixture the yield goes up. If the peptides are diluted too much in saline the yields will drop. The labeling is also very sensitive to pH. For our peptide with this ligand we have found that the optimal pH for the final formulation was pH 4.0±0.2.

The purified radiolabeled peptide in 50 µL 1:1 EtOH/H$_2$O was mixed with 150 µL of human serum and placed in the HPLC autosampler heated to 37° C. and analyzed by RP-HPLC. No detectable $^{18}F$ above background at the void volume was observed even after 4 h.

TABLE 20

IMP 485 Labeling

| Vial #/ Peptide | nmol of Peptide | Volume Saline µL | Volume EtOH µL | Activity at start mCi | Activity of isolated product mCi | % Yield | Specific Activity Ci/mmol |
|---|---|---|---|---|---|---|---|
| 1. IMP485 | 10 | 100 | 0 | 20.0 | 7.10 | 62 | |
| 2. IMP485 | 10 | 50 | 50 | 19.4 | 9.43 | 78 | |
| 3. IMP485 | 10 | 200 | 0 | 19.07 | 5.05 | 38 | |
| 4. IMP485 | 20 | 100 | 100 | 37.3 | 22.3 | 80 | |
| 5. IMP485 | 10 | 100 | 0 | 45.7 | 16.2 | 42 | |
| 6. IMP485 | 20 | 200 | 200 | 175.6 | 82.7 | 58 | 4135 |

Synthesis and Radiolabeling of IMP486: Al—OH (IMP485)

IMP485 (21.5 mg, 0.016 mmol) was dissolved in 1 mL of 2 mM NaOAc, pH 4.4 and treated with AlCl$_3$.6H$_2$O (13.2 mg, 0.055 mmol). The pH was adjusted to 4.5-5.0 and the reaction mixture was refluxed for 15 minutes. The crude mixture was purified by preparative RP-HPLC to yield a white solid (11.8 mg).

The pre-filled Al(NODA) complex (IMP486) was also radiolabeled in excellent yield after formulating into lyophilized kits. The labeling yields with IMP486 (Table 21) were as good as or better than IMP485 kits (Table 20) when labeled in saline. This high efficiency of radiolabeling with chelator preloaded with aluminum was not observed with any of the other Al(NOTA) complexes tested (data not shown). The equivalency of labeling in saline and in 1:1 ethanol/water the labeling yields was also not observed with other chelating moieties (not shown).

TABLE 21

IMP486 Labeling

| Peptide 20 nmol | Volume Saline | Volume EtOH | Activity at start mCi | Activity of isolated product mCi | % Yield | Specific Activity Ci/mmol |
|---|---|---|---|---|---|---|
| IMP486 | 100 µL | 0 | 46 | 28 | 76 | 2800 |
| IMP485 | 100 µL | 100 µL | 41 | 25 | 83 | |
| IMP486 | 100 µL | 100 µL | 43 | 22 | 81 | |
| IMP486 | 200 µL | 0 | 42 | 18 | 73 | |

Effect of Bulking Agents

An experiment was performed to compare yield using IMP485 kits (40 nmol) with different bulking agents. The peptide was labeled with 2 mCi of $^{18}F^-$ from the same batch of $^{18}F^-$ in 200 microliters saline. The bulking agents were introduced in water at a concentration of 5% by weight, with a dose of 200 microliters/vial. We tested sorbitol, trehalose, sucrose, mannitol and glycine as bulking agents. Results are shown in Table 22.

TABLE 22

Effects of Bulking Agents on Radiolabeling Yield (Refer table 15)

| Bulking Agent | Activity mCi | Yield % |
|---|---|---|
| Sorbitol | 2.17 | 82.9 |
| Glycine | 2.17 | 41.5 |
| Mannitol | 2.11 | 81.8 |
| Sucrose | 2.11 | 66.1 |
| Trehalose | 2.10 | 81.3 |

Sorbitol, mannitol and trehalose all gave radiolabeled product in the same yield. The sucrose kit and the glycine kit both had significantly lower yields. Trehalose was formulated into IMP485 kits at concentrations ranging from 2.5% to 50% by weight when reconstituted in 200 µL. The same radiolabeling yield, ~83%, was obtained for all concentrations, indicating that the $^{18}F$-radiolabeling of IMP485 was not sensitive to the concentration of the trehalose bulking agent. IMP 485 kits were formulated and stored at 2-8° C. under nitrogen for up to three days before lyophilization to assess the impact of lyophilization delays on the radiolabeling. The radiolabeling experiments indicated that yields were all ~80% at time zero, and with 1, 2, and 3 days of delay before lyophilization.

Ascorbic or gentisic acid often are added to radiopharmaceuticals during preparation to minimize radiolysis. When IMP485 (20 nmol) was formulated with 0.1, 0.5 and 1.0 mg of ascorbic acid at pH 4.1-4.2 and labeled with $^{18}F^-$ in 200 µL saline, final yields were 51, 31 and 13% isolated yields, respectively, suggesting 0.1 mg of ascorbic acid was the maximum amount that could be included in the formulation without reducing yields. Formulations containing gentisic acid did not label well. Ascorbic acid was also included in vials used to isolate the HLB purified product as an additional means of ensuring stability post-labeling. The IMP485 to $Al^{3+}$ ratio appeared to be optimal at 1:0.6, but good yields were obtained from 1:0.5 of up to a ratio of 1:1. The radiolabeling reaction was also sensitive to peptide concentration, with good yields obtained at concentrations of $1\times10^{-4}$ M and higher.

Effect of pH on Radiolabeling

The effect of pH on radiolabeling of IMP485 is shown in Table 23. The efficiency of labeling was pH sensitive and decreased at either higher or lower pH relative to the optimal pH of about 4.0.

TABLE 23

Effect of pH on IMP485 Radiolabeling Efficiency.

| pH | Yield % |
| --- | --- |
| 3.27 | 33 |
| 3.53 | 61 |
| 3.84 | 85 |
| 3.99 | 88 |
| 4.21 | 89 |
| 4.49 | 80 |
| 5.07 | 14 |

Collectively, these studies led to a final formulated kit that contained 0.5 mL of a sterile solution with 20 nmol IMP485, 12 nmoles $Al^{3+}$, 0.1 mg ascorbic acid, and 10 mg trehalose adjusted to 4.0±0.2, which was then lyophilized Biodistribution Biodistribution studies were performed in Taconic nude mice bearing subcutaneous LS174T tumor xenografts.

$Al^{18}F$(IMP485) alone: Mice bearing sc LS174T xenografts were injected with $Al^{18}F$(IMP485) (28 µCi, $5.2\times10^{-11}$ mol, 100 µL, iv). Mice were necropsied at 1 and 3 h post injection, 6 mice per time point.

TF2+$Al^{18}F$(IMP485) Pretargeting at 20:1 bsMab to peptide ratio: Mice bearing sc LS174T xenografts were injected with TF2 (163.2 µg, $1.03\times10^{-9}$ mol, iv) and allowed 16.3 h for clearance before injecting $Al^{18}F$(IMP485) (28 µCi, $5.2\times10^{-11}$ mol, 100 µL, iv). Mice were necropsied at 1 and 3 h post injection, 7 mice per time point.

TABLE 24

Biodistribution of TF2 pretargeted $Al^{18}F$(IMP485) or $Al^{18}F$(IMP485) alone at 1 and 3 h after peptide injection in nude mice bearing LS174T human colonic cancer xenografts.

| | Percent-injected dose per gram tissue (mean ± SD; N = 7) | | | |
| --- | --- | --- | --- | --- |
| | TF2 pregargeted $Al^{18}F$(IMP485) | | $Al^{18}F$(IMP485) alone | |
| Tissue | 1 h | 3 h | 1 h | 3 h |
| Tumor | 28.09 ± 4.55 | 26.52 ± 5.97 | 0.32 ± 0.11 | 0.09 ± 0.02 |
| Liver | 0.24 ± 0.04 | 0.14 ± 0.02 | 0.18 ± 0.03 | 0.10 ± 0.05 |
| Spleen | 0.25 ± 0.11 | 0.25 ± 0.11 | 0.21 ± 0.18 | 0.07 ± 0.01 |
| Kidney | 3.19 ± 0.73 | 2.22 ± 0.22 | 3.33 ± 0.56 | 2.27 ± 0.29 |
| Lung | 0.54 ± 0.15 | 0.24 ± 0.06 | 0.24 ± 0.05 | 0.07 ± 0.02 |
| Blood | 0.28 ± 0.07 | 0.02 ± 0.01 | 0.17 ± 0.06 | 0.09 ± 0.01 |
| Stomach | 0.53 ± 1.18 | 0.03 ± 0.01 | 0.13 ± 0.11 | 0.04 ± 0.02 |
| Sm. Int. | 0.69 ± 0.88 | 0.07 ± 0.03 | 0.40 ± 0.13 | 0.14 ± 0.03 |
| Lg. Int. | 0.10 ± 0.03 | 0.35 ± 0.16 | 0.08 ± 0.02 | 0.71 ± 0.22 |
| Muscle | 0.14 ± 0.10 | 0.03 ± 0.01 | 0.11 ± 0.08 | 0.01 ± 0.01 |
| Scapula | 0.5 ± 0.45 | 0.06 ± 0.02 | 0.11 ± 0.02 | 0.03 ± 0.01 |

Synthesis of IMP492 or $Al^{19}F$(IMP485)

IMP485 (16.5 mg, 0.013 mmol) was dissolved in 1 mL of 2 mM NaOAc, pH 4.43, 0.5 mL ethanol and treated with $AlF_3 \cdot 3H_2O$ (2.5 mg, 0.018 mmol). The pH was adjusted to 4.5-5.0 and the reaction mixture was refluxed for 15 minutes. On cooling the pH was once again raised to 4.5-5.0 and the reaction mixture refluxed for 15 minutes. The crude was purified by preparative RP-HPLC to yield a white solid (10.3 mg).

Synthesis of IMP490

(SEQ ID NO: 52)
NODA-MPAA-D-Phe-Cys-Phe-D-Trp-Lys-Thr-Cys-Throl

The peptide was synthesized on threoninol resin with the amino acids added in the following order: Fmoc-Cys(Trt)-OH, Fmoc-Thr(But)-OH, Fmoc-Lys(Boc)-OH, Fmoc-D-Trp(Boc)-OH, Fmoc-Phe-OH, Fmoc-Cys(Trt)-OH, Fmoc-D-Phe-OH and $(tBu)_2$NODA-MPAA. The peptide was then cleaved and purified by preparative RP-HPLC. The peptide was cyclized by treatment of the bis-thiol peptide with DMSO.

Synthesis of IMP491 or $Al^{19}F$(IMP490)

The $Al^{19}F$(IMP490) was prepared as described above (IMP492) to produce the desired peptide after HPLC purification.

Synthesis of IMP493

(SEQ ID NO: 53)
NODA-MPAA-(PEG)$_3$-Gln-Trp-Ala-Val-Gly-His-Leu-Met-NH$_2$

The peptide was synthesized on Sieber amide resin with the amino acids added in the following order: Fmoc-Met-OH, Fmoc-Leu-OH, Fmoc-His(Trt)-OH, Fmoc-Gly-OH, Fmoc-Val-OH, Fmoc-Ala-OH, Fmoc-Trp(Boc)-OH, Fmoc-Gln(Trt)-OH, Fmoc-NH-(PEG)$_3$-COOH and $(tBu)_2$NODA-MPAA. The peptide was then cleaved and purified by preparative RP-HPLC.

The affinity of the $Al^{19}F$ complex of IMP493 was $EC_{50}$=183 nm versus $EC_{50}$=59 nm for $^{125}$I-bombesin. The IMP493 kit radiolabeled with ~100 MBq of $^{18}F^-$ had a 70% yield. Radiolabeling IMP490 with 100 MBq of $^{18}F^-$ resulted in 80% yield, which was reduced to 65% when 2.11 GBq $^{18}F^-$ was used. The peptide is eluted as a single radiolabeled peak at 15.4 min using HPLC (not shown).

Synthesis of IMP494 or $Al^{19}F$(IMP493)

The $Al^{19}F$(IMP493) was prepared as described above (IMP492) to produce the desired peptide after HPLC purification.

Example 29

Other Prosthetic Group Labeling Methods Using $Al^{18}F$

In certain embodiments, the aluminum fluoride labeling method may be performed using prosthetic group labeling methods for molecules that are sensitive to heat. Prosthetic group conjugation may be carried out at lower temperatures for heat-sensitive molecules.

The prosthetic group NOTA is labeled with $^{18}F$ as described above and then it is attached to the targeting molecule. In one non-limiting example, this is performed with an aldehyde NOTA that is then attached to an amino-oxy compound on a targeting molecule. Alternatively an amino-oxy maleimide is reacted with the aldehyde and then the maleimide is attached to a cysteine on a targeting molecule (Toyokuni et al., 2003, Bioconj Chem 14:1253).

In another alternative, the AlF-chelator complexes are attached to targeting molecules through click chemistry. The ligands are first labeled with Al$^{18}$F as discussed above. The Al$^{18}$F-chelate is then conjugated to a targeting molecule through a click chemistry reaction. For example, an alkyne NOTA is labeled according to Marik and Stucliffe (2006, Tetrahedron Lett 47:6681) and conjugated to an azide containing targeting agent.

Radiolabeling of Kits with $^{18}$F$^-$ in Saline

The $^{18}$F$^-$ (0.01 mCi or higher) is received in 200 μL of saline in a 0.5 mL syringe and the solution is mixed with 200 μL of ethanol and injected into a lyophilized kit as described above. The solution is heated in the crimp sealed container at 100-110° C. for 15 min. The solution is diluted with 3 mL water and eluted through an HLB cartridge. The reaction vial and the cartridge are washed with 2×1 mL portions of water and then the product is eluted into a vial containing buffered ascorbic acid using 1:1 ethanol water in 0.5 mL fractions. Some of the ethanol may be evaporated off under a stream of inert gas. The solution is then diluted in saline and passed through a 0.2 μm sterile filter prior to injection.

Example 30

Maleimide Conjugates of NOTA for $^{18}$F-Labeling

Figure 15:
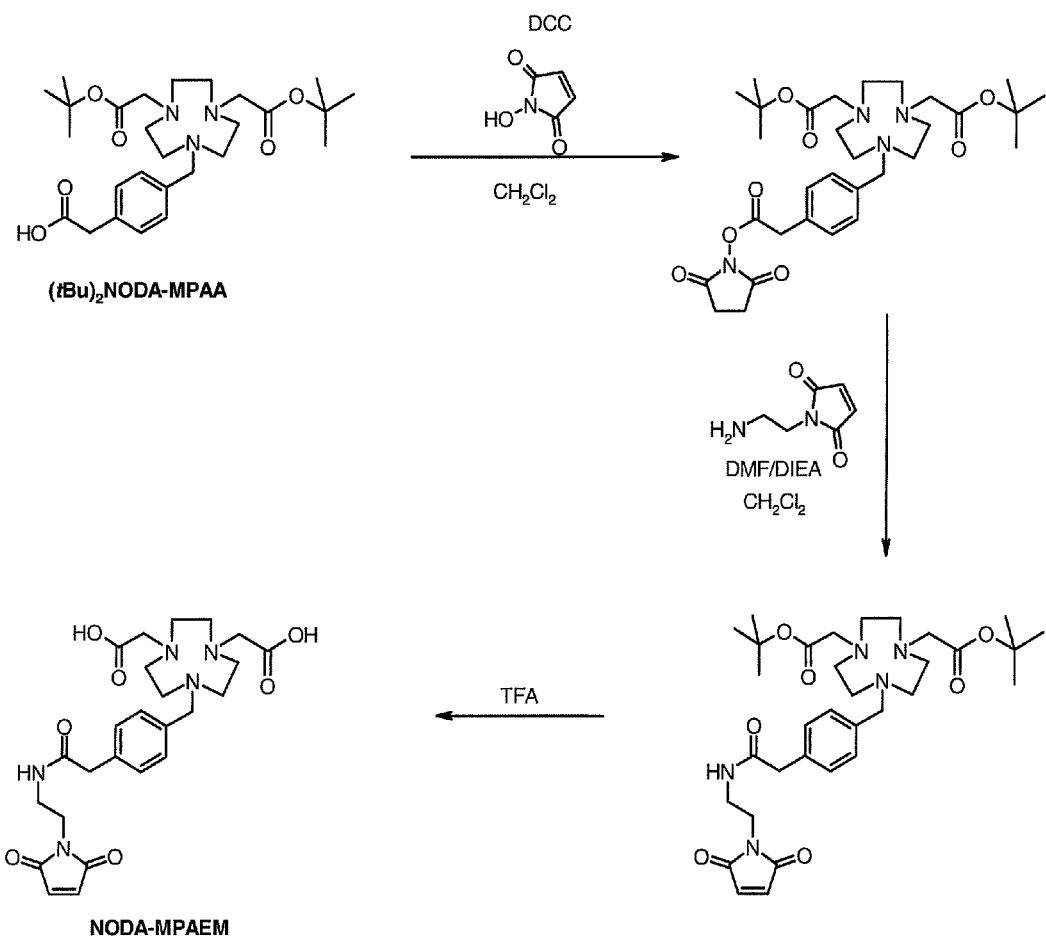
FIG. 15. Synthesis of maleimide conjugate of NOTA.

The Examples above describe a novel method of $^{18}$F-labeling, which captures a ([$^{18}$]AlF)$^{2+}$ complex, using a NOTA-derived ligand bound on a peptide. These labeled peptides were stable in vivo and retained their binding abilities (McBride et al., 2009, J. Nucl. Med. 50, 991-998; McBride et al., 2010, Bioconjug. Chem. 21, 1331-1340; Layerman et al., 2010, J. Nucl. Med. 51, 454-461; McBride et al. 2011, J. Nucl. Med. 52 (Suppl. 1), 313-314P (abstract 1489)). Although this procedure allows peptides to be radiofluorinated in one simple step within 30 min, it requires agents to be heated to ~100° C., which is unsuitable for most proteins and some peptides. We and others have found that an aromatic group attached to one of the nitrogen atoms of the triazacyl-cononane ring of NODA can enhance the yield for the ([$^{18}$F]AlF)$^{2+}$ complexation compared to some alkyl and carboxyl substituents (D'Souza et al., 2011, Bioconjug. Chem. 1793-1803; McBride et al., 2010, Bioconjug. Chem. 21, 1331-1340; Shetty et al. 2011, Chem. Comm. DOI: 10.1039/c1cc13151f). In the present Example, we explored the potential for labeling heat-labile compounds with ([$^{18}$F]AlF)$^{2+}$, using a new ([$^{18}$F]AlF)$^{2+}$-binding ligand that contains 1,4,7-triazacyclononane-1,4-diacetate (NODA) attached to a methyl phenylacetic acid group (MPAA). This was conjugated to N-(2-aminoethyl)maleimide (N-AEM) to form NODA-MPAEM. (Details of the synthesis are shown in FIG. 15.) The NODA-MPAEM was labeled with ([$^{18}$F]AlF)$^{2+}$ at 105° C. in 49-82% yield and conjugated at room temperature to an antibody Fab' fragment in 69-80% yield (total time ~50 min) and with retention of immunoreactivity. These data indicate that the rapid and simple [Al$^{18}$F]-labeling method can be easily adapted for preparing heat-sensitive compounds with $^{18}$F quickly and in high yields.

Synthesis of Bis-t-butyl-NODA-MPAA NHS ester: (tBu)$_2$NODA-MPAA NHS ester

To a solution of (tBu)$_2$NODA-MPAA (175.7 mg, 0.347 mmol) in CH$_2$Cl$_2$ (5 mL) was added 347 μL (0.347 mmol) DCC (1 M in CH$_2$Cl$_2$), 42.5 mg (0.392 mmol) N-hydroxysuccinimide (NHS), and 20 μL N,N-diisopropylethylamine (DIEA). After 3 h DCU was filtered off and solvent evaporated. The crude mixture was purified by flash chromatography on (230-400 mesh) silica gel (CH$_2$Cl$_2$:MeOH, 100:0 to 80:20) to yield (128.3 mg, 61.3%) of the NHS ester. The HRMS (ESI) calculated for C$_{31}$H$_{46}$N$_4$O$_8$ (M+H)$^+$ was 603.3388, observed was 603.3395.

Synthesis of NODA-MPAEM: (MPAEM=methyl phenyl acetamido ethyl maleimide)

To a solution of (tBu)$_2$NODA-MPAA NHS ester (128.3 mg, 0.213 mmol) in CH$_2$Cl$_2$ (5 mL) was added a solution of 52.6 mg (0.207 mmol) N-(2-aminoethyl) maleimide trifluoroacetate salt in 250 μL DMF and 20 μL DIEA. After 3 h the solvent was evaporated and the concentrate was treated with 2 mL TFA. The crude product was diluted with water and purified by preparative RP-HPLC to yield (49.4 mg, 45%) of the desired product. HRMS (ESI) calculated for C$_{25}$H$_{33}$N$_5$O$_7$ (M+H)$^+$ was 516.2453, observed was 516.2452.

$^{18}$F-Labeling of NODA-MPAEM

The NODA-MPAEM ligand (20 nmol; 10 μL), dissolved in 2 mM sodium acetate (pH 4), was mixed with AlCl$_3$ (5 μL of 2 mM solution in 2 mM acetate buffer, 200 μL of $^{18}$F$^-$ (0.73 and 1.56 GBq) in saline, and 200 μL of acetonitrile. After heating at 105-109° C. for 15-20 min, 800 μL of deionized (DI) water was added to the reaction solution, and the entire contents removed to a vial (dilution vial) containing 1 mL of deionized (DI) water. The reaction vial was washed with 2×1 mL DI water and added to the dilution vial. The crude product was then passed through a 1-mL HLB column, which was washed with 2×1 mL fractions of DI water. The labeled product was eluted from the column using 3×200 μL of 1:1 EtOH/water.

Conjugation of Al$^{18}$F(NODA-MPAEM) to hMN-14 Fab'

Fab' fragments of humanized MN-14 anti-CEACAM5 IgG (labetuzumab) were prepared by pepsin digestion, followed by TCEP (Tris(2-carboxyethyl)phosphine) reduction, and then formulated into a lyophilized kit containing 1 mg (20 nmol) of the Fab' (2.4 thiols/Fab') in 5% trehalose and 0.025 M sodium acetate, pH 6.72. The kit was reconstituted with 0.1 mL PBS, pH 7.01, and mixed with the Al$^{18}$F(NODA-MPAEM) (600 μL 1:1 EtOH/H$_2$O). After incubating for 10 min at room temperature, the product was purified on a 3-mL SEPHADEX G50-80 spin column in a 0.1 M, pH 6.5 sodium acetate buffer (5 min). The isolated yield was calculated by dividing the amount of activity in the eluent by the total activity in the eluent and the activity on the column.

Immunoreactivity of the purified product was analyzed by adding an excess of CEA and separating on SE-HPLC, comparing to a profile of the product alone. The product was also analyzed by RP-HPLC to assess percent-unbound Al$^{18}$F (NODA-MPAEM).

$^{99m}$Tc-CEA-Scan®

A CEA-SCAN® kit containing 1.2 mg of IMMU-4, a murine anti-CEACAM5 Fab' (anti-CEA, 2.4×10$^{-2}$ pima was labeled with 453 MBq $^{99m}$TcO$_4$$^-$Na$^+$ in 1 mL saline according to manufacturer's instructions and used without further purification.

Animal Study

Nude mice were inoculated subcutaneously with CaPan-1 human pancreatic adenocarcinoma (ATCC Accession No. HTB-79, Manassas, Va.). When tumors were visible, the animals were injected intravenously with 100 μL of the radiolabeled Fab'. The Al$^{18}$F(NODA-MPAES)-hMN-14 Fab' was diluted in saline to 3.7 MBq/100 μL containing ~2.8 μg of Fab'. A $^{99m}$Tc-IMMU-4 Fab' aliquot (16.9 MBq) was removed and diluted with saline (0.85 MBq/100 μL containing ~2.8 μg of Fab'). The animals were necropsied at 3 h post injection, tissues and tumors removed, weighed, and counted by gamma scintillation, together with standards prepared from the injected products. The data are expressed as percent injected dose per gram.

Results

Synthesis and Reagent Preparation

The NODA-MPAEM was produced as shown in FIG. 15, where the (tBu)$_2$NODA-MPAA was coupled to 2-aminoethyl-maleimide and then deprotected to form the desired product. The crude product was diluted with water and purified by preparative RP-HPLC to yield (49.4 mg, 45%) of the desired product [HRMS (ESI) calculated for C$_{25}$H$_{33}$N$_5$O$_7$ (M+H)$^+$ 516.2453, found 516.2452].

Radiolabeling

The NODA-MPAEM (20 nmol) was mixed with 10 nmol of Al$^{3+}$ and labeled with 0.73 GBq and 1.56 GBq of $^{18}$F$^-$ in saline. After SPE purification, the isolated yields of Al$^{18}$F(NODA-MPAEM) were 82% and 49%, respectively, with a synthesis time of about 30 min. The Al$^{18}$F(NODA-MPAES)-hMN-14 Fab' conjugate was isolated in 74% and 80% yields after spin-column purification for the low and high dose protein labeling, respectively. The total process was completed within 50 min. The specific activity for the purified Al$^{18}$F(NODA-MPAES)-hMN-14 Fab' was 19.5 GBq/μmol for the high-dose label and 10.9 GBq/μmol for the low dose label.

SE-HPLC analysis of the labeled protein for the 0.74-GBq run showed the $^{18}$F-labeled Fab' as a single peak and all of the activity shifted when excess CEA was added (not shown). RP-HPLC analysis on a C4 column showed the labeled maleimide standard eluting at 7.5 min, while the purified $^{18}$F-protein eluted at 16.6 min (not shown). There was no unbound Al$^{18}$F(NODA-MPAEM) in the spin-column purified product.

Serum Stability

The Al$^{18}$F(NODA-MPAES)-hMN-14 Fab' was mixed with fresh human serum and incubated at 37° C. SE-HPLC analysis over a 3-h period, with and without CEA showed that the product was stable and retained binding to CEA (not shown).

Biodistribution

The biodistribution of the Al$^{18}$F(NODA-MPAES)-hMN-14 Fab' and the $^{99m}$Tc-IMMU-4 murine Fab' was assessed in nude mice bearing Capan-1 pancreatic cancer xenografts. At 3 h post-injection, both agents showed an expected elevated uptake in the kidneys, since Fab' is renally filtered from the blood (Table 25). The [Al$^{18}$F]-Fab' concentration in the blood was significantly (P<0.0001) lower than the $^{99m}$Tc-Fab', with a correspondingly elevated uptake in the liver and spleen. The faster blood clearance of the [Al$^{18}$F]-Fab' likely contributed to the lower tumor uptake as compared to the $^{99m}$Tc-Fab' (2.8±0.3 vs. 6.8±0.7, respectively), but it also resulted in a more favorable tumor/blood ratio for the fluorinated Fab' (5.9±1.3 vs. 0.9±0.1, respectively). Bone uptake for both products was similar, suggesting the Al$^{18}$F(NODA) was tightly held by the Fab'.

TABLE 25

Biodistribution of Al$^{18}$F(NODA-MPAES)-hMN-14 Fab' and $^{99m}$Tc-IMMU-4 Fab' at 3 h after injection with 0.37 MBq (~3 μg) of each conjugate in nude mice bearing Capan-1 human pancreatic cancer xenografts (N = 6).

| Tissue | Al$^{18}$F(NODA-MPAES)-hMN-14 Fab' | | $^{99m}$Tc CEA Scan IMMU-4 Fab' | |
|---|---|---|---|---|
| | % ID/g | T/NT | % ID/g | T/NT |
| Capan-1 | 2.8 ± 0.3 | — | 6.8 ± 0.7 | — |
| (weight ± SD) | (0.22 ± 0.08 g) | | (0.16 ± 0.05 g) | |
| Liver | 17.5 ± 3.8 | 0.2 ± 0.04 | 4.6 ± 0.4 | 1.5 ± 0.1 |
| Spleen | 11.3 ± 1.6 | 0.3 ± 0.04 | 3.5 ± 0.5 | 2.0 ± 0.3 |
| Kidney | 216 ± 30.9 | 0.0 ± 0.0 | 183 ± 22.5 | 0.04 ± 0.01 |
| Lung | 4.2 ± 1.6 | 0.8 ± 0.5 | 4.4 ± 0.8 | 1.6 ± 0.3 |
| Blood | 0.5 ± 0.1 | 5.9 ± 1.3 | 7.6 ± 0.9 | 0.9 ± 0.1 |
| Stomach | 0.6 ± 0.1 | 4.7 ± 1.2 | 2.4 ± 0.3 | 2.9 ± 0.4 |
| Sm. Int. | 2.2 ± 0.2 | 1.3 ± 0.1 | 3.4 ± 0.4 | 2.0 ± 0.2 |
| Lg. Int. | 1.1 ± 0.4 | 2.8 ± 0.7 | 5.2 ± 1.0 | 1.3 ± 0.3 |
| Muscle | 0.4 ± 0.1 | 6.7 ± 1.3 | 1.1 ± 0.2 | 6.1 ± 1.0 |
| Scapula | 1.6 ± 0.4 | 1.8 ± 0.4 | 2.0 ± 0.2 | 3.4 ± 0.5 |

Discussion

We prepared a simple NODA-MPAEM ligand for attachment to thiols on temperature-sensitive proteins or other molecules bearing a sulfhydryl group. To avoid exposing the heat-labile compound to high temperatures, the NODA-MPAEM was first mixed with Al$^{3+}$ and $^{18}$F$^-$ in saline and heated at 100-115° C. for 15 min to form the Al$^{18}$F(NODA-MPAEM) intermediate. This intermediate was rapidly purified by SPE in 49-82% isolated yield (67.7±13.0%, n=5), depending on the amount of activity added to a fixed amount (20 nmol) of the NODA-MPAEM. The Al$^{18}$F(NODA-MPAEM) was then efficiently (69-80% isolated yield, 74.3±5.5, n=3) coupled to a reduced Fab' in 10-15 min, using a spin column gel filtration procedure to isolate the radiolabeled protein, in this case an antibody Fab' fragment. The entire two-step process was completed in ~50 min, and the labeled product retained its molecular integrity and immunoreactivity. Thus, the feasibility of extending the simplicity of the [Al$^{18}$F]-labeling procedure to heat-sensitive compounds was established.

The [Al$^{18}$F]-ligand complex has been shown to be very stable in serum in vitro, and in animal testing, minimal bone uptake is seen (McBride et al., 2009, J. Nucl. Med. 50, 991-998; D'Souza et al., 2011a, J. Nucl. Med. 52 (Suppl. 1), 171P (abstract 577)). In this series of studies, $^{18}$F associated with the NODA-MPAEM compound conjugated to a Fab' was stable in serum in vitro, and the conjugate retained binding to CEA. When injected into nude mice, there was selective localization in the tumor, providing a ~6:1 tumor/blood ratio. Bone uptake was similar for the Al$^{18}$F(NODA-MPAES)-hMN-14 Fab' and the $^{99m}$Tc-IMMU-4 murine Fab', again reflecting in vivo stability of the $^{18}$F or Al$^{18}$F complex. However, [Al$^{18}$F]-Fab' hepatic and splenic uptake was higher as compared to the $^{99m}$Tc-IMMU-4. The specific NODA derivative can be modified in different ways to accommodate conjugation to other reactive sites on peptides or proteins. However, use of this particular derivative showed that the Al$^{18}$F-labeling procedure can be adapted for use with heat-labile compounds.

Conclusions

NODA-MPAEM was labeled rapidly with $^{18}$F$^-$ in saline and then conjugated to the immunoglobulin Fab' protein in high yield. The labeling method uses only inexpensive disposable purification columns, and while not requiring an automated device to perform the labeling and purification, it can be easily adapted to such systems. Thus, the NODA-MPAEM derivative established that this or other NODA-containing derivatives can extend the capability of facile ([$^{18}$F]AlF)$^{2+}$ fluorination to heat-labile compounds.

Example 31

Improved $^{18}$F-Labeling of NOTA-Octreotide

The aim of this study was to further improve the rapid one-step method for $^{18}$F-labeling of NOTA-conjugated octreotide. Octreotide was conjugated with a NOTA ligand and was labeled with $^{18}$F in a single-step, one-pot method. Aluminum (Al$^{3+}$) was added to $^{18}$F$^-$ and the AlF$^{2+}$ was incorporated into NOTA-octreotide, as described in the Examples above. The labeling procedure was optimized with regard to aluminum:NOTA ratio, ionic strength and temperature. Radiochemical yield and specific activity were determined.

Under optimized conditions, NOTA-octreotide was labeled with Al$^{18}$F in a single step with 98% yield. The radiolabeling, including purification, was performed in 45 min. Optimal labeling yield was observed with Al:NOTA ratios around 1:20. Lower ratios led to decreased labeling efficiency. Labeling efficiencies in the presence of 0%, 25%, 50%, 67% and 80% acetonitrile in Na-acetate pH 4.1 were 36%, 43%, 49%, 70% and 98%, respectively, indicating that increasing concentrations of the organic solvent considerably improved labeling efficiency. Similar results were obtained in the presence of ethanol, DMF and THF. Labeling in the presence of DMSO failed. Labeling efficiencies in 80% MeCN at 40° C., 50° C. and 60° C. were 34%, 65%, 83%, respectively. Labeling efficiency was >98% at 80° C. and 100° C. Specific activity of the $^{18}$F-labeled peptide was higher than 45,000 GBq/mmol.

Optimal $^{18}$F-labeling of NOTA-octreotide with Al$^{18}$F was performed at 80-100° C. in Na-acetate buffer with 80% (v/v) acetonitrile and a Al:NOTA ratio between 1:20 and 1:50. Labeling efficiency was typically >98%. Since labeling efficiency at 60° C. was 83%, this method may also allow $^{18}$F-labeling of temperature-sensitive biomolecules such as proteins and antibody fragments. These conditions allow routine $^{18}$F-labeling of peptides without the need for purification prior to administration and PET imaging.

Example 32

Functionalized Triazacyclononane Ligands for Molecular Imaging

Figure 16:
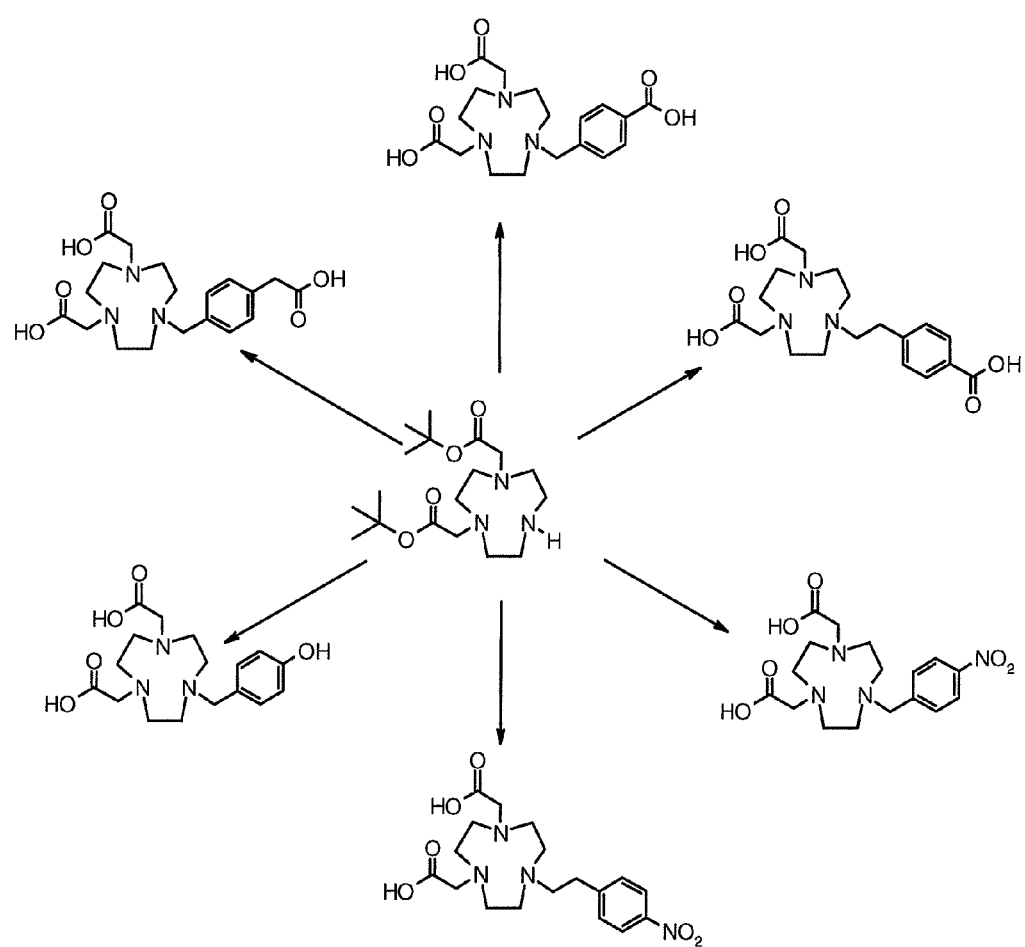
FIG. 16. Chemical structure of exemplary NODA-based bifunctional chelators.
Figure 17:
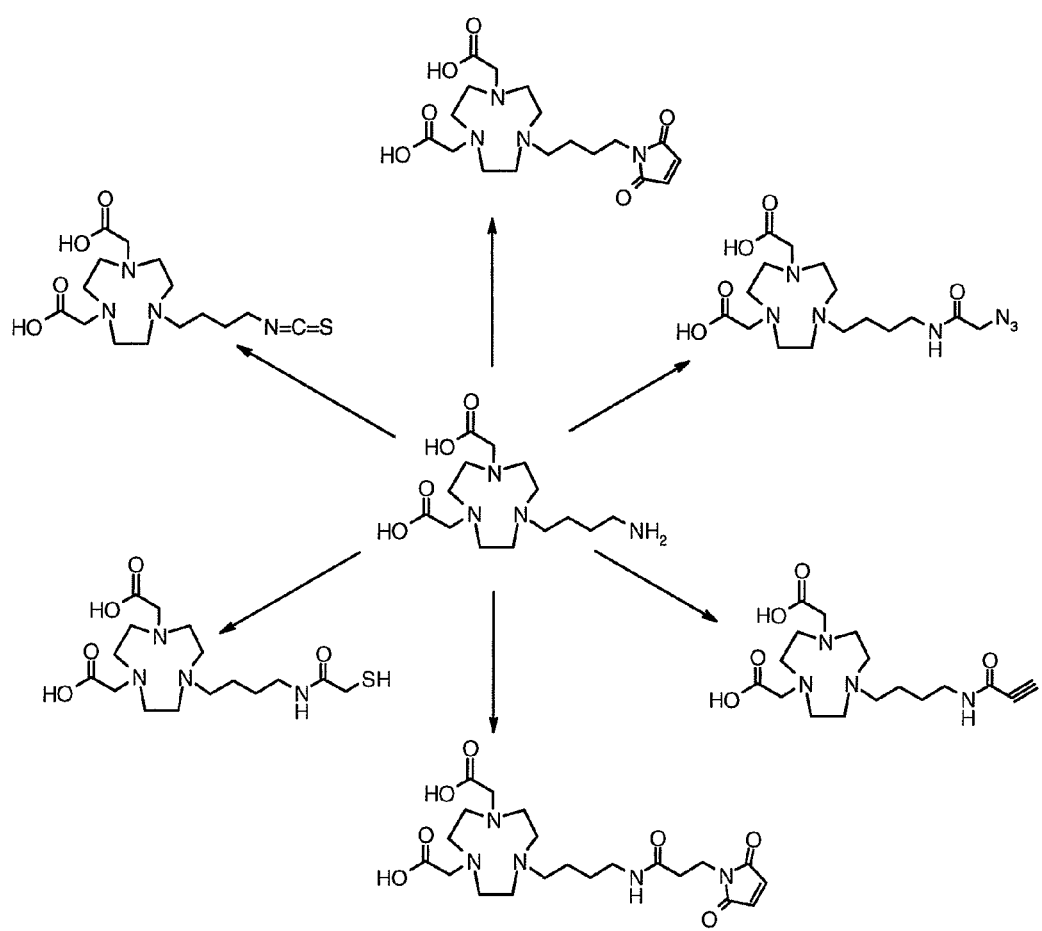
FIG. 17. Chemical structures of NODA-BM derived bifunctional chelators.
Figure 18A:
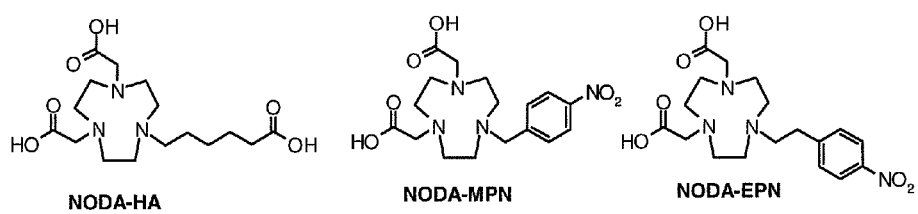
FIG. 18. Further exemplary structures of NODA-based bifunctional chelators.
Figure 18A:
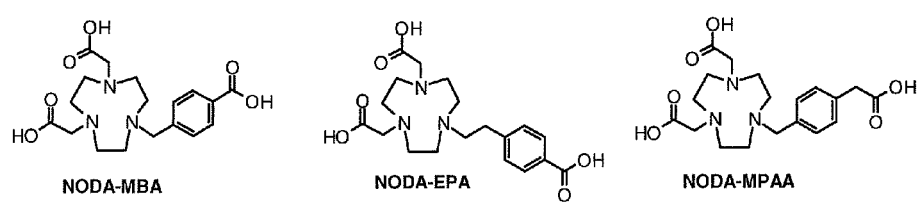
Figure 18A:
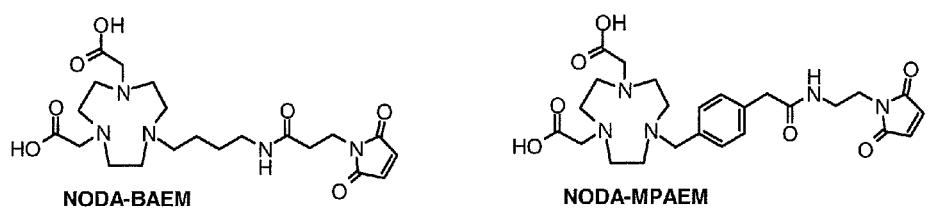
Figure 18A:
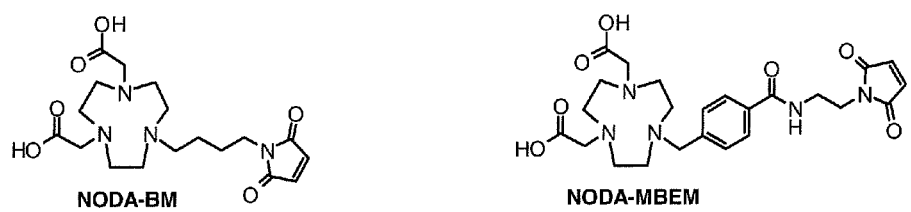
Figure 18B:
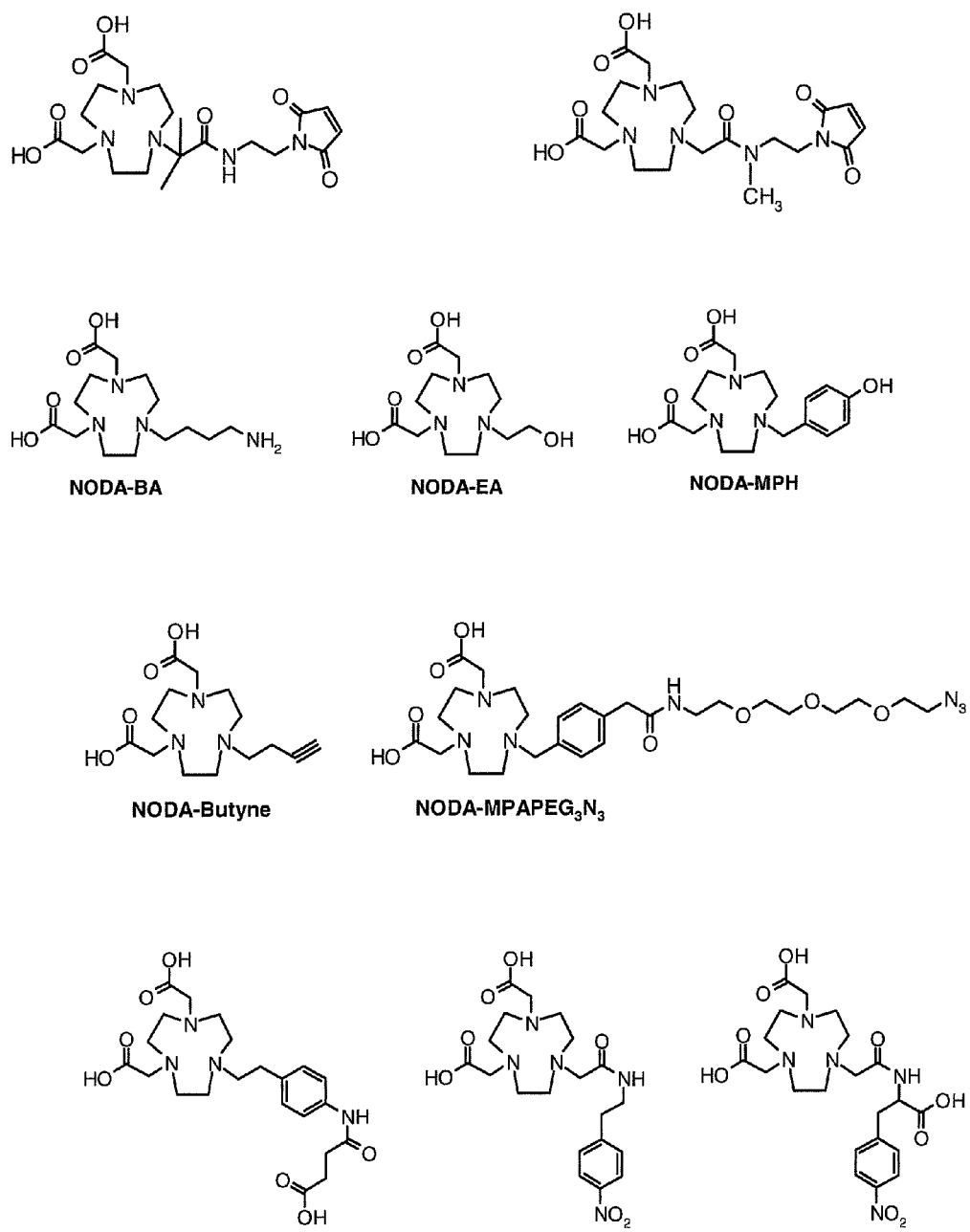
Figure 18C:
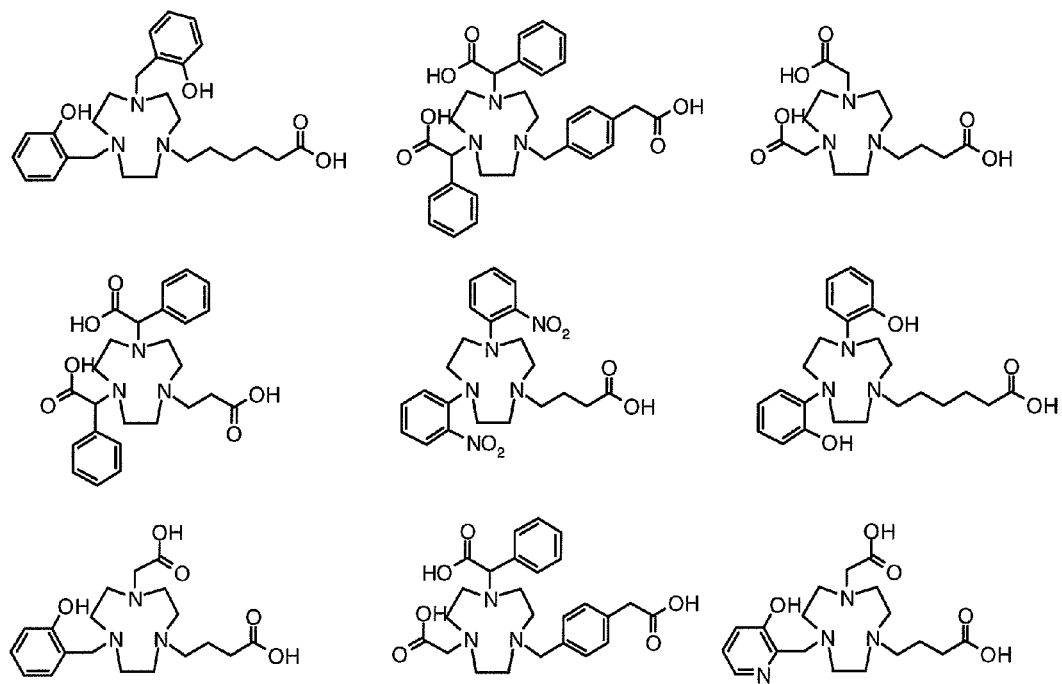
Figure 19A:
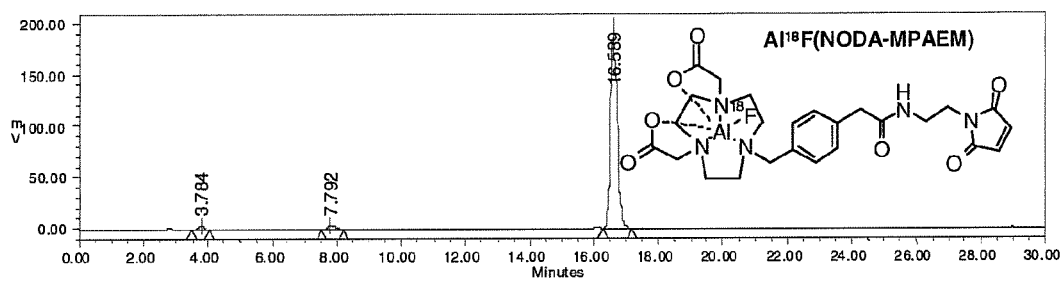
FIGS. 19(A) and 19(B). Radiochromatograms of the $^{18}$F-labeled functionalized TACN ligands.
Figure 19A:
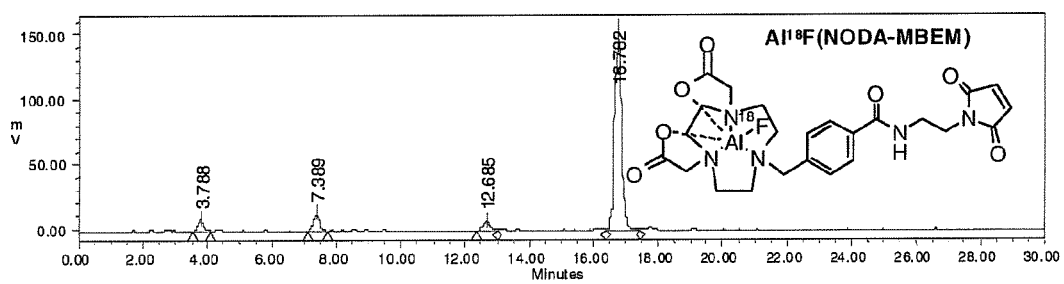
Figure 19A:
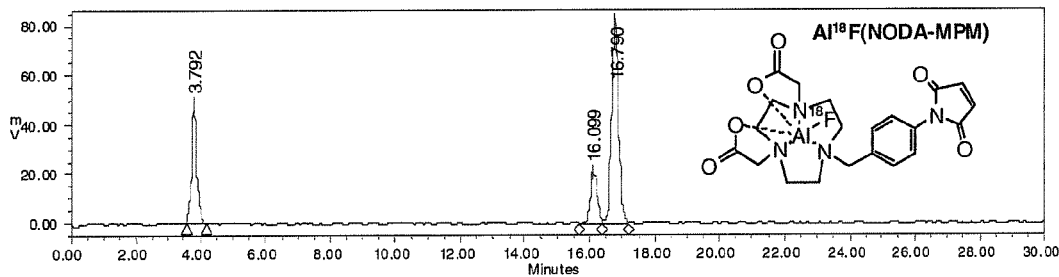
Figure 19B:
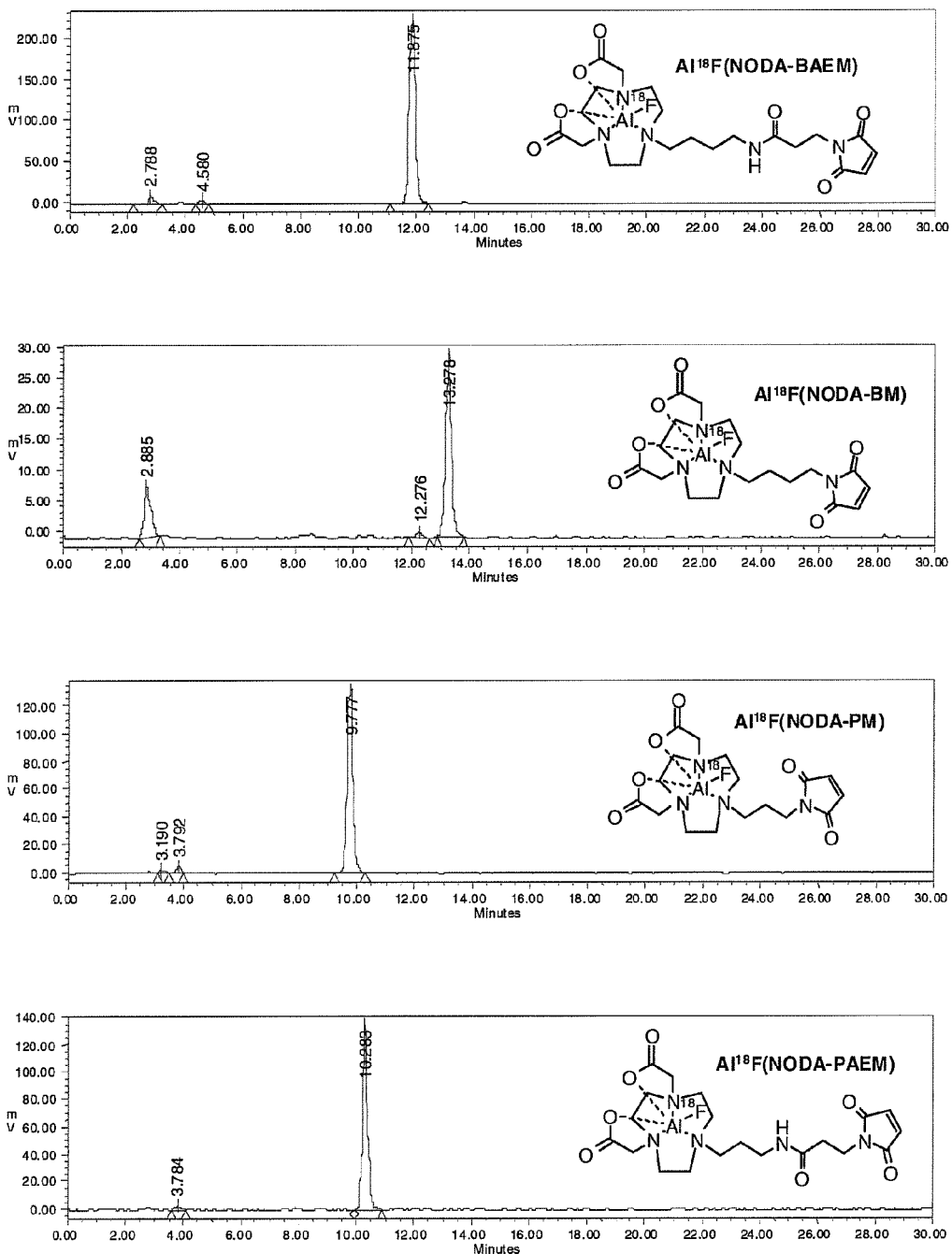
Figure 20A:
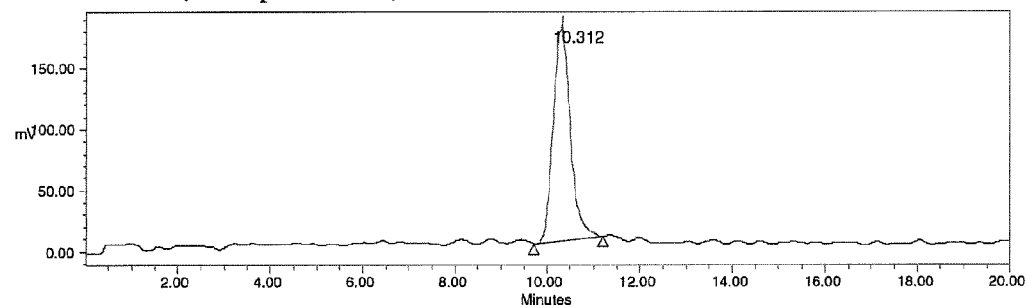
FIGS. 20(A) and 20(B). Radiochromatograms of $^{18}$F-hMN14-Fab', its stability in human serum and immunoreactivity with CEA.
Figure 20A:
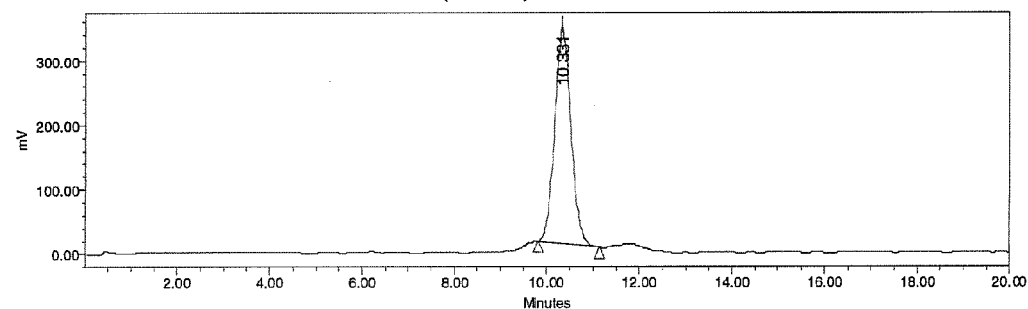
Figure 20A:
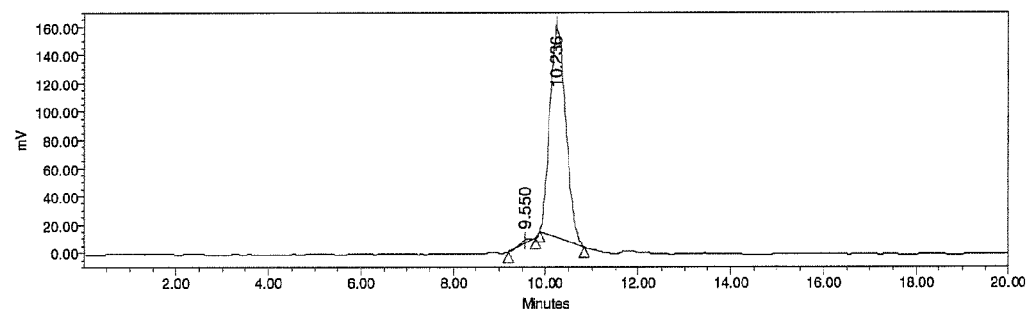
Figure 20B:
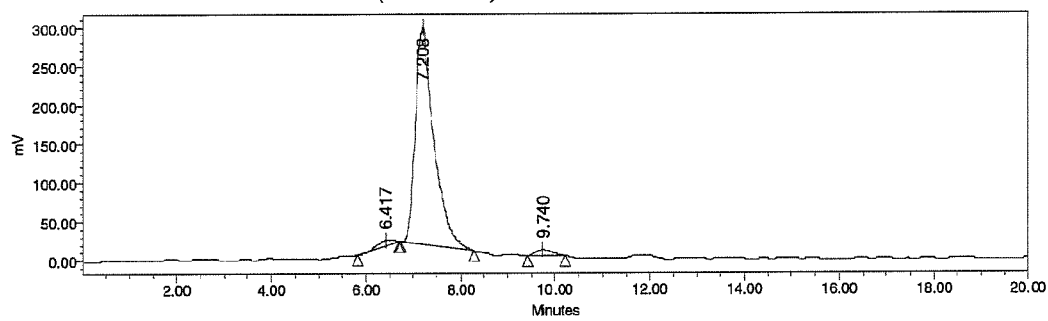
Figure 20B:
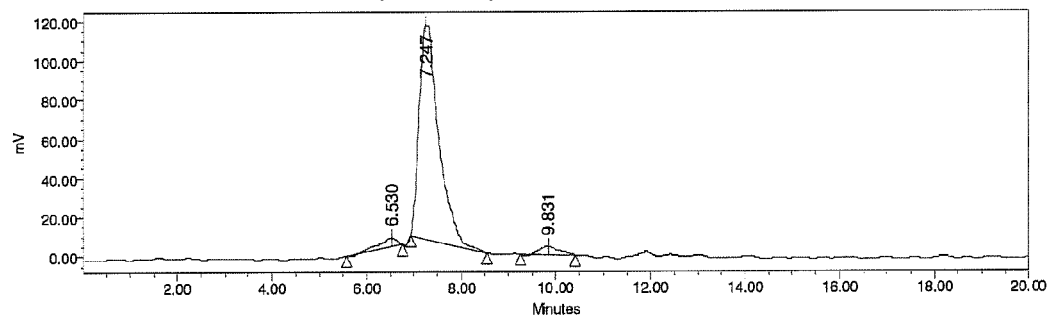

The present Example relates to synthesis and use of a new class of triazacyclonane derived ligands and their complexes useful for molecular imaging. Exemplary structures are shown in FIG. 16 to FIG. 18. The ligands may be functionalized with a $^{19}$F moiety selected from the group consisting of fluorinated alkyls, fluorinated acetates, fluoroalkyl phosphonates, fluoroanilines, trifluoromethyl anilines, and trifluoromethoxy anilines in an amount effective to provide a detectable $^{19}$F NMR signal. The complexation of these ligands with radioisotopic or paramagnetic cations renders them useful as diagnostic agents in nuclear medicine and magnetic resonance imaging (MRI). Preferably, the Al$^{18}$F and $^{68}$Ga complexes of these ligands are useful for PET imaging, while the $^{111}$In complexes can be used in SPECT imaging. Methods for conjugating these radiolabeled ligands to a targeting molecule like antibody, protein or peptide are also disclosed.

The disclosed bifunctional chelators (BFCs) can be radiolabeled with $^{111}$In, $^{68}$Ga, $^{64}$Cu, $^{177}$Lu, Al$^{18}$F, $^{99m}$Tc or $^{86}$Y or complexed with a paramagnetic metal like manganese, iron, chromium or gadolinium, and subsequently attached to a targeting molecule (biomolecule). The labeled biomolecules can be used to image the hematological system, lymphatic reticuloendothelial system, nervous system, endocrine and exocrine system, skeletomuscular system, skin, pulmonary system, gastrointestinal system, reproductive system, immune system, cardiovascular system, urinary system, auditory or olfactory system or to image affected cells or tissues in various medical conditions.

Synthesis of Bifunctional Chelators

2-{4-(carboxymethyl)-7-[2-(4-nitrophenyl)ethyl]-1,4,7-triazacyclononan-1-yl)acetic acid. NODA-EPN To a solution of 4-nitrophenethyl bromide (104.5 mg, 0.45 mmol) in anhydrous CH$_3$CN at 0° C. was added dropwise over 20 min a solution of (tBu)$_2$NODA (167.9 mg, 0.47 mmol) in CH$_3$CN (10 mL). After 1 h, anhydrous K$_2$CO$_3$ (238.9 mg, 1.73 mmol) was added to the reaction mixture and allowed to stir at room temperature overnight. Solvent was evaporated and the concentrate was acidified with 4 mL TFA. After 5 h, the reaction mixture was diluted with water and purified by preparative RP-HPLC to yield a pale yellow solid (60.8 mg, 32.8%). HRMS (ESI) calculated for C$_{18}$H$_{26}$N$_4$O$_6$ (M+H)$^+$ 395.1925; found 395.1925.

2-{4-(carboxymethyl)-7-[2-(4-nitrophenyl)methyl]-1,4,7-triazacyclononan-1-yl)acetic acid. NODA-MPN To a solution of 4-nitrobenzyl bromide (61.2 mg, 0.28 mmol) in anhydrous CH$_3$CN at 0° C. was added dropwise over 20 min a solution of (tBu)$_2$NODA (103.6 mg, 0.29 mmol) in CH$_3$CN (10 mL). After 1 h, anhydrous K$_2$CO$_3$ (57.4 mg, 0.413 mmol) was added to the reaction mixture and allowed to stir at room temperature overnight. Solvent was evaporated and the concentrate was acidified with 3 mL TFA. After 5 h, the reaction mixture was diluted with water and purified by preparative RP-HPLC to yield a pale yellow solid (19.2 mg, 17.4%). HRMS (ESI) calculated for C$_{17}$H$_{24}$N$_4$O$_6$ (M+H)$^+$ 381.1769; found 381.1774.

6-(4,7-bis{[(tert-butyl)oxycarbonyl]methyl}-1,4,7-triazacyclononan-1-yl)hexanoic acid. (tBu)$_2$NODA-HA To a solution of (tBu)$_2$NODA (208.3 mg, 0.58 mmol) in 10 mL CH$_3$CN was added 6-bromohexanoic acid (147.3 mg, 0.755 mmol) and K$_2$CO$_3$ (144.5 mg, 1.05 mmol). The reaction flask was placed in a warm water-bath for 48 h. Solvent was evaporated and the concentrate was diluted with water and purified by preparative RP-HPLC to yield a white solid (138.5 mg, 50.1%). ESMS calculated for C$_{24}$H$_{45}$N$_3$O$_6$ (M+H)$^+$ 472.3381; found 472.27.

4-[(4,7-bis{[(tert-butyl)oxycarbonyl]methyl}-1,4,7-triazacyclonoan-1-yl)methyl]benzoic acid. (tBu)$_2$NODA-MBA To a solution of α-bromo-p-toluic acid (126.2 mg, 0.59 mmol) in anhydrous CH$_3$CN was added dropwise over 20 min a solution of (tBu)$_2$NODA (208 mg, 0.58 mmol) in CH$_3$CN (10 mL) and allowed to stir at room temperature for 48 h. Solvent was evaporated and the concentrate was diluted with water/DMF and purified by preparative RP-HPLC to yield a white solid (74.6 mg). HRMS (ESI) calculated for C$_{26}$H$_{41}$N$_3$O$_6$ (M+H)$^+$ 492.3068; found 492.3071.

4-[(4,7-bis{[(tert-butyl)oxycarbonyl]methyl}-1,4,7-triazacyclononan-1-yl)ethyl]benzoic acid. (tBu)$_2$NODA-EBA To a solution of 4-(2-bromoethyl)benzoic acid (310.9 mg, 1.36 mmol) in anhydrous CH$_3$CN was added dropwise over 20 min a solution of (tBu)$_2$NODA (432.3 mg, 1.21 mmol) in CH$_3$CN (10 mL) and K$_2$CO$_3$ (122.4 mg, 0.89 mmol). The reaction was stirred at room temperature for 72 h. Solvent was evaporated and the concentrate was diluted with water/DMF and purified by preparative RP-HPLC to yield a white solid (35.1 mg). HRMS (ESI) calculated for C$_{27}$H$_{43}$N$_3$O$_6$ (M+H)$^+$ 506.3225; found 506.3234.

2-[7-but-3-ynyl-4-(carboxymethyl)-1,4,7-triazacyclonoan-1-yl)acetic acid. NODA-Butyne To a solution of (tBu)$_2$NODA (165.8 mg, 0.46 mmol) in 5 mL CH$_3$CN was added 4-bromo-1-butyne (44 µL, 62.3 mg, 0.47 mmol) and reaction mixture was stirred at room temperature for 72 h. Solvent was evaporated and the concentrate was purified by preparative RP-HPLC to yield an oil. HRMS (ESI) calculated for C$_{22}$H$_{39}$N$_3$O$_4$ (M+H)$^+$ 410.3013; found 410.3013. The purified product was acidified with 2 mL TFA and after 5 h diluted with water, frozen and lyophilized. HRMS (ESI) calculated for C$_{14}$H$_{23}$N$_3$O$_6$ (M+H)$^+$ 298.1761; found 298.1757.

tert-butyl-2-(7-(4-aminobutyl)-4-{[(tert-butyl)oxycarbonyl]methyl}-1,4,7-triazacyclononan-1-yl)acetic acid. (tBu)$_2$NODA-BA To a solution of (tBu)$_2$NODA (165.2 mg, 0.46 mmol) in 5 mL CH$_3$CN was added 4-(Boc-amino)butyl bromide (124.7 mg, 0.49 mmol), a pinch of K$_2$CO$_3$ and reaction mixture was stirred at room temperature for 72 h. Solvent was evaporated and the concentrate was treated with 1 mL CH$_2$Cl$_2$ and 0.5 mL TFA. After 5 min the solvents were evaporated and the crude oil was diluted with water/DMF and purified by preparative RP-HPLC to yield a white solid (137.2 mg, 69.3%). HRMS (ESI) calculated for C$_{22}$H$_{44}$N$_4$O$_4$ (M+H)$^+$ 429.3435; found 429.3443.

NODA-BAEM: BAEM=(butyl amido ethyl maleimide)

To a solution of (tBu)$_2$NODA-BM (29.3 mg, 0.068 mmol) in CH$_2$Cl$_2$ (3 mL) was added a β-maleimido propionic acid NHS ester (16.7 mg, 0.063 mmol), 20 µL DIEA and stirred at room temperature overnight. Solvent was evaporated and the concentrate was acidified with 1 mL TFA. After 3 h, the reaction mixture was diluted with water and purified by preparative RP-HPLC to yield a white solid. HRMS (ESI) calculated for C$_{21}$H$_{33}$N$_5$O$_7$ (M+H)$^+$ 468.2453; found 468.2441.

2-{4-[(4,7-bis-tert-butoxycarbonylmethyl)-[1,4,7]-triazacyclononan-1-yl)methyl]phenyl}acetic acid. (tBu)$_2$NODA-MPAA To a solution of 4-(bromomethyl)phenylacetic acid (593 mg, 2.59 mmol) in anhydrous CH$_3$CN (50 mL) at 0° C. were added dropwise over 1 h a solution of (tBu)$_2$NODA (1008 mg, 2.82 mmol) in CH$_3$CN (50 mL). After 4 h, anhydrous K$_2$CO$_3$ (100.8 mg, 0.729 mmol) was added to the reaction mixture and allowed to stir at room temperature overnight. Solvent was evaporated and the crude was purified by preparative RP-HPLC (Method 5) to yield a white solid (713 mg, 54.5%). $^1$H NMR (500 MHz, CDCl$_3$, 25° C., TMS) δ 1.45 (s, 18 H), 2.64-3.13 (m, 16 H), 3.67 (s, 2 H), 4.38 (s, 2 H), 7.31 (d, 2H), 7.46 (d, 2H); $^{13}$C (125.7 MHz, CDCl$_3$) δ 28.1, 41.0, 48.4, 50.9, 51.5, 57.0, 59.6, 82.3, 129.0, 130.4, 130.9, 136.8, 170.1, 173.3. HRMS (ESI) calculated for C$_{27}$H$_{43}$N$_3$O$_6$ (M+H)$^+$ 506.3225; found 506.3210.

2-(4-(carboxymethyl)-7-{[4-(carboxymethyl)phenyl]methyl}-1,4,7-triazacyclononan-1-yl)acetic acid. NODA-MPAA To a solution of 4-(bromomethyl)phenylacetic acid (15.7 mg, 0.068 mmol) in anhydrous CH$_3$CN at 0° C. was added dropwise over 20 min a solution of (tBu)$_2$NODA (26 mg, 0.073 mmol) in CH$_3$CN (5 mL). After 2 h, anhydrous K$_2$CO$_3$ (5 mg) was added to the reaction mixture and allowed to stir at room temperature overnight. Solvent was evaporated and the concentrate was acidified with 2 mL TFA. After 3 h, the reaction mixture was diluted with water and purified by preparative RP-HPLC to yield a white solid (11.8 mg, 43.7%). $^1$H NMR (500 MHz, DMSO-d$_6$, 25° C.) δ 2.65-3.13 (m, 12 H), 3.32 (d, 2H), 3.47 (d, 2H), 3.61 (s, 2 H), 4.32 (s, 2 H), 7.33 (d, 2H), 7.46 (d, 2H); $^{13}$C (125.7 MHz, DMSO-d$_6$) 40.8, 47.2, 49.6, 50.7, 55.2, 58.1, 130.4, 130.5, 130.9, 136.6, 158.4, 158.7, 172.8, 172.9. HRMS (ESI) calculated for C$_{19}$H$_{27}$N$_3$O$_6$ (M+H)$^+$ 394.1973; found 394.1979.

(tBu)$_2$NODA-MPAA NHS ester

To a solution of (tBu)$_2$NODA-MPAA (175.7 mg, 0.347 mmol) in CH$_2$Cl$_2$ (5 mL) was added (1 M in CH$_2$Cl$_2$) DCC (347 µL, 0.347 mmol), N-hydroxysuccinimide (NHS) (42.5 mg, 0.392 mmol), and 20 µL N,N-diisopropylethylamine (DIEA). After 3 h, dicyclohexylurea (DCU) was filtered off and solvent evaporated. The crude product was purified by flash chromatography on (230-400 mesh) silica gel (CH$_2$Cl$_2$: MeOH (100:0 to 80:20) to yield the NHS ester (128.3 mg, 61.3%). HRMS (ESI) calculated for C$_{31}$H$_{46}$N$_4$O$_8$ (M+H)$^+$ 603.3388; found 603.3395.

NODA-MPAEM: MPAEM=(methyl phenyl acetamido ethyl maleimide)

To a solution of (tBu)$_2$NODA-MPAA NHS ester (128.3 mg, 0.213 mmol) in CH$_2$Cl$_2$ (5 mL) was added a solution of N-(2-aminoethyl) maleimide trifluoroacetate salt (52.6 mg, 0.207 mmol) in 250 µL DMF and 20 µL DIEA. After 3 h, the solvent was evaporated and the concentrate treated with 2 mL TFA. The crude product was diluted with water and purified by preparative RP-HPLC to yield a white solid (49.4 mg, 45%). HRMS (ESI) calculated for C$_{25}$H$_{33}$N$_5$O$_7$ (M+H)$^+$ 516.2453; found 516.2452.

tert-butyl-2-(7-(4-aminopropyl)-4-{[(tert-butyl)oxycarbonyl]methyl}-1,4,7-triazacyclononan-1-yl)acetic acid. (tBu)$_2$NODA-PA To a solution of (tBu)$_2$NODA (391.3 mg, 1.09 mmol) in 5 mL CH$_3$CN was added Benzyl-3-bromo propyl carbamate (160 μL) and reaction mixture was stirred at room temperature for 28 h. Solvent was evaporated and the concentrate was dissolved in 40 mL 2-propanol, mixed with 128.7 mg of 10% Pd—C and placed under 43 psi $H_2$ overnight. The product was then filtered and the filtrate concentrated. The crude product was diluted with water/DMF and purified by preparative RP-HPLC to yield a white solid (353 mg). HRMS (ESI) calculated for $C_{21}H_{42}N_4O_4$ $(M+H)^+$ 415.3291; found 415.3279.

NODA-PAEM: (PAEM=propyl amido ethyl maleimide)

To a solution of $(tBu)_2$NODA-PM (109.2 mg, 0.263 mmol) in $CH_2Cl_2$ (3 mL) was added a β-maleimido propionic acid NHS ester (63.6 mg, 0.239 mmol), 20 μL DIEA and stirred at room temperature overnight. Solvent was evaporated and the concentrate was acidified with 1 mL TFA. After 3 h, the reaction mixture was diluted with water and purified by preparative RP-HPLC to yield a white solid (79 mg). HRMS (ESI) calculated for $C_{20}H_{31}N_5O_7$ $(M+H)^+$ 454.2319; found 454.2296.

[18]F-Labeling of Functionalized Triazacyclononane Ligands

The functionalized triazacyclononane ligand (20 nmol; 10 L), dissolved in 2 mM sodium acetate (pH 4), was mixed with $AlCl_3$ (5 L of 2 mM solution in 2 mM acetate buffer, 25-200 L of $^{18}$F in saline, and 25-200 L of ethanol. After heating at 90-105° C. for 15-20 min, 800 L of deionized (DI) water was added to the reaction solution, and the entire contents removed to a vial (dilution vial) containing 1 mL of deionized (DI) water. The reaction vial was washed with 2×1 mL DI water and added to the dilution vial. The crude product was then passed through a 1-mL HLB column, which was washed with 2×1 mL fractions of DI water. The labeled product was eluted from the column using 3×200 L of 1:1 EtOH/water. Radiochromatograms of the $^{18}$F-labeling of functionalized TACN ligands are shown in FIG. 19.

[18]F-Labeling of NODA-MPAEM

To 10 μL (20 nmol) 2 mM NODA-MPAEM solution was added 5 μL 2 mM $AlCl_3$, 200 μL [18]F[-] solution [15.94 mCi, Na[18]F, PETNET] followed by 200 μL $CH_3CN$ and heated to 110° C. for 15 minutes. The crude reaction mixture was purified by transferring the resultant solution into a Oasis® HLB 1 cc (30 mg) cartridge (P#186001879, L#099A30222A) and eluting with DI $H_2O$ to remove unbound [18]F[-] followed by 1:1 EtOH/$H_2O$ to elute the $^{18}$F-labeled peptide. The crude reaction solution was pulled through the HLB cartridge into a 10 mL vial and the cartridge washed with 6×1 mL fractions of DI $H_2O$ (4.34 mCi). The HLB cartridge was then placed on a new 3 mL vial and eluted with 4×150 L 1:1 EtOH/$H_2O$ to collect the labeled peptide (7.53 mCi). The reaction vessel retained 165.1 while the cartridge retained 270 μCi of activity. 7.53 mCi⇒ 61.2% of Al[$^{18}$F]NODA-MPAEM.

[18]F-Labeling of NODA-MPAEM:

To 10 μL (20 nmol) 2 mM NODA-MPAEM solution was added 5 μL 2 mM $AlCl_3$, 200 μL [18]F[-] solution [15.94 mCi, Na[18]F, PETNET] followed by 200 μL $CH_3CN$ and heated to 110° C. for 15 minutes. The crude reaction mixture was purified by transferring the resultant solution into a Oasis® HLB 1 cc (30 mg) cartridge (P#186001879, L#099A30222A) and eluting with DI $H_2O$ to remove unbound $^{18}$F followed by 1:1 EtOH/$H_2O$ to elute the $^{18}$F-labeled peptide. The crude reaction solution was pulled through the HLB cartridge into a 10 mL vial and the cartridge washed with 6×1 mL fractions of DI $H_2O$ (4.34 mCi). The HLB cartridge was then placed on a new 3 mL vial and eluted with 4×150 L 1:1 EtOH/$H_2O$ to collect the labeled peptide (7.53 mCi). The reaction vessel retained 165.1 μCi, while the cartridge retained 270 μCi of activity. 7.53 mCi⇒ 61.2% of Al[$^{18}$F]NODA-MPAEM.

TABLE 26

[18]F-labeling of 20 nmol NODA-MPAEM + 10 nmol $Al^{3+}$

| Activity[a] Na[18]F (mCi) | Aqueous (μL) | $CH_3CN$ (μL) | Isolated activity[b] (mCi) | RCY[c] (%) |
|---|---|---|---|---|
| 2.02 | 80 | — | 1.09 | 64.1 |
| 1.86 | 40 | 40 | 1.43 | 91.0 |
| 1.96 | 50 | 50 | 1.371 | 90.8 |
| 3.26 | 200 | 200 | 2.05 | 76.0 |
| 15.08 | 200 | 200 | 8.24 | 70.3 |
| 15.94 | 200 | 200 | 7.53 | 61.2 |

[a]10 μL NODA-MPAEM, 5 μL $Al^{3+}$, 105-110° C., 15 min.
[b]Isolated activity in (1:1) EtOH/$H_2O$ after HLB column purification (SPE).
[c]decay corrected RCY—based on synthesis time of 27-42 minutes.

Conjugation of hMN14-Fab'-SH with Al[18]F(NODA-MPAEM)

To the vial containing hMN14-Fab'-SH (1 mg, ~20 nmoles) L #112310 was added 200 μL PBS, pH 7.38 and 600 μL of the HLB purified Al[18]F(NODA-MPAEM) (EtOH:$H_2O$::1:1). The crude reaction mixture was passed through a sephadex (G-50/80, 0.1 M NaOAc, pH 6.5) 3 mL spin column. The activity in the eluate was 4.27 mCi, while 1.676 mCi was retained on the spin column and 0.178 mCi in the empty reaction vial. 4.27 mCi⇒ 68.6% of [Al[18]F]-hMN14-Fab.

To 800 μL of PBS was added 1 μL of eluate⇒ injected 40 μL (SEC-HPLC) at 2.08 p.m. Major product at 10.312 min.

Serum Stability:

In an autosampler vial 200 μL of fresh human serum+50 μL of eluate⇒ 149.6 μCi at 2.45 p.m. Incubated at 37° C.⇒ [Al[18]F]-hMN14-Fab in serum.

To 4 μL of [Al[18]F]-hMN14-Fab in serum added 280 μL of buffer B (PBS)⇒ injected 40 μL (SEC-HPLC) at 3.51 p.m. Major product at 10.331 min.

Immunoreactivity of [18]F-hMN14-Fab:

To 100 μg carcinoembryonic antigen (CEA) [L #2371505, Scripp's Labs] was added 200 μL 1% HSA in PBS, pH 7.38+100 μL PBS, pH 7.38⇒ CEA in PBS. Added 4 μL of [Al[18]F]-hMN14-Fab in serum at 37° C. to 150 μL CEA in PBS⇒ injected 40 μL (SEC-HPLC) at 4.33 p.m. Major product at 7.208 min.

Radiochromatograms of spin column purified [Al[18]F]-hMN14-Fab, stability of [Al[18]F]-hMN14-Fab in human serum and its immunoreactivity with CEA are shown in FIG. 20.

Exemplary synthetic schemes for the bifunctional chelators are shown below.

Scheme 1: Synthesis of NODA-MBA

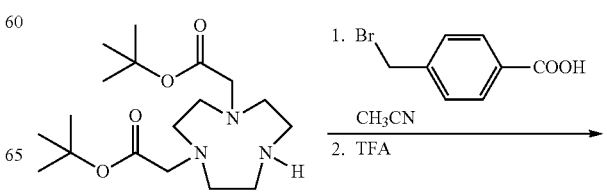

-continued
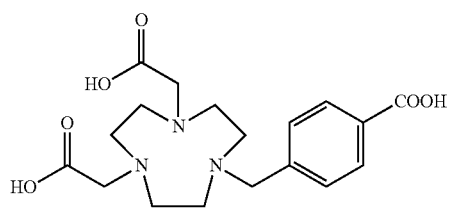
Scheme 2: Synthesis of NODA-EBA
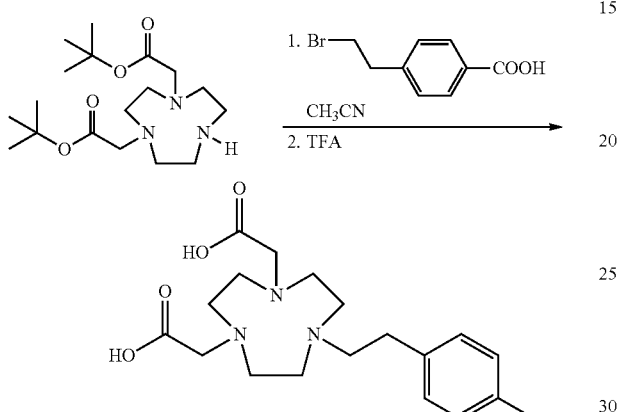
Scheme 3: Synthesis of NODA-MPN
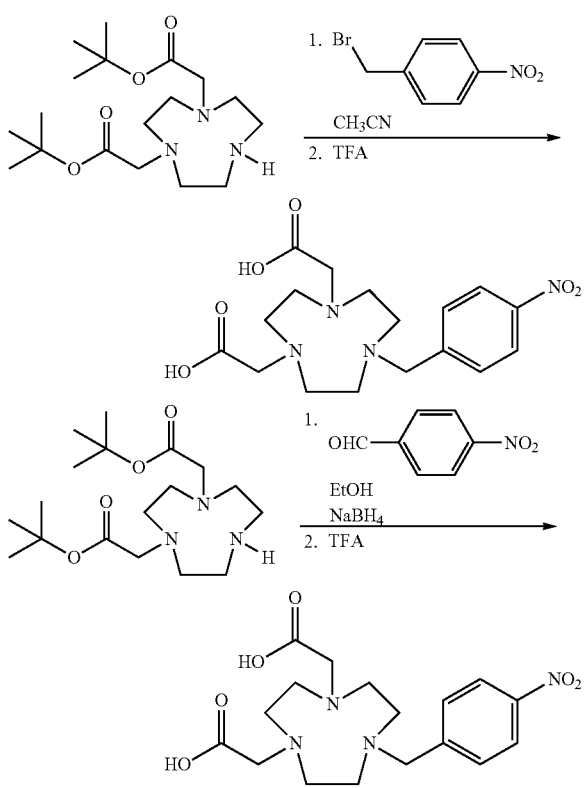
Scheme 4: Synthesis of NODA-EPN
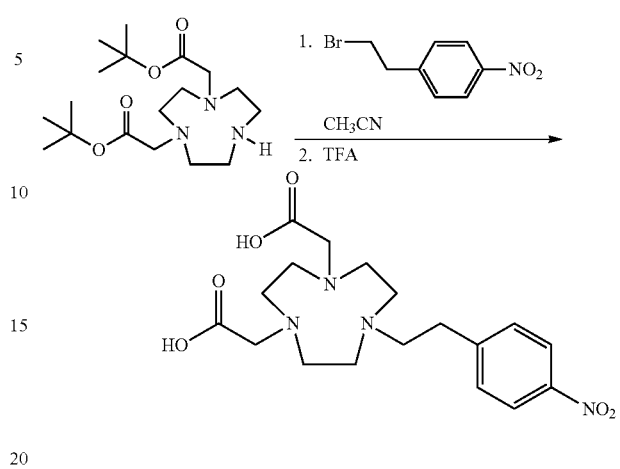
Scheme 5: Synthesis of NODA-Butyne
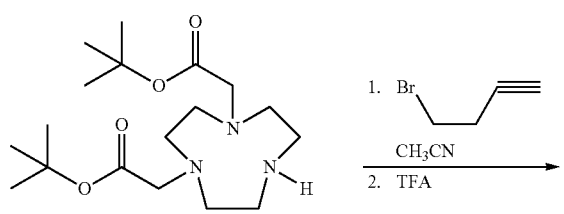
Scheme 6: Synthesis of NODA-MPH
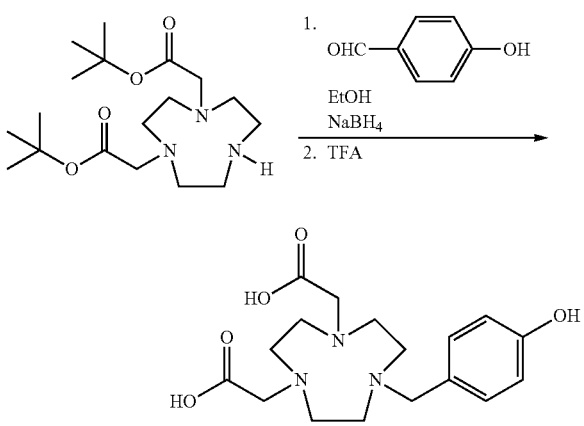

Scheme 7: Synthesis of NODA-Ethanol
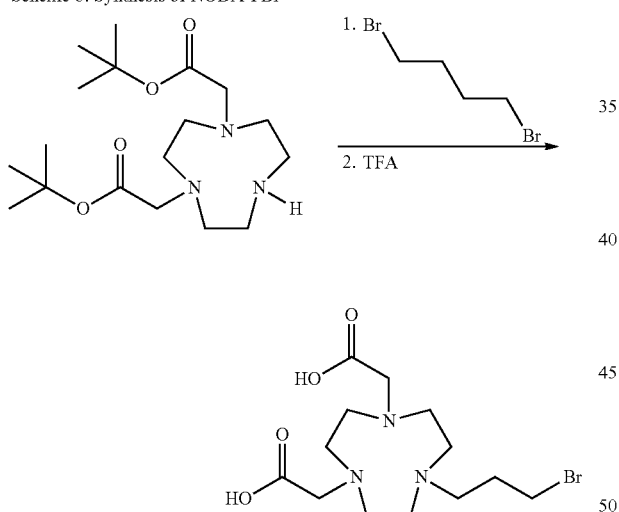
Scheme 8: Synthesis of NODA-PBr
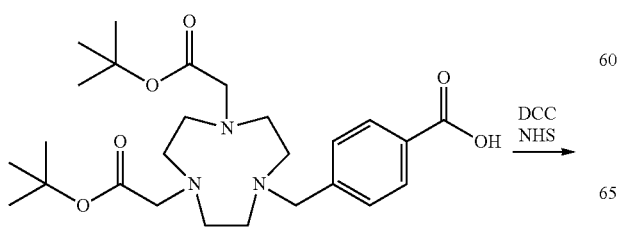
Scheme 9: Synthesis of NODA-MBEM
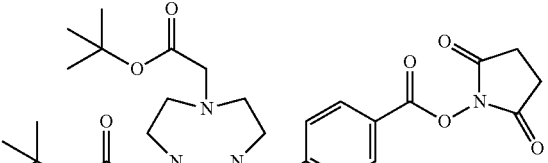
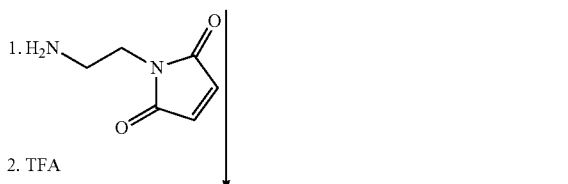
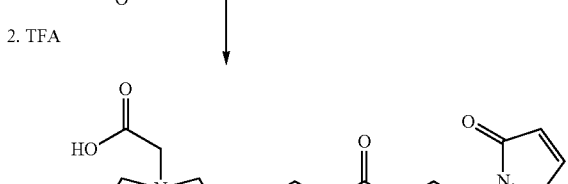
Scheme 10: Synthesis of NODA-BM
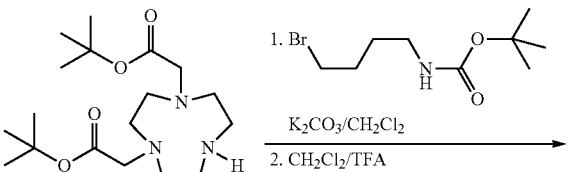
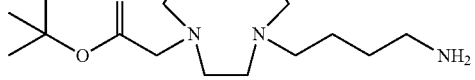
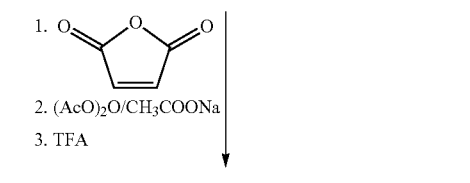
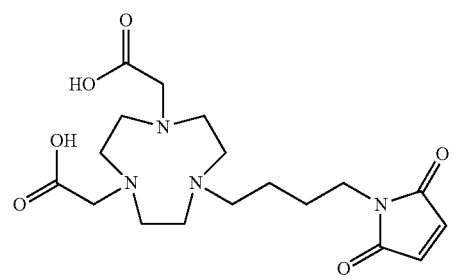

Scheme 11: Synthesis of NODA-BAEM
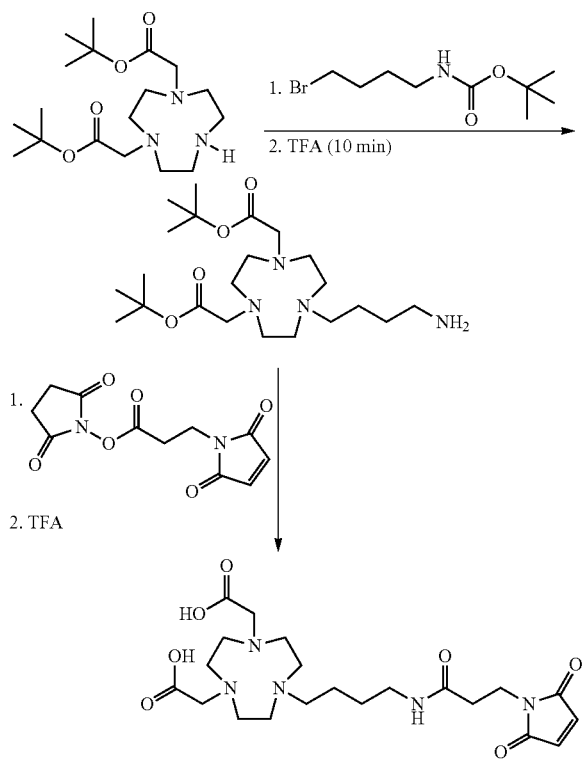
Scheme 13: Synthesis of Al$^{18}$F(NODA-MPAA NHS ester)
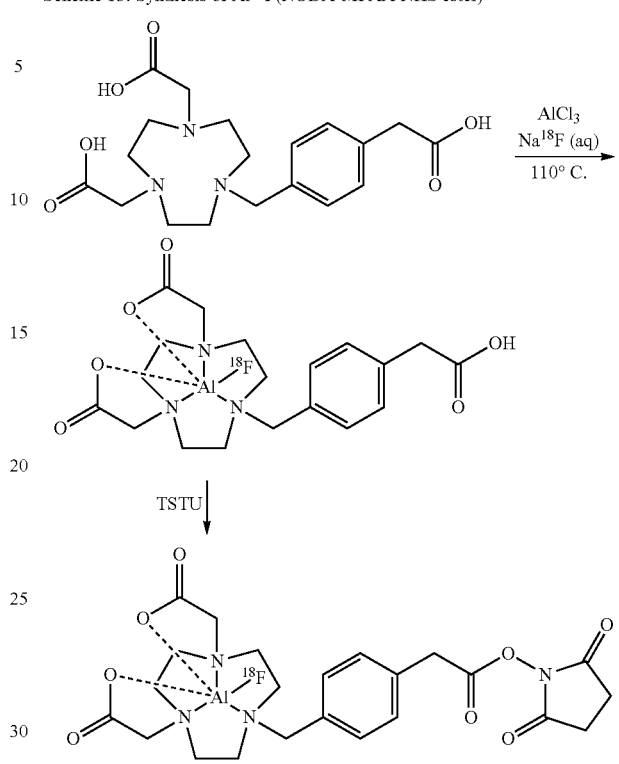
Scheme 12: Synthesis of NODA-MPAPEG$_3$N$_3$
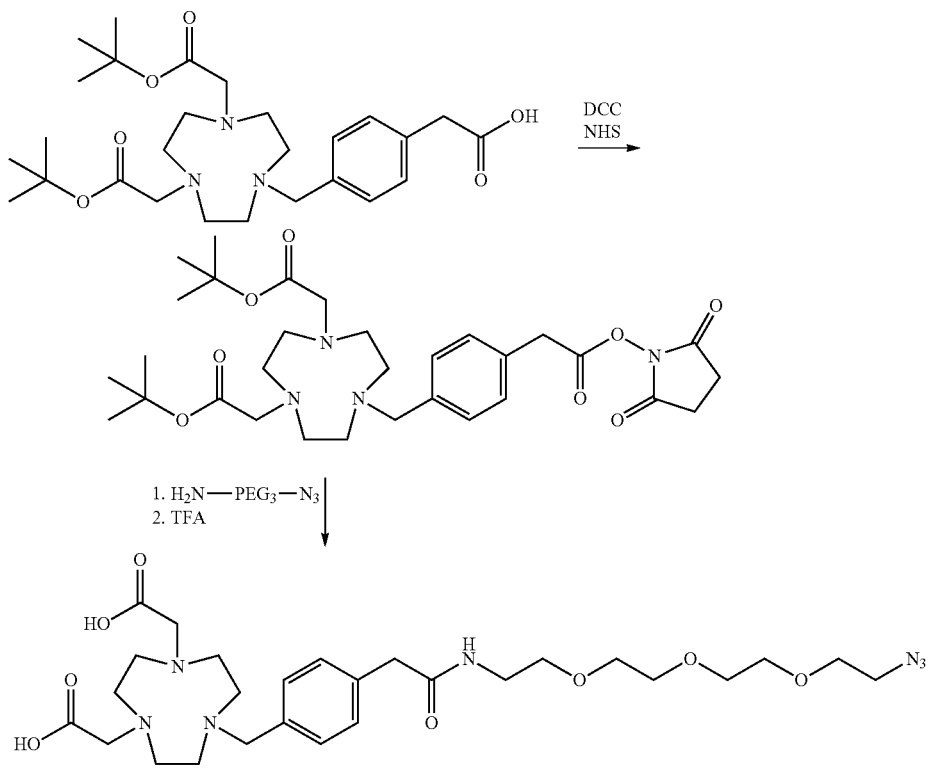

Scheme 14: Synthesis of Al$^{18}$F (NODA-BAEM)
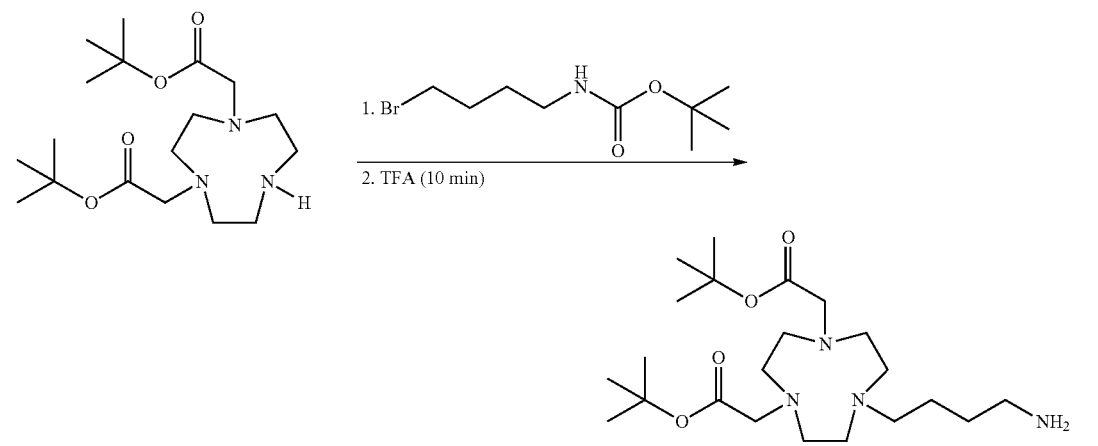
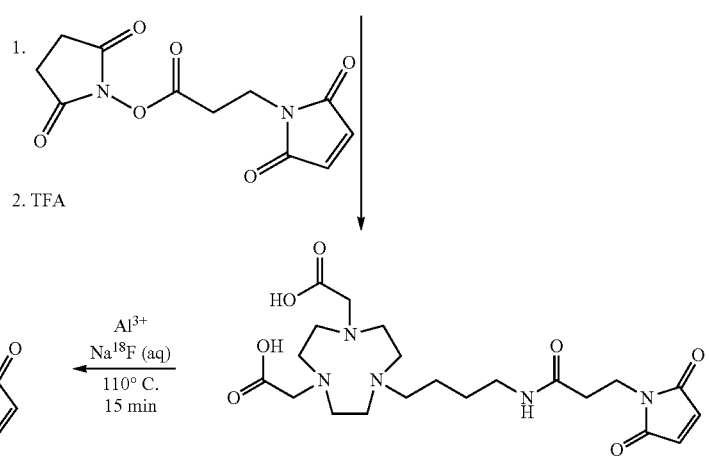
Scheme 15: Synthesis of NODA-BAMA
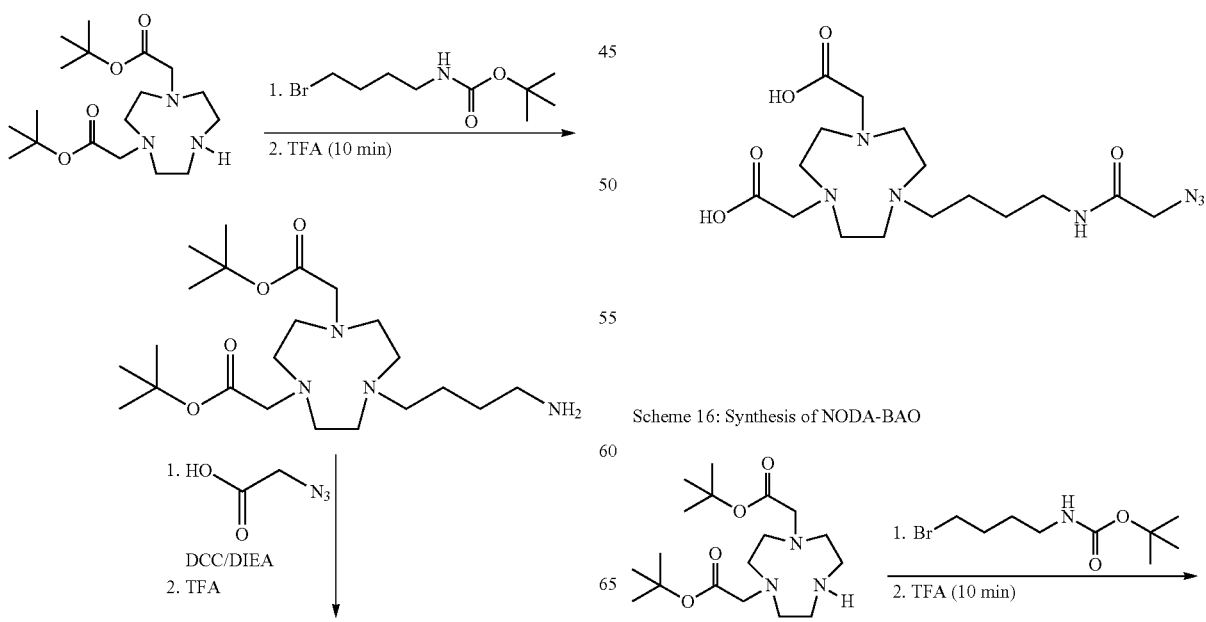
Scheme 16: Synthesis of NODA-BAO
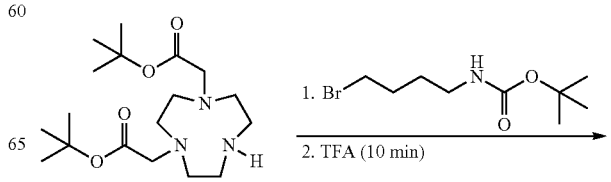

107
-continued
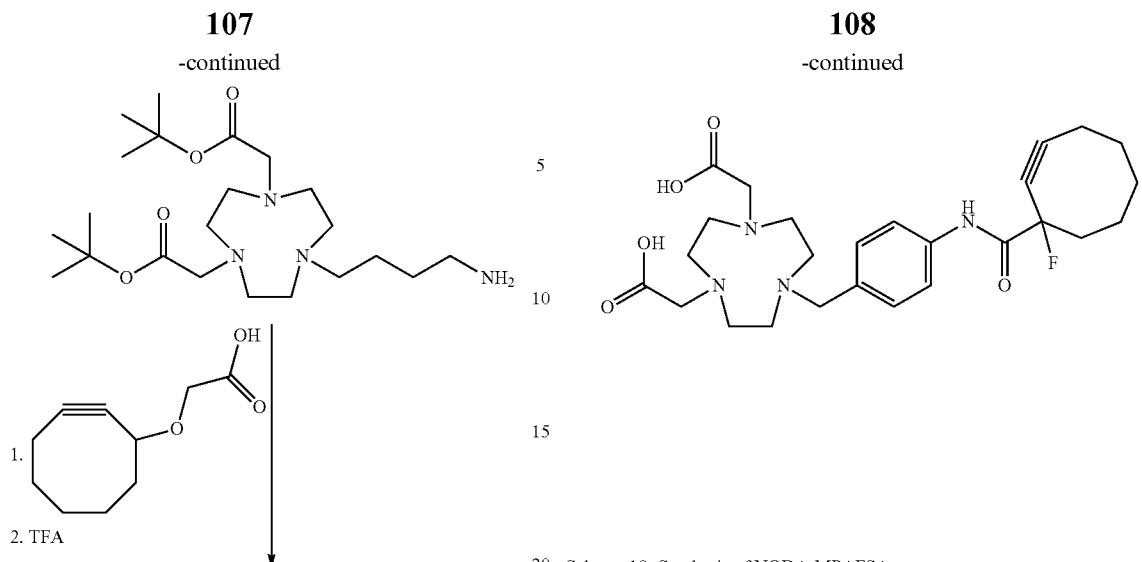
Scheme 17: Synthesis of NODA-MPAFO
108
-continued
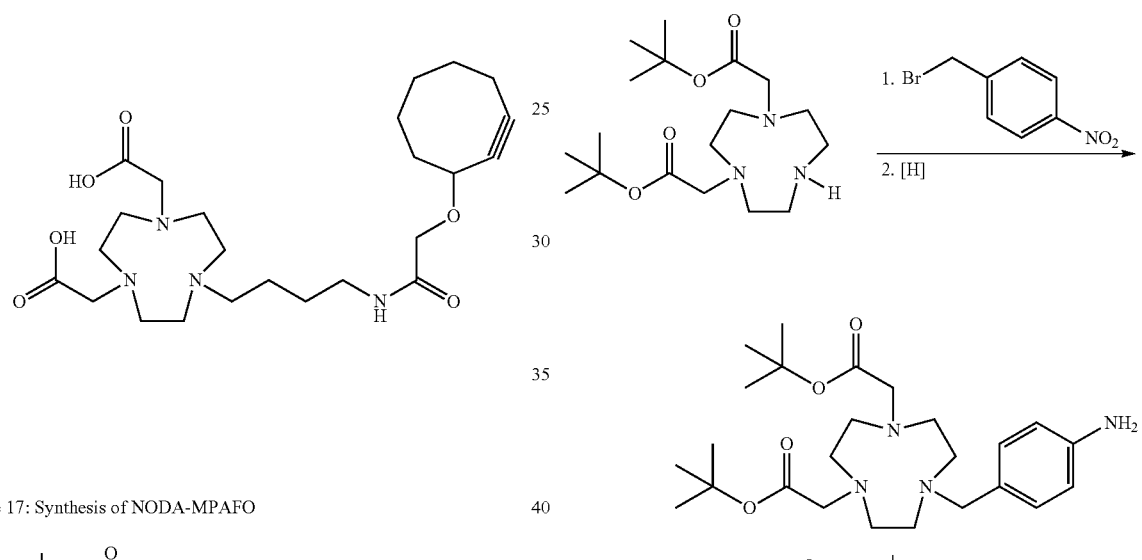
Scheme 18: Synthesis of NODA-MPAFSA
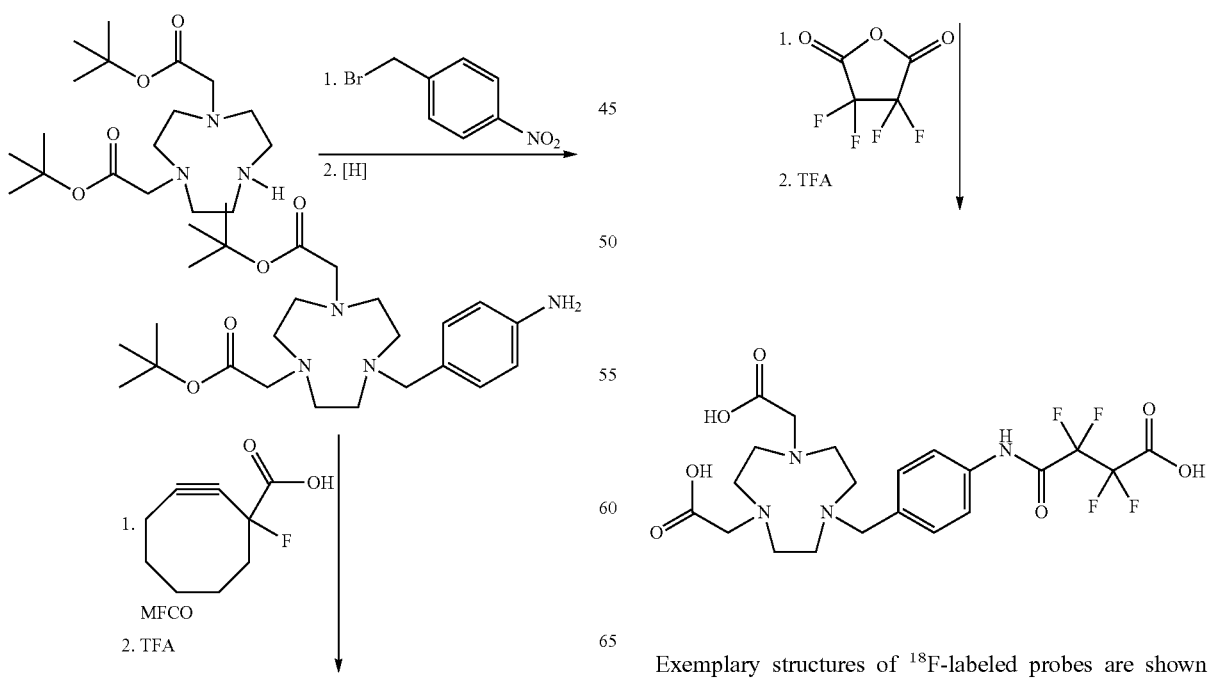
Exemplary structures of $^{18}$F-labeled probes are shown below.

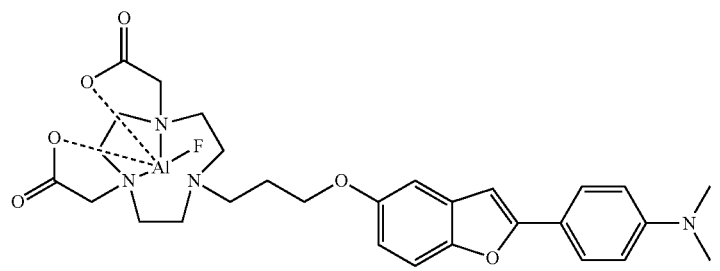
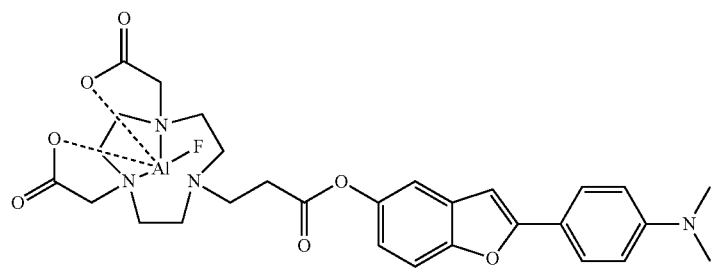
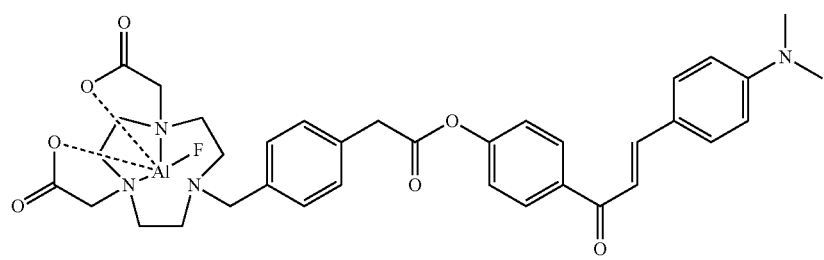
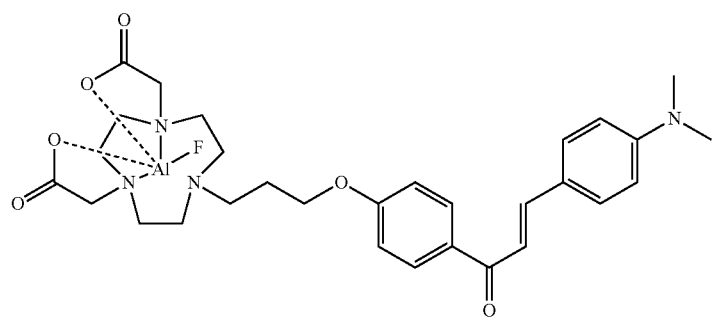
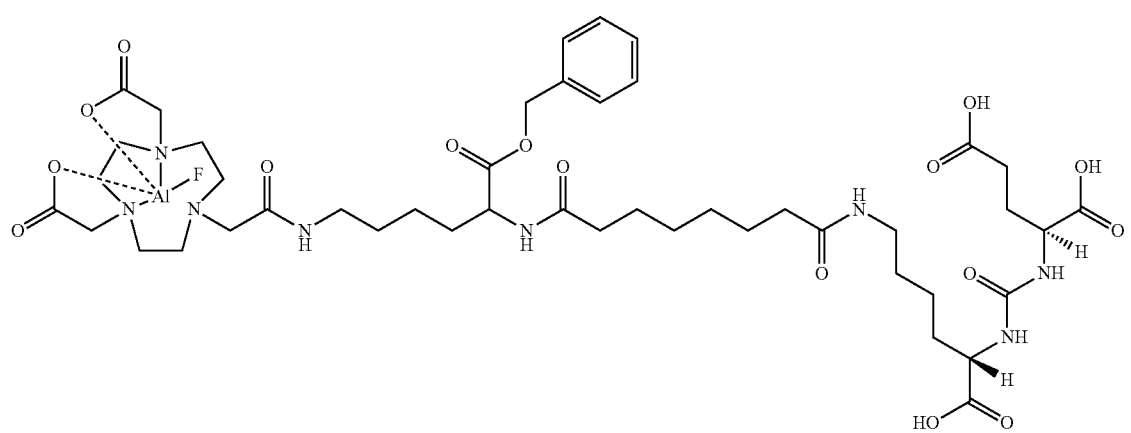

-continued
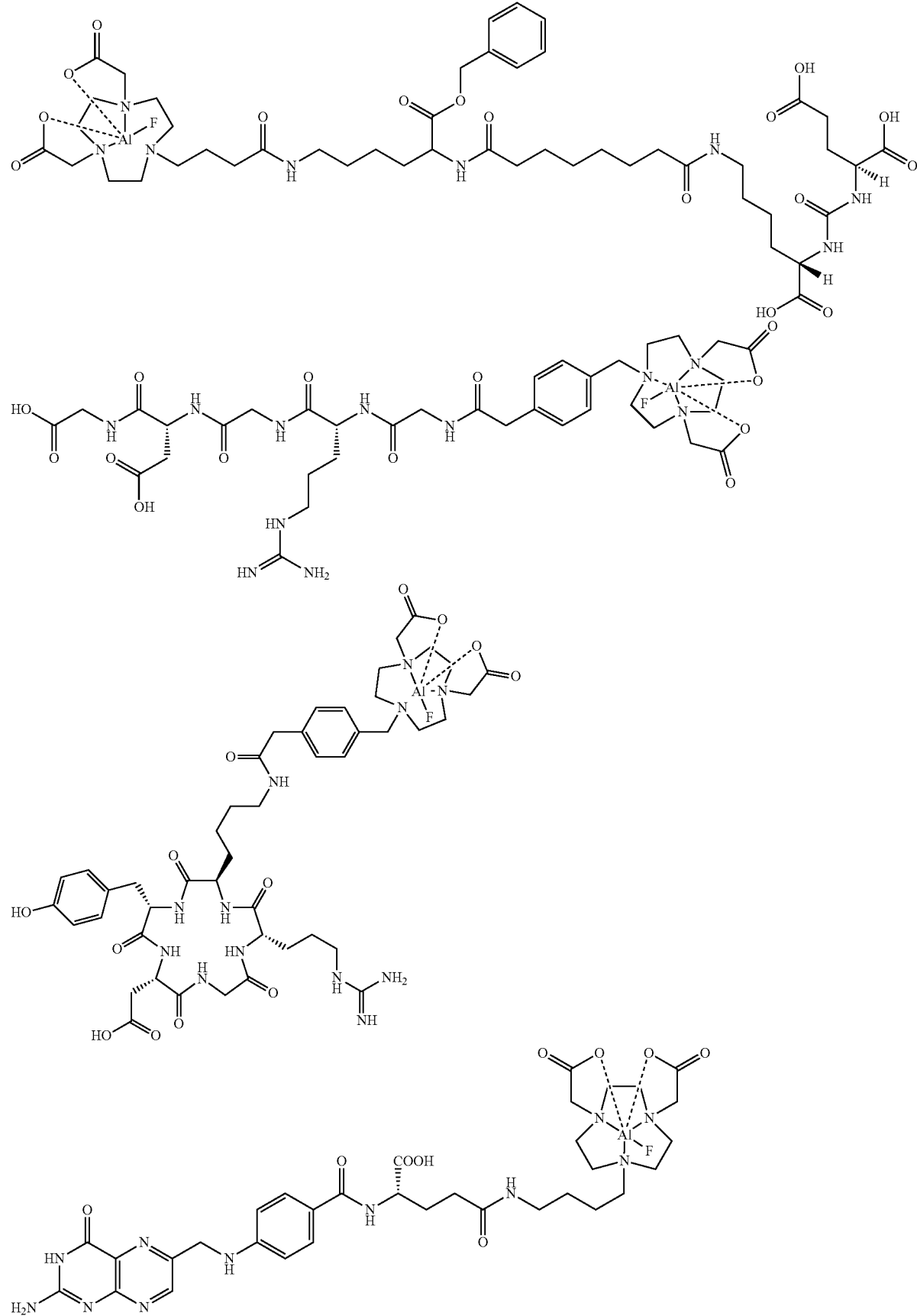

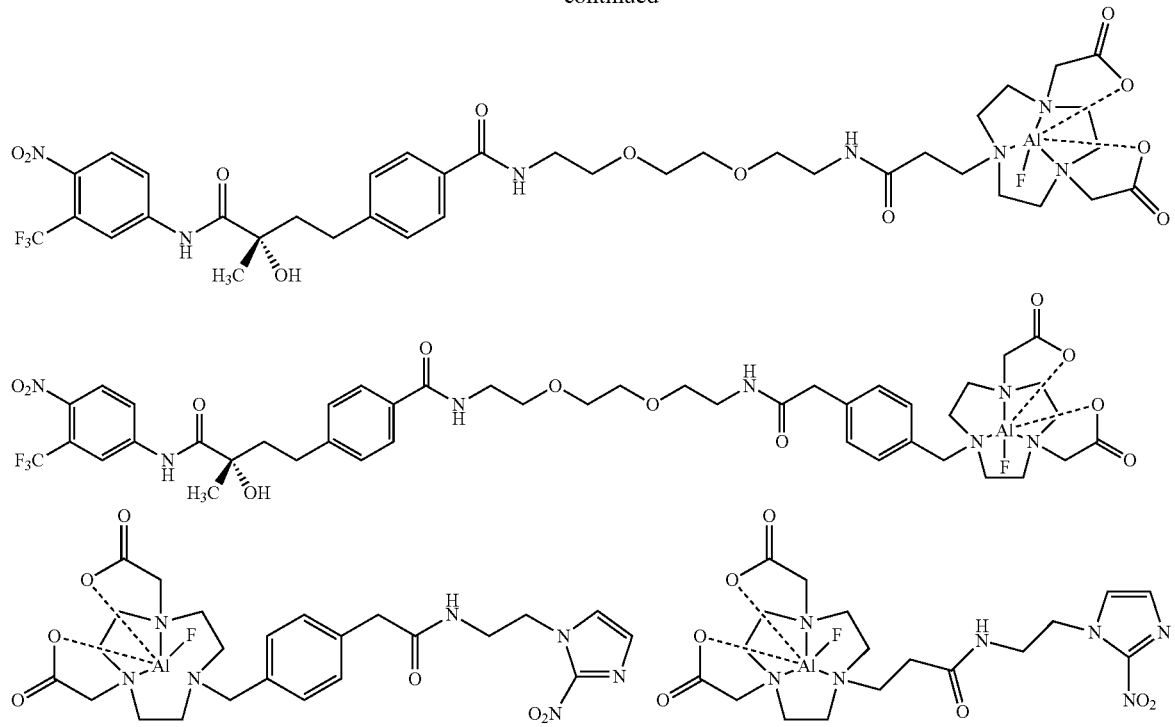

Conclusions

We have found that a novel class of triazacyclononane (TACN) derived BFCs, possessing a functionality that provides for an easy linkage onto biomolecules via solid phase or in solution, form stable complexes with a variety of metals. These BFCs also form remarkably stable $Al^{18}F$ chelates. Most $^{18}F$-labeling methods are tedious to perform, require the efforts of a specialized chemist, involve multiple purifications of the intermediates, anhydrous conditions, and generally end up with low RCYs. An advantage of this new class of BFCs is that they can be radiofluorinated rapidly in one step with high specific activity in an aqueous medium.

Example 33

Further Optimization of Kit Formulation

The effect of varying buffer composition on labeling efficiency was determined. Kits were formulated with 20 nmol IMP485 and 10 nmol $AlCl_3.6H_2O$ in 5% α,α-trehalose. The buffers and ascorbic acid were varied in the different formulations. The peptide and trehalose were dissolved in DI water and the $AlCl_3.6H_2O$ was dissolved in the buffer tested.

MES Buffer-4—morpholineethanesulfonic acid (MES, Sigma M8250), 0.3901 g (0.002 mol) was dissolved in 250 mL of DI $H_2O$ and adjusted to pH 4.06 with acetic acid (8 mM buffer).

KHP Buffer—Potassium biphthalate (KHP, Baker 2958-1), 0.4087 g (0.002 mol) was dissolved in 250 mL DI $H_2O$ pH 4.11 (8 mM buffer).

HEPES Buffer—N-2 hydroxyethylpiperazine-N'-2-ethane-sulfonic acid (HEPES, Calbiochem 391338) 0.4785 g (0.002 mol) dissolved in 250 mL DI $H_2O$ and adjusted to pH 4.13 with AcOH (8 mM buffer).

HOAc Buffer—Acetic acid (HOAc, Baker 9522-02), 0.0305 g (0.0005 mol) was dissolved in 250 mL DI $H_2O$ and adjusted to pH 4.03 with NaOH (2 mM buffer).

The $AlCl_3.6H_2O$ (Aldrich 23078) was dissolved in the buffers to obtain a 2 mM solution of $Al^{3+}$ in 2 mM buffer. IMP 485 0.0011 g (MW 1311.67, $8.39 \times 10^{-7}$ mol) was dissolved in 419 μL DI $H_2O$. Ascorbic acid, 0.1007 g (Aldrich 25,556-4, $5.72 \times 10^{-4}$ mol) was dissolved in 20 mL DI $H_2O$.

A variety of kits (summarized in Table 27) were prepared and adjusted to the proper pH by the addition of NaOH or HOAc as needed. The solution was then dispensed in 1 mL aliquots into 4, 3 mL lyophilization vials, frozen on dry ice and lyophilized. The initial shelf temperature for the lyophilization was −10° C. The samples were placed under vacuum and the shelf temperature was increased to 0° C. The samples were lyophilized for 15 hr and the shelf temperature was increased to 20° C. for 1 h before the vials were sealed under vacuum and removed from the lyophilizer. The kits were prepared with different buffers, at different pH values, with or without ascorbic acid and with or without acetate. After lyophilization, the kits were dissolved in 400 μL of saline and the pH was measured with a calibrated pH meter with a micro pH probe.

Radiolabeling—The kits were all labeled with $^{18}F^-$ in saline (200 μL, PETNET) with ethanol (200 μL) and heated to ~105° C. for 15 min. The labeled peptides were diluted with 0.6 mL DI $H_2O$ and then added to a dilution vial containing 2 mL DI $H_2O$. The reaction vial was washed with 2×1 mL portions of DI $H_2O$, which were added to the dilution vial. The diluted solution was filtered through a 1 mL (30 mg) HLB cartridge (1 mL at a time) and washed with 2 mL DI $H_2O$. The cartridge was moved to an empty vial and eluted with 3×200 μL 1:1 EtOH/DI $H_2O$. The Al[$^{18}F$]IMP485 was in the 1:1 EtOH/DI $H_2O$ fractions. The isolated yield was determined by counting the activity in the reaction vial, the dilution vial, the HLB cartridge, the DI $H_2O$ column wash and the 1:1 EtOH/DI $H_2O$ wash adding up the total and then dividing the amount in the 1:1 EtOH/DI $H_2O$ fraction by the total and multiplying by 100.

Results

The results of the studies are shown in Table 27. All the labeling in the presence of 0.1 mg of ascorbic acid went well. The ascorbic acid appears to serve as a significant non-volatile buffer that keeps the pH the same before and after lyophilization (kits 1-4). When ascorbic acid is not used (kits 5-8) the pH can change significantly along with the radiolabeling yield. The KHP buffer, kit 8, was the best kit in the second batch. Higher levels of ascorbate might also stabilize the $Al^{18}F$ complex in solution and act as a transfer ligand for $Al^{18}F$. The KHP buffer might also act as a transfer ligand for $Al^{18}F$ so the amount of KHP was increased from $5 \times 10^{-7}$ mol/kit for kit 8 to $6 \times 10^{-6}$ mol/kit for kit 11. The increase in KHP stabilized the pH better than kit 8 and gave a much better labeling yield. The kits with KHP+ascorbate (kit 12) and KHP+MES (kit 13) had slightly higher labeling yields. It may be that the higher levels of KHP and ascorbate act both as buffers and as transfer ligands to increase the labeling yields with those excipients. Citric acid is not a good buffer for $[Al^{18}F]$-labeling (kit 14), it gives low labeling yields even when only 50 µL of 2 mM citrate was used in the presence 0.1 mg of ascorbate. Increasing amounts of KHP, 0.1 M and above (kits 16-18) lead to lower labeling yields with more activity found in the aqueous wash from the HLB column.

TABLE 27

Results of labeling and pH studies

| Kit/lot Buffer | pH before lyophili-zation | pH after lyophili-zation | Isolated % yield |
|---|---|---|---|
| 1. HEPES + ascorbic | 4.07 | 3.83 | 82.6 |
| 2. MES + ascorbic | 4.08 | 3.99 | 83.5 |
| 3. NaOAc + ascorbic | 4.10 | 4.10 | 83.5 |
| 4. KHP + ascorbic | 4.12 | 4.10 | 86.1 |
| 5. HEPES No ascorbic + HOAc | 4.10 | 4.24 | 45.4 |
| 6. MES No ascorbic + HOAc | 4.07 | 4.25 | 66.4 |
| 7. HOAc No ascorbic + HOAc | 4.11 | 4.50 | 35.2 |
| 8. KHP No ascorbic + HOAc | 4.01 | 4.09 | 71 |
| 9. HEPES No ascorbic or NaOAc | 4.07 | 4.44 | 69 |
| 10. MES No ascorbic or NaOAc | 4.06 | 4.62 | 75 |
| 11. BM 20-57 KHP alone 0.015M | 4.07 | 4.05 | 83.9 |
| 12. BM 20-57 KHP 0.015M + ascorbic | 4.03 | 3.96 | 85.8 |
| 13. BM 20-57 KHP 0.015M + MES 0.015M | 4.10 | 4.09 | 87.0 |
| 14. Citric acid | 4.03 | 3.93 | 31.2 |
| 15. Ascorbic acid | 4.13 | 4.04 | 80.0 |
| 16. KHP 0.1M | 4.09 | 3.82 | 80.7 |
| 17. KHP 0.2M | 4.05 | 3.79 | 78.1 |
| 18. KHP 0.4M | 4.02 | 3.79 | 69.0 |

It appears from these results that potassium biphthalate is an optimal buffer for labeling. The peptide labeling kits were therefore reformulated to utilize KHP in the labeling buffer. The reformulated kits gave very high isolated labeling yields of about 97% when 100 nmol of peptide was labeled in 1:1 ethanol/saline. The labeling and purification time was also simplified and reduced to 20 min. In addition to using the new buffering agent, potassium biphthalate (KHP), we also added more moles of buffer, which may help stabilize the pH during labeling. The peptide is purified through an Alumina N cartridge by adding more saline to the reaction after heating and pushing crude product through the cartridge. The unbound $^{18}F^-$ and $Al^{18}F$ stick to the alumina and the labeled peptide is eluted very efficiently from the cartridge with saline. The formulation shown below is for a 20 nmol peptide kit but the same formulation is used for a 100 nmol peptide kit by adding more peptide and more $Al^{3+}$ (60 nmol $Al^{3+}$ for the 100 nmol peptide kit).

2 mM $Al^{3+}$ in 2 mM KHP—Aluminum chloride hexahydrate, 0.0196 g ($8.12 \times 10^{-5}$ mol, Aldrich 23078, MW 241.43) was dissolved in 40.6 mL of 2 mM potassium biphthalate (KHP, JT Baker 2958-1, MW 204.23). This can be stored at room temperature for months.

Ascorbic Acid—Ascorbic acid, 0.100 g was dissolved in 20 mL DI $H_2O$. This is made fresh on the day of use.

5% Trehalose—$\alpha,\alpha$-Trehalose dihydrate, 2.001 g (JT Baker, 4226-04, MW 378.33) was dissolved in 20 mL DI $H_2O$. This can be stored at room temperature for weeks.

KHP Kit Buffer—KHP, 0.2253 g was dissolved in 18 mL DI $H_2O$ (0.06 M). This solution can be kept for months at room temperature.

IMP485 solution—IMP485, 0.0049 g ($3.74 \times 10^{-6}$ mol, MW 1311.67) was dissolved in 1.494 mL DI $H_2O$ ($2.5 \times 10^{-3}$ M). This solution can be stored for months at $-20°$ C.

1M KOH—Potassium hydroxide (99.99% semiconductor grade, MW 56.11, Aldrich 306568) was dissolved in DI H2O to make a 1 M solution.

Kit Formulation (20 nmol kit, 40 kits)—The peptide, IMP485 (320 µL, $8 \times 10^{-7}$ mol) was placed in a 50 mL sterile polypropylene centrifuge tube (metal free) and mixed with 240 µL of the 2 mM $Al^{3+}$ solution ($4.8 \times 10^{-7}$ mol) 800 µL of the ascorbic acid solution, 1600 µL of the 0.06 M KHP solution, 8 mL of the 5% trehalose solution and the mixture was diluted to 40 mL with DI $H_2O$. The solution was adjusted to pH 3.99-4.03 with a few microliters of 1 M KOH. The peptide solution was dispensed 1 mL/vial with a 1 mL pipette into 3 mL glass lyophilization vials (unwashed).

Lyophilization—The vials were frozen on dry ice, fitted with lyophilization stoppers and placed on a $-20°$ C. shelf in the lyophilizer. The vacuum pump was turned on and the shelf temperature was raised to $0°$ C. after the vacuum was below 100 mtorr. The next morning the shelf temperature was raised to $20°$ C. for 4 hr before the samples were closed under vacuum and crimp sealed.

Radiolabeling—The $^{18}F^-$ in saline was received from PETNET in 200 µL saline in a 0.5 mL tuberculin syringe. Ethanol, 200 µL, was pulled into the $^{18}F^-$ solution and then the mixture was injected into a lyophilized kit containing the peptide. The solution was then heated in a $105°$ C. heating block for 15 min. Sterile saline, 0.6 mL was then added to the reaction vial and the solution was removed from the vial and pushed through an alumina N cartridge (SEP-PAK light, WAT023561, previously washed with 5 mL sterile saline) into a collection vial. The reaction vial was washed with 2×1 mL saline and the washes were pushed through the alumina column. The total labeling and purification time was about 20 min.

Example 34

Labeling at Reduced Temperature

The effect of varying the chelator structure on efficiency of labeling at reduced temperature was examined. A comparison of low temperature labeling of IMP466 (NOTA-Octreotide) with IMP485 showed that the simple NOTA ligand labels much better at low temperature than the NODA-MPAA ligand.

In one embodiment, a temperature sensitive molecule, such as a protein, may be conjugated to multiple copies of a simple NOTA ligand. The protein can then be purified and formulated for $Al^{18}F$-labeling (e.g., lyophilized). The protein kit was reconstituted with $^{18}F^-$ in saline, heated for the appropriate length of time and purified by gel filtration or an alumina column. Tables 27 and 28 show the temperature effects of labeling IMP466 vs. IMP485.

TABLE 28

Temperature-dependent labeling for Al$^{18}$F(IMP466)

| Temp ° C. | % Yield 25 µM | % Yield 50 µM | % Yield 100 µM | % Yield 250 µM | % Yield 500 µM |
|---|---|---|---|---|---|
| 50 | 3.3 | 8.6 | 14.5 | 20.5 | 37.1 |
| 70 | 21.3 | 47.4 | 58.0 | 82.8 | 93.6 |
| 90 | 29.0 | 50.7 | 70.3 | 83.0 | 93.5 |
| 100 | 34.3 | 55.8 | 77.4 | 84.0 | 94.5 |
| 110 | 34.9 | 60.3 | 78.1 | 87.9 | 90.5 |

TABLE 29

Temperature-dependent labeling for Al$^{18}$F(IMP485)

| Temp ° C. | % Yield 25 µM | % Yield 50 µM | % Yield 100 µM | % Yield 250 µM | % Yield 500 µM |
|---|---|---|---|---|---|
| 50 | 1.31 | 3.29 | 3.18 | 6.10 | 12.99 |
| 70 | 7.01 | 12.8 | 22.90 | 36.8 | 39.8 |
| 90 | 22.2 | 38.3 | 82.3 | 85.4 | 85.3 |
| 100 | 48.6 | 76.1 | 91.8 | 94.6 | 96.6 |
| 110 | 61.6 | 74.4 | 96.4 | 94.0 | 96.8 |

The data show that by switching to a different chelating moiety, the efficiency of low temperature labeling with Al$^{18}$F may be tripled at 50° C. Further modification of the chelating moiety may provide additional improvement of low temperature labeling. However, the 37% efficiency observed with IMP466 is sufficient to enable $^{18}$F PET imaging with temperature sensitive molecules if a sufficient number of chelating moieties are attached to the molecule.

We have also examined the effect of peptide concentration on low temperature labeling of IMP485. Kits were made with 10, 20, 40, 100 and 200 nmol of peptide and 0.6 equivalents of Al$^{3+}$ respectively. The rest of the formulation was the same for all of the kits. The kits were labeled with 400 µL saline/ EtOH and heated at 50-110° C. for 15 min and then purified through the Alumina N cartridge. The labeling results are reported as isolated yields in Table 30. At any temperature, increasing the concentration of peptide increased the efficiency of labeling. The results indicate that if the reaction volume can be decreased with the use of a microfluidics device then we can greatly reduce the amount of peptide and $^{18}$F$^-$ needed to prepare a single dose of labeled peptide for PET imaging.

TABLE 30

Effect of peptide concentration on efficiency of labeling as a function of temperature.

| Temp ° C. | % Yield 25 µM | % Yield 50 µM | % Yield 100 µM | % Yield 250 µM | % Yield 500 µM |
|---|---|---|---|---|---|
| 50 | 1.31 | 3.29 | 3.18 | 6.10 | 12.99 |
| 70 | 7.01 | 12.8 | 22.90 | 36.8 | 39.8 |
| 90 | 22.2 | 38.3 | 82.3 | 85.4 | 85.3 |
| 100 | 48.6 | 76.1 | 91.8 | 94.6 | 96.6 |
| 110 | 61.6 | 74.4 | 96.4 | 94.0 | 96.8 |

Example 35

Automated Synthesis of $^{18}$F-Labeled Molecules

Figure 21:
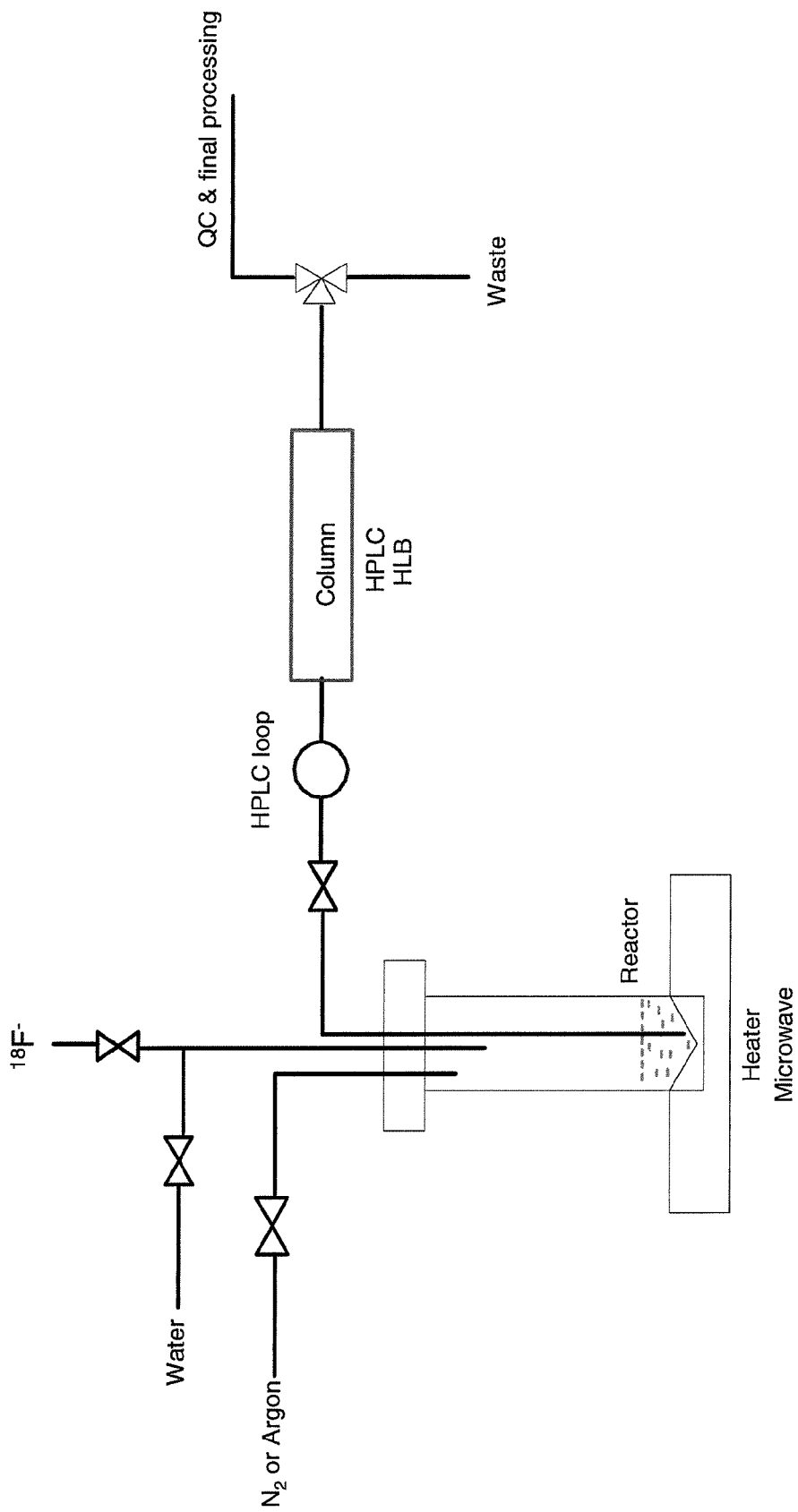
FIG. 21. Schematic diagram of automated synthesis module for $^{18}$F-labeling via [Al$^{18}$F]-chelation.

The following Example compared the automated synthesis of $^{18}$F-FBEM published by Kiesewetter et al., (2011, Appl Radiat Isot 69:410-4) to that of Al$^{18}$F(NODA-MPAEM). The automated synthesis of $^{18}$F-FBEM was accomplished using a sophisticated synthesis module (see below), with a RCY of 17% in 95 min. Our synthesis module (FIG. 21) would include a heating device and a HLB cartridge or HPLC column. With NODA-MPAEM we were able to get 67-79% RCY (decay corrected) in 40 min in one single step.

Scheme 19: Synthesis of Al$^{18}$F(NODA-MPAEM)

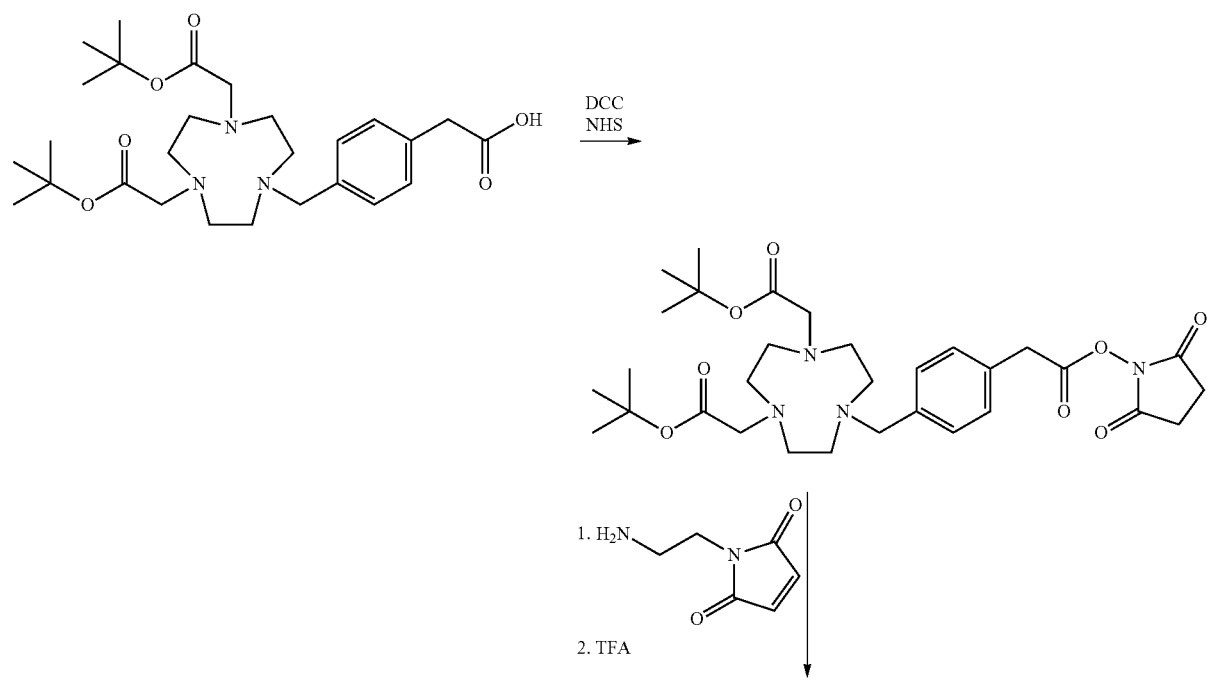

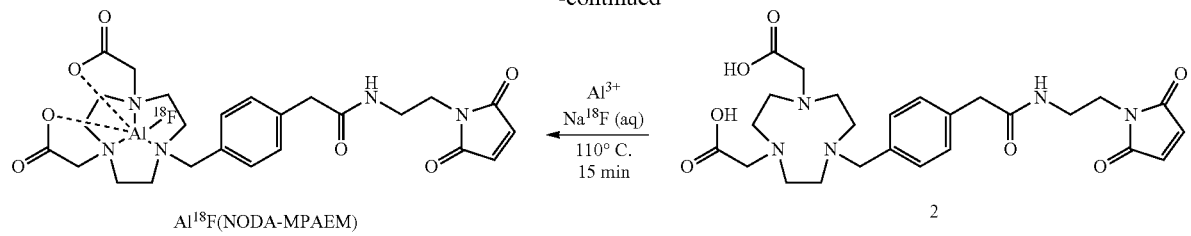

In both ¹⁸F-FBEM and ¹⁸F-FDG-MHO, the ¹⁸F is introduced first followed by a maleimide (Scheme 20 and 21). While NODA-MPAEM—a maleimide containing BFC—is ¹⁸F-labeled in one final step (Scheme 19).

Scheme 20: Synthesis of ¹⁸F-FBEM

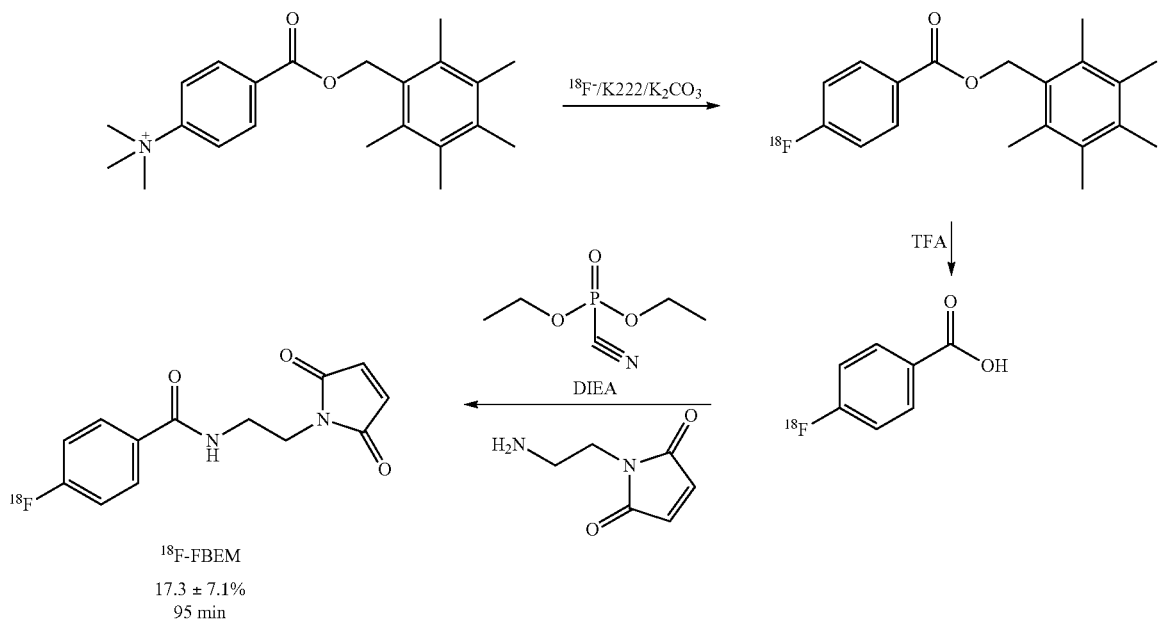

Scheme 21: Synthesis of ¹⁸F-FDG-MHO

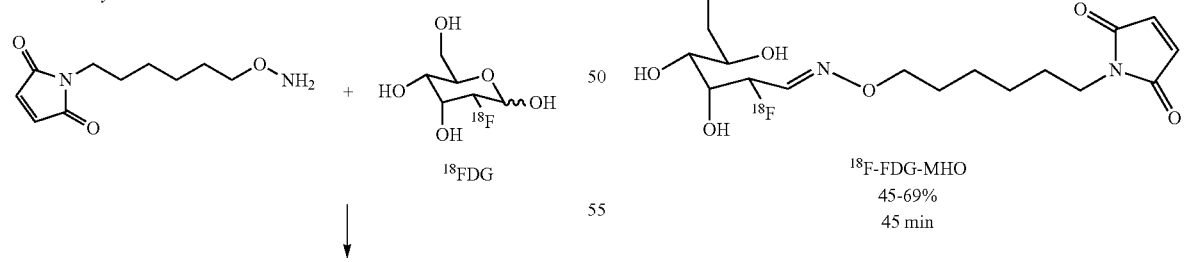

| Prosthetic group | Synthesis module | Synthesis time | RCY (%) | Specific activity |
|---|---|---|---|---|
| ¹⁸F-SFB 8-12 GBq (216-324 mCi) | TRACERlab ™ MX$_{FDG}$ | 98 min | 44.3 ± 2.5 | 250-350 GBq/μmol (6.8-9.5 Ci/μmol) |

| Prosthetic group | Synthesis module | Synthesis time | RCY* (%) | Specific activity |
|---|---|---|---|---|
| $^{18}$F-FBEM | Eckert & Ziegler | 95 min | 17.3 ± 7.1 | 181-351 GBq/μmol (4.9-9.5 Ci/μmol) |

With 8.2 GBq (222 mCi) $^{18}$F$^-$ provide 1.87 GBq (50.6 mCi) of $^{18}$F-FBEM in 96 min (22.8% uncorrected; 41.7% corrected for decay).
*not decay corrected.

What is claimed is:

1. A bifunctional chelating agent comprising a compound of the structure

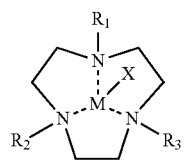

wherein $R_1$ and $R_2$ are independently selected from the group consisting of

—$CH_2$—COOH

—$CH_2$—$CH_2$—OH

—CH($CH_3$)—COOH

—CH($C_6H_5$)—COOH

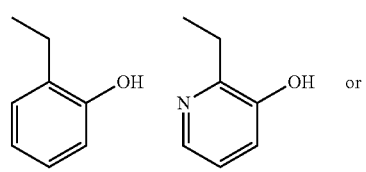

-continued

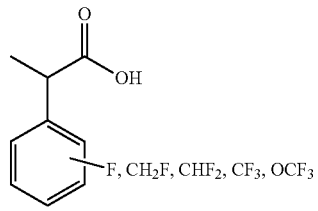

and $R_3$ is selected from the group consisting of:

—$CH_2$—$(CH_2)_n$—COOH    —$CH_2$—$(CH_2)_n$—$NH_2$

—$CH_2$—$(CH_2)_n$—OH       —$CH_2$—$(CH_2)_n$—N=C=S

—$CH_2$—$(CH_2)_n$—$N_3$    —$CH_2$—$(CH_2)_n$—N⟨maleimide⟩

—$CH_2$—$(CH_2)_n$—SH       —$CH_2$—$(CH_2)_n$—C≡CH

—$CH_2$—$(CH_2)_n$—$CONHNH_2$  —$CH_2$—$(CH_2)_n$—CHO

—$CH_2$—$(CH_2)_n$—NH—$NH_2$   —$CH_2$—$(CH_2)_n$—COOSu

—$CH_2$—$(CH_2)_n$—NH—C(O)—$(CF_2)_n$—COOH

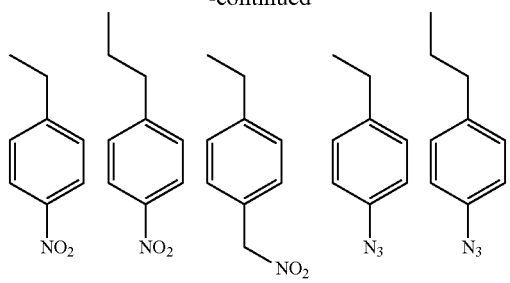
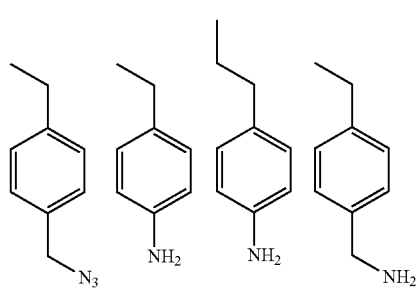
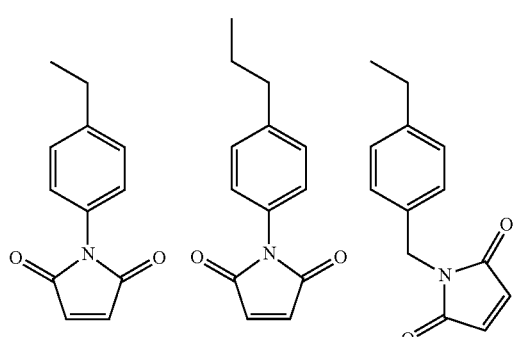
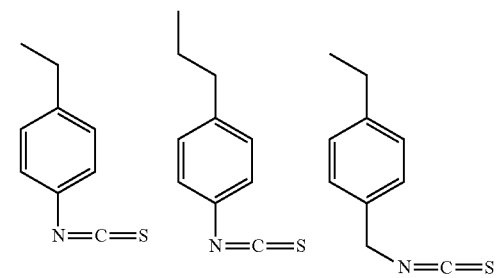
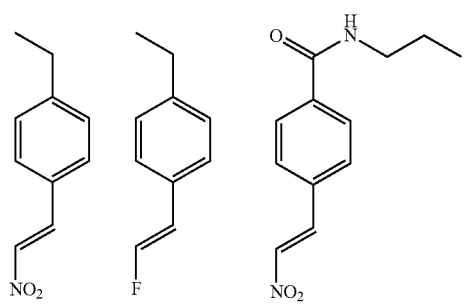

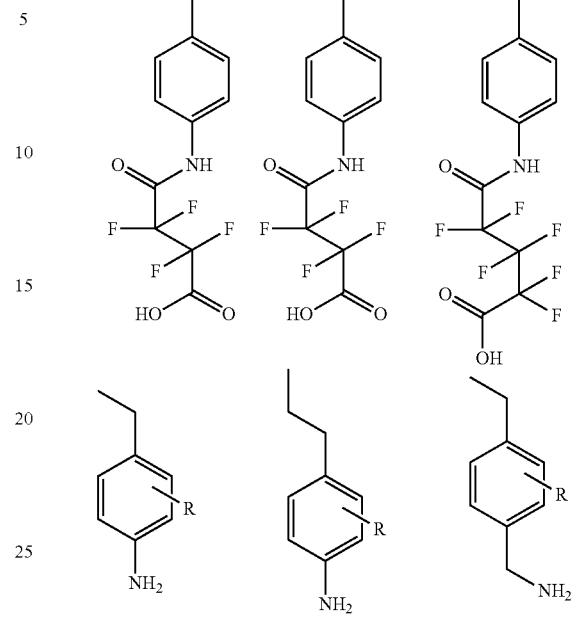
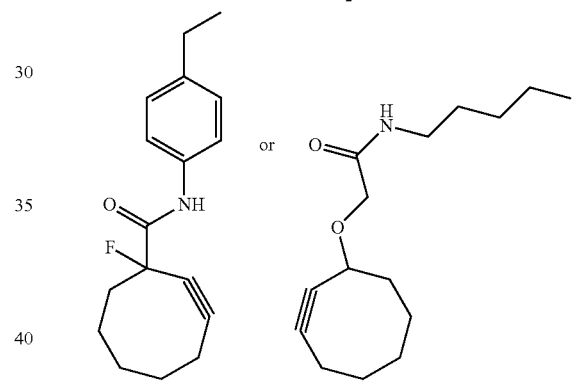

wherein M is a metal selected from the group consisting of Gd Fe, Cu, Al, Ga, In, Tl, Lu, La, Sm, Ta, Si, Ge, Sn, Co, Cr, Mn, Ti, V, Sc, Y, Tc, Zr, Mo, W, Ru, Rh, Ir and Ni and X is a coordinating species selected from the group consisting OH, Cl, Br, F, I, $NO_3$, $O_2^-$, $CH_3$, CN, $ClO_4$, $H_2O$, $BF_4$, SCN, $N_3$, RCOO, $CF_3COO$, $CH_3COO$, $HCO_3$, RSH and ROH, wherein n=1-9 and wherein R=F, CH2F, CHF2, CH3 or OCF3.

2. The bifunctional chelating agent of claim 1, further comprising a $^{19}F$ moiety selected from the group consisting of fluorinated alkyl, fluorinated acetate, fluoroalkyl phosphonate, fluoroaniline, trifluoromethyl aniline and trifluoromethoxy aniline.

3. The bifunctional chelating agent of claim 1, wherein the bifunctional chelating agent is selected from the group consisting of 1,4,7-triazacyclononane-1,4-diacetic acid-7-methyl phenyl-p-nitro; 1,4,7-triazacyclononane-1,4-diacetic acid-7-ethyl phenyl-p-nitro; 1,4,7-triazacyclononane-1,4-diacetic acid-7-methyl phenyl-p-amino; 1,4,7-triazacyclononane-1,4-diacetic acid-7-ethyl phenyl-p-amino; 1,4,7-triazacyclononane-1,4-diacetic acid-7-methyl phenyl-p-isothiocyanato; 1,4,7-triazacyclononane-1,4-diacetic acid-7-ethyl phenyl-p-isothiocyanato; 1,4,7-triazacyclononane-1,4-diacetic acid-7-butanoic acid; 1,4,7-triazacyclononane-1,4- diacetic acid-7-propanoic acid; 1,4,7-triazacyclononane-1,4-diacetic acid-7-hexanoic acid; 1,4,7-triazacyclononane-1-butylamine-4,7-diacetic acid; 1,4,7-triazacyclononane-1-propylarnine-4,7-diacetic acid; 1,4,7-triazacyclononane-1-butyne-4,7-diacetic acid; 1,4,7-triazacyclononane-1-butylamido ethyl maleimide-4,7-diacetic acid; 1,4,7-triazacyclononane-1,4-diacetic acid-7-methyl phenyl acetamido ethyl maleimide; 1,4,7-triazacyclononane-1-butyl isothiocyanato-4,7-diacetic acid; 1,4,7-triazacyclononane-1-butyl azido-4,7-diacetic acid; 1,4,7-triazacyclononane-1-ethanol-4,7-diacetic acid; 1,4,7-triazacyclononane-1-propanol-4,7-diacetic acid; and 1,4,7-triazacyclononane-1-butanol-4,7-diacetic acid.

4. The bifunctional chelating agent of claim 1, wherein M is selected from the group consisting of Al, Ga, Cu, Cr, Y, Gd, Fe, Tc and In.

5. The bifunctional chelating agent of claim 1, wherein M is selected from the group consisting of $^{64}Cu$, $^{68}Ga$, $^{111}In$, $^{27}Al$, $^{99m}Tc$ and $^{18}Y$.

6. The bifunctional chelating agent of claim 1, wherein X is OH, $^{19}F$ or $^{18}F$.

7. The bifunctional chelating agent of claim 1, wherein M-X is metal-$^{18}F$, Al$^{19}F$, Al$^{18}F$, Al—OH, Al—H$_2$O.

8. A composition comprising a bifunctional chelating agent according to claim 1 in an aqueous medium.

9. The composition of claim 8, wherein the composition is at a pH of about 3.5 to 4.5.

10. The composition of claim 8, further comprising an organic solvent.

11. The composition of claim 8, wherein the organic solvent is selected from the group consisting of acetonitrile, ethanol, dimethylformamide, methanol, acetone, propanol, isopropanol, butanol, Cert-butanol, tetrahydrofuran, dioxane and dimethylsulfoxide.

12. The composition of claim 8, further comprising ascorbic acid, potassium biphthalate, ethanol and trehalose.

13. The bifunctional chelating agent of claim 1, further comprising a radionuclide selected from group consisting of $^{18}F$, $^{64}Cu$, $^{68}Ga$, $^{111}In$, $^{99m}Tc$ and $^{86}Y$.

14. The bifunctional chelating agent of claim 1, wherein the bifunctional chelating agent is conjugated to a molecule via an amide, ester, anhydride, carbonate, carbamate, dithiocarbamate, ether, thioether, disulfide, urea, thiourea, triazoyl, amine, imine, oxime or hydrazone bond.

15. The bifunctional chelating agent of claim 14, wherein the molecule is selected from the group consisting of oligonucleotides, hormones, growth factors, cytokines, chemokines, angiogenic factors, anti-angiogenic factors, immunomodulators, peptides, polypeptides, proteins, nucleic acids, antibodies, antibody fragments, drugs, interleukins, interferons, oligosaccharides, polysaccharides, lipids, cell receptor-binding agents, siderophores and vitamins.

16. The bifunctional chelating agent of claim 14, wherein the molecule is an antibody, somatostatin, EGF, VEGF, bombesin, methotrexate, growth hormone, RGD or folic acid.

17. The bifunctional chelating agent of claim 14, wherein the molecule is radiolabeled with $^{18}F$, $^{64}Cu$, $^{68}Ga$, $^{111}In$, $^{99m}Tc$ or $^{86}Y$.

18. A kit for $^{18}F$ or $^{19}F$ labeling comprising:
a) at least one buffer;
b) a bifunctional chelating agent according to claim 1;
c) a bulking agent;
d) a radiolysis protection agent; and
e) a Group IIIA metal.

19. The kit of claim 18, wherein the bifunctional chelating agent comprises a reactive group to bind to a molecule, wherein the reactive group is selected from the group consisting of maleimide, isothiocyanate, ester, alkyne, azide, amine, aldehyde, and alkene.

20. The kit of claim 18, wherein the bulking agent is selected from the group consisting of trehalose, sorbitol, glucose, and mannitol.

21. The kit of claim 18, wherein the radiolysis protection agent is ascorbic acid.

22. The kit of claim 18, wherein the buffer is selected from the group consisting of potassium biphthalate, HEPES, MES and acetate.

23. The kit of claim 18, further comprising an organic solvent selected from the group consisting of ethanol, acetonitrile, MeCN, DMF and THF.

24. The kit of claim 18, further comprising aluminum, trehalose, potassium biphthalate, ethanol and ascorbic acid in an aqueous medium at a pH between 3.9 and 4.2.

25. The kit of claim 18, wherein the kit contents are lyophilized for storage.

26. A method of labeling a molecule with $^{18}F$ or $^{19}F$ comprising;
a) attaching a complex of $^{18}F$ or $^{19}F$ and a group IIIA metal to a bifunctional chelating agent according to claim 1, and
b) attaching the bifunctional chelating agent to the molecule.

27. The method of claim 26, wherein the molecule is selected from the group consisting of a protein, a peptide, an antibody, a monoclonal antibody, a bispecific antibody, a multispecific antibody, an antibody fusion protein, an antigen-binding antibody fragment, an affibody and a targetable construct.

28. The method of claim 26, wherein the group IIIA metal is Al.

29. The method of claim 28, wherein the Al is attached to the bifunctional chelating agent before the $^{18}F$ or $^{19}F$ is complexed to the Al.

30. The method of claim 26, wherein a metal-$^{18}F$ or metal-$^{19}F$ complex is attached to the bifunctional chelating agent by heating in an aqueous medium at a temperature between 50° C. and 110° C.

31. The method of claim 30, wherein the efficiency of labeling with $^{18}F$ is at least 35% at 50° C.

32. The method of claim 26, wherein the specific activity of the labeled molecule is at least 4,000 Ci/mmol.

33. The method of claim 26, wherein a metal-$^{18}F$ complex is attached to the bifunctional chelating agent in an aqueous medium comprising Al, trehalose, potassium biphthalate, ethanol and ascorbic acid at a pH between 3.9 and 4.2.

34. The method of claim 26, wherein multiple copies of the bifunctional chelating agent are attached to the molecule.

35. The method of claim 26, wherein the $^{18}F$-labeled molecule is produced in less than 30 minutes from the start of the method.

36. The method of claim 26, further comprising using positron emission tomography (PET), magnetic resonance imaging (MRI) and/or single photon emission computer tomography (SPECT) to image the distribution of the labeled molecule in a subject.

37. The method of claim 26, wherein the bifunctional chelating agent is attached to the molecule by a click chemistry reaction or by a maleimide-sulfhydryl reaction.

38. The method of claim 26, wherein the yield of labeled molecule is at least 95%.

39. The method of claim 27, wherein the labeled molecule is an antibody selected from the group consisting of hR1 (anti-IGF-1R), hPAM4 m (anti-pancreatic cancer mucin), hA20 (anti-CD20), hA19 (anti-CD19), hIMMU31 (anti-AFP), hLL1 (anti-CD74), hLL2 (anti-CD22), hMu-9 (anti-CSAp), hL243 (anti-HLA-DR), hMN-14 (anti-CEACAM5), hMN-15 (anti-CEACAM6), hRS7 (anti-EGP-1) and hMN-3 (anti-CEACAM6).

40. The method of claim 26, wherein the bifunctional chelating agent is attached to the molecule before the complex of $^{18}F$ or $^{19}F$ and group MA metal is attached to the bifunctional chelating agent.

41. The method of claim 26, wherein the complex of $^{18}F$ or $^{19}F$ and group IIIA metal is attached to the bifunctional chelating agent before the bifunctional chelating agent is attached to the molecule.

* * * * *

SEQUENCE LISTING

<160> NUMBER OF SEQ ID NOS: 58

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term DOTA
<220> FEATURE:
<221> NAME/KEY: MOD_RES
<222> LOCATION: (2)..(2)
<223> OTHER INFORMATION: Lys(HSG)
<220> FEATURE:
<221> NAME/KEY: MOD_RES
<222> LOCATION: (4)..(4)
<223> OTHER INFORMATION: Lys(HSG)
<220> FEATURE:
<223> OTHER INFORMATION: C-term amidated
<220> FEATURE:
<223> OTHER INFORMATION: see specification as filed for detailed description of substitutions and preferred embodiments

<400> SEQUENCE: 1

Phe Lys Tyr Lys
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Lys(DTPA)
<220> FEATURE:
<221> NAME/KEY: MOD_RES
<222> LOCATION: (3)..(3)
<223> OTHER INFORMATION: Lys(DTPA)
<220> FEATURE:
<221> NAME/KEY: MOD_RES
<222> LOCATION: (4)..(4)
<223> OTHER INFORMATION: Lys(Tscg-Cys); branched sequence with C-term Lys which has a (Tscg-Cys) side-chain; Cys is not the C-term residue
<220> FEATURE:
<223> OTHER INFORMATION: C-term amidated

<400> SEQUENCE: 2

Lys Tyr Lys Lys
1

```
<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term DTPA
<220> FEATURE:
<221> NAME/KEY: MOD_RES
<222> LOCATION: (3)..(3)
<223> OTHER INFORMATION: Lys(HSG)
<220> FEATURE:
<221> NAME/KEY: MOD_RES
<222> LOCATION: (4)..(4)
<223> OTHER INFORMATION: D-Tyr
<220> FEATURE:
<221> NAME/KEY: MOD_RES
<222> LOCATION: (5)..(5)
<223> OTHER INFORMATION: Lys(HSG)
<220> FEATURE:
<223> OTHER INFORMATION: C-term amidated

<400> SEQUENCE: 3

Gln Ala Lys Tyr Lys
1               5

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NOTA-ITC benzyl-ITC
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-Lys(HSG)
<220> FEATURE:
<221> NAME/KEY: MOD_RES
<222> LOCATION: (3)..(3)
<223> OTHER INFORMATION: D-Tyr
<220> FEATURE:
<221> NAME/KEY: MOD_RES
<222> LOCATION: (4)..(4)
<223> OTHER INFORMATION: D-Lys(HSG)
<220> FEATURE:
<223> OTHER INFORMATION: C-term amidated

<400> SEQUENCE: 4

Ala Lys Tyr Lys
1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-Lys(HSG)
<220> FEATURE:
```

```
<221> NAME/KEY: MOD_RES
<222> LOCATION: (3)..(3)
<223> OTHER INFORMATION: D-Tyr
<220> FEATURE:
<221> NAME/KEY: MOD_RES
<222> LOCATION: (4)..(4)
<223> OTHER INFORMATION: D-Lys(HSG)
<220> FEATURE:
<223> OTHER INFORMATION: C-term amidated

<400> SEQUENCE: 5

Ala Lys Tyr Lys
1

<210> SEQ ID NO 6
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 7
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
        35                  40                  45

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Ile Glu Tyr Leu Ala Lys Gln Ile Val Asp Asn Ala Ile Gln Gln
1               5                   10                  15

Ala

<210> SEQ ID NO 9
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 9

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 10
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gly Ser Gly Gly Gly Ser Gly Gly Gly Ser His Ile Gln Ile
1               5                   10                  15

Pro Pro Gly Leu Thr Glu Leu Leu Gln Gly Tyr Thr Val Glu Val Leu
            20                  25                  30

Arg Gln Gln Pro Pro Asp Leu Val Glu Phe Ala Val Glu Tyr Phe Thr
        35                  40                  45

Arg Leu Arg Glu Ala Arg Ala
    50                  55

<210> SEQ ID NO 11
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Ser Gly Gly Gly Ser Gly Gly Gly Ser Gln Ile Glu Tyr
1               5                   10                  15

Leu Ala Lys Gln Ile Val Asp Asn Ala Ile Gln Gln Ala
            20                  25

<210> SEQ ID NO 12
<211> LENGTH: 51
<212> TYPE: PRT
<213> ORGANISM: Homo sapiens

<400> SEQUENCE: 12

Ser Leu Arg Glu Cys Glu Leu Tyr Val Gln Lys His Asn Ile Gln Ala
1               5                   10                  15

Leu Leu Lys Asp Val Ser Ile Val Gln Leu Cys Thr Ala Arg Pro Glu
            20                  25                  30

Arg Pro Met Ala Phe Leu Arg Glu Tyr Phe Glu Lys Leu Glu Lys Glu
        35                  40                  45

Glu Ala Lys
    50

<210> SEQ ID NO 13
<211> LENGTH: 54
<212> TYPE: PRT
<213> ORGANISM: Homo sapiens

<400> SEQUENCE: 13

Ser Leu Lys Gly Cys Glu Leu Tyr Val Gln Leu His Gly Ile Gln Gln
1               5                   10                  15

Val Leu Lys Asp Cys Ile Val His Leu Cys Ile Ser Lys Pro Glu Arg
```

-continued

```
                20                  25                  30
Pro Met Lys Phe Leu Arg Glu His Phe Glu Lys Leu Glu Lys Glu Glu
            35                  40                  45

Asn Arg Gln Ile Leu Ala
        50

<210> SEQ ID NO 14
<211> LENGTH: 44
<212> TYPE: PRT
<213> ORGANISM: Homo sapiens

<400> SEQUENCE: 14

Ser His Ile Gln Ile Pro Pro Gly Leu Thr Glu Leu Leu Gln Gly Tyr
1               5                   10                  15

Thr Val Glu Val Gly Gln Gln Pro Pro Asp Leu Val Asp Phe Ala Val
            20                  25                  30

Glu Tyr Phe Thr Arg Leu Arg Glu Ala Arg Arg Gln
        35                  40

<210> SEQ ID NO 15
<211> LENGTH: 44
<212> TYPE: PRT
<213> ORGANISM: Homo sapiens

<400> SEQUENCE: 15

Ser Ile Glu Ile Pro Ala Gly Leu Thr Glu Leu Leu Gln Gly Phe Thr
1               5                   10                  15

Val Glu Val Leu Arg His Gln Pro Ala Asp Leu Leu Glu Phe Ala Leu
            20                  25                  30

Gln His Phe Thr Arg Leu Gln Gln Glu Asn Glu Arg
        35                  40

<210> SEQ ID NO 16
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (2)..(2)
<223> OTHER INFORMATION: His, Lys or Arg
<220> FEATURE:
<221> NAME/KEY: MOD_RES
<222> LOCATION: (4)..(4)
<223> OTHER INFORMATION: Gln or Asn
<220> FEATURE:
<221> NAME/KEY: MOD_RES
<222> LOCATION: (8)..(8)
<223> OTHER INFORMATION: Gly or Ala
<220> FEATURE:
<221> NAME/KEY: MOD_RES
<222> LOCATION: (10)..(10)
<223> OTHER INFORMATION: Thr or Ser
<220> FEATURE:
<221> NAME/KEY: MOD_RES
<222> LOCATION: (11)..(11)
<223> OTHER INFORMATION: Glu or Asp
<220> FEATURE:
<221> NAME/KEY: MOD_RES
<222> LOCATION: (14)..(14)
<223> OTHER INFORMATION: Gln or Asn
<220> FEATURE:
<221> NAME/KEY: MOD_RES
```

```
<222> LOCATION: (15)..(15)
<223> OTHER INFORMATION: Gly or Ala
<220> FEATURE:
<221> NAME/KEY: MOD_RES
<222> LOCATION: (17)..(17)
<223> OTHER INFORMATION: Thr or Ser
<220> FEATURE:
<221> NAME/KEY: MOD_RES
<222> LOCATION: (19)..(19)
<223> OTHER INFORMATION: Glu or Asp
<220> FEATURE:
<221> NAME/KEY: MOD_RES
<222> LOCATION: (22)..(22)
<223> OTHER INFORMATION: Arg or Lys
<220> FEATURE:
<221> NAME/KEY: MOD_RES
<222> LOCATION: (23)..(24)
<223> OTHER INFORMATION: Gln or Asn
<220> FEATURE:
<221> NAME/KEY: MOD_RES
<222> LOCATION: (27)..(27)
<223> OTHER INFORMATION: Asp or Glu
<220> FEATURE:
<221> NAME/KEY: MOD_RES
<222> LOCATION: (30)..(30)
<223> OTHER INFORMATION: Glu or Asp
<220> FEATURE:
<221> NAME/KEY: MOD_RES
<222> LOCATION: (32)..(32)
<223> OTHER INFORMATION: Ala, Leu, Ile or Val
<220> FEATURE:
<221> NAME/KEY: MOD_RES
<222> LOCATION: (34)..(34)
<223> OTHER INFORMATION: Glu or Asp
<220> FEATURE:
<221> NAME/KEY: MOD_RES
<222> LOCATION: (37)..(37)
<223> OTHER INFORMATION: Thr or Ser
<220> FEATURE:
<221> NAME/KEY: MOD_RES
<222> LOCATION: (38)..(38)
<223> OTHER INFORMATION: Arg or Lys
<220> FEATURE:
<221> NAME/KEY: MOD_RES
<222> LOCATION: (40)..(40)
<223> OTHER INFORMATION: Arg or Lys
<220> FEATURE:
<221> NAME/KEY: MOD_RES
<222> LOCATION: (41)..(41)
<223> OTHER INFORMATION: Glu or Asp
<220> FEATURE:
<221> NAME/KEY: MOD_RES
<222> LOCATION: (42)..(42)
<223> OTHER INFORMATION: Ala, Leu, Ile or Val
<220> FEATURE:
<221> NAME/KEY: MOD_RES
<222> LOCATION: (43)..(43)
<223> OTHER INFORMATION: Arg or Lys
<220> FEATURE:
<221> NAME/KEY: MOD_RES
<222> LOCATION: (44)..(44)
<223> OTHER INFORMATION: Ala, Leu, Ile or Val

<400> SEQUENCE: 16

Xaa Xaa Ile Xaa Ile Pro Pro Xaa Leu Xaa Xaa Leu Leu Xaa Xaa Tyr
 1               5                  10                  15

Xaa Val Xaa Val Leu Xaa Xaa Xaa Pro Pro Xaa Leu Val Xaa Phe Xaa
            20                  25                  30

Val Xaa Tyr Phe Xaa Xaa Leu Xaa Xaa Xaa Xaa Xaa
        35                  40

<210> SEQ ID NO 17
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln or Asn
<220> FEATURE:
<221> NAME/KEY: MOD_RES
<222> LOCATION: (2)..(2)
<223> OTHER INFORMATION: Ile, Leu or Val
<220> FEATURE:
<221> NAME/KEY: MOD_RES
<222> LOCATION: (3)..(3)
<223> OTHER INFORMATION: Glu or Asp
<220> FEATURE:
<221> NAME/KEY: MOD_RES
<222> LOCATION: (4)..(4)
<223> OTHER INFORMATION: Tyr, Phe, Thr or Ser
<220> FEATURE:
<221> NAME/KEY: MOD_RES
<222> LOCATION: (5)..(5)
<223> OTHER INFORMATION: Leu, Ile or Val
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Gln or Asn
<220> FEATURE:
<221> NAME/KEY: MOD_RES
<222> LOCATION: (11)..(11)
<223> OTHER INFORMATION: Asp or Glu
<220> FEATURE:
<221> NAME/KEY: MOD_RES
<222> LOCATION: (12)..(12)
<223> OTHER INFORMATION: Asn or Gln
<220> FEATURE:
<221> NAME/KEY: MOD_RES
<222> LOCATION: (15)..(16)
<223> OTHER INFORMATION: Gln or Asn
<220> FEATURE:
<221> NAME/KEY: MOD_RES
<222> LOCATION: (17)..(17)
<223> OTHER INFORMATION: Ala, Leu, Ile or Val

<400> SEQUENCE: 17

Xaa Xaa Xaa Xaa Xaa Ala Xaa Xaa Ile Val Xaa Xaa Ala Ile Xaa Xaa
1               5                   10                  15

Xaa

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Ile Glu Tyr Val Ala Lys Gln Ile Val Asp Tyr Ala Ile His Gln
1               5                   10                  15

Ala

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19
```

-continued

```
Gln Ile Glu Tyr Lys Ala Lys Gln Ile Val Asp His Ala Ile His Gln
1               5                   10                  15

Ala

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Ile Glu Tyr His Ala Lys Gln Ile Val Asp His Ala Ile His Gln
1               5                   10                  15

Ala

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Ile Glu Tyr Val Ala Lys Gln Ile Val Asp His Ala Ile His Gln
1               5                   10                  15

Ala

<210> SEQ ID NO 22
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asp Leu Ile Glu Glu Ala Ala Ser Arg Ile Val Asp Ala Val Ile Glu
1               5                   10                  15

Gln Val Lys Ala Ala Gly Ala Tyr
                20

<210> SEQ ID NO 23
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Leu Glu Gln Tyr Ala Asn Gln Leu Ala Asp Gln Ile Ile Lys Glu Ala
1               5                   10                  15

Thr Glu

<210> SEQ ID NO 24
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 24

Phe Glu Glu Leu Ala Trp Lys Ile Ala Lys Met Ile Trp Ser Asp Val
1               5                   10                  15

Phe Gln Gln Cys
            20

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Ile Glu Tyr Leu Ala Lys Gln Ile Pro Asp Asn Ala Ile Gln Gln
1               5                   10                  15

Ala

<210> SEQ ID NO 26
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Lys Gly Ala Asp Leu Ile Glu Glu Ala Ala Ser Arg Ile Val Asp Ala
1               5                   10                  15

Val Ile Glu Gln Val Lys Ala Ala Gly
            20                  25

<210> SEQ ID NO 27
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Lys Gly Ala Asp Leu Ile Glu Glu Ala Ala Ser Arg Ile Pro Asp Ala
1               5                   10                  15

Pro Ile Glu Gln Val Lys Ala Ala Gly
            20                  25

<210> SEQ ID NO 28
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Pro Glu Asp Ala Glu Leu Val Arg Leu Ser Lys Arg Leu Val Glu Asn
1               5                   10                  15

Ala Val Leu Lys Ala Val Gln Gln Tyr
            20                  25

<210> SEQ ID NO 29
<211> LENGTH: 25
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 29

Pro Glu Asp Ala Glu Leu Val Arg Thr Ser Lys Arg Leu Val Glu Asn
1               5                   10                  15

Ala Val Leu Lys Ala Val Gln Gln Tyr
            20                  25

<210> SEQ ID NO 30
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Pro Glu Asp Ala Glu Leu Val Arg Leu Ser Lys Arg Asp Val Glu Asn
1               5                   10                  15

Ala Val Leu Lys Ala Val Gln Gln Tyr
            20                  25

<210> SEQ ID NO 31
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Pro Glu Asp Ala Glu Leu Val Arg Leu Ser Lys Arg Leu Pro Glu Asn
1               5                   10                  15

Ala Val Leu Lys Ala Val Gln Gln Tyr
            20                  25

<210> SEQ ID NO 32
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Pro Glu Asp Ala Glu Leu Val Arg Leu Ser Lys Arg Leu Pro Glu Asn
1               5                   10                  15

Ala Pro Leu Lys Ala Val Gln Gln Tyr
            20                  25

<210> SEQ ID NO 33
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Pro Glu Asp Ala Glu Leu Val Arg Leu Ser Lys Arg Leu Val Glu Asn
1               5                   10                  15

Ala Val Glu Lys Ala Val Gln Gln Tyr
            20                  25
```

```
<210> SEQ ID NO 34
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Glu Glu Gly Leu Asp Arg Asn Glu Glu Ile Lys Arg Ala Ala Phe Gln
1               5                   10                  15

Ile Ile Ser Gln Val Ile Ser Glu Ala
            20                  25

<210> SEQ ID NO 35
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Leu Val Asp Asp Pro Leu Glu Tyr Gln Ala Gly Leu Leu Val Gln Asn
1               5                   10                  15

Ala Ile Gln Gln Ala Ile Ala Glu Gln
            20                  25

<210> SEQ ID NO 36
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Tyr Glu Thr Leu Leu Ile Glu Thr Ala Ser Ser Leu Val Lys Asn
1               5                   10                  15

Ala Ile Gln Leu Ser Ile Glu Gln Leu
            20                  25

<210> SEQ ID NO 37
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Leu Glu Lys Gln Tyr Gln Glu Gln Leu Glu Glu Val Ala Lys Val
1               5                   10                  15

Ile Val Ser Met Ser Ile Ala Phe Ala
            20                  25

<210> SEQ ID NO 38
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Asn Thr Asp Glu Ala Gln Glu Glu Leu Ala Trp Lys Ile Ala Lys Met
```

```
                1               5                  10                 15
Ile Val Ser Asp Ile Met Gln Gln Ala
            20                  25

<210> SEQ ID NO 39
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Val Asn Leu Asp Lys Lys Ala Val Leu Ala Glu Lys Ile Val Ala Glu
1               5                   10                  15

Ala Ile Glu Lys Ala Glu Arg Glu Leu
            20                  25

<210> SEQ ID NO 40
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asn Gly Ile Leu Glu Leu Glu Thr Lys Ser Ser Lys Leu Val Gln Asn
1               5                   10                  15

Ile Ile Gln Thr Ala Val Asp Gln Phe
            20                  25

<210> SEQ ID NO 41
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Thr Gln Asp Lys Asn Tyr Glu Asp Glu Leu Thr Gln Val Ala Leu Ala
1               5                   10                  15

Leu Val Glu Asp Val Ile Asn Tyr Ala
            20                  25

<210> SEQ ID NO 42
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Glu Thr Ser Ala Lys Asp Asn Ile Asn Ile Glu Glu Ala Ala Arg Phe
1               5                   10                  15

Leu Val Glu Lys Ile Leu Val Asn His
            20                  25

<210> SEQ ID NO 43
<211> LENGTH: 44
<212> TYPE: PRT
<213> ORGANISM: Artificial Sequence
<220> FEATURE:
<223> OTHER INFORMATION: Description of Artificial Sequence: Synthetic
```

```
        polypeptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (4)..(4)
<223> OTHER INFORMATION: Gln or Asn
<220> FEATURE:
<221> NAME/KEY: MOD_RES
<222> LOCATION: (10)..(10)
<223> OTHER INFORMATION: Thr or Ser
<220> FEATURE:
<221> NAME/KEY: MOD_RES
<222> LOCATION: (18)..(18)
<223> OTHER INFORMATION: Val, Ile, Leu or Ala
<220> FEATURE:
<221> NAME/KEY: MOD_RES
<222> LOCATION: (23)..(23)
<223> OTHER INFORMATION: Gln or Asn
<220> FEATURE:
<221> NAME/KEY: MOD_RES
<222> LOCATION: (33)..(33)
<223> OTHER INFORMATION: Val, Ile, Leu or Ala
<220> FEATURE:
<221> NAME/KEY: MOD_RES
<222> LOCATION: (34)..(34)
<223> OTHER INFORMATION: Glu or Asp
<220> FEATURE:
<221> NAME/KEY: MOD_RES
<222> LOCATION: (37)..(37)
<223> OTHER INFORMATION: Thr or Ser
<220> FEATURE:
<221> NAME/KEY: MOD_RES
<222> LOCATION: (38)..(38)
<223> OTHER INFORMATION: Arg or Lys
<220> FEATURE:
<221> NAME/KEY: MOD_RES
<222> LOCATION: (40)..(40)
<223> OTHER INFORMATION: Arg or Lys
<220> FEATURE:
<221> NAME/KEY: MOD_RES
<222> LOCATION: (42)..(42)
<223> OTHER INFORMATION: Ala, Leu, Ile or Val
<220> FEATURE:
<221> NAME/KEY: MOD_RES
<222> LOCATION: (44)..(44)
<223> OTHER INFORMATION: Ala, Leu, Ile or Val

<400> SEQUENCE: 43

Xaa His Ile Xaa Ile Pro Pro Gly Leu Xaa Glu Leu Leu Gln Gly Tyr
1               5                   10                  15

Thr Xaa Glu Val Leu Arg Xaa Gln Pro Pro Asp Leu Val Glu Phe Ala
            20                  25                  30

Xaa Xaa Tyr Phe Xaa Xaa Leu Xaa Glu Xaa Arg Xaa
        35                  40

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NODA-Ga
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-Lys(HSG)
<220> FEATURE:
```

```
<221> NAME/KEY: MOD_RES
<222> LOCATION: (3)..(3)
<223> OTHER INFORMATION: D-Tyr
<220> FEATURE:
<221> NAME/KEY: MOD_RES
<222> LOCATION: (4)..(4)
<223> OTHER INFORMATION: D-Lys(HSG)
<220> FEATURE:
<223> OTHER INFORMATION: C-term amidated

<400> SEQUENCE: 44

Ala Lys Tyr Lys
1

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NOTA
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-Lys(HSG)
<220> FEATURE:
<221> NAME/KEY: MOD_RES
<222> LOCATION: (3)..(3)
<223> OTHER INFORMATION: D-Tyr
<220> FEATURE:
<221> NAME/KEY: MOD_RES
<222> LOCATION: (4)..(4)
<223> OTHER INFORMATION: D-Lys(HSG)
<220> FEATURE:
<223> OTHER INFORMATION: C-term amidated

<400> SEQUENCE: 45

Ala Lys Tyr Lys
1

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NOTA
<220> FEATURE:
<221> NAME/KEY: MOD_RES
<222> LOCATION: (1)..(1)
<223> OTHER INFORMATION: D-Asp
<220> FEATURE:
<221> NAME/KEY: MOD_RES
<222> LOCATION: (2)..(2)
<223> OTHER INFORMATION: D-Lys(HSG)
<220> FEATURE:
<221> NAME/KEY: MOD_RES
<222> LOCATION: (3)..(3)
<223> OTHER INFORMATION: D-Tyr
<220> FEATURE:
<221> NAME/KEY: MOD_RES
<222> LOCATION: (4)..(4)
<223> OTHER INFORMATION: D-Lys(HSG)
<220> FEATURE:
<223> OTHER INFORMATION: C-term amidated

<400> SEQUENCE: 46
```

```
Asp Lys Tyr Lys
1

<210> SEQ ID NO 47
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term C-NETA-succinyl
<220> FEATURE:
<221> NAME/KEY: MOD_RES
<222> LOCATION: (1)..(1)
<223> OTHER INFORMATION: D-Lys(HSG)
<220> FEATURE:
<221> NAME/KEY: MOD_RES
<222> LOCATION: (2)..(2)
<223> OTHER INFORMATION: D-Tyr
<220> FEATURE:
<221> NAME/KEY: MOD_RES
<222> LOCATION: (3)..(3)
<223> OTHER INFORMATION: D-Lys(HSG)
<220> FEATURE:
<223> OTHER INFORMATION: C-term amidated

<400> SEQUENCE: 47

Lys Tyr Lys
1

<210> SEQ ID NO 48
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NOTA
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-Lys(HSG)
<220> FEATURE:
<221> NAME/KEY: MOD_RES
<222> LOCATION: (3)..(3)
<223> OTHER INFORMATION: D-Tyr
<220> FEATURE:
<221> NAME/KEY: MOD_RES
<222> LOCATION: (4)..(4)
<223> OTHER INFORMATION: D-Lys(HSG)
<220> FEATURE:
<223> OTHER INFORMATION: C-term amidated

<400> SEQUENCE: 48

Ala Lys Tyr Lys
1

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NOTA-NH-(CH2)7CO
<220> FEATURE:
<223> OTHER INFORMATION: C-term amidated
```

-continued

```
<400> SEQUENCE: 49

Gln Trp Val Trp Ala Val Gly His Leu Met
1               5                   10

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NOTA
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (8)..(8)
<223> OTHER INFORMATION: Threoninol

<400> SEQUENCE: 50

Phe Cys Phe Trp Lys Thr Cys Thr
1               5

<210> SEQ ID NO 51
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term DOTA
<220> FEATURE:
<221> NAME/KEY: MOD_RES
<222> LOCATION: (1)..(1)
<223> OTHER INFORMATION: D-Tyr
<220> FEATURE:
<221> NAME/KEY: MOD_RES
<222> LOCATION: (2)..(2)
<223> OTHER INFORMATION: D-Lys(HSG)
<220> FEATURE:
<221> NAME/KEY: MOD_RES
<222> LOCATION: (3)..(3)
<223> OTHER INFORMATION: D-Glu
<220> FEATURE:
<221> NAME/KEY: MOD_RES
<222> LOCATION: (4)..(4)
<223> OTHER INFORMATION: D-Lys(HSG)
<220> FEATURE:
<223> OTHER INFORMATION: C-term amidated

<400> SEQUENCE: 51

Tyr Lys Glu Lys
1

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NODA-MPAA
<220> FEATURE:
<221> NAME/KEY: MOD_RES
<222> LOCATION: (1)..(1)
```

```
<223> OTHER INFORMATION: D-Phe
<220> FEATURE:
<221> NAME/KEY: misc_feature
<222> LOCATION: (2)..(7)
<223> OTHER INFORMATION: Cyclic
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (8)..(8)
<223> OTHER INFORMATION: Threoninol

<400> SEQUENCE: 52

Phe Cys Phe Trp Lys Thr Cys Thr
1               5

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NODA-MPAA-(PEG)3
<220> FEATURE:
<223> OTHER INFORMATION: C-term amidated

<400> SEQUENCE: 53

Gln Trp Ala Val Gly His Leu Met
1               5

<210> SEQ ID NO 54
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NODA-HA
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-Lys(HSG)
<220> FEATURE:
<221> NAME/KEY: MOD_RES
<222> LOCATION: (3)..(3)
<223> OTHER INFORMATION: D-Tyr
<220> FEATURE:
<221> NAME/KEY: MOD_RES
<222> LOCATION: (4)..(4)
<223> OTHER INFORMATION: D-Lys(HSG)
<220> FEATURE:
<223> OTHER INFORMATION: C-term amidated

<400> SEQUENCE: 54

Ala Lys Tyr Lys
1

<210> SEQ ID NO 55
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

-continued

```
<223> OTHER INFORMATION: N-term NODA-MPAA
<220> FEATURE:
<221> NAME/KEY: MOD_RES
<222> LOCATION: (1)..(1)
<223> OTHER INFORMATION: D-Lys(HSG)
<220> FEATURE:
<221> NAME/KEY: MOD_RES
<222> LOCATION: (2)..(2)
<223> OTHER INFORMATION: D-Tyr
<220> FEATURE:
<221> NAME/KEY: MOD_RES
<222> LOCATION: (3)..(3)
<223> OTHER INFORMATION: D-Lys(HSG)
<220> FEATURE:
<223> OTHER INFORMATION: C-term amidated

<400> SEQUENCE: 55

Lys Tyr Lys
1

<210> SEQ ID NO 56
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NODA-EPA-succinyl
<220> FEATURE:
<221> NAME/KEY: MOD_RES
<222> LOCATION: (1)..(1)
<223> OTHER INFORMATION: D-Lys(HSG)
<220> FEATURE:
<221> NAME/KEY: MOD_RES
<222> LOCATION: (2)..(2)
<223> OTHER INFORMATION: D-Tyr
<220> FEATURE:
<221> NAME/KEY: MOD_RES
<222> LOCATION: (3)..(3)
<223> OTHER INFORMATION: D-Lys(HSG)
<220> FEATURE:
<223> OTHER INFORMATION: C-term amidated

<400> SEQUENCE: 56

Lys Tyr Lys
1

<210> SEQ ID NO 57
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NODA-EBA
<220> FEATURE:
<221> NAME/KEY: MOD_RES
<222> LOCATION: (1)..(1)
<223> OTHER INFORMATION: D-Glu
<220> FEATURE:
<221> NAME/KEY: MOD_RES
<222> LOCATION: (2)..(2)
<223> OTHER INFORMATION: D-Lys(HSG)
<220> FEATURE:
<221> NAME/KEY: MOD_RES
<222> LOCATION: (3)..(3)
<223> OTHER INFORMATION: D-Tyr
<220> FEATURE:
<221> NAME/KEY: MOD_RES
<222> LOCATION: (4)..(4)
<223> OTHER INFORMATION: D-Lys(HSG)
<220> FEATURE:
<223> OTHER INFORMATION: C-term amidated
```

```
<400> SEQUENCE: 57

Glu Lys Tyr Lys
1

<210> SEQ ID NO 58
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NODA-MBA
<220> FEATURE:
<221> NAME/KEY: MOD_RES
<222> LOCATION: (1)..(1)
<223> OTHER INFORMATION: D-Glu
<220> FEATURE:
<221> NAME/KEY: MOD_RES
<222> LOCATION: (2)..(2)
<223> OTHER INFORMATION: D-Lys(HSG)
<220> FEATURE:
<221> NAME/KEY: MOD_RES
<222> LOCATION: (3)..(3)
<223> OTHER INFORMATION: D-Tyr
<220> FEATURE:
<221> NAME/KEY: MOD_RES
<222> LOCATION: (4)..(4)
<223> OTHER INFORMATION: D-Lys(HSG)
<220> FEATURE:
<223> OTHER INFORMATION: C-term amidated

<400> SEQUENCE: 58

Glu Lys Tyr Lys
1
```